United States Patent
Spector et al.

(10) Patent No.: US 12,263,155 B2
(45) Date of Patent: Apr. 1, 2025

(54) COMBINATIONS OF MONOAMINE OXIDASE INHIBITORS AND SEROTONIN RECEPTOR AGONISTS AND THEIR THERAPEUTIC USE

(71) Applicant: Remedi, Inc., Norwell, MA (US)

(72) Inventors: Tom Spector, Chapel Hill, NC (US); Jeremy Ford, Norwell, MA (US); Thomas A. Krenitsky, Chapel Hill, NC (US)

(73) Assignee: Remedi, Inc., Norwell, MA (US)

( * ) Notice: Subject to any disclaimer, the term of this patent is extended or adjusted under 35 U.S.C. 154(b) by 0 days.

(21) Appl. No.: 18/616,046

(22) Filed: Mar. 25, 2024

(65) Prior Publication Data
US 2024/0285578 A1    Aug. 29, 2024

Related U.S. Application Data

(63) Continuation of application No. PCT/US2023/080419, filed on Nov. 17, 2023.
(Continued)

(51) Int. Cl.
*A61K 31/39* (2006.01)
*A61K 31/4045* (2006.01)
*A61P 25/24* (2006.01)

(52) U.S. Cl.
CPC .......... *A61K 31/39* (2013.01); *A61K 31/4045* (2013.01); *A61P 25/24* (2018.01)

(58) Field of Classification Search
CPC .. A61K 2300/00; A61K 31/23; A61K 31/231; A61K 31/352; A61K 31/36;
(Continued)

(56) References Cited

U.S. PATENT DOCUMENTS

| 6,110,961 A | 8/2000 | White et al. |
| 7,812,050 B2 | 10/2010 | Brot et al. |

(Continued)

FOREIGN PATENT DOCUMENTS

| CA | 3166511 A1 | 7/2021 |
| EP | 2774991 A1 | 9/2014 |

(Continued)

OTHER PUBLICATIONS

Adams CE, et al. Contingency Management for Patients with Cooccurring Disorders: Evaluation of a Case Study and Recommendations for Practitioners, Case Reports in Psychiatry, 2012, Article ID 731638.
(Continued)

*Primary Examiner* — Savitha M Rao
(74) *Attorney, Agent, or Firm* — CALYX LAW; Graham Pechenik

(57) ABSTRACT

Disclosed are methods of treating a subject having a disease or disorder by administering a monoamine oxidase inhibitor in combination with a serotonin receptor agonist, which in some embodiments is a deuterated serotonin receptor agonist. In some aspects, the disclosure further relates to pharmaceutical compositions and kits comprising a monoamine oxidase inhibitor and a serotonin receptor agonist. In some embodiments, the monoamine oxidase inhibitor is a MAO-A-selective inhibitor such as CX157, and the serotonin receptor agonist is a serotonin 2A receptor agonist such as N,N-dimethyltryptamine (DMT), or deuterated DMT.

19 Claims, 12 Drawing Sheets

Related U.S. Application Data

(60) Provisional application No. 63/472,532, filed on Jun. 12, 2023, provisional application No. 63/426,266, filed on Nov. 17, 2022.

(58) Field of Classification Search
CPC ............ A61K 31/4045; A61K 31/4406; A61K 31/675; A61K 31/704; A61K 31/7048; A61K 45/06; A61P 25/00; A61P 25/22; A61P 25/24
See application file for complete search history.

(56) References Cited

U.S. PATENT DOCUMENTS

| | | |
|---|---|---|
| 8,313,766 B2 | 11/2012 | Chen et al. |
| 11,242,318 B2 | 2/2022 | Nivorozhkin et al. |
| 11,406,619 B2 | 8/2022 | Layzell et al. |
| 11,471,417 B2 | 10/2022 | Rands et al. |
| 11,578,039 B2 | 2/2023 | Rands et al. |
| 11,643,390 B2 | 5/2023 | Rands et al. |
| 11,660,289 B2 | 5/2023 | Rands et al. |
| 11,697,638 B2 | 7/2023 | Rands et al. |
| 11,724,985 B2 | 8/2023 | Nivorozhkin et al. |
| 11,746,088 B2 | 9/2023 | Nivorozhkin et al. |
| 11,771,681 B2 | 10/2023 | Rands et al. |
| 11,773,062 B2 | 10/2023 | Rands et al. |
| 11,834,410 B2 | 12/2023 | Nivorozhkin et al. |
| 2008/0009542 A1 | 1/2008 | Brot et al. |
| 2012/0003274 A1 | 1/2012 | Brand et al. |
| 2012/0003303 A1 | 1/2012 | Brand et al. |
| 2021/0346347 A1 | 11/2021 | Witowski et al. |
| 2022/0062237 A1 | 3/2022 | Layzell et al. |
| 2022/0081396 A1 | 3/2022 | Rands et al. |
| 2022/0168274 A1 | 6/2022 | Rands et al. |
| 2022/0169606 A1 | 6/2022 | Rands et al. |
| 2022/0313660 A1 | 10/2022 | Layzell et al. |
| 2023/0081892 A1 | 3/2023 | Nozuki et al. |
| 2023/0126298 A1 | 4/2023 | Nivorozhkin et al. |
| 2023/0149293 A1 | 5/2023 | Rands et al. |
| 2023/0159456 A1 | 5/2023 | Duncton et al. |
| 2023/0167056 A1 | 6/2023 | Rands et al. |
| 2023/0181530 A1 | 6/2023 | Rands et al. |
| 2023/0283364 A1 | 9/2023 | Shen et al. |

FOREIGN PATENT DOCUMENTS

| | | |
|---|---|---|
| JP | 2012214443 A | 11/2012 |
| WO | 1998012190 A2 | 3/1998 |
| WO | 2010080970 A2 | 7/2010 |
| WO | 2010080977 A2 | 7/2010 |
| WO | 2011069051 A1 | 6/2011 |
| WO | 2011096953 A1 | 8/2011 |
| WO | 2012018759 A3 | 2/2012 |
| WO | 2020198613 A1 | 10/2020 |
| WO | 2020245133 A1 | 12/2020 |
| WO | 2021116503 A2 | 6/2021 |
| WO | 2021234608 A1 | 11/2021 |
| WO | 2021243461 A1 | 12/2021 |
| WO | 2021244831 A1 | 12/2021 |
| WO | 2021259962 A1 | 12/2021 |
| WO | 2022117359 A1 | 6/2022 |
| WO | 2022212854 A1 | 10/2022 |
| WO | 2022235587 A1 | 11/2022 |
| WO | 2023023347 | 2/2023 |
| WO | 2023081892 A1 | 5/2023 |
| WO | 2023108174 A1 | 6/2023 |
| WO | 2023135237 A1 | 7/2023 |
| WO | 2023186963 A1 | 10/2023 |

OTHER PUBLICATIONS

Armstrong R. What causes neurodegenerative disease?. Folia Neuropathol. 2020;58(2):93-112.
Barker SA. Administration of N,N-dimethyltryptamine (DMT) in psychedelic therapeutics and research and the study of endogenous DMT. Psychopharmacology (Berl). 2022;239(6):1749-1763.
Berge et al., Pharmaceutical Salts. J.Pharm. Sci., 1977;66:1-19.
Borbely et al. Novel drug developmental strategies for treatment-resistant depression. Br J Pharmacol. 2022; 179 (6):1146-1186.
Boulle et al. Epigenetic regulation of the BDNF gene: implications for psychiatric disorders. Mol Psychiatry. 2012;17(6):584-596.
Brierley & Davidson. Developments in harmine pharmacology—implications for ayahuasca use and drug—dependence treatment. Prog Neuropsychopharmacol Biol Psychiatry. 2012;39(2):263-272.
Brito-Da-Costa et al. Toxicokinetics and Toxicodynamics of Ayahuasca Alkaloids N,N-Dimethyltryptamine (DMT), Harmine, Harmaline and Tetrahydroharmine: Clinical and Forensic Impact. Pharmaceuticals (Basel). 2020;13 (11):334.
Bunag RD. Validation in awake rats of a tail-cuff method for measuring systolic pressure. J Appl Physiol. 1973;34 (2):279-282.
Burch et al. Lack of tyramine pressor response effect with oral CX157: A specific reversible MAOI. Clin Pharmacol Drug Dev. 2014;3(1):4-12.
Cameron and Olson. Dark Classics in Chemical Neuroscience: N,N-Dimethyltryptamine (DMT). ACS Chem Neurosci. 2018;9(10):2344-2357.
Cameron et al. Chronic, Intermittent Microdoses of the Psychedelic N,N-Dimethyltryptamine (DMT) Produce Positive Effects on Mood and Anxiety in Rodents. ACS Chem Neurosci. 2019;10(7):3261-3270.
Carbonario & Gatch. Neuropharmacology of N,N-dimethyltryptamine. Brain Res Bull. 2016;126(Pt 1):74-88.
Carradori et al. Patent-related survey on new monoamine oxidase inhibitors and their therapeutic potential. Expert Opin Ther Pat. 2012;22(7):759-801.
Cenerx Biophrma Inc. A Study of CX157 (TriRima) for the Treatment of Depression (CX157-200). NCT00739908. Jun. 17, 2012.
Cenerx Biophrma Inc. Efficacy, Safety and Tolerability of CX157 in Treatment Resistant Depression (CX157-201) NCT01246908. Jul. 10, 2012.
Cenerx Biophrma Inc. Oral Tyramine Pressor Response Study of CX157 Tablets in Healthy Male Volunteers (CX157-112). NCT01633437. Jul. 4, 2012.
Chan FK, et al., Programmed Necrosis in the Cross Talk of Cell Death and Inflammation, Annu Rev Immunol. 2015; 33:79-10.
Chi et al. Neuronal cell death mechanisms in major neurodegenerative diseases. Int J Mol Sci. 2018;19(10):3082.
Chiuccariello et al. Monoamine Oxidase-A Occupancy by Moclobemide and Phenelzine: Implications for the Development of Monoamine Oxidase Inhibitors. Int J Neuropsychopharmacol. 2015;19(1):pyv078.
Chou & Talalay. Quantitative analysis of dose-effect relationships: the combined effects of multiple drugs or enzyme inhibitors. Adv Enzyme Regul. 1984;22:27-55.
Cloez-Tayarani et al. Differential effect of serotonin on cytokine production in lipopolysaccharide-stimulated human peripheral blood mononuclear cells: involvement of 5-hydroxytryptamine2A receptors. Int Immunol. 2003;15 (2):233-240.
Crits-Cristoph P, et al., Psychosocial treatments for cocaine dependence: National Institute on Drug Abuse collaborative cocaine.
Dugger BN & Dickson DW, Pathology of Neurodegenerative Diseases. Cold Spring Harb Perspect Biol. 2017;9(7): a028035.
Entzeroth & Ratty. Monoamine Oxidase Inhibitors-Revisiting a Therapeutic Principle. Open Journal of Depression. 2017;6(2):31-68.
Finberg & Rabey. Inhibitors of MAO-A and MAO-B in Psychiatry and Neurology. Front Pharmacol. 2016;7:340.
Finberg & Tenne. Relationship between tyramine potentiation and selective inhibition of monoamine oxidase types A and B in the rat vas deferens. Br J Pharmacol. 1982;77(1):13-21.
Finberg JP. Update on the pharmacology of selective inhibitors of MAO-A and MAO-B: focus on modulation of CNS monoamine neurotransmitter release. Pharmacol Ther. 2014;143(2):133-152.
Flanagan & Nichols. Psychedelics as anti-inflammatory agents. Int Rev Psychiatry. 2018;30(4):363-375.
Fowler et al. Monoamine oxidase: radiotracer chemistry and human studies. J Labelled Comp Radiopharm. 2015;58(3):51-64.

(56) References Cited

OTHER PUBLICATIONS

Fowler et al. Reversible inhibitors of monoamine oxidase-A (RIMAs): robust, reversible inhibition of human brain MAO-A by CX157. Neuropsychopharmacology. 2010;35(3):623-631.
Gerardy J. Effect of moclobemide on rat brain monoamine oxidase A and B: comparison with harmaline and clorgyline. Prog Neuropsychopharmacol Biol Psychiatry. 1994; 18(4):793-802.
Germolec et al. Markers of Inflammation. Methods Mol Biol. 2018;1803:57-79.
Gleiter et al. Effect of the selective MAO-A inhibitors brofaromine, clorgyline and moclobemide on human platelet MAO-B activity. J Neural Transm Gen Sect. 1992;89(1-2):129-133.
Glennon R, Arylalkylamine Drugs of Abuse: An Overview of Drug Discrimination Studies, Pharmacology Biochemistry and Behavior, 1999; 64, 251-56.
Glennon R. Serotonin Interactions of Harmaline and Several Related B-Carbolines. Life Sciences. 1981;29:861-865.
Grob CS & Grigsby J, Handbook of Medical Hallucinogens, 2021.
Grof et al. LSD-assisted psychotherapy in patients with terminal cancer. Int Pharmacopsychiatry. 1973;8 (3):129-144.
Gwaltney et al. Self-efficacy and smoking cessation: a meta-analysis. Psychol Addict Behav. 2009;23(1):56-66.
Handforth. Harmaline Tremor: Underlying Mechanisms in a Potential Animal Model of Essential Tremor. Tremor and Other Hyperkinetic Movements. 2012;2:02-92-769.
Holford & Sheiner. Understanding the dose-effect relationship: clinical application of pharmacokinetic-pharmacodynamic models. Clin Pharmacokinet. 1981;6(6):429-453.
Holze et al. Safety pharmacology of acute LSD administration in healthy subjects [published correction appears in Psychopharmacology (Berl). Feb. 2022;239(2):661]. Psychopharmacology (Berl). 2022;239(6):1893-1905.
House et al. Comparison of the hallucinogenic indole alkaloids ibogaine and harmaline for potential immunomodulatory activity. Pharmacology. 1995;51(1):56-65.
Huang et al. Isobologram Analysis: A Comprehensive Review of Methodology and Current Research. Front Pharmacol. 2019;10:1222.
Hung CI, Factors predicting adherence to antidepressant treatment, Curr. Opin. Psychiatry 2014;27:344-9.
Katz et al. Characterizing the psychological state produced by LSD. J Abnorm Psychol. 1968;73(1):1-14.
Koulu et al. Inhibition of monoamine oxidase by moclobemide: effects on monoamine metabolism and secretion of anterior pituitary hormones and cortisol in healthy volunteers. Br J Clin Pharmacol. 1989;27(2):243-255.
Kozlowska et al. From psychiatry to neurology: Psychedelics as prospective therapeutics for neurodegenerative disorders. J Neurochem. 2022;162(1):89-108.
Laban & Abdolreza. Monoamine Oxidase Inhibitors (MAOI). StatPearls [Internet]. 2023.
Lotufo-Neto et al. Meta-Analysis of the Reversible Inhibitors of Monoamine Oxidase Type A Moclobemide and Brofaromine for the Treatment of Depression. Neuropsychopharmacology. 1999;20:226-247.
Luethi D & Liechti ME, Designer drugs: mechanism of action and adverse effects, Arch. Toxicol., 2020; 94, 1085-133.
Lum & Stahl. Opportunities for reversible inhibitors of monoamine oxidase-A (RIMAs) in the treatment of depression. CNS Spectr. 2012;17(3):107-120.
Luo et al. Normal Reference Intervals of Neutrophil-To-Lymphocyte Ratio, Platelet-To-Lymphocyte Ratio, Lymphocyte-To-Monocyte Ratio, and Systemic Immune Inflammation Index in Healthy Adults: a Large Multi-Center Study from Western China . Clin Lab. 2019 1;65(3).
Ly et al. Transient Stimulation with Psychoplastogens Is Sufficient to Initiate Neuronal Growth. ACS Pharmacol Transl Sci. 2020;4(2):452-460.
Mithoefer MC, et al., A Manual for MDMA-Assisted Therapy in the Treatment of Posttraumatic Stress Disorder. 2017 Ver 8.1.

Moliner et al. Psychedelics promote plasticity by directly binding to BDNF receptor TrkBNat. Neurosci. 2023;26:1032-1041.
Morales-Garcia et al. N,N-dimethyltryptamine compound found in the hallucinogenic tea ayahuasca, regulates adult neurogenesis in vitro and in vivo. Transl Psychiatry. 2020;10(1):331.
Nasehi et al. Interaction between harmane, a class of β-carboline alkaloids, and the CA1 serotonergic system in modulation of memory acquisition. Neurosci Res. 2017;122:17-24.
NCT00739908. A Study of CX157 (TriRima) for the Treatment of Depression (CX157-200). Aug. 22, 2008.
NCT01246908. Efficacy, Safety and Tolerability of CX157 in Treatment Resistant Depression (CX157-201). Nov. 24, 2010.
NCT01633437. Oral Tyramine Pressor Response Study of CX157 Tablets in Healthy Male Volunteers (CX157-112). Jul. 4, 2012.
Nichols DE, Psychedelics, Pharmacological Reviews, 2016; 68(2):264-355.
Ott J. Pharmahuasca: human pharmacology of oral DMT plus harmine. J Psychoactive Drugs. 1999;31(2):171-177.
Ott. Pharmahuasca: On Phenethylamines and Potentiation. Newsletter of the Multidisciplinary Association for Psychedelic Studies. 1996;6(3):32-34.
Petry et al. "Prize reinforcement contingency management for cocaine dependence: integration with group therapy in a methadone clinic." Journal of consulting and clinical psychology. 2005;73(2):354.
Pusefidelity. Beyond the Void: An Experience with Huasca Combo (Syrian Rue & DMT) (exp103790). Erowid. Jul. 11, 2016.
Reckweg et al. A Phase 1, Dose-Ranging Study to Assess Safety and Psychoactive Effects of a Vaporized 5-Methoxy-N, N-Dimethyltryptamine Formulation (GH001) in Healthy Volunteers. Front Pharmacol. 2021;12:760671.
Reckweg et al. The clinical pharmacology and potential therapeutic applications of 5-methoxy-N,N-dimethyltryptamine (5-MeO-DMT). J Neurochem. 2022;162(1):128-146.
Richards et al. DPT as an adjunct in brief psychotherapy with cancer patients. Omega. 1979;10(1):9-26.
Robinson et al. The Monoamine Oxidase Inhibitor, Phenelzine, in the Treatment of Depressive-Anxiety States A Controlled Clinical Trial. Arch Gen Psychiatry. 1973;29(3):407-413.
Rohsenhow et al, Brief coping skills treatment for cocaine abuse: 12-month substance use outcomes. J. Consul. Clin. Psychol. 2000; 68(3): 515-2.
Saeger & Olson. Psychedelic-inspired approaches for treating neurodegenerative disorders. J Neurochem. 2022;162(1):109-127.
Samorini G. The oldest archeological data evidencing the relationship of *Homo sapiens* with psychoactive plants: A worldwide overview. Journal of Psychedelic Studies. 2019;1-18.
Schenberg EE, Psychedelic-Assisted Psychotherapy: A Paradigm Shift in Psychiatric Research and Development. Neuropharmacology, 2018;9:733.
Shen et al. Psychedelic 5-methoxy-N,N-dimethyltryptamine: metabolism, pharmacokinetics, drug interactions, and pharmacological actions. Curr Drug Metab. 2010;11(8):659-666.
Shulgin & Shulgin. PiHKAL: A Chemical Love Story, 1992 Transform Press, Berkeley CA.
Shulgin & Shulgin. TiHKAL: The Continuation, 1997 Transform Press.
Stefulj et al. mRNA expression of serotonin receptors in cells of the immune tissues of the rat. Brain Behav Immun. 2000;14(3):219-224.
Stotts AL, et al., Motivational Interviewing with Cocaine-Dependent Patients: A Pilot Study, J. Consul. Clin. Psychol. 2001;69(5):858-62.
Strassman et al. Dose-response study of N,N-dimethyltryptamine in humans. II. Subjective effects and preliminary results of a new rating scale. Archives of General Psychiatry. 1994;51(2):98-108.
Szabo & Slavish. Measuring salivary markers of inflammation in health research: A review of methodological considerations and best practices. Psychoneuroendocrinology. 2021;124:105069.
Tarawneh R, et al., Cerebrospinal Fluid Markers of Neurodegeneration and Rates of Brain Atrophy in Early Alzheimer Disease, Neurol. 2015; 72(6): 656-65.

(56) References Cited

OTHER PUBLICATIONS

Toh EA, et al., Comparison of cognitive and UHDRS measures in monitoring disease progression in Huntington's disease: a 12-month longitudinal study, Transl Neurodegener. 2014;3:15.

Tyagi et al. The Psychedelic N,N-Dipropyltryptamine Prevents Seizures in a Mouse Model of Fragile X Syndrome via a Mechanism that Appears Independent of Serotonin and Sigma1 Receptors. ACS Pharmacol Transl Sci. 2023;6 (10):1480-1491.

Vargas et al. Psychedelics promote neuroplasticity through the activation of intracellular 5-HT2A receptors. Science. 2023;379(6633):700-706.

White & Scates. Mechanism of monoamine oxidase-A inhibition by BW 1370U87. Drug Development Research. 1992;25(3):191-199.

Zhang et al. Brain-derived Neurotrophic Factor (BDNF)-TrkB Signaling in Inflammation-related Depression and Potential Therapeutic Targets. Curr Neuropharmacol. 2016;14(7):721-731.

Zhao et al. Inhibition of Human Cytochrome P450 Enzymes 3A4 and 2D6 by β-Carboline Alkaloids, Harmine Derivatives. Phytotherapy Research. 2011;25(11):1671-1677.

Brian Gormley, CeNeRx BioPharma Winds Down as Placebo Effect Dooms Antidepressant Study, Jun. 20, 2013. WSJ Pro.

CeNeRx BioPharma Announces $18.5 Million Series A Financing, BioSpace, Nov. 29, 2005.

CeNeRX BioPharma Completes $13 Million Series C Financing, PR Newswire, Aug. 13, 2020.

CeNeRX BioPharma, Inc. Completes $15 Million Series B Financing, Fierce Biotech, Oct. 17, 2008.

Cenerx Biopharma, Inc., CeNeRx's Novel Antidepressant TriRima™ Demonstrates Key Safety Benefit in Pivotal Safety Study, PR Newswire, Nov. 2, 2010.

Fowler, J., Logan, J., Azzaro, A. et al. Reversible Inhibitors of Monoamine Oxidase-A (RIMAs): Robust, Reversible Inhibition of Human Brain MAO-A by CX157. Neuropsychopharmacol 35, 623-631 (2010).

Frank Vinluan, CeNeRx, expecting trial results and drug partner in 2012, raises $4.8M, MedCityNews, Dec. 9, 2011.

Loewe S. T. Effect of combinations: mathematical basis of problem. Arch. Exp. Pathol. Pharmakol., 1926;114:313-326.

Mahnaz Asgharnejad, Pharm. D; Daniel Burch, M.D., Clinical Study Report for CX157-201 A Randomized, Double-Blind, Placebo-Controlled, Parallel-Group, Assessment of the Efficacy, Safety and Tolerability of CX157 Modified Release Tablet, 125 mg Twice Per Day in Subjects with Treatment Resistant Depression, Sep. 25, 2012.

Mahnaz Asgharnejad, Pharm. D; Mark Sale, MD; Brian Yan, Ph.D; Daniel Burch, M.D., Clinical Study Report for CX157-200 A Randomized, Double-Blind, Placebo-Controlled, Parallel-Group, Assessment of the Efficacy, Safety and Tolerability of CX157 60 mg TID in Subjects with Major Depressive Disorder, Mar. 15, 2010.

Targum S. Early symptomatic improvement affects treatment outcome in a study of major depressive disorder. Journal of Psychiatric Research. 2017;95:276-281.

Targum S. et al., Use of band-pass filter analysis to evaluate outcomes in an antidepressant trial for treatment resistant patients, European Neuropsychopharmacology, vol. 24, Issue 8, 2014, pp. 1188-1195,.

The Daily Startup: Placebo Effect Makes CeNeRx Shutdown Real, The Wall Street Journal, Jun. 20, 2013.

COMBINATIONS OF MONOAMINE OXIDASE INHIBITORS AND SEROTONIN RECEPTOR AGONISTS AND THEIR THERAPEUTIC USE

CROSS-REFERENCE

This application is a continuation of International Application No. PCT/US2023/80419, filed in the U.S. Receiving Office on Nov. 17, 2023, which claims the benefit of priority under PCT Article 8(1) and Rule 4.10 to U.S. Provisional App. No. 63/426,266, filed Nov. 17, 2022, and U.S. Provisional App. No. 63/472,532, filed Jun. 12, 2023, both of which are incorporated by reference for all purposes as if fully set forth herein.

FIELD OF THE INVENTION

The disclosure relates to methods of treating a subject having a disease or disorder by administering a monoamine oxidase inhibitor (MAOI) together with a serotonin (5-HT) receptor agonist, which in some embodiments is deuterated. In some aspects, the disclosure further relates to pharmaceutical compositions and kits comprising a MAOI and a 5-HT receptor agonist, such as a serotonin 2A (5-HT$_{2A}$) receptor agonist.

BACKGROUND OF THE INVENTION

Dimethyltryptamine (DMT) is a natural endogenous agonist for the serotonin 2A (5-HT$_{2A}$) receptor with considerable therapeutic potential. Investigators are exploring using DMT to treat several disorders and diseases such as major depressive disorder (MDD), treatment-resistant depression (TRD), generalized anxiety disorder (GAD), post-traumatic stress disorder (PTSD), obsessive-compulsive disorder (OCD), and post-cerebral infarction (ischemic stroke) recovery, among others.

DMT, like many other psychedelics, has variable bioavailability and duration of action that may limit clinical use and can undermine treatment accessibility. Furthermore, rapid metabolic clearance of DMT and certain other psychedelics precludes oral administration, significantly reduces bioavailability, and requires more invasive routes of administration (e.g., injection, inhalation).

There is accordingly an ongoing need for the development of effective and safe methods for reliably administering psychedelic compounds, such as DMT, especially methods that minimize side effects, optimize efficacy, and allow for greater access, including through greater ease of administration. Provided herein are methods, compositions, uses, and pharmaceutical kits to meet these needs and others, and having such advantages and improvements as will become readily apparent through the disclosure below.

INCORPORATION BY REFERENCE

Each cited patent, publication, and non-patent literature is incorporated by reference in its entirety, as if each was incorporated individually, and as if each is fully set forth herein. However, no such citation should be construed as an admission that a cited reference comes from an area that is analogous or directly applicable to the invention, nor should a citation be construed as an admission that a document or underlying information, in any jurisdiction, is prior art or forms part of the common general knowledge in the art.

BRIEF SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

In some aspects are disclosed pharmaceutical compositions and pharmaceutical kits or kits of parts, which are useful to treat a disease or disorder in a human subject, and which comprise therapeutically effective amounts of 3-fluoro-7(2,2,2-trifluorethoxy)phenoxathiine-10,10-dioxide (i.e., the compound CX157):

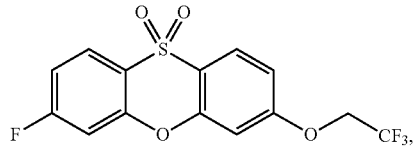 [SMILES: O=S1(=O)c2ccc(F)cc2Oc2cc(OCC(F)(F)F)ccc21]

or a pharmaceutically acceptable salt thereof, together with a serotonin 2A (5-HT$_{2A}$) receptor agonist, or a pharmaceutically acceptable salt thereof, preferably but optionally wherein the 5-HT$_{2A}$ receptor agonist is susceptible to degradation by monoamine oxidase A (MAO-A).

In some embodiments, the 5-HT$_{2A}$ receptor agonist is a tryptamine. In some embodiments, the tryptamine is a psychedelic tryptamine. In some embodiments, the tryptamine is any of 6-allyl-N,N-diethyl-norlysergamide (AL-LAD), N,N-dibutyltryptamine (DBT), N,N-diethyltryptamine (DET), N,N-diisopropyl-tryptamine (DiPT), 5-methoxy-α-methyltryptamine (α,O-DMS), N,N-dimethyltryptamine (DMT), 2,α-dimethyltryptamine (2,α-DMT), α,N-dimethyltryptamine (α,N-DMT), N,N-dipropyltryptamine (DPT), N-ethyl-N-isopropyltryptamine (EiPT), α-ethyltryptamine (AET), 6,N,N-triethylnorlysergamide (ETH-LAD), N,N-dibutyl-4-hydroxytryptamine (4-HO-DBT), N,N-diethyl-4-hydroxytryptamine (4-HO-DET), N,N-diisopropyl-4-hydroxytryptamine (4-HO-DiPT), N,N-dimethyl-4-hydroxytryptamine (4-HO-DMT), N,N-dimethyl-5-hydroxytryptamine (5-HO-DMT, bufotenine), N,N-dipropyl-4-hydroxytryptamine (4-HO-DPT), N-ethyl-4-hydroxy-N-methyltryptamine (4-HO-MET), 4-hydroxy-N-isopropyl-N-methyltryptamine (4-HO-MiPT), 4-hydroxy-N-methyl-N-propyl-tryptamine (4-HO-MPT), 4-hydroxy-N,N-tetramethylene-tryptamine (4-HO-pyr-T), 12-methoxyibogamine (Ibogaine), N-butyl-N-methyltryptamine (MBT), N,N-diisopropyl-4,5-methylenedioxytryptamine (4,5-MDO-DiPT), N,N-diisopropyl-5,6-methylenedioxy-tryptamine (5,6-MDO-DiPT), N,N-dimethyl-4,5-methylenedioxytryptamine (4,5-MDO-DMT), N,N-dimethyl-5,6-methylenedioxytryptamine (5,6-MDO-DMT), N-isopropyl-N-methyl-5,6-methylenedioxy-tryptamine (5,6-MDO-MiPT), N,N-diethyl-2-methyltryptamine (2-Me-DET), 2,N,N-trimethyltryptamine (2-Me-DMT), N-acetyl-5-methoxytryptamine (melatonin), N,N-diethyl-5-methoxytryptamine (5-MeO-DET), N,N-diisopropyl-5-methoxytryptamine (5-MeO-DiPT), 5-methoxy-N,N-dimethyltryptamine (5-MeO-DMT), N-isopropyl-4-methoxy-N-methyltryptamine (4-MeO-MiPT), N-isopropyl-5-methoxy-N-methyltryptamine (5-MeO- MiPT), 5,6-dimethoxy-N-isopropyl-N-methyltryptamine (5,6-MeO-MiPT), 5-methoxy-N-methyl-tryptamine (5-MeO-NMT), 5-methoxy-N,N-tetramethylenetryptamine (5-MeO-pyr-T), 6-methoxy-1-methyl-1,2,3,4-tetrahydrocarboline (6-MeO-THH), 5-methoxy-2,N,N-trimethyltryptamine (5-MeO-TMT), N,N-dimethyl-5-methylthio-tryptamine (5-MeS-DMT), N-isopropyl-N-methyltryptamine (MiPT), α-methyl-tryptamine (α-MT), N-ethyltryptamine (NET), N-methyltryptamine (NMT), 6-propylnorlysergamide (PRO-LAD), N,N-tetramethylenetryptamine (pyr-T), 7-methoxy-1-methyl-1,2,3,4-tetrahydrocarboline (tetrahydroharmine), α,N-dimethyl-5-methoxytryptamine (α,N,O-TMS), bufotenine, psilocin, or psilocybin; or a pharmaceutically acceptable salt thereof.

In some embodiments, the 5-HT$_{2A}$ receptor agonist is any of DMT, 5-MeO-DMT, DPT, psilocin, or psilocybin; or a pharmaceutically acceptable salt thereof. In some embodiments, the 5-HT$_{2A}$ receptor agonist is DPT, or a pharmaceutically acceptable salt thereof. In some embodiments, the 5-HT$_{2A}$ receptor agonist is 5-MeO-DMT, or a pharmaceutically acceptable salt thereof. In some embodiments, the 5-HT$_{2A}$ receptor agonist is DMT, or a pharmaceutically acceptable salt thereof.

In some embodiments, the 5-HT$_{2A}$ receptor agonist is a deuterated 5-HT$_{2A}$ agonist. In some embodiments, the deuterated 5-HT$_{2A}$ agonist is a deuterated tryptamine, or a pharmaceutically acceptable salt thereof. In some embodiments, the deuterated tryptamine is a deuterated psychedelic tryptamine, or a pharmaceutically acceptable salt thereof. In some embodiments, the deuterated psychedelic tryptamine is deuterated DMT, or a pharmaceutically acceptable salt thereof.

In some embodiments, the deuterated 5-HT$_{2A}$ agonist has the structure of Formula (I):

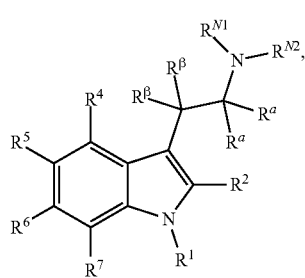

(I)

wherein: $R^{N1}$ and $R^{N2}$ are each independently H, $C_1$-$C_6$ alkyl, $C_1$-$C_6$ deuteroalkyl, $C_2$-$C_6$ alkenyl, $C_2$-$C_6$ deuteroalkenyl, $C_2$-$C_6$ alkynyl, $C_2$-$C_6$ deuteroalkynyl, $C_3$-$C_{10}$ cycloalkyl, or $C_3$-$C_{10}$ deuterocycloalkyl; or $R^{N1}$ and $R^{N2}$ are taken together with the intervening nitrogen to form a $C_4$-$C_{10}$ heterocyclyl, or $C_4$-$C_{10}$ deuteroheterocyclyl; each $R^\alpha$ is independently H, D, $C_1$-$C_6$ alkyl, or $C_1$-$C_6$ deuteroalkyl; each RR is independently H or D; $R^1$ is H or D; $R^2$, $R^4$, $R^5$, $R^6$, and $R^7$ are each independently H, D, $C_1$-$C_6$ alkyl, $C_1$-$C_6$ deuteroalkyl, —OPO$_3$H$_2$, $C_1$-$C_6$ acyl, $C_1$-$C_6$ deuteroacyl, OH, $C_1$-$C_6$ alkoxy, or $C_1$-$C_6$ deuteroalkoxy; provided that at least one of $R^{N1}$, $R^{N2}$, $R^1$, $R^\alpha$, $R^\beta$, $R^2$, $R^4$, $R^5$, $R^6$, and $R^7$ is D, $C_1$-$C_6$ deuteroalkyl, $C_1$-$C_6$ deuteroalkoxy, or $C_1$-$C_6$ deuteroacyl; or a pharmaceutically acceptable salt thereof.

In some embodiments, the deuterated 5-HT$_{2A}$ agonist has the structure of Formula (II):

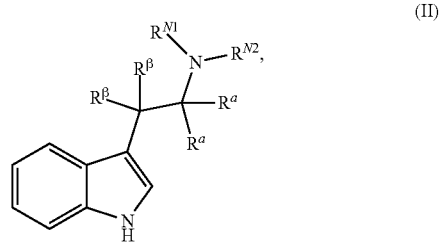

(II)

wherein $R^{N1}$, $R^{N2}$, $R^\alpha$, and $R^\beta$, are as defined for Formula (I); or a pharmaceutically acceptable salt thereof.

In some embodiments, the deuterated 5-HT$_{2A}$ agonist has the structure of Formula (III):

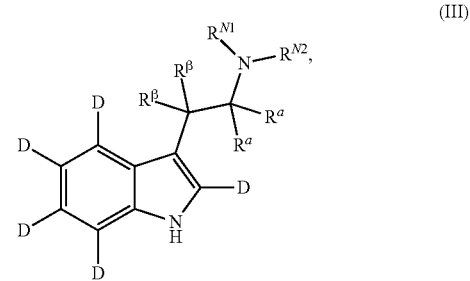

(III)

wherein $R^{N1}$, $R^{N2}$, $R^\alpha$, and $R^\beta$, are as defined for Formula (I); or a pharmaceutically acceptable salt thereof.

In some embodiments, the deuterated 5-HT$_{2A}$ agonist has the structure of Formula (IV):

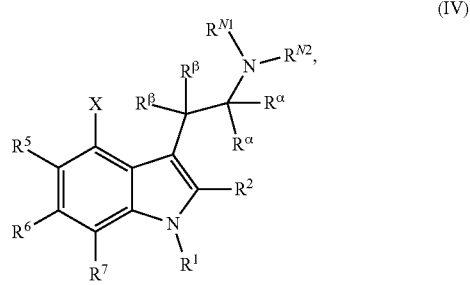

(IV)

wherein and $R^{N1}$, $R^{N2}$, $R^\alpha$, $R^\beta$, $R^1$, $R^2$, $R^5$, $R^6$, and $R^7$ are as defined for Formula (I); and X is —OPO$_3$H$_2$, $C_1$-$C_6$ acyl, $C_1$-$C_6$ deuteroacyl, or OH; or a pharmaceutically acceptable salt thereof.

In some embodiments, the deuterated 5-HT$_{2A}$ agonist has the structure of Formula (V):

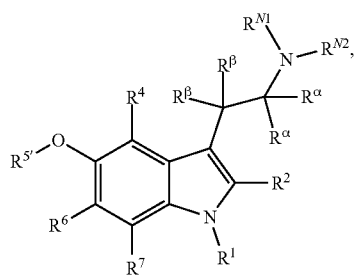

(V)

wherein $R^{N1}$, $R^{N2}$, $R^{\alpha}$, $R^{\beta}$, $R^1$, $R^2$, $R^4$, $R^6$, and $R^7$ are as defined for Formula (I); and $R^{5'}$ is $C_1$-$C_6$ alkyl or $C_1$-$C_6$ deuteroalkyl; or a pharmaceutically acceptable salt thereof.

In some embodiments, the deuterated 5-HT$_{2A}$ agonist has the structure of Formula (VI):

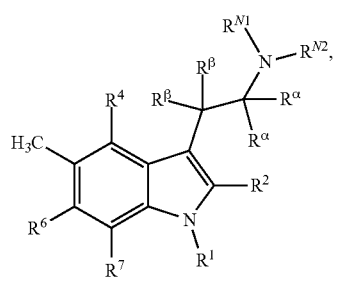

(VI)

wherein $R^{N1}$, $R^{N2}$, $R^{\alpha}$, $R^{\beta}$, $R^1$, $R^2$, $R^5$, $R^6$, and $R^7$ are as defined for Formula (I); or a pharmaceutically acceptable salt thereof.

In some embodiments, the deuterated 5-HT$_{2A}$ agonist is any of:

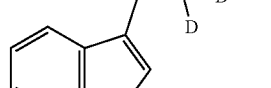
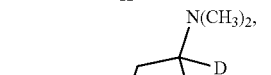
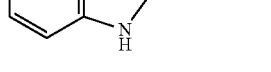
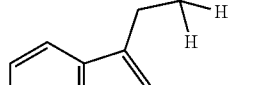

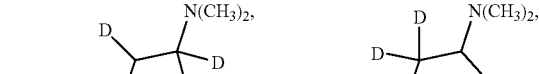
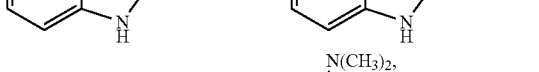
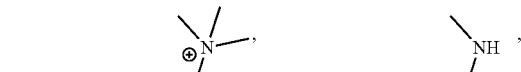
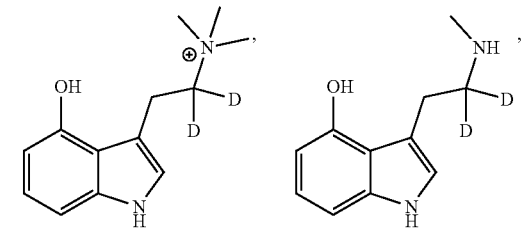

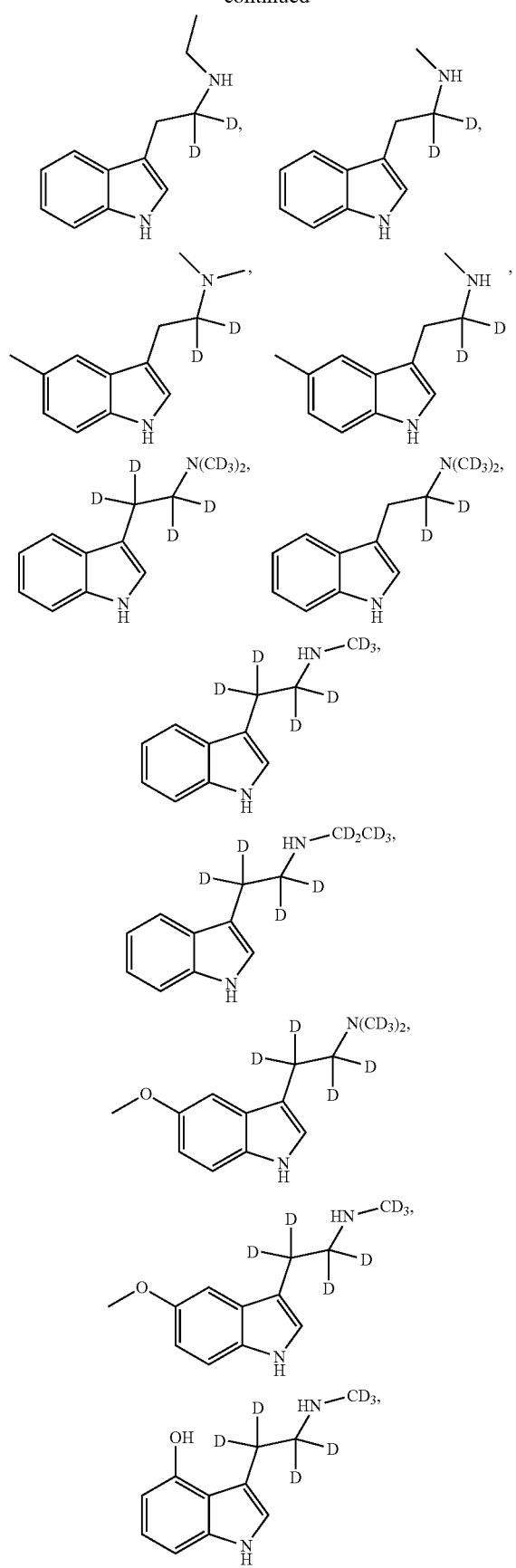
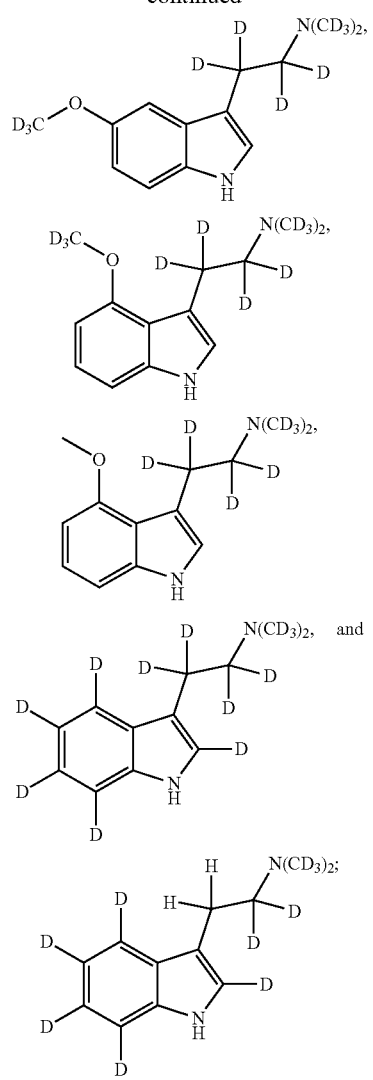
or a pharmaceutically acceptable salt thereof.
In some embodiments, the deuterated 5-HT$_{2A}$ agonist is any of:
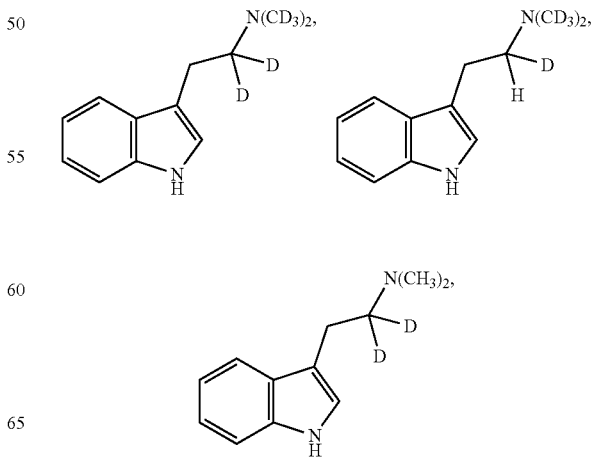

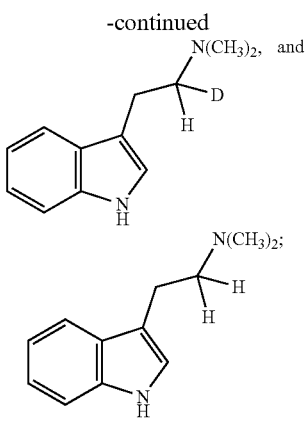

or a pharmaceutically acceptable salt thereof.

In some embodiments, the pharmaceutical composition or kit of parts comprises between 50 and 300 mg, between 75 and 200 mg, between 100 and 150, about 125 mg, or about 175 mg of CX157. In some embodiments, the pharmaceutical composition or kit of parts comprises 175 mg of CX157.

In some embodiments, the pharmaceutical composition or kit of parts comprises between 1 and 10 mg, between 2 and 8 mg, or about 5 mg of the 5-HT$_{2A}$ receptor agonist. In some embodiments, the pharmaceutical composition or kit of parts comprises between 15 and 300 mg, between 25 and 200 mg, or between 50 and 100 mg of the 5-HT$_{2A}$ receptor agonist.

In some embodiments, the pharmaceutical composition or kit of parts comprises a microdose of the 5-HT$_{2A}$ receptor agonist. In some embodiments, the pharmaceutical composition or kit of parts comprises a microdose of DMT. In some embodiments, the pharmaceutical composition or kit of parts comprises a microdose of deuterated DMT.

In some embodiments, the pharmaceutical composition or kit of parts comprises a psycholytic dose of the 5-HT$_{2A}$ receptor agonist. In some embodiments, the pharmaceutical composition or kit of parts comprises a psycholytic dose of DMT. In some embodiments, the pharmaceutical composition or kit of parts comprises a psycholytic dose of deuterated DMT.

In some embodiments, the pharmaceutical composition or kit of parts comprises a psychedelic dose of the 5-HT$_{2A}$ receptor agonist. In some embodiments, the pharmaceutical composition or kit of parts comprises a psychedelic dose of DMT. In some embodiments, the pharmaceutical composition or kit of parts comprises a psychedelic dose of deuterated DMT.

In some embodiments, the pharmaceutical composition or kit of parts is formulated as an immediate release, controlled release, sustained release, extended release, or modified release formulation.

In some aspects are disclosed pharmaceutical compositions and pharmaceutical kits or kits of parts, useful to treat a disease or disorder in a human, comprising therapeutically effective amounts of: a monoamine oxidase (MAO) inhibitor, or a pharmaceutically acceptable salt thereof; and a 5-HT$_{2A}$ receptor agonist, or a pharmaceutically acceptable salt thereof; preferably but optionally wherein the 5-HT$_{2A}$ receptor agonist is susceptible to degradation by monoamine oxidase A (MAO-A).

In embodiments, the MAO inhibitor is any of isocarboxazid, pargyline, selegiline, furazolidone, phenelzine, amiflamine, iproniazid, nialamide, tranylcypromine, octamoxin, phenoxypropazine, pivalyl benzhydrazine, iproclozide, iproniazide, bifemelane, prodipine, benmoxin, etryptamine, fenoxypropazine, mebanazine, pheniprazine, safrazine, hypericine, iproniazid phosphate, phenelzine sulphate, tranylcypromine sulphate, methylene blue, moclobemide, brofaromine, befloxatone, toloxatone, clorgyline, cimoxatone, bazinaprine, harmine, harmaline, sercloremine, esuprone, pirlindole, metralindole, tetrindole, or clorgyline hydrochloride; or a pharmaceutically acceptable salt thereof. In some embodiments, the MAO inhibitor is metralindole, pirlindole, or tetrindole; or a pharmaceutically acceptable salt thereof.

In some embodiments, the MAO inhibitor is the compound CX157:

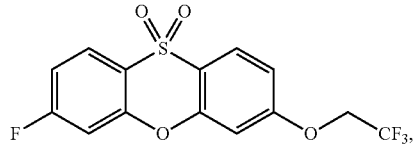 [SMILES: O=S1(=O)c2ccc(F)cc2Oc2cc(OCC(F)(F)F)ccc21]

or a pharmaceutically acceptable salt thereof.

In some embodiments, the MAO inhibitor is the compound CX009:

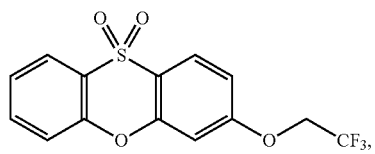 [SMILES: O=S1(=O)c2ccccc2Oc2cc(OCC(F)(F)F)ccc21]

or a pharmaceutically acceptable salt thereof.

In some embodiments, the MAO inhibitor is a reversible inhibitor of MAO-A. In some embodiments, the MAO inhibitor is a monoamine oxidase A (MAO-A) selective inhibitor. In some embodiments, the MAO inhibitor has a selectivity for MAO-A inhibition over monoamine oxidase B (MAO-B) inhibition of at least 5-fold, 10-fold, 50-fold, 100-fold, 150-fold, 200-fold, 300-fold, 500-fold, or 1000-fold.

In some embodiments, administering the therapeutically effective amount of the MAO inhibitor does not result in a detectable amount of MAO-B inhibition. In some embodiments, the MAO inhibitor has a $K_i$ for MAO-B of greater than 10 μM. In some embodiments, the MAO inhibitor has a $K_i$ for MAO-A of less than 50 nM, less than 30 nM, less than 20 nM, less than 10 nM, or less than 5 nM. In some embodiments, the MAO inhibitor has a $K_i$ for MAO-A of about 10 nM.

In some embodiments, the MAO inhibitor has a $K_i$ for CYP2D6 of greater than 100 nM. In some embodiments, administering the therapeutically effective amount of the MAO inhibitor does not result in a detectable amount of CYP2D6 inhibition.

In some embodiments, the MAO inhibitor has a $K_i$ for acetylcholinesterase of greater than 100 nM. In some embodiments, administering the therapeutically effective amount of the MAO inhibitor does not result in a detectable amount of acetylcholinesterase inhibition.

In some embodiments, the MAO inhibitor does not require the subject to restrict intake of tyramine-rich food.

In some embodiments, the 5-HT$_{2A}$ receptor agonist is metabolized by MAO-A.

In some embodiments, the MAO inhibitor and the 5-HT$_{2A}$ receptor agonist are formulated in a single pharmaceutical composition, together with at least one pharmaceutically acceptable carrier, diluent, or excipient. In embodiments, the single pharmaceutical composition is formulated for oral administration. In embodiments, the MAO inhibitor and the 5-HT$_{2A}$ receptor agonist are formulated in separate pharmaceutical compositions, together with at least one pharmaceutically acceptable carrier, diluent, or excipient. In embodiments, the separate pharmaceutical compositions are both formulated for oral administration.

In some aspects are disclosed methods of treating a disease or disorder in a subject, the method comprising: administering to the subject a therapeutically effective amount of a monoamine oxidase (MAO) inhibitor, or a pharmaceutically acceptable salt thereof; and administering to the subject a therapeutically effective amount of a 5-HT$_{2A}$ receptor agonist, or a pharmaceutically acceptable salt thereof; wherein, preferably, the 5-HT$_{2A}$ receptor agonist is susceptible to degradation by monoamine oxidase A (MAO-A).

In some embodiments, the MAO inhibitor is CX157 and the 5-HT$_{2A}$ receptor agonist is DPT; or pharmaceutically acceptable salts thereof. In some embodiments, the MAO inhibitor is CX157 and the 5-HT$_{2A}$ receptor agonist is 5-MeO-DMT; or pharmaceutically acceptable salts thereof. In some embodiments, the MAO inhibitor is CX157 and the 5-HT$_{2A}$ receptor agonist is DMT; or pharmaceutically acceptable salts thereof. In some embodiments, the MAO inhibitor is CX009 and the 5-HT$_{2A}$ receptor agonist is DPT; or pharmaceutically acceptable salts thereof. In embodiments, the MAO inhibitor is CX009 and the 5-HT$_{2A}$ receptor agonist is 5-MeO-DMT; or pharmaceutically acceptable salts thereof. In embodiments, the MAO inhibitor is CX009 and the 5-HT$_{2A}$ receptor agonist is DMT; or pharmaceutically acceptable salts thereof.

In some embodiments, the MAO inhibitor is CX157 and, the 5-HT$_{2A}$ receptor agonist is a deuterated 5-HT$_{2A}$ agonist. In some embodiments, the MAO inhibitor is CX157 and, the deuterated 5-HT$_{2A}$ agonist is a deuterated tryptamine, or a pharmaceutically acceptable salt thereof. In some embodiments, the MAO inhibitor is CX157 and, the deuterated tryptamine is a deuterated psychedelic tryptamine, or a pharmaceutically acceptable salt thereof. In some embodiments, the MAO inhibitor is CX157 and, the deuterated psychedelic tryptamine is deuterated DMT, or a pharmaceutically acceptable salt thereof. In some embodiments, the MAO inhibitor is CX157 and, the deuterated 5-HT$_{2A}$ agonist has the structure of Formula (I), as described above and herein. In some embodiments, the MAO inhibitor is CX157 and, the deuterated 5-HT$_{2A}$ agonist has the structure of Formula (II), as described above and herein. In some embodiments, the MAO inhibitor is CX157 and, the deuterated 5-HT$_{2A}$ agonist has the structure of Formula (III), as described above and herein. In some embodiments, the MAO inhibitor is CX157 and, the deuterated 5-HT$_{2A}$ agonist has the structure of Formula (IV), as described above and herein. In some embodiments, the MAO inhibitor is CX157 and, the deuterated 5-HT$_{2A}$ agonist has the structure of Formula (V), as described above and herein. In some embodiments, the MAO inhibitor is CX157 and, the deuterated 5-HT$_{2A}$ agonist has the structure of Formula (VI), as described above and herein. In some embodiments, the MAO inhibitor is CX157 and, the deuterated 5-HT$_{2A}$ agonist is any of the specific structures disclosed above and herein.

In some embodiments, the MAOI is CX157 or CX009 and the deuterated 5-HT$_{2A}$ agonist is any of:

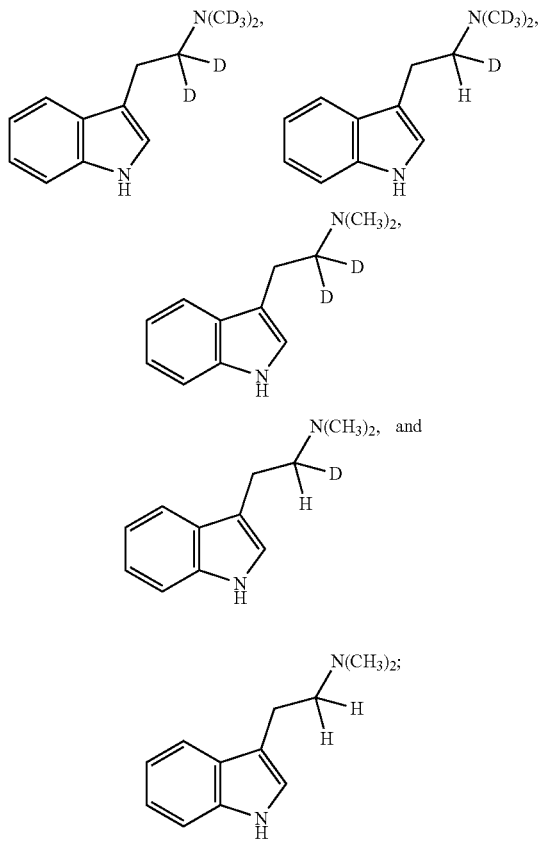

or pharmaceutically acceptable salts thereof.

In some embodiments, the MAO inhibitor is CX157 and the deuterated 5-HT$_{2A}$ agonist is

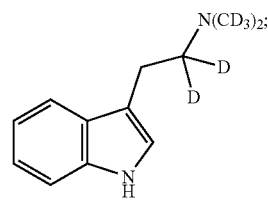

or pharmaceutically acceptable salts thereof.

In some embodiments, the MAO inhibitor is CX157 and the deuterated 5-HT$_{2A}$ agonist is,

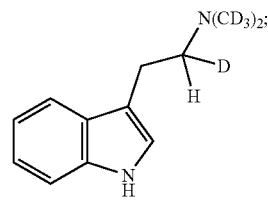

or pharmaceutically acceptable salts thereof.

In some embodiments, the MAO inhibitor is CX157 and the deuterated 5-HT$_{2A}$ agonist is,

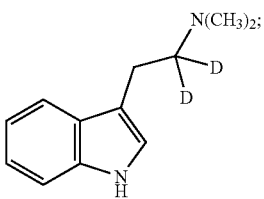 [SMILES: [2H]C([2H])(Cc1c[nH]c2ccccc12)N(C)C]

or pharmaceutically acceptable salts thereof.

In some embodiments, the MAO inhibitor is CX157 and the deuterated 5-$HT_{2A}$ agonist is

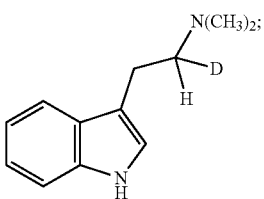 [SMILES: [2H]C(Cc1c[nH]c2ccccc12)N(C)C]

or pharmaceutically acceptable salts thereof.

In some embodiments, the MAO inhibitor is CX157 and the deuterated 5-$HT_{2A}$ agonist is

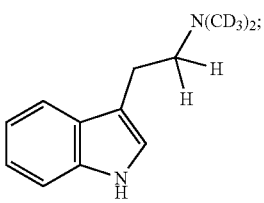

or pharmaceutically acceptable salts thereof.

In some embodiments, the MAO inhibitor is CX157 and the deuterated 5-$HT_{2A}$ agonist is deuterated DMT; or pharmaceutically acceptable salts thereof.

In some embodiments, administering to the subject a therapeutically effective amount of a MAO inhibitor results in an increase in the oral bioavailability of the 5-$HT_{2A}$ receptor agonist. In some embodiments, administering to the subject a therapeutically effective amount of a MAO inhibitor is capable of decreasing the in vivo rate of degradation of the 5-$HT_{2A}$ receptor agonist. In some embodiments, the in vivo degradation of the 5-$HT_{2A}$ receptor agonist is reduced by at least 20%, 50%, 75%, 90%, 95%, or 99%.

In some embodiments, the in vivo half-life of the 5-$HT_{2A}$ receptor agonist is increased by at least 1.2-fold, 1.5-fold, 1.7-fold, 2-fold, 5-fold, 10-fold, 20-fold, 50-fold, or 100-fold.

In some embodiments, the MAO inhibitor is administered prior to administration of the 5-$HT_{2A}$ receptor agonist. In some embodiments, the MAO inhibitor is administered simultaneously with administration of the 5-$HT_{2A}$ receptor agonist.

In some embodiments, the MAO inhibitor and the 5-$HT_{2A}$ receptor agonist are administered in a single pharmaceutical composition.

In some embodiments, the MAO inhibitor is administered orally. In some embodiments, the 5-$HT_{2A}$ receptor agonist is administered orally.

In some embodiments, the disease or disorder is linked to dysregulation or inadequate functioning of neurotransmission. In some embodiments, the disease or disorder linked to dysregulation or inadequate functioning of neurotransmission is that of monoaminergic neurotransmission. In some embodiments, the disease or disorder linked to dysregulation or inadequate functioning of neurotransmission is that of serotonergic, dopaminergic, or noradrenergic neurotransmission.

In some embodiments, the disease or disorder is a mental health disorder. In some embodiments, the mental health disorder is any of post-traumatic stress disorder (PTSD), adjustment disorder, affective disorder, depressive disorders, major depressive disorder (MDD), treatment resistant depression (TRD), atypical depression, postpartum depression, catatonic depression, a depressive disorder due to a medical condition, premenstrual dysphoric disorder, seasonal affective disorder, dysthymia, anxiety related disorders, generalized anxiety disorder (GAD), phobia disorders, binge disorders, body dysmorphic disorder, alcohol or drug abuse or dependence disorders, a substance use disorder, substance-induced mood disorder, a mood disorder related to another health condition, disruptive behavior disorders, eating disorders, impulse control disorders, obsessive compulsive disorder (OCD), attention deficit hyperactivity disorder (ADHD), prolonged grief disorder, personality disorders, autism, autism spectrum disorders, social anxiety in autism, attachment disorders, and dissociative disorders. In some embodiments, the substance use disorder is any of alcohol use disorder, nicotine dependency, opioid use disorder, sedative, hypnotic, or anxiolytic use disorder, stimulant use disorder, or tobacco use disorder.

In some embodiments, the disease or disorder is a neurodegenerative disease. In some embodiments, the neurodegenerative disease is any of Alzheimer's disease (AD), corticobasal degeneration (CBD), a form of dementia, Huntington's disease, Lytico-Bodig disease, mild cognitive impairment (MCI), a motor neuron disease, progressive supranuclear palsy (PSP), multiple sclerosis, Parkinson's disease, traumatic brain injury (TBI), ischemic cerebral infarction, hemorrhagic cerebral infarction, frontotemporal lobar degeneration, Lewy body dementia, primary progressive aphasia, multiple systems atrophy, and Creutzfeld-Jakob disease.

In some embodiments, the disease or disorder is pain or a pain disorder. In some embodiments, the pain disorder is any of arthritis, allodynia, atypical trigeminal neuralgia, trigeminal neuralgia, somatoform disorder, hypoesthesia, hyperalgesia, neuralgia, neuritis, neurogenic pain, phantom limb pain, analgesia, anesthesia dolorosa, causalgia, sciatic nerve pain disorder, degenerative joint disorder, fibromyalgia, visceral disease, chronic pain disorders, headache disorders, migraine headaches, chronic cluster headaches, concussion headache, short-lasting unilateral neuralgiform headache attacks, chronic fatigue syndrome, complex regional pain syndrome, neurodystrophy, plantar fasciitis, or pain associated with cancer.

In some embodiments, the disease or disorder is inflammation or an inflammatory disorder. In some embodiments, the inflammatory disorder is characterized by any one or more of skin inflammation, muscle inflammation, tendon inflammation, ligament inflammation, bone inflammation, cartilage inflammation, lung inflammation, heart inflammation, liver inflammation, pancreatic inflammation, kidney inflammation, bladder inflammation, gastric inflammation, intestinal inflammation, neuroinflammation, and brain inflammation.

In some embodiments, the methods further comprise improving the mental health or functioning of the subject. In some embodiments, the methods further comprise psychotherapy or psychological support.

In some embodiments, the methods comprise administering to the subject a total amount of between 50 and 300 mg, between 75 and 200 mg, or about 175 mg of the MAO inhibitor. In some embodiments, the methods comprise administering to the subject a total amount of 175 mg of the MAO inhibitor, wherein the MAO inhibitor is CX157. In some embodiments, the methods comprise administering to the subject a total amount of between 100 and 150 mg, or about 125 mg of the MAO inhibitor.

In some embodiments, the methods comprise administering to the subject a total amount of between 1 and 10 mg, between 2 and 8 mg, or about 5 mg of the $5\text{-}HT_{2A}$ receptor agonist. In some embodiments, the methods comprise administering to the subject a total amount of between 15 and 300 mg, between 25 and 200 mg, or between 50 and 100 mg of the $5\text{-}HT_{2A}$ receptor agonist.

In some embodiments, the methods comprise administering to the subject a microdose of the $5\text{-}HT_{2A}$ receptor agonist. In some embodiments, the methods comprise administering to the subject a microdose of the $5\text{-}HT_{2A}$ receptor agonist, wherein the $5\text{-}HT_{2A}$ receptor agonist is DMT. In some embodiments, the methods comprise administering to the subject a microdose of DMT and CX157. In some embodiments, the methods comprise administering to the subject a microdose of the $5\text{-}HT_{2A}$ receptor agonist, wherein the $5\text{-}HT_{2A}$ receptor agonist is deuterated DMT. In some embodiments, the methods comprise administering to the subject a microdose of deuterated DMT and CX157.

In some embodiments, the methods comprise administering to the subject a psycholytic dose of the $5\text{-}HT_{2A}$ receptor agonist. In some embodiments, the methods comprise administering to the subject a psycholytic dose of the $5\text{-}HT_{2A}$ receptor agonist, wherein the $5\text{-}HT_{2A}$ receptor agonist is DMT. In some embodiments, the methods comprise administering to the subject a psycholytic dose of DMT and CX157. In some embodiments, the methods comprise administering to the subject a psycholytic dose of the $5\text{-}HT_{2A}$ receptor agonist, wherein the $5\text{-}HT_{2A}$ receptor agonist is deuterated DMT. In some embodiments, the methods comprise administering to the subject a psycholytic dose of deuterated DMT and CX157.

In some embodiments, the methods comprise administering to the subject a psychedelic dose of the $5\text{-}HT_{2A}$ receptor agonist. In some embodiments, the methods comprise administering to the subject a psychedelic dose of the $5\text{-}HT_{2A}$ receptor agonist, wherein the $5\text{-}HT_{2A}$ receptor agonist is DMT. In some embodiments, the methods comprise administering to the subject a psychedelic dose of DMT and CX157. In some embodiments, the methods comprise administering to the subject a psychedelic dose of the $5\text{-}HT_{2A}$ receptor agonist, wherein the $5\text{-}HT_{2A}$ receptor agonist is deuterated DMT. In some embodiments, the methods comprise administering to the subject a psychedelic dose of deuterated DMT and CX157.

In some embodiments, the methods comprise administering to the subject the MAO inhibitor as an immediate release, controlled release, sustained release, extended release, or modified release formulation. In some embodiments, the methods comprise administering to the subject the $5\text{-}HT_{2A}$ receptor agonist as an immediate release, controlled release, sustained release, extended release, or modified release formulation.

In some aspects is disclosed the use of a disclosed pharmaceutical composition or kit of parts to treat a disease or disorder in a human.

In some aspects is disclosed the use of a disclosed pharmaceutical composition or kit of parts to treat a mental health disorder in a human, wherein the mental health disorder is any of post-traumatic stress disorder (PTSD), adjustment disorder, affective disorder, depressive disorders, major depressive disorder (MDD), treatment resistant depression (TRD), atypical depression, postpartum depression, catatonic depression, a depressive disorder due to a medical condition, premenstrual dysphoric disorder, seasonal affective disorder, dysthymia, anxiety related disorders, generalized anxiety disorder (GAD), phobia disorders, binge disorders, body dysmorphic disorder, alcohol or drug abuse or dependence disorders, a substance use disorder, substance-induced mood disorder, a mood disorder related to another health condition, disruptive behavior disorders, eating disorders, impulse control disorders, obsessive compulsive disorder (OCD), attention deficit hyperactivity disorder (ADHD), prolonged grief disorder, personality disorders, autism, autism spectrum disorders, social anxiety in autism, attachment disorders, and dissociative disorders.

In some aspects is disclosed the use of a disclosed pharmaceutical composition or kit of parts to treat a neurodegenerative disease in a human, wherein the neurodegenerative disease is any of Alzheimer's disease (AD), corticobasal degeneration (CBD), a form of dementia, Huntington's disease, Lytico-Bodig disease, mild cognitive impairment (MCI), a motor neuron disease, progressive supranuclear palsy (PSP), multiple sclerosis, Parkinson's disease, traumatic brain injury (TBI), ischemic cerebral infarction, hemorrhagic cerebral infarction, frontotemporal lobar degeneration, Lewy body dementia, primary progressive aphasia, multiple systems atrophy, and Creutzfeld-Jakob disease.

In some aspects is disclosed the use of a disclosed pharmaceutical composition or kit of parts to treat a pain disorder in a human, wherein the pain disorder is any of arthritis, allodynia, atypical trigeminal neuralgia, trigeminal neuralgia, somatoform disorder, hypoesthesia, hyperalgesia, neuralgia, neuritis, neurogenic pain, phantom limb pain, analgesia, anesthesia dolorosa, causalgia, sciatic nerve pain disorder, degenerative joint disorder, fibromyalgia, visceral disease, chronic pain disorders, headache disorders, migraine headaches, chronic cluster headaches, concussion headache, short-lasting unilateral neuralgiform headache attacks, chronic fatigue syndrome, complex regional pain syndrome, neurodystrophy, plantar fasciitis, or pain associated with cancer.

In some aspects is disclosed the use of a disclosed pharmaceutical composition or kit of parts to treat an inflammatory disorder in a human, wherein the inflammatory disorder is characterized by any one or more of skin inflammation, muscle inflammation, tendon inflammation, ligament inflammation, bone inflammation, cartilage inflammation, lung inflammation, heart inflammation, liver inflammation, pancreatic inflammation, kidney inflammation, bladder inflammation, gastric inflammation, intestinal inflammation, neuroinflammation, and brain inflammation. In some aspects is disclosed the use of a disclosed pharmaceutical composition or kit of parts to improve the mental health or functioning of a human.

The foregoing has outlined broadly and in summary certain pertinent features of the disclosure so that the detailed description of the invention that follows may be better understood, and so that the present contribution to the art can be more fully appreciated. Hence, this summary is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled. Additional features of the invention are described hereinafter. It should be appreciated by those in the art that all disclosed specific compositions and methods are only exemplary, and may be readily utilized as a basis for modifying or designing other compositions and methods for carrying out the same purposes. Such equivalent compositions and methods will be appreciated to be also within the scope and spirit of the invention as set forth in the claims.

It will be appreciated that the headings within this document are being utilized only to expedite its review by the reader. They should not be construed as limiting the invention in any manner whatsoever.

BRIEF DESCRIPTION OF THE FIGURES

To further clarify various aspects of the invention, a more particular description is rendered by reference to certain exemplary embodiments illustrated in the figures. It will be appreciated that these figures depict only illustrated embodiments of the invention and should not be considered limiting of its scope. They are merely provided as exemplary illustrations of certain concepts of some embodiments of the invention. Certain aspects of the invention are therefore further described and explained with additional specificity and detail, but still by way of example only, with reference to the accompanying figures in which.

DETAILED DESCRIPTION OF THE INVENTION

Figure 1:
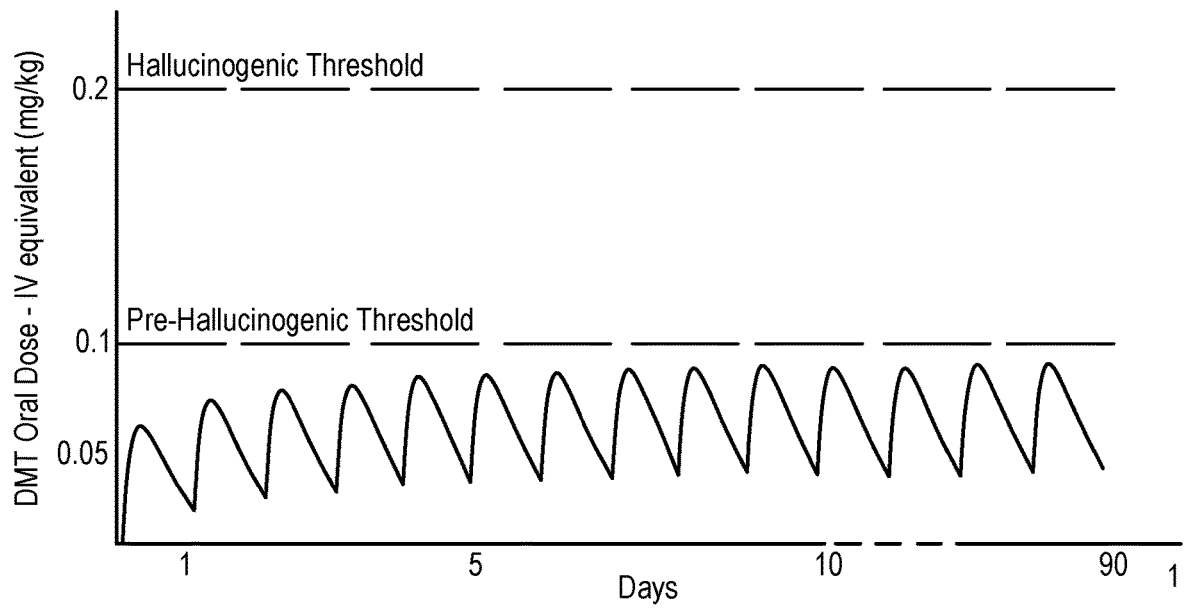
FIG. 1 illustrates an exemplary dosing regimen, wherein a subject takes a given microdose of DMT daily and an effective amount of CX157 daily.

While various aspects and features of certain embodiments are summarized above, this detailed description illustrates several exemplary embodiments in further detail to enable one of skill in the art to practice such embodiments, and to make and use the full scope of the invention. The examples are provided for illustrative purposes and are not intended to limit the scope of the invention or its applications. It will be understood that many modifications, substitutions, changes, and variations in the described examples, embodiments, applications, and details of the invention illustrated herein can be made by those skilled in the art without departing from the spirit of the invention, or the scope of the invention as described in the claims.

It will be appreciated that the headings within this document are being utilized only to expedite its review by a reader. They should not be construed as limiting the invention in any manner.

I. GENERAL DEFINITIONS AND TERMS

As used in this specification and the appended claims, the singular forms "a," "an," and "the" include plural referents unless the context clearly dictates otherwise. Thus, for example, reference to "an active agent" includes reference to a combination of two or more active agents, and reference to "an excipient" includes reference to a combination of two or more excipients. While the term "one or more" may be used, its absence (or its replacement by the singular) does not signify the singular only, but simply underscores the possibility of multiple agents or ingredients in particular embodiments.

The terms "comprising," "including," "such as," and "having" are intended to be inclusive and not exclusive (i.e., there may be other elements in addition to the recited elements), e.g., the term "including" is used to mean, and is used interchangeably with, the phrase "including but not limited to." "Or" is used to mean, and is used interchangeably with, the term "and/or," unless context clearly indicates otherwise.

"Alkyl" will be understood to include straight or branched radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" can also be used. Preferably, an alkyl group comprises from 1 to 10 carbon atoms, more preferably from 1 to 6 carbon atoms, more preferably from 1 to 4 carbon atoms, and most preferably from 1 to 3 carbon atoms. Alkyl groups can be substituted or unsubstituted, meaning that in some embodiments an alkyl may be optionally substituted at one or more positions by deuterium, halogen, alkyl, alkyl ester, hydroxy, alkoxy, carboxy, formyl, aryl, cycloalkyl, heterocycloalkyl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, $OP(O)(OH)_2$, $OC(O)H$, $OSO_2OH$, $OC(O)NH_2$, and $SONH_2$.

"Alkenyl" refers to an unsaturated branched, straight-chain, or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include ethenyl; propenyls such as prop-1-en-1-yl, prop-1-en-2-yl, prop-2-en-1-yl (allyl), prop-2-en-2-yl, cycloprop-1-en-1-yl, and cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2yl, buta-1,3-dien-1-yl, buta-1,3-dien-2-yl, cyclobut-1-en-1-yl, cyclobut-1-en-3-yl, and cyclobuta-1,3-dien-1-yl; and the like. Alkenyl groups can be substituted or unsubstituted.

"Alkynyl" refers to an unsaturated branched, straight-chain, or cyclic alkyl radical having at least one carbon-carbon triple bond derived by the removal of one hydrogen atom from a single carbon atom of a parent alkyne. Typical alkynyl groups include ethynyl; propynyls such as prop-1-yn-1-yl, and prop-2-yn-1-yl; butynyls such as but-1-yn-1-yl, but-1-yn-3-yl, and but-3-yn-1-yl; and the like. Aklynyl groups can be substituted or unsubstituted.

"Aryl" refers to a monovalent aromatic hydrocarbon radical derived by the removal of one hydrogen atom from a single carbon atom of a parent aromatic ring system. Typical aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. Preferably, an aryl group comprises from 6 to 20 carbon atoms, more preferably, between 6 to 12 carbon atoms. Aryl groups can be substituted or unsubstituted.

"Cycloalkyl" refers to a saturated monocyclic, bicyclic, fused bicyclic or bridged polycyclic ring assembly containing from 3 to 12 ring atoms, or the number of atoms indicated. Cycloalkyl can include any number of carbons, such as 3 to 6 carbon atoms, 4 to 6 carbon atoms, 5 to 6 carbon atoms, 3 to 8 carbon atoms, 4 to 8 carbon atoms, 5 to 8 carbon atoms, 6 to 8 carbon atoms, 7 to 8 carbon atoms, 3 to 9 carbon atoms, 4 to 9 carbon atoms, 5 to 9 carbon atoms, 6 to 9 carbon atoms, 7 to 9 carbon atoms, 8 to 9 carbon atoms, 3 to 10 carbon atoms, 4 to 10 carbon atoms, 5 to 10 carbon atoms, 6 to 10 carbon atoms, 7 to 10 carbon atoms, 8 to 10 carbon atoms, 9 to 10 carbon atoms, 3 to 11 carbon atoms, 4 to 11 carbon atoms, 5 to 11 carbon atoms, 6 to 11 carbon atoms, 7 to 11 carbon atoms, 8 to 11 carbon atoms, 9 to 11 carbon atoms, 10 to 11 carbon atoms, 3 to 12 carbon atoms, 4 to 12 carbon atoms, 5 to 12 carbon atoms, 6 to 12 carbon atoms, 7 to 12 carbon atoms, 8 to 12 carbon atoms, 9 to 12 carbon atoms, 10 to 12 carbon atoms, and 11 to 12 carbon atoms. Monocyclic cycloalkyl rings include, for example, cyclopropyl, cyclobutyl, cyclopentyl, cyclohexyl, and cyclooctyl. Bicyclic compounds include spirocyclic compounds, fused bicyclic compounds and bridged bicyclic compounds. Bicyclic and polycyclic cycloalkyl rings include, for example, norbornane, bicyclooctane, decahydronaphthalene and adamantane. When cycloalkyl is a monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Cycloalkenyl" refers to a mono- or multi-cyclic hydrocarbon ring system that contains one or more double bonds in at least one ring. However, if there is more than one double bond, the double bonds cannot form a fully delocalized pi-electron system throughout all the rings (otherwise the group would be "aryl," as defined herein). When composed of two or more rings, the rings may be connected together in a fused fashion. Cycloalkenyl can include any number of carbons, such as 3 to 6 carbon atoms, 4 to 6 carbon atoms, 5 to 6 carbon atoms, 3 to 8 carbon atoms, 4 to 8 carbon atoms, 5 to 8 carbon atoms, 6 to 8 carbon atoms, 7 to 8 carbon atoms, 3 to 9 carbon atoms, 4 to 9 carbon atoms, 5 to 9 carbon atoms, 6 to 9 carbon atoms, 7 to 9 carbon atoms, 8 to 9 carbon atoms, 3 to 10 carbon atoms, 4 to 10 carbon atoms, 5 to 10 carbon atoms, 6 to 10 carbon atoms, 7 to 10 carbon atoms, 8 to 10 carbon atoms, 9 to 10 carbon atoms, 3 to 11 carbon atoms, 4 to 11 carbon atoms, 5 to 11 carbon atoms, 6 to 11 carbon atoms, 7 to 11 carbon atoms, 8 to 11 carbon atoms, 9 to 11 carbon atoms, 10 to 11 carbon atoms, 3 to 12 carbon atoms, 4 to 12 carbon atoms, 5 to 12 carbon atoms, 6 to 12 carbon atoms, 7 to 12 carbon atoms, 8 to 12 carbon atoms, 9 to 12 carbon atoms, 10 to 12 carbon atoms, and 11 to 12 carbon atoms. Representative Cycloalkenyl groups include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. A cycloalkenyl group may be unsubstituted or substituted.

"Deuteroalkyl" will be understood to include any alkyl group as defined above, wherein one or more hydrogen atoms are replaced by a deuterium (i.e., $^2H$, or D). Where an alkyl radical is substituted by more than one deuterium, it may be referred to using a prefix corresponding to the number of deuterium substitutions. For example, trideuteroalkyl refers to an alkyl in which three hydrogens have been replaced by deuteriums. A deuteroalkyl can be fully deuterated (i.e., all of the hydrogens have been replaced by deuteriums) or partially deuterated (i.e., only some of the hydrogens have been replaced by deuteriums). For example, a deuteromethyl (i.e., a $C_1$ deuteroalkyl) group refers to $CH_2D$, $CHD_2$, or $CD_3$. A deuteroethyl (i.e., a $C_2$ deuteroalkyl) group refers to $CH_2CH_2D$, $CHDCH_2D$, $CD_2CH_2D$, $CH_2CHD_2$, $CHDCHD_2$, $CD_2CHD_2$, $CH_2CD_3$, $CHDCD_3$, or $CD_2CD_3$. A deuteropropyl group (i.e., a $C_3$ deuteroalkyl) refers to any partially or fully substituted n-propyl or iso-propyl group.

"Deuteroalkenyl" refers to any alkenyl group as defined above, wherein one or more hydrogen atoms are replaced by a deuterium (i.e., $^2H$, or D). Where an alkenyl radical is substituted by more than one deuterium, it may be referred to using a prefix corresponding to the number of deuterium substitutions. For example, trideuteroalkenyl refers to an alkenyl in which three hydrogens have been replaced by deuteriums. A deuteroalkenyl can be fully deuterated (i.e., all of the hydrogens have been replaced by deuteriums) or partially deuterated (i.e., only some of the hydrogens have been replaced by deuteriums). For example, a deuteroeth-enyl (i.e., a $C_2$ deuteroalkenyl) group refers to CHCHD, $CHCD_2$, or CDCHD, $CDCH_2$, or $CDCD_2$. A deuteroalkenyl group may be in either the cis or trans conformation about the double bond(s).

"Deuteroalkynyl" refers to any alkynyl group as defined above, wherein one or more hydrogen atoms are replaced by a deuterium (i.e., $^2H$, or D). Where an alkynyl radical is substituted by more than one deuterium, it may be referred to using a prefix corresponding to the number of deuterium substitutions. A deuteroalkynyl can be fully deuterated (i.e., all of the hydrogens have been replaced by deuteriums) or partially deuterated (i.e., only some of the hydrogens have been replaced by deuteriums). For example, a deuteroprop-argyl (i.e., a $C_3$ deuteroalkynyl) group refers to —$CH_2CD$, —CHDCH, or —$CD_2CD$.

"Deuteroalkoxy" refers to any alkoxy group as defined above, wherein one or more hydrogen atoms are replaced by a deuterium (i.e., $^2H$, or D). Where an alkoxy radical is substituted by more than one deuterium, it may be referred to using a prefix corresponding to the number of deuterium substitutions. A deuteroalkoxy can be fully deuterated (i.e., all of the hydrogens have been replaced by deuteriums) or partially deuterated (i.e., only some of the hydrogens have been replaced by deuteriums). For example, a deuter-omethoxy (i.e., a $C_1$ deuteroalkoxy) group refers to —$OCH_2D$, —$OCHD_2$, or —$OCD_3$.

"Halogen" refers to fluorine, chlorine, bromine, and iodine.

"Heterocycloalkyl" or "heterocyclyl" refers to a cycloal-kyl as defined above, having from 3 to 12 ring members and from 1 to 4 heteroatoms of N, O and S. Heterocycloalkyl includes bicyclic compounds which include a heteroatom. Bicyclic compounds includes spirocyclic compounds, fused bicyclic compounds, and bridged bicyclic compounds The heteroatoms can also be oxidized, such as —S(O)— and —$S(O)_2$—. A heterocycloalkyl group can include any num-ber of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. A heterocycloalkyl group can include groups such as aziridine, azetidine, pyrrolidine, piperidine, azepane, azocane, quinu-clidine, pyrazolidine, imidazolidine, piperazine (1,2-, 1,3-and 1,4-isomers), oxirane, oxetane, tetrahydrofuran, oxane (tetrahydropyran), oxepane, thiirane, thietane, thiolane (tet-rahydrothiophene), thiane (tetrahydrothiopyran), oxazoli-dine, isoxazolidine, thiazolidine, isothiazolidine, dioxolane, dithiolane, morpholine, thiomorpholine, dioxane, or dithi-ane. A heterocycloalkyl group can be fused to aromatic or non-aromatic ring systems to form members including indo-line. A heterocycloalkyl group can be unsubstituted or substituted. For example, a heterocycloalkyl group can be substituted with $C_1$-6 alkyl or oxo (=O), among many others.

"Alkoxy" refers to the formula —OR, wherein R is an alkyl, an alkenyl, an alkynyl, a cycloalkyl, a cycloalkenyl, aryl, or heterocyclyl, as defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

"β-carboxy" refers to a —RC(=O)O— group in which R can be hydrogen, alkyl, alkenyl, alkynyl, cycloalkyl, cycloalkenyl, aryl, or heterocyclyl, as defined herein. An β-carboxy may be substituted or unsubstituted.

"Ester" and "C-carboxy" refer to a —C(=O)OR group in which R can be the same as defined with respect to β-car-boxy. Ester and C-carboxy groups may be substituted or unsubstituted.

"Thiocarbonyl" refers to a C(=S)R group in which R can be the same as defined with respect to O-carboxy. A thio-carbonyl may be substituted or unsubstituted.

A comprehensive list of the abbreviations utilized by organic chemists of ordinary skill in the art appears in the first issue of each volume of the *Journal of Organic Chem-istry*; this list is typically presented in a table entitled Standard List of Abbreviations; the current list as of the date of this filing is hereby incorporated by reference as if fully set forth herein.

Unless otherwise indicated, all numbers expressing quan-tities of ingredients, properties such as concentration, reac-tion conditions, and so forth, used to describe and claim certain embodiments of the invention are to be understood as being modified in some instances by the term "about." Accordingly, in some embodiments (equivalently, and as shorthand, "in embodiments"), the numerical parameters set forth in the description and claims are approximations that can vary depending upon the desired properties sought to be obtained by a particular embodiment. In some embodiments, "about" refers to plus or minus five percent (±5%) of the recited unit of measure. The term "substantially," where it is applied to modify a feature or limitation herein, will be read in the context of the invention and in light of the knowledge in the art to provide the appropriate certainty, e.g., by using a standard that is recognized in the art for measuring the meaning of "substantially" as a term of degree, or by ascertaining the scope as would one of skill in the art.

In some embodiments, the numerical parameters should be construed in light of the number of reported significant digits and by applying ordinary rounding techniques. Not-withstanding that the numerical ranges and parameters set-ting forth the broad scope of some embodiments of the invention are approximations, the numerical values set forth in the specific examples are reported as precisely as practi-cable. The numerical values presented in embodiments may contain certain errors necessarily resulting from the standard deviation found in their respective testing measurements.

Unless defined otherwise, all technical and scientific terms herein have the meaning as commonly understood by one having ordinary skill in the art to which this invention belongs, who as a shorthand may be referred to simply as "one of skill." Further definitions that may assist the reader in understanding the disclosed embodiments are as follows; however, it will be appreciated that such definitions are not intended to limit the scope of the invention, which shall be properly interpreted and understood by reference to the full specification (as well as any plain meaning known to one of skill in the relevant art) in view of the language used in the appended claims. The terminology used herein is for the purpose of describing particular embodiments only and is not intended to be limiting.

Generally, the nomenclature used and procedures performed herein are those known in fields relating to one or more aspects of the invention, such as biology, pharmacology, neuroscience, organic chemistry, synthetic chemistry, and/or medicinal chemistry, and are those that will be well known and commonly employed in such fields. Standard techniques and procedures will be those generally performed according to conventional methods in the art.

Still additional definitions and abbreviations are provided elsewhere herein.

II. THERAPEUTIC METHODS

Dimethyltryptamine (N,N-dimethyltryptamine, "DMT") is principally administered by intravenous (IV) infusion, intramuscular (IM) injection, and most typically inhalation (e.g., by combustion or vaporization).

Oral administration of DMT is highly desirable, but is not possible because DMT, as with certain other psychedelics, are not orally active as they are rapidly inactivated by monoamine oxidase (MAO) enzymes during first-pass metabolism (Nichols, Pharmacological Reviews, 2016; 68(2):264-355).

There are two isoforms of MAO, monoamine oxidase-A (MAO-A) and monoamine oxidase-B (MAO-B). MAO-A has been shown to break down serotonin, melatonin, norepinephrine, epinephrine, and other monoamines ingested in food. MAO-B metabolizes similar compounds with a preference to oxidize phenylethylamines, such as dopamine. (Shih et al., Pol J Pharmacol. 1999; 51(1):25-29). Certain substrates, like tyramine, are metabolized by both MAO-A and MAO-B. (Finberg et al., Br. J Pharmacol, 1982; 77(1): 13).

Co-administration of DMT and a monoamine oxidase inhibitor (i.e., a MAO inhibitor, or "MAOI") is an approach that has been used to render DMT orally active. Decoctions made from botanicals containing DMT combined with other botanicals containing beta-carboline (O-carboline) type MAO inhibitors (e.g., harmine and/or harmaline) have been used as psychoactive medicines by Indigenous tribes of South America for at least hundreds of years. These teas are called yage, caapi, hoasca, or ayahuasca (Samorini, J Psychedelic Studies, 2019; 3(2):63-80). Unfortunately, the dosing of DMT when taken as ayahuasca is not precise and is often accompanied by unpleasant side effects. Vomiting and diarrhea are often reported as adverse effects resulting from ayahuasca consumption (Cameron et al., ACS Chem Neurosci., 2018; 9:2344-2357).

Mixtures of pharmaceutical grade DMT and the MAO inhibitors harmine and/or harmaline, called "pharmahuasca" (Ott, 1999; Brierley and Davidson, 2012), have been tested as an orally administered substitute for ayahuasca with fewer extraneous excipients and other ingredients. However, the β-carbolines harmaline and harmine are psychoactive (Glennon et al., Life Sci., 1981; 29(8):861-865) and can also produce physiological effects such as tremors (Airaksinen et al., Pharmacol Toxicol. 1987; 60:5-8). Certain β-carbolines are also associated with induced convulsion, respiratory paralysis, hypothermia, CNS depression, visual trouble, delirium, loss of coordination, and paralysis when consumed at higher doses (Brito-da-Costa et al. Pharmaceuticals, 2020; 13(11):334). In addition, ayahuasca β-carboline alkaloids can act on the immune system resulting in a dose-related suppression of all immune functions examined except macrophage function (House et al., Pharmacol., 1995; 51(1):56-65). Suppression of IL-2 and IL-4 production, CD8 activity, B cell proliferation, and NK cell activity also have been observed following exposure to harmaline (id.). Some β-carboline alkaloids (e.g., harmine) also can impair memory acquisition (Nasehi et al., Neurosci Res., 2017; 122:17-24) and inhibit human cytochrome P450 (e.g., CYP2D6), resulting in additional adverse effects (Zhao et al., Phytotherapy Res., 2011; 25(11):1671-1677).

Other MAO inhibitors with antidepressant properties have been developed, targeting MAO-A and MAO-B. (Robinson et al., Arch Gen Psych., 1973; 29(3):407-413). However these existing MAOIs have been associated with significant downsides. For example, existing MAOIs, such as moclobemide, also can potentiate cardiovascular effects of dietary amine tyramine (e.g., hypertension) and require dietary counseling (Finberg & Rabey, Frontiers Pharmacol., 2016).

Thus, there remains a need for therapeutic combinations of DMT and other 5-$HT_{2A}$ receptor agonists, with MAOIs, especially those which minimize side effects and optimize efficacy by increasing oral bioavailability of the 5-$HT_{2A}$ receptor agonist to an extent sufficient for oral administration. This need is recognized in recent primary literature: "Indeed, there seems to be no ideal or conveniently unobtrusive route for routine administration of DMT for general or common therapeutic use" (Barker, S A, Psychopharmacol., 2022; 239:1749-1763). This need is among those solved by the present disclosure.

A. Monoamine Oxidase Inhibitors

In one aspect of the disclosure is a method of treating a disease or disorder in a subject, the method comprising: administering to the subject a therapeutically effective amount of a MAO inhibitor (equivalently, and simply as shorthand, "MAOI"), or a pharmaceutically acceptable salt thereof (equivalently, and simply as shorthand, "a salt thereof," as every "salt" herein shall be understood to be a "pharmaceutically acceptable salt," unless the context clearly demands otherwise); and administering to the subject a therapeutically effective amount of a 5-$HT_{2A}$ receptor agonist (equivalently, and simply as shorthand, "5-$HT_{2A}$ agonist"), or a salt thereof. In some embodiments, including some preferred embodiments, the method comprises administration of a 5-$HT_{2A}$ agonist which is susceptible to degradation by MAO-A, for example by oxidative deamination by MAO-A under normal metabolic conditions in a subject after administration. Determination of susceptibility to degradation by MAO-A for any disclosed 5-$HT_{2A}$ agonist may be by ordinary skill.

Herein, "MAO inhibitor" or "MAOI" refers to any compound, whether natural or synthetic, that exhibits the ability to inhibit the enzymatic activity of MAO, including MAO-A and MAO-B. It encompasses all chemical structures, including organic molecules, peptides, proteins, nucleic acids, derivatives, analogs, and combinations thereof, capable of interfering with the catalytic function of monoamine oxidase enzymes, thereby preventing or reducing the metabolism or breakdown of monoamine neurotransmitters. The term "MAO inhibitor" or "MAOI" further encompasses reversible, irreversible, competitive, non-competitive, selective, and non-selective inhibitors, as well as any substance that indirectly modulates or regulates monoamine oxidase activity through allosteric, regulatory, or indirect mechanisms. In some embodiments, the MAOI is an MAO-A-selective inhibitor. In some embodiments, the MAOI is an MAO-B-selective inhibitor. In some embodiments, the MAOI is a non-selective inhibitor.

In some embodiments, the MAOI is selected from the group consisting of isocarboxazid, pargyline, selegiline, furazolidone, phenelzine, amiflamine, iproniazid, nialamide, tranylcypromine, octamoxin, phenoxypropazine, pivalyl benzhydrazine, iproclozide, iproniazide, bifemelane, prodipine, benmoxin, etryptamine, fenoxypropazine, mebanazine, pheniprazine, safrazine, hypericine, iproniazid phosphate, phenelzine sulphate, tranylcypromine sulphate, methylene blue, moclobemide, brofaromine, befloxatone, toloxatone, clorgyline, CX157, cimoxatone, bazinaprine, harmine, harmaline, sercloremine, esuprone, pirlindole, metralindole, tetrindole, and clorgyline hydrochloride. In some embodiments, the MAOI is selected from the group consisting of moclobemide, brofaromine, caroxazone, eprobemide, metralindole, minaprine, pirlindole, harmaline, harmine, rosiridin, amiflamine, befloxatone, cimoxatone, esuprone, sercloremine, tetrindole, CX157, and CX009. In some embodiments, the MAOI is selected from the group consisting of moclobemide, metralindole, pirlindole, harmaline, harmine, tetrindole, CX157, and CX009.

In some embodiments, the MAOI is selected from the group consisting of isocarboxazid, pargyline, selegiline, furazolidone, phenelzine, amiflamine, iproniazid, nialamide, tranylcypromine, octamoxin, phenoxypropazine, pivalyl benzhydrazine, iproclozide, iproniazide, bifemelane, prodipine, benmoxin, etryptamine, fenoxypropazine, mebanazine, pheniprazine, safrazine, hypericine, iproniazid phosphate, phenelzine sulphate, tranylcypromine sulphate, methylene blue, moclobemide, brofaromine, befloxatone, toloxatone, clorgyline, CX157, cimoxatone, bazinaprine, sercloremine, esuprone, pirlindole, metralindole, tetrindole, and clorgyline hydrochloride. In some embodiments, the MAOI is selected from the group consisting of moclobemide, brofaromine, caroxazone, eprobemide, metralindole, minaprine, pirlindole, rosiridin, amiflamine, befloxatone, cimoxatone, esuprone, sercloremine, tetrindole, CX157, and CX009.

In some embodiments, the MAOI is selected from the group consisting of moclobemide, metralindole, pirlindole, tetrindole, CX157, and CX009. In some embodiments, the MAOI is selected from the group consisting of metralindole, pirlindole, tetrindole, CX157, and CX009. In some embodiments, the MAOI is selected from the group consisting of metralindole, pirlindole, and tetrindole. In some embodiments, the MAOI is CX157 or CX009. In embodiments, the MAOI is CX009. In embodiments, the MAOI is CX157.

In some embodiments, the MAOI is not moclobemide. In some embodiments, when the 5-HT$_{2A}$ agonist is DMT, the MAOI is not moclobemide. In some embodiments, when the 5-HT$_{2A}$ agonist is deuterated DMT, the MAOI is not moclobemide.

In some embodiments, the MAOI is not harmine. In some embodiments, the MAOI is not harmaline. In some embodiments, the MAOI is not tetrahydroharmine. In some embodiments, the MAOI is not a naturally occurring MAOI, such as a naturally occurring harmala alkaloid, a naturally occurring β-carboline, or a naturally occurring MAOI found in a natural plant source such as Banisteriopsis caapi. In embodiments, when the 5-HT$_{2A}$ agonist is DMT, the MAOI is not harmine. In embodiments, when the 5-HT$_{2A}$ agonist is deuterated DMT, the MAOI is not harmine. In embodiments, when the 5-HT$_{2A}$ agonist is DMT, the MAOI is not harmaline. In embodiments, when the 5-HT$_{2A}$ agonist is deuterated DMT, the MAOI is not harmaline. In embodiments, when the 5-HT$_{2A}$ agonist is DMT, the MAOI is not tetrahydroharmine. In embodiments, when the 5-HT$_{2A}$ agonist is deuterated DMT, the MAOI is not tetrahydroharmine. In embodiments, when the 5-HT$_{2A}$ agonist is DMT, the MAOI is not a naturally occurring MAOI, such as a naturally occurring harmala alkaloid, a naturally occurring β-carboline, or a naturally occurring MAOI found in a natural plant source such as Banisteriopsis caapi. In embodiments, when the 5-HT$_{2A}$ agonist is deuterated DMT, the MAOI is not a naturally occurring MAOI, such as a naturally occurring harmala alkaloid, a naturally occurring β-carboline, or a naturally occurring MAOI found in a natural plant source such as Banisteriopsis caapi.

In another aspect, provided herein is a method of treating a disease or disorder in a subject, the method comprising: administering to the subject a therapeutically effective amount of a MAOI, or a salt thereof; and administering to the subject a therapeutically effective amount of a 5-HT$_{2A}$ agonist, or a salt thereof; wherein the MAOI is a MAO-A-selective inhibitor; and in some preferred embodiments wherein the 5-HT$_{2A}$ agonist is susceptible to degradation by MAO-A.

Herein, "MAO-A-selective inhibitor" refers to an MAOI that exhibits selectivity for inhibiting monoamine oxidase A (MAO-A) over monoamine oxidase B (MAO-B). For a MAO inhibitor, selectivity can be calculated by comparing the inhibitory constant ($K_i$) for MAO-A and MAO-B. For example, if an inhibitor has a $K_i$ of 0.2 µM for MAO-A and a $K_i$ of 1.0 µM for MAO-B, it can be said that the inhibitor has a 5-fold selectivity for MAO-A (i.e., the inhibitor exhibits a 5-fold higher potency for MAO-A inhibition over MAO-B inhibition). $K_i$ can be measured according to methods known to those of skill in the art.

Selective inhibitors of MAO-A can exhibit advantageous properties over non-selective inhibitors. For example, patients who consume non-selective MAOIs and also consume tyramine-rich foods or drinks (e.g., aged, cured, pickled, smoked, and fermented foods, such as cheese; fermented drinks, such as beer and wine; dried fruit; and fresh citrus) can develop dangerously high serum levels of tyramine. This can result in adverse effects, such as headache, hypertension, gastrointestinal upset, rapid heartbeat, shortness of breath, and neurological problems. (McCabe, *J Am Dietetic Assoc.*, 1986; 86(8):1059-1064.)

Tyramine is metabolized by both MAO-A and MAO-B; thus, compounds that selectively inhibit MAO-A but not MAO-B can allow for continued MAO-B-mediated metabolism of tyramine (Finberg et al., Br J Pharmacol, 1982; 77(1):13). Without being bound by theory, this can provide a better safety profile and improved patient quality of life, as patients may be treated with MAO-A-selective inhibitors with less (or no) modification of their existing diets. If a compound inhibits both MAO-A and -B, ingestion of foods containing tyramine (e.g., cheese) may produce tyramine-induced pressor effects, and result in a hypertensive crisis.

In some embodiments, the MAOI, or a salt thereof, is a MAO-A-selective inhibitor (i.e., the MAO inhibitor exhibits higher potency for MAO-A over MAO-B; or, in other words, the MAO-inhibitor has a lower $K_i$ for MAO-A inhibition than for MAO-B inhibition).

In some embodiments, the MAOI, or a salt thereof, has a selectivity for MAO-A inhibition over MAO-B inhibition of at least 5-fold, 10-fold, 50-fold, 100-fold, 150-fold, 200-fold, 300-fold, 500-fold, or 1,000-fold. In embodiments, the MAOI, or a salt thereof, has a selectivity for MAO-A inhibition over MAO-B inhibition of at least 5-fold. In embodiments, the MAOI, or a salt thereof, has a selectivity for MAO-A inhibition over MAO-B inhibition of at least 10-fold. In embodiments, the MAOI, or a salt thereof, has a selectivity for MAO-A inhibition over MAO-B inhibition of at least 20-fold. In embodiments, the MAOI, or a salt thereof, has a selectivity for MAO-A inhibition over MAO-B inhibition of at least 50-fold. In embodiments, the MAOI, or a salt thereof, has a selectivity for MAO-A inhibition over MAO-B inhibition of at least 100-fold. In embodiments, the MAOI, or a salt thereof, has a selectivity for MAO-A inhibition over MAO-B inhibition of at least 150-fold. In embodiments, the MAOI, or a salt thereof, has a selectivity for MAO-A inhibition over MAO-B inhibition of at least 200-fold. In embodiments, the MAOI, or a salt thereof, has a selectivity for MAO-A inhibition over MAO-B inhibition of at least 300-fold. In embodiments, the MAOI, or a salt thereof, has a selectivity for MAO-A inhibition over MAO-B inhibition of at least 500-fold. In embodiments, the MAOI, or a salt thereof, has a selectivity for MAO-A inhibition over MAO-B inhibition of at least 1000-fold. In embodiments, the MAOI, or a salt thereof, does not result in a detectable amount of MAO-B inhibition.

In some embodiments, the MAO inhibitor is CX157, or a salt thereof. Herein "CX157" and "TriRima™" are used interchangeably to refer to the compound having the formula:

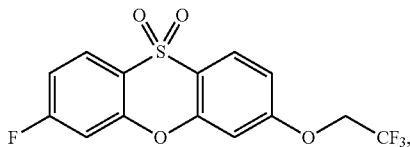 [SMILES: O=S1(=O)c2ccc(F)cc2Oc2cc(OCC(F)(F)F)ccc21]

(i.e., 3-fluoro-7(2,2,2-trifluorethoxy)phenoxathiiine-10,10-dioxide), or a salt thereof. CX157 can exist as an amorphous or crystalline structure, including polymorphic forms (see, e.g., U.S. Pat. No. 7,812,050); all physical forms of CX157, including polymorphs, are included in the present disclosure. Also included are formulations of CX157 for either rapid or extended release (see, e.g., WO2010/080977); with or without stabilizers and/or excipients (see, e.g., U.S. Pat. No. 8,313,766); and in various formulations with or without coatings, such as enteric coatings (see, e.g., WO2010/080970). The disclosures of each of the patent references above are incorporated as if fully set forth herein.

CX157 exhibits a $K_i$ for MAO-A of 10 nM in human brain homogenates and no detectable MAO-B inhibition at the tested concentration of 10 μM (i.e., $K_i$ for MAO-B inhibition >10 PM), thus displaying a >1000-fold selectivity for MAO-A inhibition over MAO-B inhibition (see Example 14). In contrast, a single 100 mg dose of moclobemide in human subjects reversibly inhibited platelet MAO-B by 27% (Koulu et al., *Br J Clinical Pharmacol.*, 1989; 27:243-255). A 450 mg moclobemide dose produced 32% inhibition (Gleiter et al., *J Neural Transmission/General Section JNT*, 1992; 89:129-133).

In some embodiments, the MAOI is CX009, which refers to the compound having the formula:

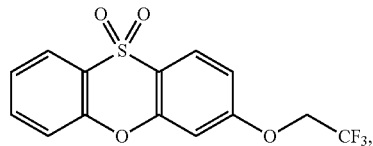 [SMILES: O=S1(=O)c2ccccc2Oc2cc(OCC(F)(F)F)ccc21]

(3-(2,2,2-trifluoroethoxy)phenoxathiin-10,10-dioxide, "CX009"), or a salt thereof.

In some embodiments, the MAOI is CX2614, which refers to the compound having the formula:

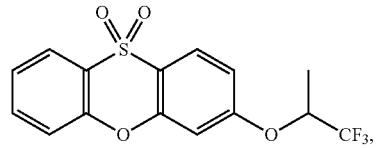

(3-(2,2,2-trifluoro-1-methylethoxy)phenoxathiin-10,10-dioxide, "CX2614"), or a salt thereof.

In some embodiments, the MAOI is a phenoxathiin-based MAO-A inhibitor of the following formula:

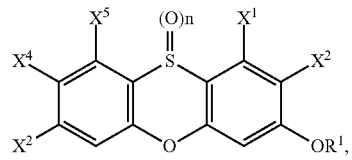

wherein n is 0, 1 or 2; $R^1$ is a branched or straight chain $C_1$-5 alkyl or $C_3$-6 cycloalkyl optionally substituted with hydroxyl, or one or more halogens; and $X^1$, $X^2$, $X^3$, $X^4$, and $X^5$ are either all hydrogens or one or two of $X^1$, $X^2$, $X^3$, $X^4$, and $X^5$ are halogen and the remainder are hydrogens, with the proviso that when n is 0 or 1 and each X is hydrogen, $R^1$ is not methyl; as in U.S. Pub. No. 2012/0003303A1, the disclosure of which is incorporated by reference as if fully set forth herein.

In some embodiments, the MAOI, or a salt thereof, has a $K_i$ for MAO-A of less than 50 nM, less than 30 nM, less than 20 nM, less than 10 nM, or less than 5 nM. In embodiments, the MAOI, or a salt thereof, has a $K_i$ for MAO-A of about 10 nM. Determining $K_i$ for MAO-A, for a MAOI or a salt thereof, may be according to methods known in the art.

In some embodiments, the MAOI, or a salt thereof, has a $K_i$ for MAO-B of greater than 1 μM, greater than 5 μM, greater than 10 μM, or greater than 20 PM. In embodiments, the MAOI, or a salt thereof, has a $K_i$ for MAO-B of greater than 1 μM. In embodiments, the MAOI, or a salt thereof, has a $K_i$ for MAO-B of greater than 5 μM. In embodiments, the MAOI, or a salt thereof, has a $K_i$ for MAO-B of greater than 10 μM. In embodiments, the MAOI, or a salt thereof, has a $K_i$ for MAO-B of greater than 20 μM. Determining $K_i$ for MAO-B, for a MAOI or a salt thereof, may be according to methods known in the art.

In some embodiments, the MAOI, or a salt thereof, does not inhibit human cytochrome P450 (e.g., CYP3A4, CYP1A2, CYP2A6, $CYP2C_{19}$, $CYP2C_{9*1}$, or CYP2D6). In embodiments, the MAOI, or a salt thereof, has a $K_i$ for CYP2D6 of greater than 10 nM, greater than 20 nM, greater than 50 nM, or greater than 100 nM. In embodiments, the MAOI, or a salt thereof, has a $K_i$ for CYP2D6 of greater than 10 nM. In embodiments, the MAOI, or a salt thereof, has a $K_i$ for CYP2D6 of greater than 20 nM. In embodiments, the MAOI, or a salt thereof, has a $K_i$ for CYP2D6 of greater than 50 nM. In embodiments, the MAOI, or a salt thereof, has a $K_i$ for CYP2D6 of greater than 100 nM. Determining inhibition of human cytochrome P450, such as CYP2D6, for a MAOI or a salt thereof, may be according to methods known in the art.

In some embodiments, the MAOI, or a salt thereof, has a $K_i$ for acetylcholinesterase of greater than 10 nM, greater than 20 nM, greater than 50 nM, or greater than 100 nM. In embodiments, the MAOI, or a salt thereof, has a $K_i$ for acetylcholinesterase of greater than 10 nM. In embodiments, the MAOI, or a salt thereof, has a $K_i$ for acetylcholinesterase of greater than 20 nM. In embodiments, the MAOI, or a salt thereof, has a $K_i$ for acetylcholinesterase of greater than 50 nM. In embodiments, the MAOI, or a salt thereof, has a $K_i$ for acetylcholinesterase of greater than 100 nM. Determining the $K_i$ for acetylcholinesterase, for a MAOI or a salt thereof, may be according to methods known in the art.

In some embodiments, the MAOI, or a salt thereof, is a reversible inhibitor of MAO-A. Herein, a "reversible inhibitor of MAO-A" is a compound that does not bind irreversibly to MAO-A and can be removed, for example, by in vitro techniques such as dilution or dialysis, or by competing substrates in vivo. Reversible MAO inhibitors are also capable of dissociating from the enzyme over time. Reversible inhibitors of MAO-A can bind to MAO-A with non-covalent interactions (e.g., hydrogen bonds, hydrophobic interactions, ionic bonds). Reversible inhibitors of MAO-A can alternatively bind to MAO-A by forming a chemical bond between the inhibitor and MAO-A; however, in such cases, the chemical bond can be cleaved under physiological conditions, rendering the inhibitor binding reversible. Reversible inhibitors of MAO-A include competitive inhibitors, non-competitive inhibitors, and inhibitors that exhibit a combination of competitive and non-competitive inhibition. Determining reversible inhibition of MAO-A, for a MAOI or a salt thereof, may be according to methods known in the art.

In embodiments, the MAOI, or a salt thereof, is a competitive inhibitor of MAO-A. Reversible inhibitors of MAO-A may also exhibit better safety profiles and fewer adverse effects, as compared to irreversible inhibitors (Lotufo-Neto et al., *Neuropsychopharmacol.*, 1999; 20:226-247). Determining competitive inhibition of MAO-A, for a MAOI or a salt thereof, may be according to methods known in the art.

As discussed above, CX157 is known to be a highly selective MAO-A-selective inhibitor (MAO-A $K_i$=10 nM) with no apparent affinity for the MAO-B isoform. CX157 is highly potent for MAO-A inhibition: more than 100 times more potent than moclobemide (Entzeroth et al., *Open J Depression*, 2017; 6:31-68). In addition to its potency, CX157 exhibits the desirable property of binding to MAO-A in a reversible fashion, thus allowing for greater safety margins and improved patient quality of life (id.). Accordingly, clinical studies have shown that CX157 can be used with an adequate safety margin without dietary tyramine restrictions (Burch et al. *Clinical Pharmacol Drug Devel.*, 2013; 3(1):4-12). This feature of CX157 is a major advantage that is not present in comparable MAO inhibitors. For example, tyramine-caused pressor effects have been demonstrated with therapeutic doses of moclobemide (Koulu et al., *Br J Clinical Pharmacol.*, 1989; 27:243-255); Gleiter et al., *J Neural Transmission/General Section JNT*, 1992; 89:129-133). The advantageous properties of CX157 led to its investigation in two Phase II clinical trials in treatment-resistant depression and major depressive disorders (see Clinical Trial Nos. NCT00739908 and NCT01246908).

In some embodiments, the MAOI, or a salt thereof, rapidly penetrates into the brain. Brain penetration can be assessed by determining the concentration of the MAOI in the brain compared to the plasma concentration. In embodiments, quantifying brain penetration comprises determining the brain/plasma (concentration) ratio of the MAOI. For example, brain/plasma ratios of CX157 were determined at oral doses of 1 mg/kg (FIG. 14), 5 mg/kg (FIG. 17), and 10 mg/kg (FIG. 15). These data indicate that CX157 brain/plasma ratios are high, with brain concentrations of up to 10-fold higher than plasma concentrations (e.g., 4 hours after a 1 mg/kg oral dose). In embodiments, following an oral dose of the MAOI, the brain concentration of the MAOI is at least 2-fold, 4-fold, 6-fold, 8-fold, or 10-fold higher than the plasma concentration (i.e., the MAOI exhibits a brain/plasma ratio of at least 2, 4, 6, 8, or 10).

Without being bound by theory, a MAOI with a high brain/plasma ratio may confer certain benefits in the context of disclosed methods. For example, therapeutic efficacy may be improved at a given plasma concentration, as the brain concentration is relatively higher. Accordingly, at a therapeutically effective brain concentration, a MAOI with a high brain/plasma ratio will have lower plasma concentrations (e.g., as compared to a MAOI with a lower brain/plasma ratio). The lower plasma concentration may reduce off-target effects of the MAOI. This may improve safety, for example, by reducing the potential for interference with metabolism (e.g., of dietary tyramine, or medications metabolized by MAO). In embodiments, a MAOI with a high brain/plasma ratio is subject to fewer pharmaceutical contraindications.

High brain/plasma ratios may also provide greater potential for increasing the therapeutic efficacy of a disclosed method or composition by lengthening the effects of the MAOI within the brain. For example, FIGS. 14-18 show that at each dose tested (i.e., 1, 5, and 10 mg/kg), CX157 concentrations in the brain are maintained over the 24-hour time course of the experiments, and that CX157 appeared to demonstrate a longer pharmacokinetic half-life in the brain than in plasma—particularly at a dose of 10 mg/kg, where an increase in brain/plasma ratio was observed at the later post-treatment time points. This may indicate CX157 has improved binding and/or slower clearance of CX157 in the brain, as compared to in plasma. These pharmacokinetic advantages may provide greater flexibility for the dose and/or timing of MAOI administration, e.g., in embodiments wherein the MAOI is administered prior to the $5\text{-HT}_{2A}$ agonist.

B. $5\text{-HT}_{2A}$ Receptor Agonists

The serotonin 2 ($5\text{-HT}_2$) receptor family consists of the three distinct receptor subtypes: $5\text{-HT}_{2A}$, $5\text{-HT}_{2B}$, and $5\text{-HT}_{2C}$. While these receptors are found throughout the human body, the $5\text{-HT}_{2A}$ and $5\text{-HT}_{2C}$ receptor subtypes are more highly expressed in the brain than the $5\text{-HT}_{2B}$ subtype.

Psychedelics are thought to exert their psychoactive effects principally by acting as $5\text{-HT}_{2A}$ receptor agonists. Herein, a "$5\text{-HT}_{2A}$ receptor agonist" (or "$5\text{-HT}_{2A}$ agonist") is a compound that binds to a $5\text{-HT}_{2A}$ receptor in an activating fashion, thereby producing a biological response. The $5\text{-HT}_{2A}$ agonist can be a full agonist or a partial agonist. In some embodiments, the $5\text{-HT}_{2A}$ agonist is a full agonist. In some embodiments, the $5\text{-HT}_{2A}$ agonist is a partial agonist. The term "$5\text{-HT}_{2A}$ receptor agonist" (or "$5\text{-HT}_{2A}$ agonist") as used herein also includes compounds that agonize intracellular $5\text{-HT}_{2A}$ receptors, instead of or in addition to cell-surface $5\text{-HT}_{2A}$ receptors (see, e.g., Vargas et al., *Science* 2023; 379(6633):700-706).

Certain $5\text{-HT}_{2A}$ agonists, such as LSD and psilocin, have been shown to bind directly to TrkB with very high affinity (Moliner et al., *Nature* 2023; 26:1032-1041). TrkB (Tropomyosin receptor kinase B) is a receptor protein that plays a significant role in the functioning and development of the nervous system. TrkB acts as a receptor for Brain-Derived Neurotrophic Factor (BDNF). Neurotrophic factors are a group of proteins that support the survival, growth, and differentiation of neurons in the nervous system. BDNF is one of the most widely studied neurotrophic factors, and it is particularly important for the development, maintenance, and plasticity of neurons in various regions of the brain. Both TrkB and BDNF have been studied due to their critical roles in various physiological and pathological processes (Zhang et al., *Current Neuropharmacol.* 2016; 14(7):721-731; Boulle et al., *Mol. Psychol.* 2012; 17:584-596). Dysregulation or deficiencies in TrkB or BDNF signaling is implicated in several neurological and psychiatric disorders, including depression, Alzheimer's disease, and epilepsy (id.). Directly binding TrkB with a 5-HT$_{2A}$ agonist may produce therapeutic effects in the treatment of such diseases. In some embodiments, the 5-HT$_{2A}$ agonist, or a salt thereof, is a compound that binds to TrkB.

Certain 5-HT$_{2A}$ agonists, including DMT and 5-MeO-DMT, have little to no oral bioactivity. For example, DMT is not orally active, likely due to rapid degradation by peripheral monoamine oxidase, the enzyme responsible for catalyzing the oxidative deamination of endogenous biogenic amines (see, e.g, Carbonaro et al., *Brain Res. Bull.* 2016; 126(1), 74-88). For hallucinogenic or psychedelic effects to occur in a subject, plasma concentration must be between 12-90 µg/L with an apparent volume of distribution of 36-55 L/kg, which roughly corresponds to a plasma concentration of 0.06-0.50 µM (id.). 5-MeO-DMT is likewise metabolized by monoamine oxidase and is therefore not orally active (see, e.g., Reckweg et al., *J Neurochem.* 2022; 162(1):128-146; and Shen et al. Curr Drug Metab. 2010; 11:659-666).

Other 5-HT$_{2A}$ agonists may require high oral doses to achieve a desired (e.g., therapeutic) effect due to metabolism by monoamine oxidase reducing oral bioavailability. For example, intravenous N,N-dipropyltryptamine (DPT) has been used as an adjunct to psychotherapy for the treatment of alcoholism (Grof et al. *Int. Pharmacopsychiatry.* 1973; 8(1-2):104-115) and cancer-associated psychological distress (Richards et al. *Omega (Westport).* 1980; 10(1):9-26). DPT may also be useful in preventing seizures (Tyagi et al. *ACS Pharmacol. Transl. Sci.* 2023; 6(10):1480-1491). However, despite DPT's nanomolar potency at the 5-HT$_{2A}$ receptor (id.), DPT is considerably less active when administered orally, as compared to other routes of administration (e.g., inhalation, intramuscular or intravenous injection) (see, e.g., Shulgin and Shulgin, TiHKAL: The Continuation, Transform Press (1997)).

"Bioavailability" can be defined as the fraction of an administered dose of unchanged drug that reaches the systemic circulation. When a drug is administered intravenously, its bioavailability is defined to be 100%. "Oral bioavailability" refers to the bioavailability of a drug (e.g., a disclosed 5-HT$_{2A}$ agonist) that reaches the systemic circulation after the drug is orally administered. As will be known to a person of skill in the art, drug bioavailability can be measured by area under the curve (AUC) or Cmax. AUC is a determination of the Area Under the Curve plotting the serum or plasma concentration of the drug along the ordinate (y-axis) against time along the abscissa (x-axis). Cmax is a measurement of the maximum concentration that a drug achieves after administration.

Those of skill will understand how to use such standard techniques in the art to identify 5-HT$_{2A}$ agonists having little to no, little, no, or low oral bioactivity. The same techniques may be used to measure an increase in oral bioavailability of a 5-HT$_{2A}$ agonist when administered according to a disclosed method or in a disclosed composition. For example, in some embodiments, an increase in oral bioavailability is indicated by an increase in AUC relative to the same 5-HT$_{2A}$ agonist when administered alone. In embodiments, an increase in oral bioavailability is indicated by an increase in Cmax relative to the same 5-HT$_{2A}$ agonist when administered alone.

In some embodiments, the 5-HT$_{2A}$ agonist has a AUC of less than about 25 ng/ml. In embodiments, the 5-HT$_{2A}$ agonist has a AUC of less than about 50 ng/ml. In embodiments, the 5-HT$_{2A}$ agonist has a AUC of less than about 75 ng/ml. In embodiments, administration of a 5-HT$_{2A}$ agonist according to a disclosed method or in a disclosed composition increases the AUC of the 5-HT$_{2A}$ agonist by about 25 ng/ml. In embodiments, administration of a 5-HT$_{2A}$ agonist according to a disclosed method or in a disclosed composition increases the AUC of the 5-HT$_{2A}$ agonist by about 50 ng/ml. In embodiments, administration of a 5-HT$_{2A}$ agonist according to a disclosed method or in a disclosed composition increases the AUC of the 5-HT$_{2A}$ agonist by about 75 ng/ml. In embodiments, administration of a 5-HT$_{2A}$ agonist according to a disclosed method or in a disclosed composition increases the AUC of the 5-HT$_{2A}$ agonist by about 100 ng/ml.

In embodiments, the 5-HT$_{2A}$ agonist has a Cmax of less than about 350 ng-min/ml. In embodiments, the 5-HT$_{2A}$ agonist has a Cmax of less than about 500 ng-min/ml. In embodiments, the 5-HT$_{2A}$ agonist has a Cmax of less than about 750 ng-min/ml. In embodiments, the 5-HT$_{2A}$ agonist has a Cmax of less than about 900 ng-min/ml. In embodiments, administration of a 5-HT$_{2A}$ agonist according to a disclosed method or in a disclosed composition increases the Cmax of the 5-HT$_{2A}$ agonist by about 350 ng-min/ml. In embodiments, administration of a 5-HT$_{2A}$ agonist according to a disclosed method or in a disclosed composition increases the Cmax of the 5-HT$_{2A}$ agonist by about 500 ng-min/ml. In embodiments, administration of a 5-HT$_{2A}$ agonist according to a disclosed method or in a disclosed composition increases the Cmax of the 5-HT$_{2A}$ agonist by about 750 ng-min/ml. In embodiments, administration of a 5-HT$_{2A}$ agonist according to a disclosed method or in a disclosed composition increases the Cmax of the 5-HT$_{2A}$ agonist by about 900 ng-min/ml.

In embodiments, the 5-HT$_{2A}$ agonist, or a salt thereof, is a compound that is metabolized by MAO-A. In embodiments, the 5-HT$_{2A}$ agonist is a tryptamine, or a salt thereof "Tryptamines" are as readily understood by those in the art. In embodiments, the 5-HT$_{2A}$ agonist is 6-allyl-N,N-diethylnorlysergamide (AL-LAD), N,N-dibutyltryptamine (DBT), N,N-diethyltryptamine (DET), N,N-diisopropyltryptamine (DiPT), 5-methoxy-α-methyltryptamine (α,O-DMS), N,N-dimethyltryptamine (DMT), 2,α-dimethyltryptamine (2,α-DMT), α,N-dimethyltryptamine (α,N-DMT), N,N-dipropyltryptamine (DPT), N-ethyl-N-isopropyltryptamine (EiPT), α-ethyltryptamine (AET), 6,N,N-triethylnorlysergamide (ETH-LAD), 3,4-dihydro-7-methoxy-1-methylcarboline (Harmaline), 7-methoxy-1-methylcarboline (Harmine), N,N-dibutyl-4-hydroxytryptamine (4-HO-DBT), N,N-diethyl-4-hydroxytryptamine (4-HO-DET), N,N-diisopropyl-4-hydroxytryptamine (4-HO-DiPT), N,N-dimethyl-4-hydroxytryptamine (4-HO-DMT), N,N-dimethyl-5-hydroxytryptamine (5-HO-DMT, bufotenine), N,N-dipropyl-4-hydroxytryptamine (4-HO-DPT), N-ethyl-4-hydroxy-N-methyltryptamine (4-HO-MET), 4-hydroxy-N-isopropyl-N-methyltryptamine (4-HO-MiPT), 4-hydroxy-N-methyl-N-propyl-tryptamine (4-HO-MPT), 4-hydroxy-N,N-tetramethylenetryptamine (4-HO-pyr-T), 12-methoxyibogamine (Ibogaine), N-butyl-N-methyltryptamine (MBT), N,N-diisopropyl-4,5-methylenedioxy-tryptamine (4,5-MDO-DiPT), N,N-diisopropyl-5,6-methylenedioxytryptamine (5,6-MDO-DiPT), N,N-dimethyl-4,5-methylenedioxytryptamine (4,5-MDO-DMT), N,N-dimethyl-5,6-methylenedioxytryptamine (5,6-MDO-DMT), N-isopropyl-N-methyl-5,6-methylenedioxytryptamine (5,6-MDO-MiPT), N,N-diethyl-2-methyl-tryptamine (2-Me-DET), 2,N,N-trimethyltryptamine (2-Me-DMT), N-acetyl-5-methoxytryptamine (melatonin), N,N-diethyl-5-methoxytryptamine (5-MeO-DET), N,N-diisopropyl-5-methoxytryptamine (5-MeO-DiPT), 5-methoxy-N,N-dimethyltryptamine (5-MeO-DMT), N-isopropyl-4-methoxy-N-methyltryptamine (4-MeO-MiPT), N-isopropyl-5-methoxy-N-methyltryptamine (5-MeO-MiPT), 5,6-dimethoxy-N-isopropyl-N-methyl-tryptamine (5,6-MeO-MiPT), 5-methoxy-N-methyl-tryptamine (5-MeO-NMT), 5-methoxy-N,N-tetramethylene-tryptamine (5-MeO-pyr-T), 6-methoxy-1-methyl-1,2,3,4-tetrahydrocarboline (6-MeO-THH), 5-methoxy-2,N,N-trimethyl-tryptamine (5-MeO-TMT), N,N-dimethyl-5-methylthiotryptamine (5-MeS-DMT), N-isopropyl-N-methyltryptamine (MiPT), α-methyltryptamine (α-MT), N-ethyltryptamine (NET), N-methyltryptamine (NMT), 6-propylnorlysergamide (PRO-LAD), N,N-tetra-methylenetryptamine (pyr-T), Tryptamine (T), 7-methoxy-1-methyl-1,2,3,4-tetrahydrocarboline (tetrahydroharmine), or α,N-dimethyl-5-methoxytryptamine (α,N,O-TMS), or a salt, hydrate, solvate, prodrug, stereoisomer, or tautomer thereof, or a combination thereof. See Shulgin and Shulgin, TiHKAL: The Continuation, Transform Press (1997) ("TiHKAL"), which is incorporated by reference as if fully set forth herein (and the above tryptamines, together, referred to herein as the "TiHKAL tryptamines"). In some preferred embodiments, the tryptamine has little to no oral bioactivity, such as one metabolized by monoamine oxidase. In some other preferred embodiments, the tryptamine requires high oral doses to achieve a desired (e.g., therapeutic) effect due to metabolism by MAO, reducing oral bioavailability.

In embodiments, the $5\text{-HT}_{2A}$ agonist is 6-allyl-N,N-diethyl-norlysergamide (AL-LAD). In embodiments, the $5\text{-HT}_{2A}$ agonist is N,N-dibutyltryptamine (DBT). In embodiments, the $5\text{-HT}_{2A}$ agonist is N,N-diethyltryptamine (DET). In embodiments, the $5\text{-HT}_{2A}$ agonist is N,N-diisopropyltryptamine (DiPT). In embodiments, the $5\text{-HT}_{2A}$ agonist is 5-methoxy-α-methyltryptamine (α,O-DMS). In embodiments, the $5\text{-HT}_{2A}$ agonist is N,N-dimethyltryptamine (DMT). In embodiments, the $5\text{-HT}_{2A}$ agonist is 2,α-dimethyltryptamine (2,α-DMT). In embodiments, the $5\text{-HT}_{2A}$ agonist is α,N-dimethyltryptamine (α,N-DMT). In embodiments, the $5\text{-HT}_{2A}$ agonist is N,N-dipropyltryptamine (DPT). In embodiments, the $5\text{-HT}_{2A}$ agonist is N-ethyl-N-isopropyltryptamine (EiPT). In embodiments, the $5\text{-HT}_{2A}$ agonist is α-ethyltryptamine (AET). In embodiments, the $5\text{-HT}_{2A}$ agonist is 6,N,N-triethylnorlysergamide (ETH-LAD). In embodiments, the $5\text{-HT}_{2A}$ agonist is N,N-dibutyl-4-hydroxytryptamine (4-HO-DBT). In embodiments, the $5\text{-HT}_{2A}$ agonist is N,N-diethyl-4-hydroxytryptamine (4-HO-DET). In embodiments, the $5\text{-HT}_{2A}$ agonist is N,N-diisopropyl-4-hydroxytryptamine (4-HO-DiPT). In embodiments, the $5\text{-HT}_{2A}$ agonist is N,N-dimethyl-4-hydroxytryptamine (4-HO-DMT). In embodiments, the $5\text{-HT}_{2A}$ agonist is N,N-dimethyl-5-hydroxytryptamine (5-HO-DMT, bufotenine). In embodiments, the $5\text{-HT}_{2A}$ agonist is N,N-dipropyl-4-hydroxytryptamine (4-HO-DPT). In embodiments, the $5\text{-HT}_{2A}$ agonist is N-ethyl-4-hydroxy-N-methyltryptamine (4-HO-MET). In embodiments, the $5\text{-HT}_{2A}$ agonist is 4-hydroxy-N-isopropyl-N-methyltryptamine (4-HO-MiPT). In embodiments, the $5\text{-HT}_{2A}$ agonist is 4-hydroxy-N-methyl-N-propyl-tryptamine (4-HO-MPT). In embodiments, the $5\text{-HT}_{2A}$ agonist is 4-hydroxy-N,N-tetramethylenetryptamine (4-HO-pyr-T). In embodiments, the $5\text{-HT}_{2A}$ agonist is 12-methoxyibogamine (Ibogaine). In embodiments, the $5\text{-HT}_{2A}$ agonist is N-butyl-N-methyltryptamine (MBT). In embodiments, the $5\text{-HT}_{2A}$ agonist is N,N-diisopropyl-4,5-methylenedioxytryptamine (4,5-MDO-DiPT). In embodiments, the $5\text{-HT}_{2A}$ agonist is N,N-diisopropyl-5,6-methylenedioxytryptamine (5,6-MDO-DiPT). In embodiments, the $5\text{-HT}_{2A}$ agonist is N,N-dimethyl-4,5-methylenedioxytryptamine (4,5-MDO-DMT). In embodiments, the $5\text{-HT}_{2A}$ agonist is N,N-dimethyl-5,6-methylenedioxytryptamine (5,6-MDO-DMT). In embodiments, the $5\text{-HT}_{2A}$ agonist is N-isopropyl-N-methyl-5,6-methylenedioxytryptamine (5,6-MDO-MiPT). In embodiments, the $5\text{-HT}_{2A}$ agonist is N,N-diethyl-2-methyl-tryptamine (2-Me-DET). In embodiments, the $5\text{-HT}_{2A}$ agonist is 2,N,N-trimethyltryptamine (2-Me-DMT). In embodiments, the $5\text{-HT}_{2A}$ agonist is N-acetyl-5-methoxytryptamine (melatonin). In embodiments, the $5\text{-HT}_{2A}$ agonist is N,N-diethyl-5-methoxytryptamine (5-MeO-DET). In embodiments, the $5\text{-HT}_{2A}$ agonist is N,N-diisopropyl-5-methoxytryptamine (5-MeO-DiPT). In embodiments, the $5\text{-HT}_{2A}$ agonist is 5-methoxy-N,N-dimethyltryptamine (5-MeO-DMT). In embodiments, the $5\text{-HT}_{2A}$ agonist is N-isopropyl-4-methoxy-N-methyltryptamine (4-MeO-MiPT). In embodiments, the $5\text{-HT}_{2A}$ agonist is N-isopropyl-5-methoxy-N-methyltryptamine (5-MeO-MiPT). In embodiments, the $5\text{-HT}_{2A}$ agonist is 5,6-dimethoxy-N-isopropyl-N-methyltryptamine (5,6-MeO-MiPT). In embodiments, the $5\text{-HT}_{2A}$ agonist is 5-methoxy-N-methyltryptamine (5-MeO-NMT). In embodiments, the $5\text{-HT}_{2A}$ agonist is 5-methoxy-N,N-tetramethylenetryptamine (5-MeO-pyr-T). In embodiments, the $5\text{-HT}_{2A}$ agonist is 6-methoxy-1-methyl-1,2,3,4-tetrahydrocarboline (6-MeO-THH). In embodiments, the $5\text{-HT}_{2A}$ agonist is 5-methoxy-2,N,N-trimethyltryptamine (5-MeO-TMT). In embodiments, the $5\text{-HT}_{2A}$ agonist is N,N-dimethyl-5-methylthiotryptamine (5-MeS-DMT). In embodiments, the $5\text{-HT}_{2A}$ agonist is N-isopropyl-N-methyltryptamine (MiPT). In embodiments, the $5\text{-HT}_{2A}$ agonist is.

In embodiments, the $5\text{-HT}_{2A}$ agonist is α-methyltryptamine (α-MT). In embodiments, the $5\text{-HT}_{2A}$ agonist is N-ethyltryptamine (NET). In embodiments, the $5\text{-HT}_{2A}$ agonist is N-methyltryptamine (NMT). In embodiments, the $5\text{-HT}_{2A}$ agonist is 6-propylnorlysergamide (PRO-LAD). In embodiments, the $5\text{-HT}_{2A}$ agonist is N,N-tetramethylenetryptamine (pyr-T). In embodiments, the $5\text{-HT}_{2A}$ agonist is Tryptamine (T). In embodiments, the $5\text{-HT}_{2A}$ agonist is 7-methoxy-1-methyl-1,2,3,4-tetrahydrocarboline (Tetrahydroharmine). In embodiments, the $5\text{-HT}_{2A}$ agonist is α,N-dimethyl-5-methoxytryptamine (α,N,O-TMS). In embodiments, the $5\text{-HT}_{2A}$ agonist is psilocin (4-OH-T). In embodiments, the $5\text{-HT}_{2A}$ agonist is psilocybin (4-OPO$_3$H$_2$-T). In embodiments, the $5\text{-HT}_{2A}$ agonist is bufotenine (5-OH-T). All above $5\text{-HT}_{2A}$ agonists will include their pharmaceutically acceptable salts.

In embodiments, the $5\text{-HT}_{2A}$ agonist is a (substituted) tryptamine having the structure below, wherein $R^{N1}$, $R^{N2}$, $R^{\alpha}$, $R^{\beta}$, $R^2$, $R^4$, $R^5$, $R^6$, and $R^7$ are as taught herein and as generally understood in the art:

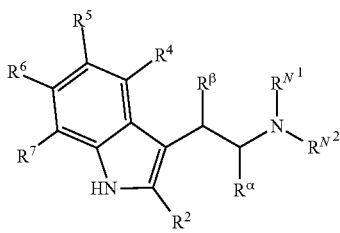

In some embodiments, $R^{N1}$, $R^{N2}$, $R^{\alpha}$, $R^{\beta}$, $R^2$, $R^4$, $R^5$, $R^6$, and $R^7$ are each independently hydrogen, deuterium, halogen (F, Cl, Br, or I), OH, phosphoryloxy, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl. Additionally, any two of $R^{N1}$, $R^{N2}$, $R^{\alpha}$, $R^{\beta}$, $R^2$, $R^4$, $R^5$, $R^6$, and $R^7$ and the intervening atoms can be taken together to form an optionally substituted optionally substituted cycloalkyl, optionally substituted cycloalkenyl, optionally substituted aryl, or optionally substituted heterocyclyl. In embodiments, the tryptamine is a quaternary salt, in which an additional $R^{N3}$ is connected to the nitrogen to which $R^{N1}$ and $R^{N2}$ are bound; wherein $R^{N3}$ is optionally substituted alkyl, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl. In some embodiments, at least one of $R^{N1}$, $R^{N2}$, $R^{\alpha}$, $R^{\beta}$, $R^2$, $R^4$, $R^5$, $R^6$, and $R^7$ is deuterium. In some preferred embodiments, the substituted tryptamine has little to no oral bioactivity, such as a substituted tryptamine metabolized by monoamine oxidase.

In embodiments, the 5-$HT_{2A}$ agonist is selected from the group consisting of DMT, 5-MeO-DMT, DPT, psilocin, and psilocybin; or a salt thereof (i.e., a salt of any in the group). In some preferred embodiments, the 5-$HT_{2A}$ agonist is DMT, or a salt thereof. In embodiments, the 5-$HT_{2A}$ agonist is 5-MeO-DMT, or a salt thereof. In embodiments, the 5-$HT_{2A}$ agonist is DPT, or a salt thereof. In embodiments, the 5-$HT_{2A}$ agonist is psilocin, or a salt thereof. In embodiments, the 5-$HT_{2A}$ agonist is psilocybin, or a salt thereof. In embodiments, the 5-$HT_{2A}$ agonist is psilocin, psilocybin, or a salt thereof. In embodiments, the 5-$HT_{2A}$ agonist is a psilocin prodrug other than psilocybin, such as psilacetin, or a salt thereof. In embodiments, the 5-$HT_{2A}$ agonist is selected from the group consisting of DMT, 5-MeO-DMT, and DPT, or a salt thereof. In embodiments, the 5-$HT_{2A}$ agonist is DMT or 5-MeO-DMT, or a salt thereof. In embodiments, the 5-$HT_{2A}$ agonist is DMT or DPT, or a salt thereof. In embodiments, the 5-$HT_{2A}$ agonist is 5-MeO-DMT or DPT, or a salt thereof.

1. Deuterated 5-$HT_{2A}$ Receptor Agonists

In embodiments, the 5-$HT_{2A}$ agonist is deuterated. Hence, in embodiments, a disclosed method, as an example, comprises administering to a subject a deuterated 5-$HT_{2A}$ agonist, or a salt thereof. Also provided herein are pharmaceutical compositions comprising a deuterated 5-$HT_{2A}$ agonist, or a salt thereof.

Herein, a compound (such as a 5-$HT_{2A}$ agonist) that is "deuterated" refers to the compound wherein one or more hydrogen (protium) atoms are replaced by a deuterium (i.e., $^2H$, or D). "Deuterated" compounds may be fully deuterated or partially deuterated. In general, and without being bound by theory, deuterated drugs can show promising advantages in pharmacokinetics, such as improved metabolic stability and prolonged half-life, and can lead to enhanced drug exposure and potentially reduce dosing frequency (Lu et al., *J Med Chem.* 2018; 61(6):2111-2127). Deuterated drugs can offer improved bioavailability and tissue distribution compared to their non-deuterated counterparts, potentially resulting in enhanced therapeutic efficacy and reduced interpatient variability (Hruska et al., *Expert Opin Drug Metab Toxicol.*, 2020; 16(2):87-98). Deuteration can reduce off-target interactions and minimize drug-drug interactions by altering the physicochemical properties of the drug, potentially leading to improved safety and tolerability (Shimizu et al., *J Med Chem.*, 2020; 63(13):6751-6776). Various deuterated 5-$HT_{2A}$ agonists have been explored. For example, deuterated tryptamines, such as deuterated DMT and DMT analogs, are described in at least WO2021/116503, WO2021/234608, WO2021/245133, and U.S. Pat. No. 11,471,417. To the best of Applicant's knowledge however, there is no evidence that any deuterated form of DMT is orally active, or that deuteration renders any other non-orally active compound orally active.

In embodiments, the deuterated 5-$HT_{2A}$ agonist has a AUC of less than about 25 ng/ml. In embodiments, the deuterated 5-$HT_{2A}$ agonist has a AUC of less than about 50 ng/ml. In embodiments, the deuterated 5-$HT_{2A}$ agonist has a AUC of less than about 75 ng/ml. In embodiments, administration of a deuterated 5-$HT_{2A}$ agonist according to a disclosed method or in a disclosed composition increases the AUC of the deuterated 5-$HT_{2A}$ agonist by about 25 ng/ml. In embodiments, administration of a deuterated 5-$HT_{2A}$ agonist according to a disclosed method or in a disclosed composition increases the AUC of the deuterated 5-$HT_{2A}$ agonist by about 50 ng/ml. In embodiments, administration of a deuterated 5-$HT_{2A}$ agonist according to a disclosed method or in a disclosed composition increases the AUC of the deuterated 5-$HT_{2A}$ agonist by about 75 ng/ml. In embodiments, administration of a deuterated 5-$HT_{2A}$ agonist according to a disclosed method or in disclosed composition increases the AUC of the deuterated 5-$HT_{2A}$ agonist by about 100 ng/ml.

In embodiments, the deuterated 5-$HT_{2A}$ agonist has a Cmax of less than about 350 ng-min/ml. In embodiments, the deuterated 5-$HT_{2A}$ agonist has a Cmax of less than about 500 ng-min/ml. In embodiments, the deuterated 5-$HT_{2A}$ agonist has a Cmax of less than about 750 ng-min/ml. In embodiments, the deuterated 5-$HT_{2A}$ agonist has a Cmax of less than about 900 ng-min/ml. In embodiments, administration of a deuterated 5-$HT_{2A}$ agonist according to a disclosed method or in a disclosed composition increases the Cmax of the deuterated 5-$HT_{2A}$ agonist by about 350 ng-min/ml. In embodiments, administration of a deuterated 5-$HT_{2A}$ agonist according to a disclosed method or in a disclosed composition increases the Cmax of the deuterated 5-$HT_{2A}$ agonist by about 500 ng-min/ml. In embodiments, administration of a deuterated 5-$HT_{2A}$ agonist according to a disclosed method or in a disclosed composition increases the Cmax of the deuterated 5-$HT_{2A}$ agonist by about 750 ng-min/ml. In embodiments, administration of a deuterated 5-$HT_{2A}$ agonist according to a disclosed method or in a disclosed composition increases the Cmax of the deuterated 5-$HT_{2A}$ agonist by about 900 ng·min/ml.

In embodiments, the deuterated 5-$HT_{2A}$ agonist is a deuterated compound that is metabolized by MAO-A. In embodiments, the deuterated 5-$HT_{2A}$ agonist is a deuterated tryptamine, or a salt thereof. In general, the deuterated 5-$HT_{2A}$ agonist can be any 5-$HT_{2A}$ agonist disclosed herein, having any amount of deuterium substitution (i.e., the compound may be fully deuterated or partially deuterated, and may have any isotopic purity).

a. Isotopic Purity

In some embodiments, the deuterated 5-HT$_{2A}$ agonist, or a salt thereof, has a deuterium isotopic purity of at least 50%, 55%, 60%, 65%, 70%, 75%, 80%, 85%, 90%, 91%, 92%, 93%, 94%, 95%, 96%, 97%, 98%, 99%, 99.5%, 99.6%, 99.7%, 99.8%, 99.9%, or 100%. In one embodiment, the deuterated 5-HT$_{2A}$ agonist, or a salt thereof, has an isotopic purity of at least 50%. In an embodiment, the deuterated 5-HT$_{2A}$ agonist, or a salt thereof, has an isotopic purity of at least 55%. In another embodiment, the deuterated 5-HT$_{2A}$ agonist, or a salt thereof, has an isotopic purity of at least 60%. In yet another embodiment, the compound of any, or a salt thereof, has an isotopic purity of at least 65%. In another embodiment, the deuterated 5-HT$_{2A}$ agonist, or a salt thereof, has an isotopic purity of at least 70%. In another embodiment, the deuterated 5-HT$_{2A}$ agonist, or a salt thereof, has an isotopic purity of at least 75%. In another embodiment, the compound of any, or a salt thereof, has an isotopic purity of at least 80%. In another embodiment, the deuterated 5-HT$_{2A}$ agonist, or a salt thereof, has an isotopic purity of at least 85%. In another embodiment, the deuterated 5-HT$_{2A}$ agonist, or a salt thereof, has an isotopic purity of at least 90%. In another embodiment, the deuterated 5-HT$_{2A}$ agonist, or a salt thereof, has an isotopic purity of at least 91%. In another embodiment, the deuterated 5-HT$_{2A}$ agonist, or a salt thereof, has an isotopic purity of at least 92%. In another embodiment, the deuterated 5-HT$_{2A}$ agonist, or a salt thereof, has an isotopic purity of at least 93%. In another embodiment, the deuterated 5-HT$_{2A}$ agonist, or a salt thereof, has an isotopic purity of at least 94%. In another embodiment, the deuterated 5-HT$_{2A}$ agonist, or a salt thereof, has an isotopic purity of at least 95%. In another embodiment, the deuterated 5-HT$_{2A}$ agonist, or a salt thereof, has an isotopic purity of at least 96%. In another embodiment, the deuterated 5-HT$_{2A}$ agonist, or a salt thereof, has an isotopic purity of at least 97%. In another embodiment, the deuterated 5-HT$_{2A}$ agonist, or a salt thereof, has an isotopic purity of at least 98%. In another embodiment, the deuterated 5-HT$_{2A}$ agonist, or a salt thereof, has an isotopic purity of at least 99%. In another embodiment, the deuterated 5-HT$_{2A}$ agonist, or a salt thereof, has an isotopic purity of at least 99.5%. In another embodiment, the deuterated 5-HT$_{2A}$ agonist, or a salt thereof, has an isotopic purity of at least 99.6%. In another embodiment, the deuterated 5-HT$_{2A}$ agonist, or a salt thereof, has an isotopic purity of at least 99.7%. In another embodiment, the deuterated 5-HT$_{2A}$ agonist, or a salt thereof, has an isotopic purity of at least 99.8%. In another embodiment, the deuterated 5-HT$_{2A}$ agonist, or a salt thereof, has an isotopic purity of at least 99.9%. For such isotopically-labeled molecules, isotopic enrichment may be described as a percentage indicating the percent of isotopic atoms at a particular site on the molecule. The percentage can be referred to as the "isotopic purity" of the isotopically-labeled compound.

In some embodiments, the deuterated 5-HT$_{2A}$ agonist, or a salt thereof, will be a mixture of the deuterated 5-HT$_{2A}$ agonist (i.e., a deuterium-substituted compound, of any isotopic purity) and a corresponding non-substituted compound (i.e., the corresponding compound wherein none of the hydrogens are substituted by a deuterium, e.g., at no position of the compound will the presence of deuterium be higher than the natural abundance of deuterium isotope), or a salt thereof. In such mixtures, at least 1%, 2%, 3%, 4%, 5%, 10%, 20%, 30%, 40%, 50%, 55%, 60%, 65%, 70%, 75%, 80%, 85%, 90%, 91%, 92%, 93%, 94%, 95%, 96%, 97%, 98%, 99%, 99.5%, 99.6%, 99.7%, 99.8%, 99.9%, or 100% are deuterium-substituted 5-HT$_{2A}$ agonists of any, or a salt thereof (wherein the other compounds in such mixtures are the corresponding non-substituted compounds). In an embodiment, at least 1% of the deuterated 5-HT$_{2A}$ agonists of any, or a salt thereof, are deuterium-substituted. In an embodiment, at least 2% of the deuterated 5-HT$_{2A}$ agonists of any, or a salt thereof, are deuterium-substituted. In an embodiment, at least 3% of the deuterated 5-HT$_{2A}$ agonists of any, or a salt thereof, are deuterium-substituted. In an embodiment, at least 4% of the deuterated 5-HT$_{2A}$ agonists of any, or a salt thereof, are deuterium-substituted. In an embodiment, at least 5% of the deuterated 5-HT$_{2A}$ agonists of any, or a salt thereof, are deuterium-substituted. In an embodiment, at least 10% of the deuterated 5-HT$_{2A}$ agonists of any, or a salt thereof, are deuterium-substituted. In an embodiment, at least 20% of the deuterated 5-HT$_{2A}$ agonists of any, or a salt thereof, are deuterium-substituted. In an embodiment, at least 30% of the deuterated 5-HT$_{2A}$ agonists of any, or a salt thereof, are deuterium-substituted. In an embodiment, at least 40% of the deuterated 5-HT$_{2A}$ agonists of any, or a salt thereof, are deuterium-substituted. In an embodiment, at least 50% of the deuterated 5-HT$_{2A}$ agonists of any, or a salt thereof, are deuterium-substituted. In an embodiment, the deuterated 5-HT$_{2A}$ agonists of any, or a salt thereof, at least 55% are deuterium-substituted. In another embodiment, the deuterated 5-HT$_{2A}$ agonists of any, or a salt thereof, at least 60% are deuterium-substituted. In yet another embodiment, the deuterated 5-HT$_{2A}$ agonists of any, or a salt thereof, at least 65% are deuterium-substituted. In another embodiment, the deuterated 5-HT$_{2A}$ agonists of any, or a salt thereof, at least 70% are deuterium-substituted. In another embodiment, the deuterated 5-HT$_{2A}$ agonists of any, or a salt thereof, at least 75% are deuterium-substituted. In another embodiment, the deuterated 5-HT$_{2A}$ agonists of any, or a salt thereof, at least 80% are deuterium-substituted. In another embodiment, the deuterated 5-HT$_{2A}$ agonists of any, or a salt thereof, at least 85% are deuterium-substituted. In another embodiment, the deuterated 5-HT$_{2A}$ agonists of any, or a salt thereof, at least 90% are deuterium-substituted. In another embodiment, the deuterated 5-HT$_{2A}$ agonists of any, or a salt thereof, at least 91% are deuterium-substituted. In another embodiment, the deuterated 5-HT$_{2A}$ agonists of any, or a salt thereof, at least 92% are deuterium-substituted. In another embodiment, the deuterated 5-HT$_{2A}$ agonists of any, or a salt thereof, at least 93% are deuterium-substituted. In another embodiment, the deuterated 5-HT$_{2A}$ agonists of any, or a salt thereof, at least 94% are deuterium-substituted. In another embodiment, the deuterated 5-HT$_{2A}$ agonists of any, or a salt thereof, at least 95% are deuterium-substituted. In another embodiment, the deuterated 5-HT$_{2A}$ agonists of any, or a salt thereof, at least 96% are deuterium-substituted. In another embodiment, the deuterated 5-HT$_{2A}$ agonists of any, or a salt thereof, at least 97% are deuterium-substituted. In another embodiment, the deuterated 5-HT$_{2A}$ agonists of any, or a salt thereof, at least 98% are deuterium-substituted. In another embodiment, the deuterated 5-HT$_{2A}$ agonists of any, or a salt thereof, at least 99% are deuterium-substituted. In another embodiment, the deuterated 5-HT$_{2A}$ agonists of any, or a salt thereof, at least 99.5% are deuterium-substituted. In another embodiment, the deuterated 5-HT$_{2A}$ agonists of any, or a salt thereof, at least 99.6% are deuterium-substituted. In another embodiment, the deuterated 5-HT$_{2A}$ agonists of any, or a salt thereof, at least 99.7% are deuterium-substituted. In another embodiment, the deuterated 5-HT$_{2A}$ agonists of any, or a salt thereof, at least 99.8% are deuterium-substituted. In another embodiment, the deuterated 5-HT$_{2A}$ agonists of any, or a salt thereof, at least 99.9% are deuterium-substituted. In any of the embodiments described above, a non-substituted or non-deuterated 5-HT$_{2A}$ agonist may be described as a compound of any, or a salt thereof, wherein all of the deuterium atoms are replaced with hydrogen atoms.

b. Mixtures of Deuterated and Undeuterated Compounds

In some embodiments, a composition comprising a deuterated 5-HT$_{2A}$ agonist used in a disclosed method or contained within a disclosed pharmaceutical composition will be a mixture of one or more deuterium-substituted 5-HT$_{2A}$ agonists and corresponding non-substituted 5-HT$_{2A}$ agonists in a fixed ratio, and will contain a ratio of deuterium-substituted to non-substituted compounds (as mole ratio or mass ratio), including a salt, hydrate, solvate or prodrug thereof, of 1:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, at least 2.0:1, at least 2.5:1, at least 3.0:1, at least 4.0:1, at least 5.0:1, at least 6.0:1, at least 7.0:1, at least 8.0:1, at least 9.0:1, and at least 10:1, at least 11:1, at least 12:1, at least 13:1, at least 14:1, at least 15:1, at least 16:1, at least 17:1, at least 18:1, at least 19:1, at least 20:1, at least 25:1, at least 30:1, at least 40:1, at least 50:1, at least 60:1, at least 70:1, at least 80:1, at least 90:1, and at least 100:1, including all exact above-listed ratios.

In some embodiments, a composition comprising a deuterated 5-HT$_{2A}$ agonist used in a disclosed method or contained within a disclosed pharmaceutical composition will be a mixture of one or more deuterium-substituted 5-HT$_{2A}$ agonists and corresponding non-substituted 5-HT$_{2A}$ agonists in a fixed ratio, and will contain a ratio of non-substituted to deuterium-substituted compounds (as mole ratio or mass ratio), including a salt, hydrate, solvate or prodrug thereof, of 1:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, at least 2.0:1, at least 2.5:1, at least 3.0:1, at least 4.0:1, at least 5.0:1, at least 6.0:1, at least 7.0:1, at least 8.0:1, at least 9.0:1, and at least 10:1, at least 11:1, at least 12:1, at least 13:1, at least 14:1, at least 15:1, at least 16:1, at least 17:1, at least 18:1, at least 19:1, at least 20:1, at least 25:1, at least 30:1, at least 40:1, at least 50:1, at least 60:1, at least 70:1, at least 80:1, at least 90:1, and at least 100:1, including all exact above-listed ratios.

c. Deuterated Compounds

In some embodiments, the deuterated 5-HT$_{2A}$ agonist is selected from the group consisting of deuterated DMT, deuterated 5-MeO-DMT, deuterated DPT, deuterated psilocin, deuterated psilocybin, or a salt thereof. In some preferred embodiments, the deuterated 5-HT$_{2A}$ agonist is deuterated DMT, or a salt thereof. In embodiments, the 5-HT$_{2A}$ agonist is deuterated 5-MeO-DMT, or a salt thereof. In embodiments, the 5-HT$_{2A}$ agonist is deuterated DPT, or a salt thereof. In embodiments, the deuterated 5-HT$_{2A}$ agonist is deuterated psilocin, or a salt thereof. In embodiments, the 5-HT$_{2A}$ agonist is deuterated psilocybin, or a salt thereof. In embodiments, the deuterated 5-HT$_{2A}$ agonist is selected from the group consisting of deuterated DMT, deuterated 5-MeO-DMT, and deuterated DPT, or a salt thereof. In embodiments, the deuterated 5-HT$_{2A}$ agonist is deuterated DMT or deuterated 5-MeO-DMT, or a salt thereof.

In some aspects are disclosed deuterated 5-HT$_{2A}$ agonists with the structure of Formula (I):

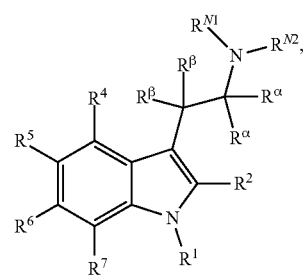

or a salt thereof, wherein:
$R^{N1}$ and $R^{N2}$ are each independently H, $C_1$-$C_6$ alkyl, $C_1$-$C_6$ deuteroalkyl, $C_2$-$C_6$ alkenyl, $C_2$-$C_6$ deuteroalkenyl, $C_2$-$C_6$ alkynyl, $C_2$-$C_6$ deuteroalkynyl, $C_3$-$C_{10}$ cycloalkyl, or $C_3$-$C_{10}$ deuterocycloalkyl; or
$R^{N1}$ and $R^{N2}$ are taken together with the intervening nitrogen to form a $C_4$-$C_{10}$ heterocyclyl, or $C_4$-$C_{10}$ deuteroheterocyclyl; each $R^\alpha$ is independently H (protium), D (deuterium), $C_1$-$C_6$ alkyl, or $C_1$-$C_6$ deuteroalkyl; each $R^\beta$ is independently H or D; $R^1$ is H or D; $R^2$, $R^4$, $R^5$, $R^6$, and $R^7$ are each independently H, D, $C_1$-$C_6$ alkyl, $C_1$-$C_6$ deuteroalkyl, —OPO$_3$H$_2$, $C_1$-$C_6$ acyl, $C_1$-$C_6$ deuteroacyl, OH, $C_1$-$C_6$ alkoxy, or $C_1$-$C_6$ deuteroalkoxy; provided that at least one of $R^{N1}$, $R^{N2}$, $R^1$, $R^\alpha$, $R^\beta$, $R^2$, $R^4$, $R^5$, $R^6$, and $R^7$ is D, $C_1$-$C_6$ deuteroalkyl, $C_1$-$C_6$ deuteroalkoxy, or $C_1$-$C_6$ deuteroacyl.

In some embodiments, the deuterated 5-HT$_{2A}$ agonist has the structure of Formula (II):

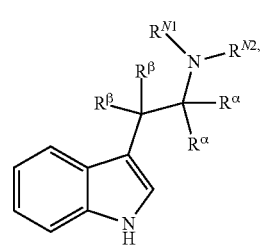

or a salt thereof, wherein $R^{N1}$, $R^{N2}$, $R^\alpha$, and $R^\beta$, are as defined for Formula (I).

In some embodiments, the deuterated 5-HT$_{2A}$ agonist has the structure of Formula (III):

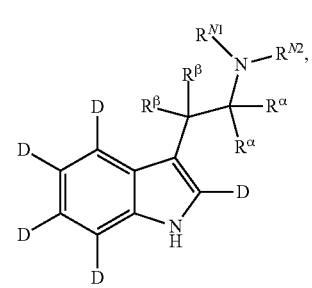

or a salt thereof, wherein $R^{N1}$, $R^{N2}$, $R^\alpha$, and $R^\beta$, are as defined for Formula (I).

In some embodiments, the deuterated 5-HT$_{2A}$ agonist is selected from TABLE 1 below.

TABLE 1
Exemplary deuterated 5-HT$_{2A}$ agonists.
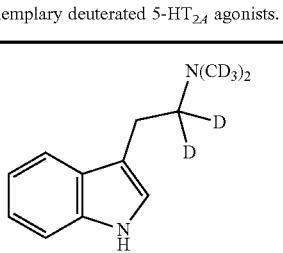
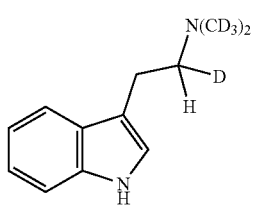
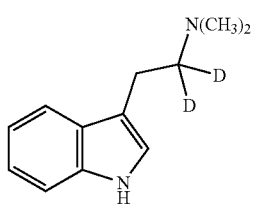
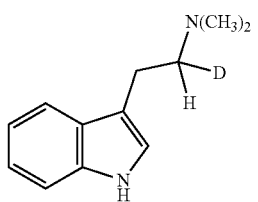 [SMILES: [2H]C(Cc1c[nH]c2ccccc12)N(C)C]
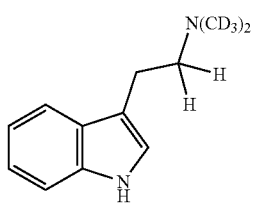
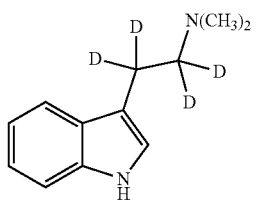 [SMILES: [2H]C([2H])(c1c[nH]c2ccccc12)C([2H])([2H])N(C)C]
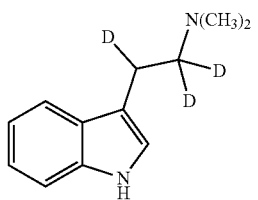 [SMILES: [2H]C(c1c[nH]c2ccccc12)C([2H])([2H])N(C)C]
TABLE 1-continued
Exemplary deuterated 5-HT$_{2A}$ agonists.
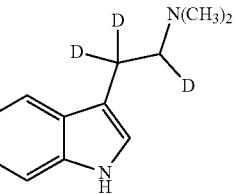
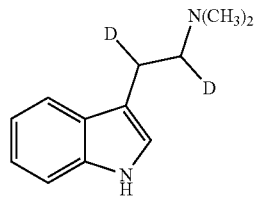 [SMILES: [2H]C(c1c[nH]c2ccccc12)C([2H])N(C)C]
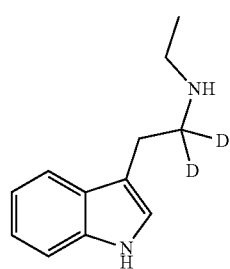 [SMILES: [2H]C([2H])(Cc1c[nH]c2ccccc12)NCC]
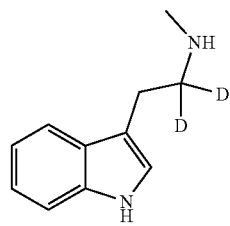
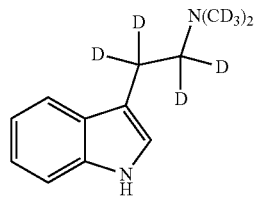
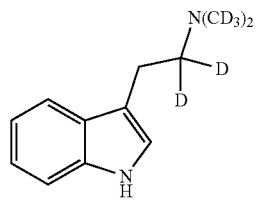
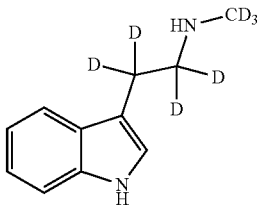 [SMILES: [2H]C([2H])([2H])NC([2H])([2H])C([2H])([2H])c1c[nH]c2ccccc12]

TABLE 1-continued
Exemplary deuterated 5-HT$_{2A}$ agonists.
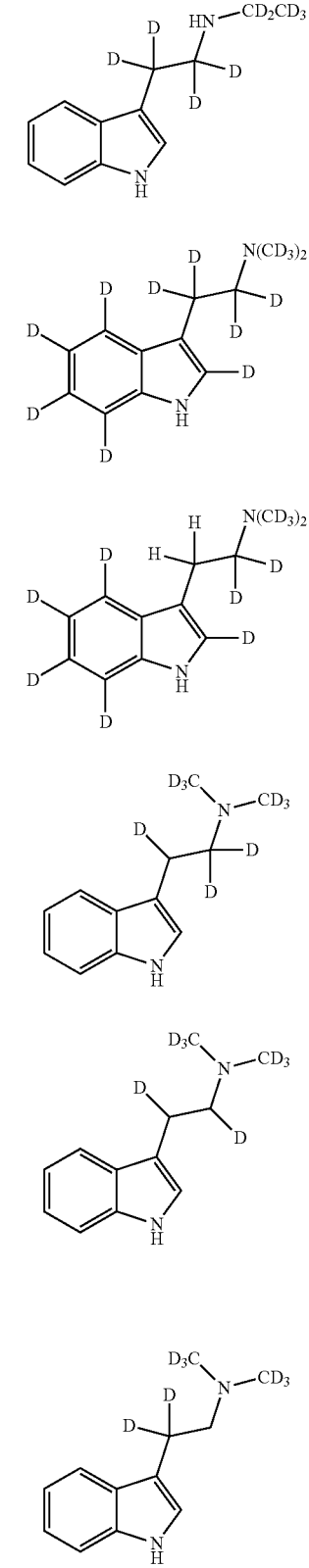
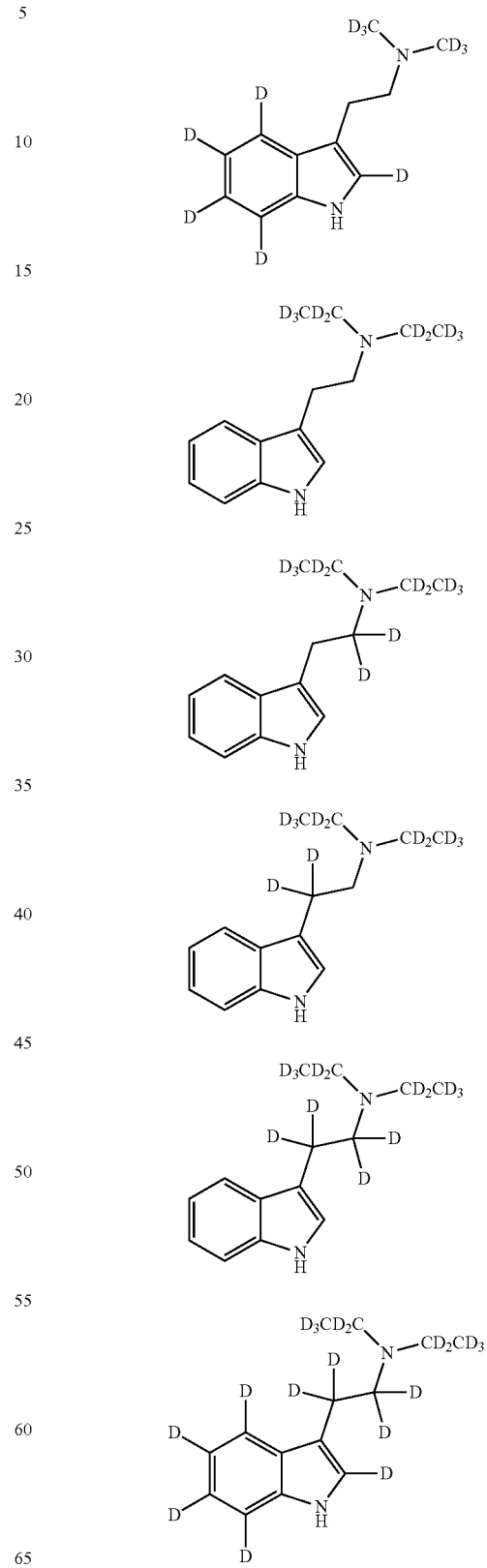

TABLE 1-continued

Exemplary deuterated 5-HT$_{2A}$ agonists.

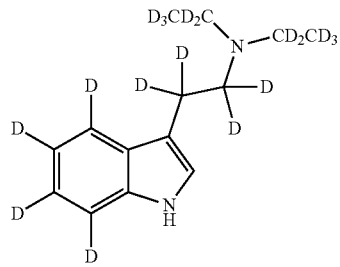

In some embodiments, the deuterated 5-HT$_{2A}$ agonist has the structure of Formula (IV):

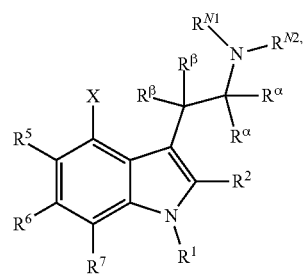

(IV)

or a salt thereof, wherein X is —OPO$_3$H$_2$, C$_1$-C$_6$ acyl, C$_1$-C$_6$ deuteroacyl, or OH; and R$^{N1}$, R$^{N2}$, R$^{\alpha}$, R$\beta$, R$^1$, R$^2$, R$^5$, R$^6$, and R$^7$ are as defined for Formula (I).

In some embodiments, the deuterated 5-HT$_{2A}$ agonist is selected from TABLE 2 below.

TABLE 2

Exemplary deuterated 5-HT$_{2A}$ agonists.

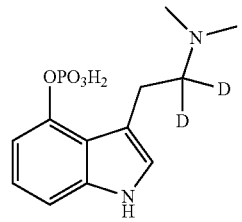

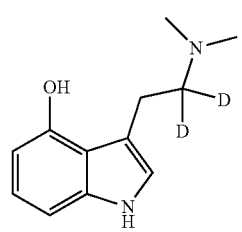 [SMILES: [2H]C([2H])(Cc1c[nH]c2cccc(O)c12)N(C)C]

TABLE 2-continued

Exemplary deuterated 5-HT$_{2A}$ agonists.

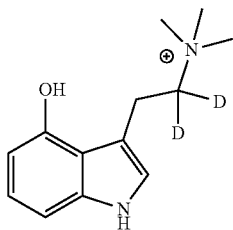 [SMILES: [2H]C([2H])(Cc1c[nH]c2cccc(O)c12)[N+](C)(C)C]

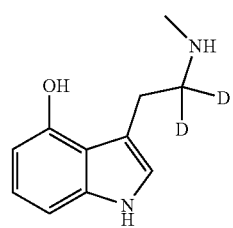 [SMILES: [2H]C([2H])(Cc1c[nH]c2cccc(O)c12)NC]

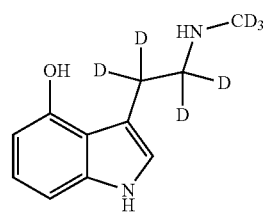 [SMILES: [2H]C([2H])([2H])NC([2H])([2H])C([2H])([2H])c1c[nH]c2cccc(O)c12]

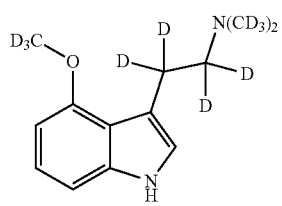

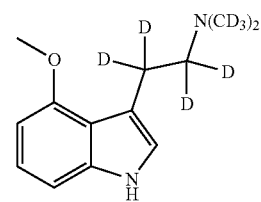

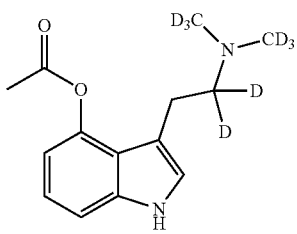 [SMILES: [2H]C([2H])([2H])N(C([2H])([2H])[2H])C([2H])([2H])Cc1c[nH]c2cccc(OC(C)=O)c12]

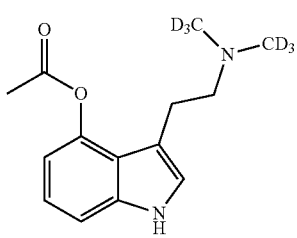 [SMILES: [2H]C([2H])([2H])N(CCc1c[nH]c2cccc(OC(C)=O)c12)C([2H])([2H])[2H]]

TABLE 2-continued

Exemplary deuterated 5-HT$_{2A}$ agonists.

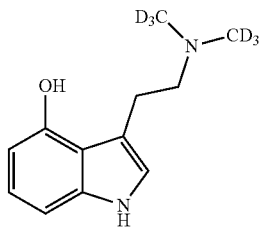 [SMILES: [2H]C([2H])([2H])N(CCc1c[nH]c2cccc(O)c12)C([2H])([2H])[2H]]
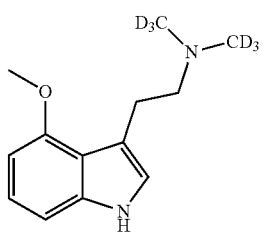 [SMILES: [2H]C([2H])([2H])N(CCc1c[nH]c2cccc(OC)c12)C([2H])([2H])[2H]]
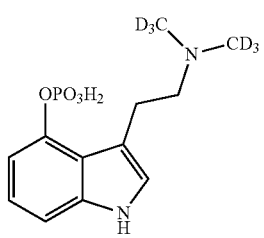
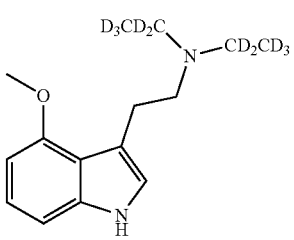
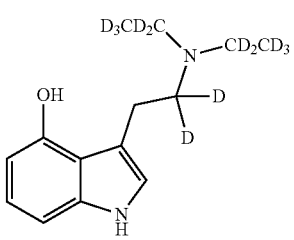
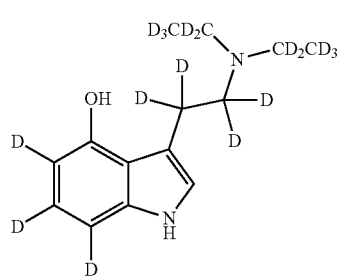

In some embodiments, the deuterated 5-HT$_{2A}$ agonist has the structure of Formula (V):

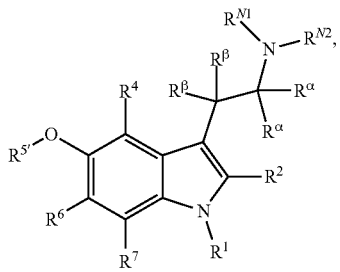

or a salt thereof, wherein $R^{5'}$ is $C_1$-$C_6$ alkyl or $C_1$-$C_6$ deuteroalkyl, such as $CH_3$ or $CD_3$; and $R^{N1}$, $R^{N2}$, $R^\alpha$, $R^\beta$, $R^1$, $R^2$, $R^4$, $R^6$, and $R^7$ are as defined for Formula (I).

In some embodiments, the deuterated 5-HT$_{2A}$ agonist is selected from TABLE 3 below.

TABLE 3

Exemplary deuterated 5-HT$_{2A}$ agonists.

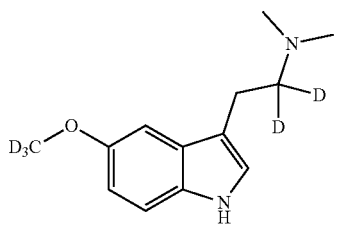 [SMILES: [2H]C([2H])([2H])Oc1ccc2[nH]cc(CC([2H])([2H])N(C)C)c2c1]
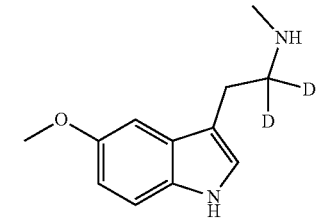 [SMILES: [2H]C([2H])(Cc1c[nH]c2ccc(OC)cc12)NC]
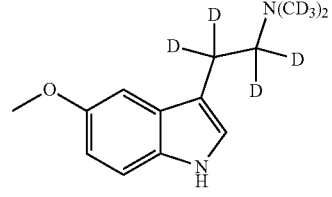
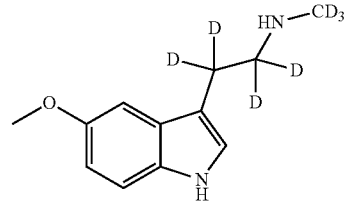 [SMILES: [2H]C([2H])([2H])NC([2H])([2H])C([2H])([2H])c1c[nH]c2ccc(OC)cc12]

TABLE 3-continued

Exemplary deuterated 5-HT$_{2A}$ agonists.

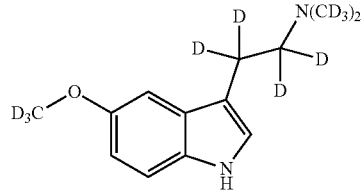
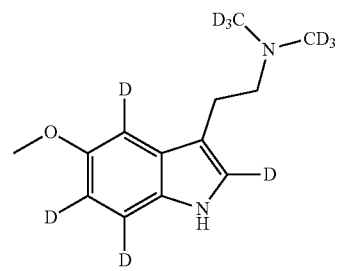 [SMILES: [2H]c1[nH]c2c([2H])c([2H])c(OC)c([2H])c2c1CCN(C([2H])([2H])[2H])C([2H])([2H])[2H]]
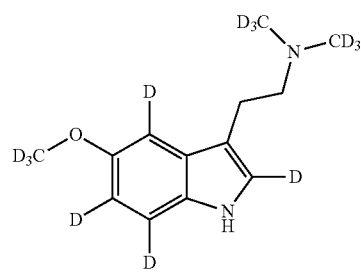 [SMILES: [2H]c1[nH]c2c([2H])c([2H])c(OC([2H])([2H])[2H])c([2H])c2c1CCN(C([2H])([2H])[2H])C([2H])([2H])[2H]]
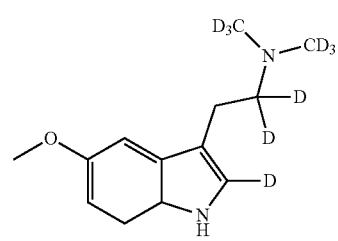 [SMILES: [2H]C1=C(CC([2H])([2H])N(C([2H])([2H])[2H])C([2H])([2H])[2H])C2=CC(OC)=CCC2N1]
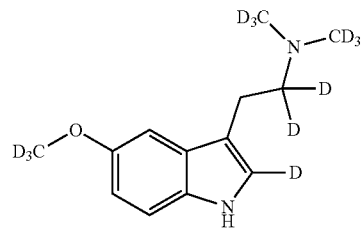 [SMILES: [2H]c1[nH]c2ccc(OC([2H])([2H])[2H])cc2c1CC([2H])([2H])N(C([2H])([2H])[2H])C([2H])([2H])[2H]]
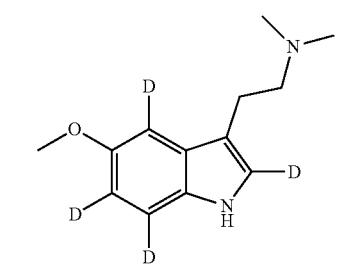

TABLE 3-continued

Exemplary deuterated 5-HT$_{2A}$ agonists.

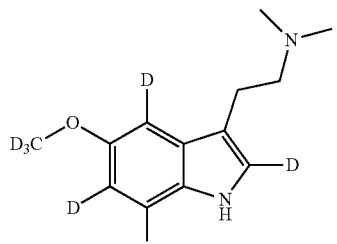

In some embodiments, the deuterated 5-HT$_{2A}$ agonist has the structure of Formula (VI):

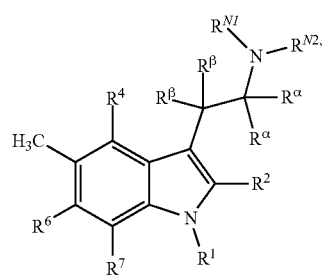

(VI)

or a salt thereof, wherein $R^{N1}$, $R^{N2}$, $R^{\alpha}$, $R^{\beta}$, $R^{1}$, $R^{2}$, $R^{5}$, $R^{6}$, and $R^{7}$ are as defined for Formula (I).

In some embodiments, the deuterated 5-HT$_{2A}$ agonist is selected from TABLE 4 below.

TABLE 4

Exemplary deuterated 5-HT$_{2A}$ agonists.

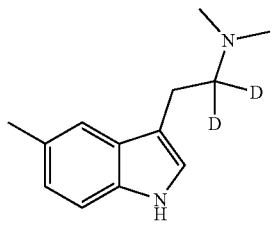
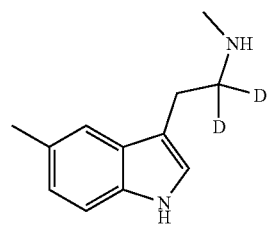 [SMILES: [2H]C([2H])(Cc1c[nH]c2ccc(C)cc12)NC]

TABLE 4-continued
Exemplary deuterated 5-HT$_{2A}$ agonists.
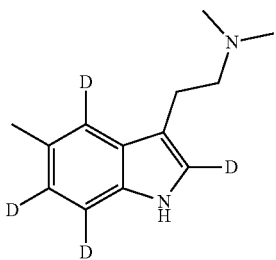
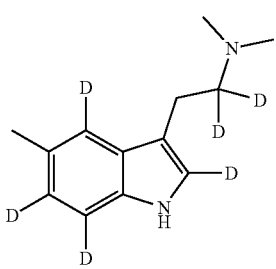
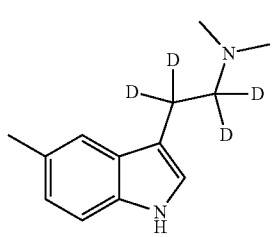
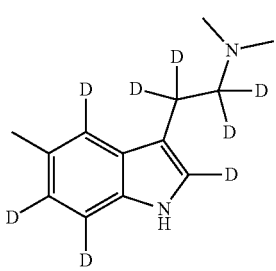
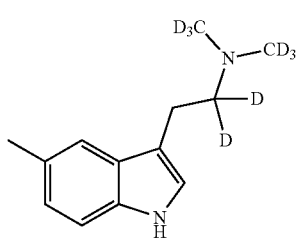 [SMILES: [2H]C([2H])([2H])N(C([2H])([2H])[2H])C([2H])([2H])Cc1c[nH]c2ccc(C)cc12]
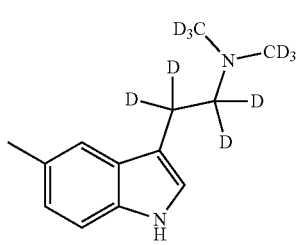 [SMILES: [2H]C([2H])([2H])N(C([2H])([2H])[2H])C([2H])([2H])C([2H])([2H])c1c[nH]c2ccc(C)cc12]
TABLE 4-continued
Exemplary deuterated 5-HT$_{2A}$ agonists.
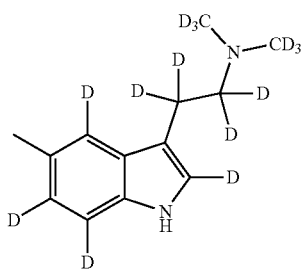 [SMILES: [2H]c1[nH]c2c([2H])c([2H])c(C)c([2H])c2c1C([2H])([2H])C([2H])([2H])N(C([2H])([2H])[2H])C([2H])([2H])[2H]]
In some embodiments, the deuterated 5-HT$_{2A}$ agonist is selected from TABLE 5 below.
TABLE 5
Exemplary deuterated 5-HT$_{2A}$ agonists.
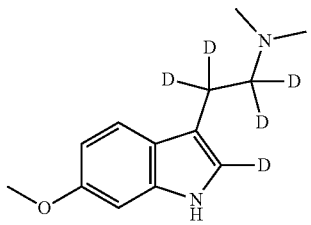
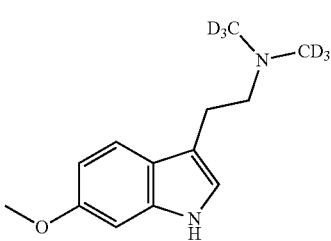 [SMILES: [2H]C([2H])([2H])N(CCc1c[nH]c2cc(OC)ccc12)C([2H])([2H])[2H]]
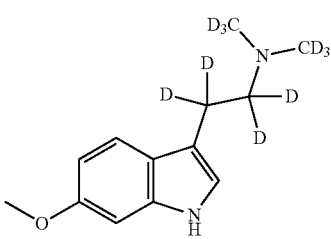 [SMILES: [2H]C([2H])([2H])N(C([2H])([2H])[2H])C([2H])([2H])C([2H])([2H])c1c[nH]c2cc(OC)ccc12]
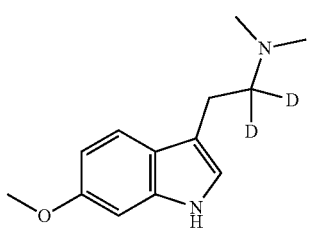

TABLE 5-continued
Exemplary deuterated 5-HT$_{2A}$ agonists.
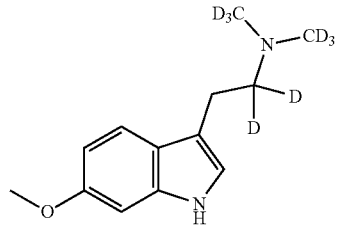 [SMILES: [2H]C([2H])([2H])N(C([2H])([2H])[2H])C([2H])([2H])Cc1c[nH]c2cc(OC)ccc12]
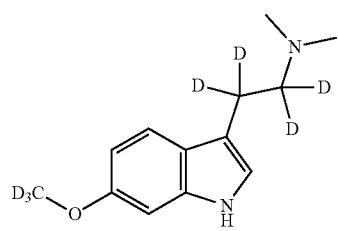 [SMILES: [2H]C([2H])([2H])Oc1ccc2c(C([2H])([2H])C([2H])([2H])N(C)C)c[nH]c2c1]
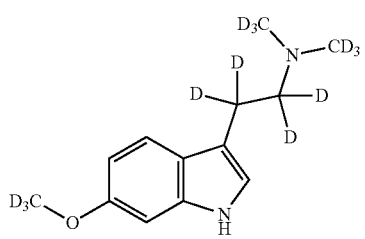 [SMILES: [2H]C([2H])([2H])Oc1ccc2c(C([2H])([2H])C([2H])([2H])N(C([2H])([2H])[2H])C([2H])([2H])[2H])c[nH]c2c1]
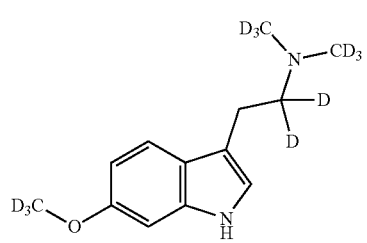 [SMILES: [2H]C([2H])([2H])Oc1ccc2c(CC([2H])([2H])N(C([2H])([2H])[2H])C([2H])([2H])[2H])c[nH]c2c1]
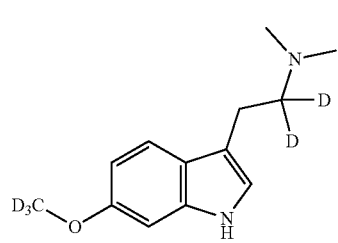 [SMILES: [2H]C([2H])([2H])Oc1ccc2c(CC([2H])([2H])N(C)C)c[nH]c2c1]
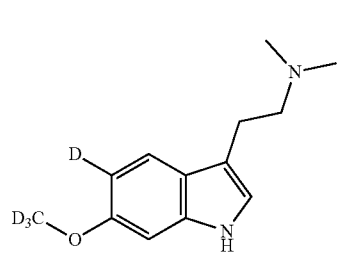 [SMILES: [2H]c1cc2c(CCN(C)C)c[nH]c2cc1OC([2H])([2H])[2H]]
TABLE 5-continued
Exemplary deuterated 5-HT$_{2A}$ agonists.
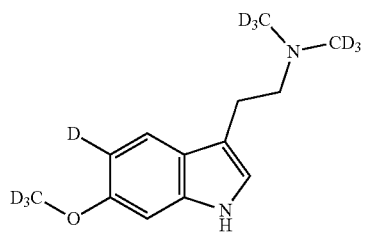 [SMILES: [2H]c1cc2c(CCN(C([2H])([2H])[2H])C([2H])([2H])[2H])c[nH]c2cc1OC([2H])([2H])[2H]]
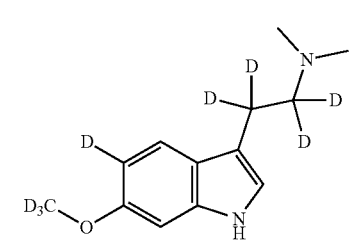 [SMILES: [2H]c1cc2c(C([2H])([2H])C([2H])([2H])N(C)C)c[nH]c2cc1OC([2H])([2H])[2H]]
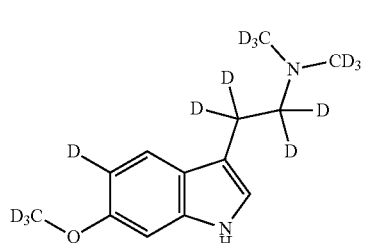
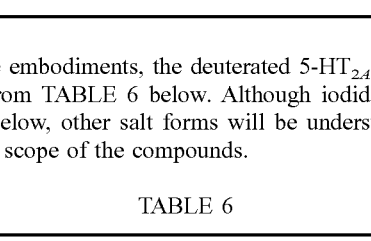
In some embodiments, the deuterated 5-HT$_{2A}$ agonist is selected from TABLE 6 below. Although iodide salts are depicted below, other salt forms will be understood to be within the scope of the compounds.
TABLE 6
Exemplary deuterated 5-HT$_{2A}$ agonists.
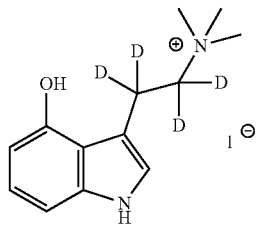 [SMILES: [2H]C([2H])(c1c[nH]c2cccc(O)c12)C([2H])([2H])[N+](C)(C)C]
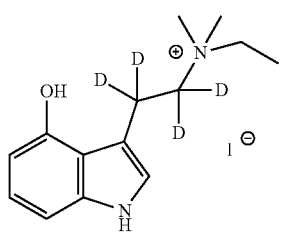 [SMILES: [2H]C([2H])(c1c[nH]c2cccc(O)c12)C([2H])([2H])[N+](C)(C)CC]

TABLE 6-continued
Exemplary deuterated 5-HT$_{2A}$ agonists.
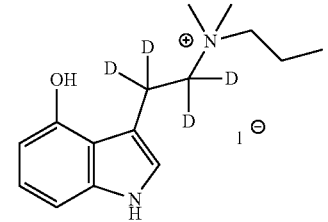 [SMILES: [2H]C([2H])(c1c[nH]c2cccc(O)c12)C([2H])([2H])[N+](C)(C)CCC]
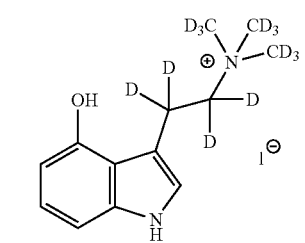 [SMILES: [2H]C([2H])(c1c[nH]c2cccc(O)c12)C([2H])([2H])[N+](C([2H])([2H])[2H])(C([2H])([2H])[2H])C([2H])([2H])[2H]]
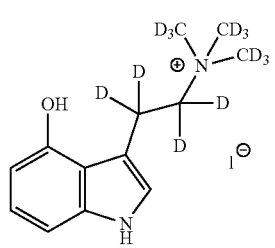 [SMILES: [2H]C([2H])(c1c[nH]c2cccc(O)c12)C([2H])([2H])[N+](C([2H])([2H])[2H])(C([2H])([2H])[2H])C([2H])([2H])[2H]]
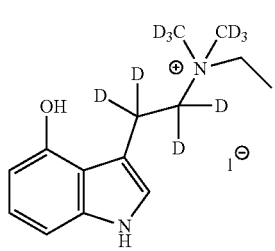 [SMILES: [2H]C([2H])(c1c[nH]c2cccc(O)c12)C([2H])([2H])[N+](CC)(C([2H])([2H])[2H])C([2H])([2H])[2H]]
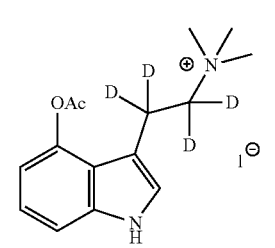 [SMILES: [2H]C([2H])(c1c[nH]c2cccc(OC(C)=O)c12)C([2H])([2H])[N+](C)(C)C]
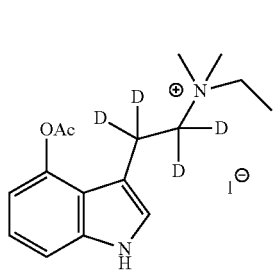 [SMILES: [2H]C([2H])(c1c[nH]c2cccc(OC(C)=O)c12)C([2H])([2H])[N+](C)(C)CC]
TABLE 6-continued
Exemplary deuterated 5-HT$_{2A}$ agonists.
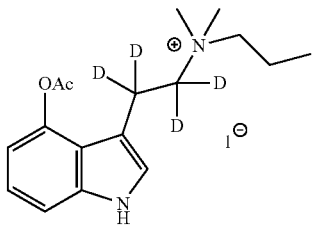 [SMILES: [2H]C([2H])(c1c[nH]c2cccc(OC(C)=O)c12)C([2H])([2H])[N+](C)(C)CCC]
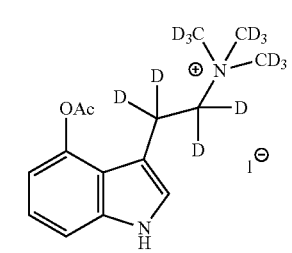 [SMILES: [2H]C([2H])(c1c[nH]c2cccc(OC(C)=O)c12)C([2H])([2H])[N+](C([2H])([2H])[2H])(C([2H])([2H])[2H])C([2H])([2H])[2H]]
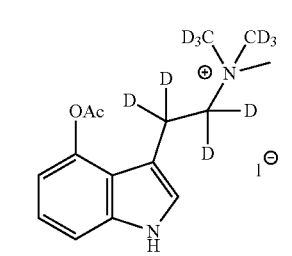 [SMILES: [2H]C([2H])(c1c[nH]c2cccc(OC(C)=O)c12)C([2H])([2H])[N+](C)(C([2H])([2H])[2H])C([2H])([2H])[2H]]
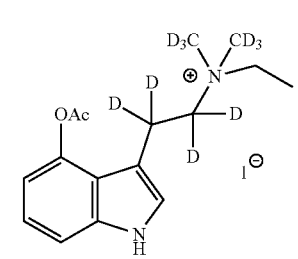 [SMILES: [2H]C([2H])(c1c[nH]c2cccc(OC(C)=O)c12)C([2H])([2H])[N+](CC)(C([2H])([2H])[2H])C([2H])([2H])[2H]]
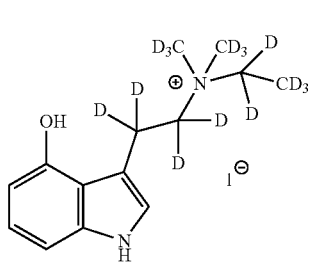 [SMILES: [2H]C([2H])([2H])C([2H])([2H])[N+](C([2H])([2H])[2H])(C([2H])([2H])[2H])C([2H])([2H])C([2H])([2H])c1c[nH]c2cccc(O)c12]
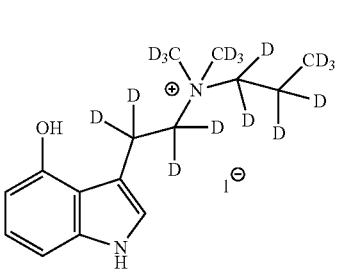 [SMILES: [2H]C([2H])([2H])C([2H])([2H])C([2H])([2H])[N+](C([2H])([2H])[2H])(C([2H])([2H])[2H])C([2H])([2H])C([2H])([2H])c1c[nH]c2cccc(O)c12]

TABLE 6-continued
Exemplary deuterated 5-HT$_{2A}$ agonists.
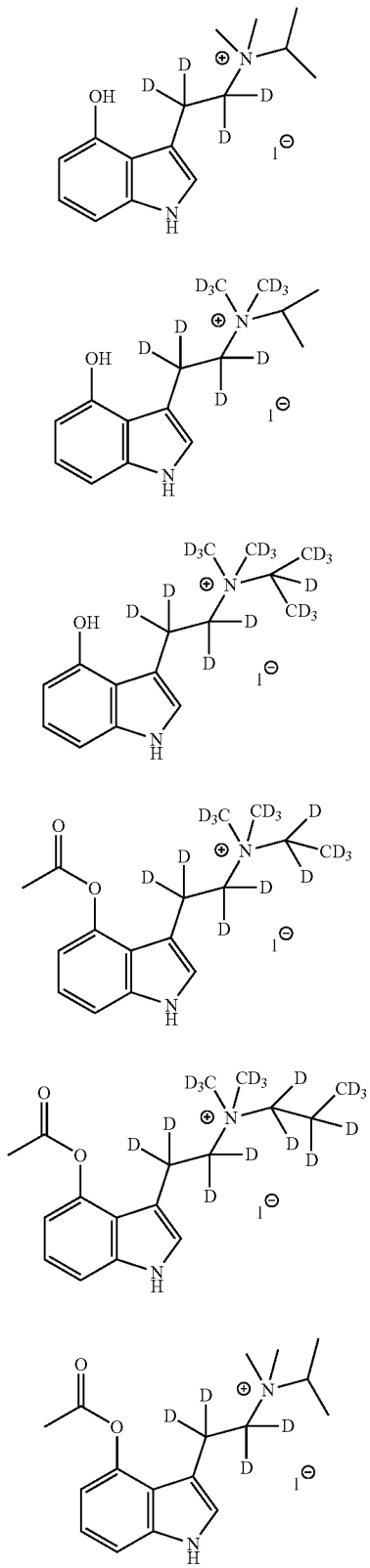
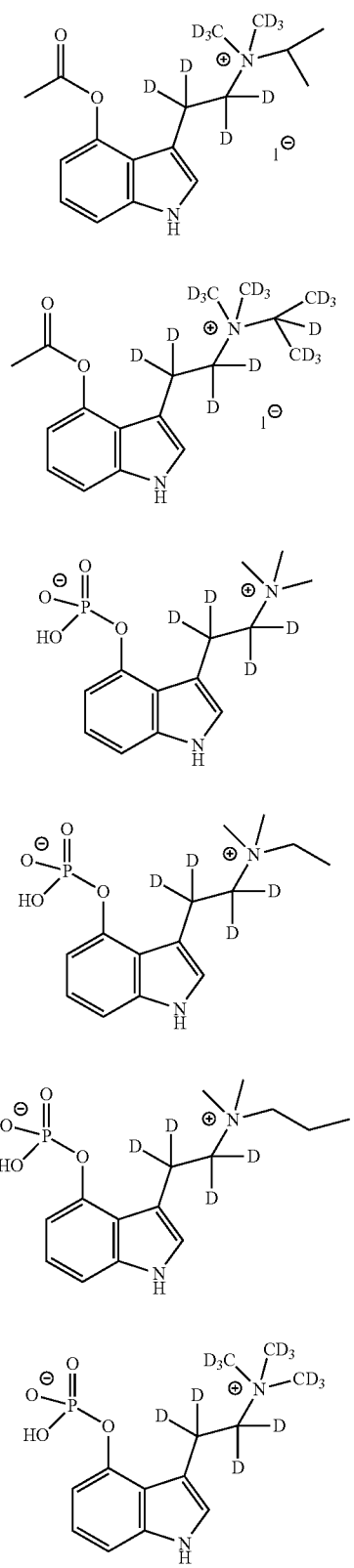

TABLE 6-continued
Exemplary deuterated 5-HT$_{2A}$ agonists.
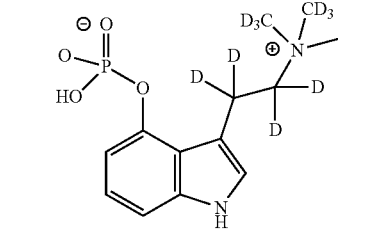
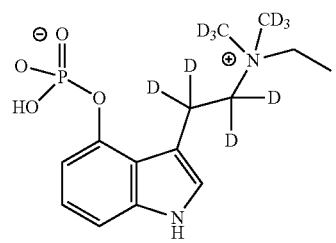
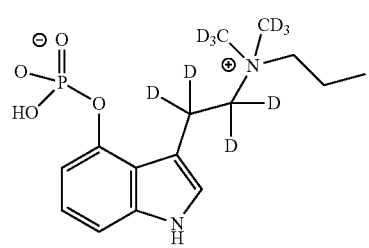
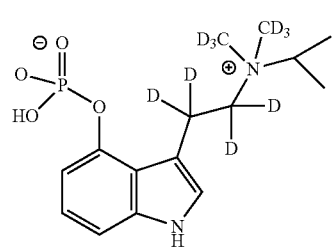
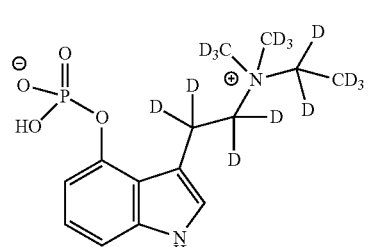
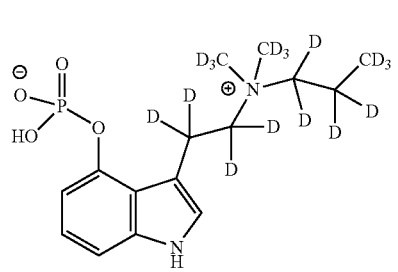 [SMILES: [2H]C([2H])([2H])C([2H])([2H])C([2H])([2H])[N+](C([2H])([2H])[2H])(C([2H])([2H])[2H])C([2H])([2H])C([2H])([2H])c1c[nH]c2cccc(OP(=O)([O-])O)c12]
TABLE 6-continued
Exemplary deuterated 5-HT$_{2A}$ agonists.
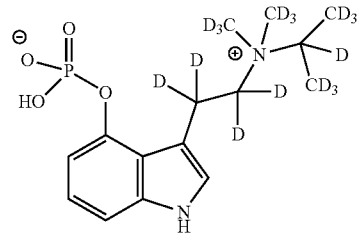 [SMILES: [2H]C([2H])([2H])C([2H])(C([2H])([2H])[2H])[N+](C([2H])([2H])[2H])(C([2H])([2H])[2H])C([2H])([2H])C([2H])([2H])c1c[nH]c2cccc(OP(=O)([O-])O)c12]
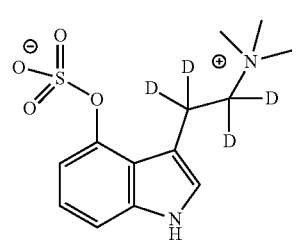
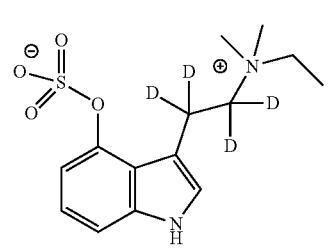
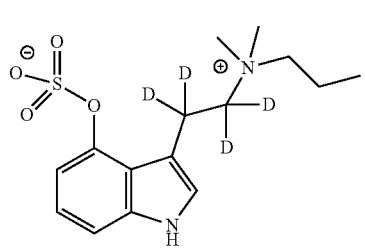 [SMILES: [2H]C([2H])(c1c[nH]c2cccc(OS(=O)(=O)[O-])c12)C([2H])([2H])[N+](C)(C)CCC]
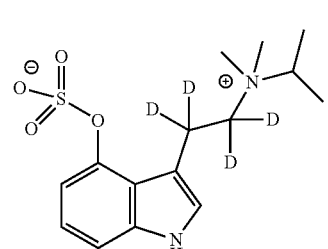
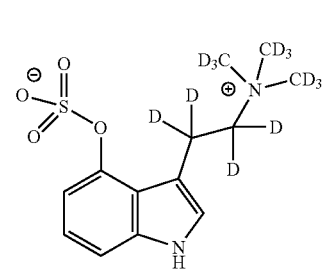

TABLE 6-continued

Exemplary deuterated 5-HT$_{2A}$ agonists.

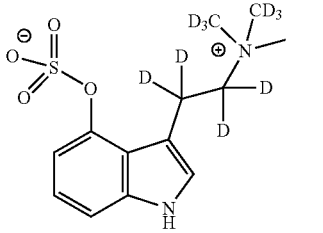

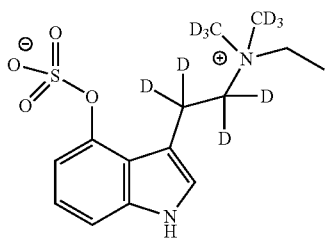

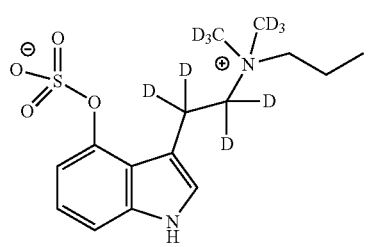

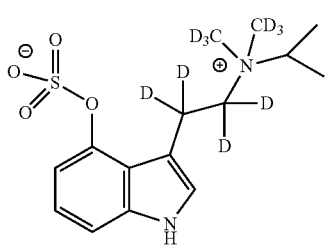

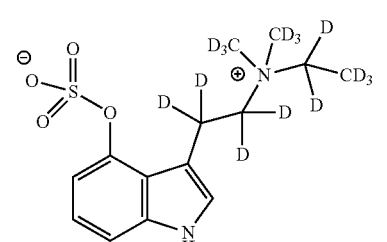

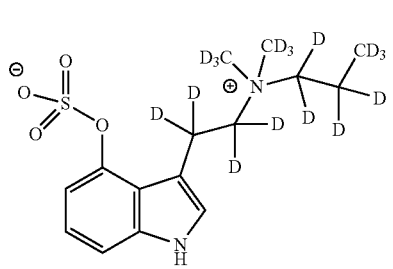

TABLE 6-continued

Exemplary deuterated 5-HT$_{2A}$ agonists.

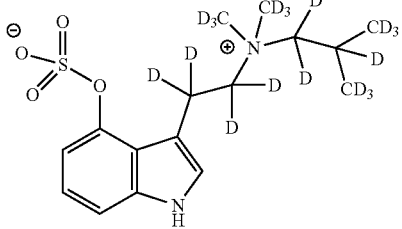

In some embodiments, the MAOI is CX157, or a salt thereof; and the deuterated 5-HT$_{2A}$ agonist is selected from TABLE 1, or a salt thereof.

In some embodiments, the MAOI is CX157, or a salt thereof; and the deuterated 5-HT$_{2A}$ agonist is selected from TABLE 2, or a salt thereof.

In some embodiments, the MAOI is CX157, or a salt thereof; and the deuterated 5-HT$_{2A}$ agonist is selected from TABLE 3, or a salt thereof.

In some embodiments, the MAOI is CX157, or a salt thereof; and the deuterated 5-HT$_{2A}$ agonist is selected from TABLE 4, or a salt thereof.

In some embodiments, the MAOI is CX157, or a salt thereof; and the deuterated 5-HT$_{2A}$ agonist is selected from TABLE 5, or a salt thereof.

In some embodiments, the MAOI is CX157, or a salt thereof; and the deuterated 5-HT$_{2A}$ agonist is selected from TABLE 6, or a salt thereof.

In some embodiments, the MAOI is CX157, or a salt thereof; and the 5-HT$_{2A}$ agonist is deuterated DMT, or a salt thereof. In some embodiments, the MAOI is CX157, or a salt thereof; and the 5-HT$_{2A}$ agonist is deuterated 5-MeO-DMT, or a salt thereof. In some embodiments, the MAOI is CX157, or a salt thereof; and the 5-HT$_{2A}$ agonist is deuterated DPT, or a salt thereof.

In embodiments, the 5-HT$_{2A}$ receptor agonist is a deuterated 5-HT$_{2A}$ agonist selected from the group consisting of:

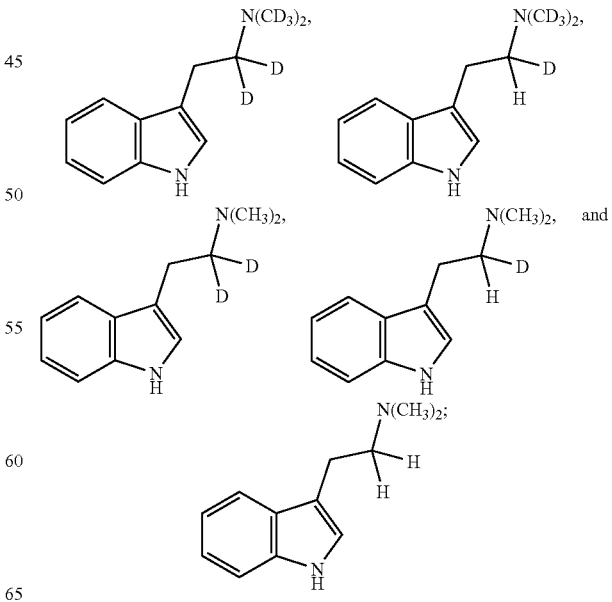

or a salt thereof.

In some embodiments, the 5-HT$_{2A}$ agonist is

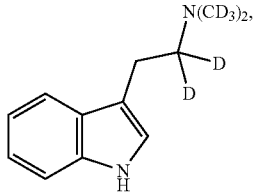

or a salt thereof.

In some embodiments, the 5-HT$_{2A}$ agonist is

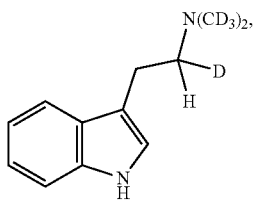

or a salt thereof.

In some embodiments, the 5-HT$_{2A}$ agonist is

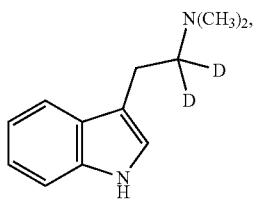 [SMILES: [2H]C([2H])(Cc1c[nH]c2ccccc12)N(C)C]

or a salt thereof.

In some embodiments, the 5-HT$_{2A}$ agonist is

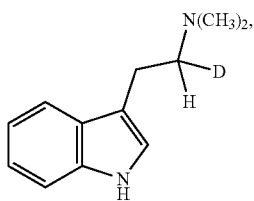 [SMILES: [2H]C(Cc1c[nH]c2ccccc12)N(C)C]

or a salt thereof.

In some embodiments, the 5-HT$_{2A}$ agonist is

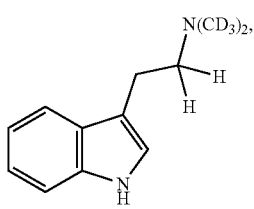

or a salt thereof.

In embodiments, the MAOI is CX157 or CX009; or a salt thereof; and the 5-HT$_{2A}$ agonist is a deuterated 5-HT$_{2A}$ agonist selected from the group consisting of:

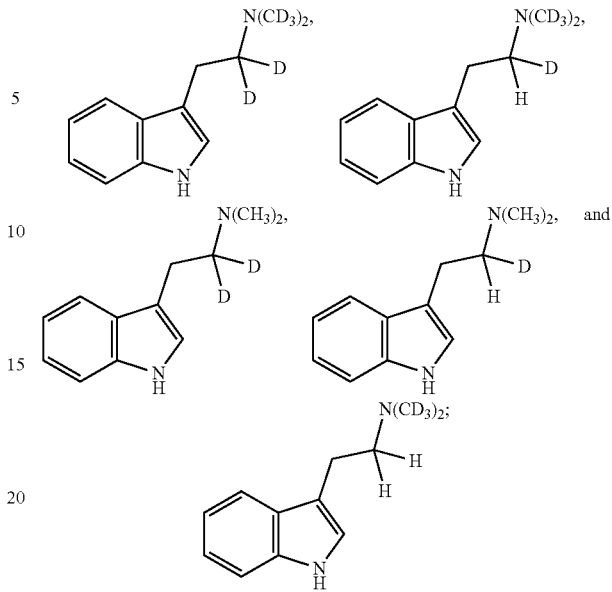

or a salt thereof.

In some embodiments, the MAOI is CX157, or a salt thereof; and the 5-HT$_{2A}$ agonist is

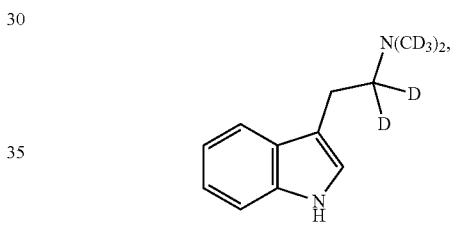

or a salt thereof. In some embodiments, the MAOI is CX157, or a salt thereof; and the 5-HT$_{2A}$ agonist is

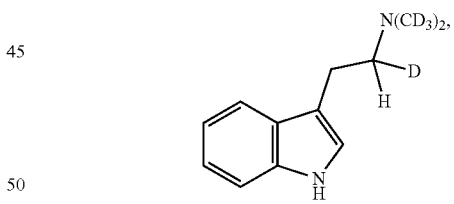

or a salt thereof. In some embodiments, the MAOI is CX157, or a salt thereof; and the 5-HT$_{2A}$ agonist is

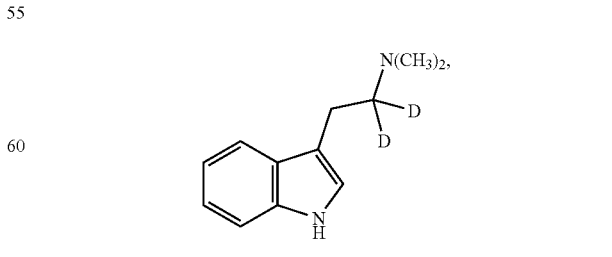

or a salt thereof. In some embodiments, the MAOI is CX157, or a salt thereof; and the 5-HT$_{2A}$ agonist is

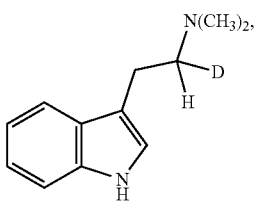 [SMILES: [2H]C([2H])(Cc1c[nH]c2ccccc12)N(C)C]

or a salt thereof. In some embodiments, the MAOI is CX157, or a salt thereof; and the 5-HT$_{2A}$ agonist is

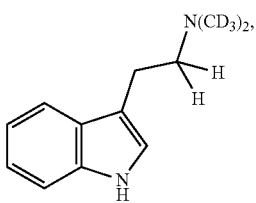

or a salt thereof.

In some embodiments, including where the MAO inhibitor is as disclosed herein, such as CX157 or CXOO9, or CX157 specifically, the 5-HT$_{2A}$ agonist is not a deuterated 5-HT$_{2A}$ agonist selected from the group consisting of:

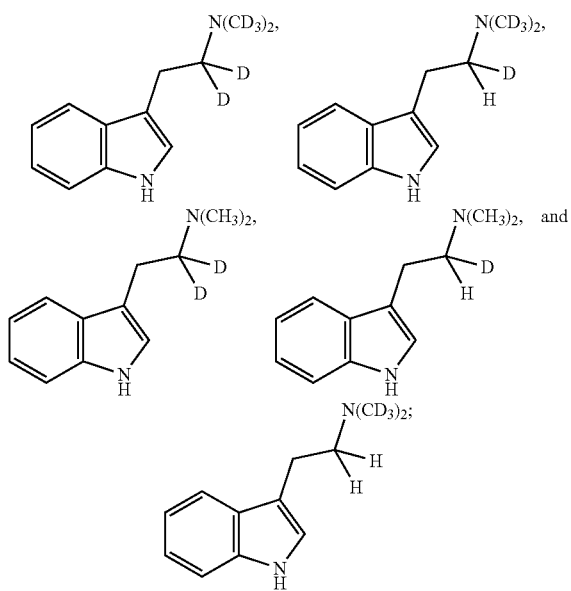

or a salt thereof.

III. EXEMPLARY FEATURES OF DISCLOSED METHODS

In some embodiments, administering to the subject a therapeutically effective amount of a MAOI, or a salt thereof, results in an increase of the oral bioavailability, a decrease of the (in vitro or in vivo) rate of degradation, or an increase of the (in vitro or in vivo) half-life of the 5-HT$_{2A}$ agonist, or a salt thereof.

Without being bound by theory, it is proposed that administering to the subject a therapeutically effective amount of a MAOI, or a salt thereof, results in inhibiting MAO (e.g., MAO-A) to an extent sufficient to allow the 5-HT$_{2A}$ agonist, or a salt thereof, to enter the systemic circulation without being rapidly metabolized by MAO to a therapeutically ineffective concentration. After entering systemic circulation, the 5-HT$_{2A}$ agonist can distribute to tissues in which a target therapeutic effect is desired; for example, crossing the blood-brain barrier and thereafter producing a psychedelic effect. The rate of degradation of 5-HT$_{2A}$ agonist, or a salt thereof, is also proposed to decrease as metabolism by MAO is inhibited, resulting in an increase in the half-life of the 5-HT$_{2A}$ agonist.

In some embodiments, the oral bioavailability of the 5-HT$_{2A}$ agonist, or a salt thereof, is increased by at least 1.2-fold, 1.5-fold, 1.7-fold, 2-fold, 5-fold, 10-fold, 20-fold, 50-fold, or 100-fold. In embodiments, the oral bioavailability of the 5-HT$_{2A}$ agonist, or a salt thereof, is increased by at least 1.2-fold. In embodiments, the oral bioavailability of the 5-HT$_{2A}$ agonist, or a salt thereof, is increased by at least 1.5-fold. In embodiments, the oral bioavailability of the 5-HT$_{2A}$ agonist, or a salt thereof, is increased by at least 2-fold. In embodiments, the oral bioavailability of the 5-HT$_{2A}$ agonist, or a salt thereof, is increased by at least 5-fold. In embodiments, the oral bioavailability of the 5-HT$_{2A}$ agonist, or a salt thereof, is increased by at least 10-fold. In embodiments, the oral bioavailability of the 5-HT$_{2A}$ agonist, or a salt thereof, is increased by at least 20-fold. In embodiments, the oral bioavailability of the 5-HT$_{2A}$ agonist, or a salt thereof, is increased by at least 50-fold. In embodiments, the oral bioavailability of the 5-HT$_{2A}$ agonist, or a salt thereof, is increased by at least 100-fold.

In some embodiments, the in vivo rate of degradation of the 5-HT$_{2A}$ agonist, or a salt thereof, is decreased by at least 20%, 50%, 75%, 90%, 95%, or 99%. In embodiments, the in vivo rate of degradation of the 5-HT$_{2A}$ agonist, or a salt thereof, is decreased by at least 20%. In embodiments, the in vivo rate of degradation of the 5-HT$_{2A}$ agonist, or a salt thereof, is decreased by at least 50%. In embodiments, the in vivo rate of degradation of the 5-HT$_{2A}$ agonist, or a salt thereof, is decreased by at least 75%. In embodiments, the in vivo rate of degradation of the 5-HT$_{2A}$ agonist, or a salt thereof, is decreased by at least 90%. In embodiments, the in vivo rate of degradation of the 5-HT$_{2A}$ agonist, or a salt thereof, is decreased by at least 95%. In embodiments, the in vivo rate of degradation of the 5-HT$_{2A}$ agonist, or a salt thereof, is decreased by at least 99%.

In some embodiments, the in vivo half-life of the 5-HT$_{2A}$ agonist, or a salt thereof, is increased by at least 1.2-fold, 1.5-fold, 1.7-fold, 2-fold, 5-fold, 10-fold, 20-fold, 50-fold, or 100-fold. In embodiments, the in vivo half-life of the 5-HT$_{2A}$ agonist, or a salt thereof, is increased by at least 1.2-fold. In embodiments, the in vivo half-life of the 5-HT$_{2A}$ agonist, or a salt thereof, is increased by at least 1.5-fold. In embodiments, the in vivo half-life of the 5-HT$_{2A}$ agonist, or a salt thereof, is increased by at least 2-fold. In embodiments, the in vivo half-life of the 5-HT$_{2A}$ agonist, or a salt thereof, is increased by at least 5-fold. In embodiments, the in vivo half-life of the 5-HT$_{2A}$ agonist, or a salt thereof, is increased by at least 10-fold. In embodiments, the in vivo half-life of the 5-HT$_{2A}$ agonist, or a salt thereof, is increased by at least 20-fold. In embodiments, the in vivo half-life of the 5-HT$_{2A}$ agonist, or a salt thereof, is increased by at least 50-fold. In embodiments, the in vivo half-life of the 5-HT$_{2A}$ agonist, or a salt thereof, is increased by at least 100-fold.

In some embodiments, disclosed methods and compositions induce a psychedelic experience or psychedelic effects (e.g., in a human). "Psychedelic effects" refer to certain cognitive, emotional, perceptual, physiological, psychological, and other effects induced by a psychedelic substance, such as comprise an altered state of consciousness, and which include vivid visual and auditory perceptual changes, often accompanied by intense emotional, mystical, or "spiritual" experiences. Some subcomponents of psychedelic effects include effects on the mind, effects on mood, and visual effects. Herein, "psychedelic" effects may be used interchangeably with "hallucinogenic" effects. "Psychedelic experience" refers to the overall state of an individual induced by a psychedelic substance, including the individual's emotional, psychological, and physiological state. The psychedelic experience constitutes the aggregate of all individual psychedelic effects an individual may encounter or experience after consuming a psychedelic substance, such as DMT.

In embodiments, the subject administered a disclosed compound has psychedelic effects that last at least 1 hour, at least 2 hours, at least 3 hours, at least 4 hours, at least 5 hours, at least 6 hours, at least 7 hours, at least 8 hours, at least 9 hours, at least 10 hours, at least 11 hours, or at least 12 hours post-administration of a disclosed method or composition.

In some embodiments, disclosed methods and compositions do not induce a psychedelic experience or psychedelic effects (e.g., in a human).

In some embodiments, psychedelic effects are assessed using one or more of a Peak Experience Scale (PES), e.g., as described in Reckweg et al., *Front Pharmacol.* 2021; 12:760671, the Mystical Experience Questionnaire (MEQ), the Ego Dissolution Inventory (EDI), the Challenging Experience Questionnaire (CEQ), and the 5-Dimensional Altered States of Consciousness Questionnaire (5D-ASC). In some embodiments, psychedelic effects are assessed using the Hallucinogen Rating Scale (HRS). In some embodiments, onset and duration of psychedelic effects may be determined by observing and/or interviewing the subject, such as by using a self-report symptom questionnaire, or by asking the subject to document subjective psychedelic effects, i.e., the subject's experience. In some embodiments, the self-report symptom questionnaire is the Subjective Drug Effects Questionnaire (SDEQ), a 272-item questionnaire measuring perceptual, mood, and somatic changes caused by psychedelics (Katz et al., *J Abnorm Psych,* 1968; 73:1-14). In some embodiments, the self-report symptom questionnaire is the List of Complaints (LC), a 66-item questionnaire that reliably measures physical and general discomfort (see, e.g., Holze et al., *Psychopharmacol,* 2022; 239:1893-1905). Psychedelic effects and the onset and duration of such effects may additionally be determined according to methods known to one of skill in the art.

IV. MANNER OF ADMINISTRATION

In some embodiments, including some preferred embodiments, the MAOI, or a salt thereof, is administered prior to administration of the 5-HT$_{2A}$ agonist, or a salt thereof; or the MAOI, or a salt thereof, is administered simultaneously with administration of the 5-HT$_{2A}$ agonist, or a salt thereof.

In embodiments, the MAOI, or a salt thereof, is administered prior to administration of the 5-HT$_{2A}$ agonist, or a salt thereof. In embodiments, the MAOI, or a salt thereof, is administered simultaneously with administration of the 5-HT$_{2A}$ agonist, or a salt thereof. While one of skill will appreciate that the MAOI, or a salt thereof, is preferably administered prior to or simultaneously with administration of the 5-HT$_{2A}$ agonist, or a salt thereof, in some embodiments, the MAOI, or a salt thereof, is administered after administration of the 5-HT$_{2A}$ agonist, or a salt thereof.

In some embodiments, the MAOI, or a salt thereof, is administered to the subject while the subject is in a fasted state (i.e., the subject has not eaten a meal or substantial amount of food during a time window of e.g. at least 2 hours, at least 4 hours, at least 6 hours, or at least 8 hours preceding administration). In other embodiments, the MAOI, or a salt thereof, is administered to the subject while the subject is in a fed state (i.e., the subject has eaten a meal or substantial amount of food within e.g. 1 hour, 2 hours, or 3 hours of administration).

In some embodiments, the MAOI, or a salt thereof, is administered to the subject prior to administration of the 5-HT$_{2A}$ agonist, or a salt thereof. In some embodiments, the MAOI is administered at least 1 hour, 2 hours, 4 hours, 6 hours, 8 hours, 12 hours, or 24 hours before administration of the 5-HT$_{2A}$ agonist. In some embodiments, the MAOI is administered between about 1 hour and 12 hours before administration of the 5-HT$_{2A}$ agonist. In some embodiments, the MAOI is administered between about 2 hours and 8 hours before administration of the 5-HT$_{2A}$ agonist. In some embodiments, the MAOI is administered between about 3 hours and 6 hours before administration of the 5-HT$_{2A}$ agonist. In some embodiments, the MAOI is administered about 2 hours before administration of the 5-HT$_{2A}$ agonist. In some embodiments, the MAOI is administered about 4 hours before administration of the 5-HT$_{2A}$ agonist. As will be appreciated by one of skill, the timing of administration of the MAOI may be selected based on the properties and release profile of the pharmaceutical composition comprising MAOI. For example, in embodiments wherein the MAOI is formulated as an extended-release composition, the MAOI may be administered earlier (e.g., at least 8 hours, 12 hours, or 24 hours prior to administration of the 5-HT$_{2A}$ agonist). As another example, in embodiments wherein the MAOI is formulated as a rapid-release composition, the MAOI may be administered within about 8 hours, 4 hours, 3 hours, 2 hours, 1 hour, or less than 1 hour prior to administration of the 5-HT$_{2A}$ agonist; or simultaneously with the 5-HT$_{2A}$ agonist.

In embodiments, administration to a subject of an effective amount of a MAOI, or a salt thereof, "simultaneously" with treatment with a 5-HT$_{2A}$ agonist refers to administration to a subject of an effective amount of a first MAOI, or a salt thereof, at substantially the same time as administration to the subject of treatment with a 5-HT$_{2A}$ agonist. In some embodiments, "simultaneously" refers to administration of the MAOI, or a salt thereof, within not more than 15 minutes, 10 minutes, preferably 5 minutes, or more preferably 1 minute of administration of the 5-HT$_{2A}$ agonist. In embodiments, the MAOI is administered less than 15 minutes before administration of the 5-HT$_{2A}$ agonist. In some embodiments, the MAOI is administered less than 10 minutes before administration of the 5-HT$_{2A}$ agonist. In some embodiments, the MAOI is administered less than 5 minutes before administration of the 5-HT$_{2A}$ agonist. In some embodiments, the MAOI is administered less than 1 minute before administration of the 5-HT$_{2A}$ agonist.

In embodiments an effective amount of a 5-HT$_{2A}$ agonist, or salt thereof, is administered to a subject every third day, and an effective amount of a MAOI, or salt thereof, is administered simultaneously therewith. In some embodiments, an effective amount of a 5-HT$_{2A}$ agonist, or salt thereof, is administered to a subject weekly, and an effective amount of a MAOI, or salt thereof, is administered simultaneously therewith.

In some embodiments, the MAOI, or a salt thereof, and the 5-$HT_{2A}$ agonist, or a salt thereof, are administered with a delaying buffer or delaying layer. In embodiments, the MAOI, or a salt thereof, and the 5-$HT_{2A}$ agonist, or a salt thereof, are administered as an extended-release product, a delayed-release product, or a targeted-release product.

The MAOI, or a salt thereof, and the 5-$HT_{2A}$ agonist, or a salt thereof, can be administered in the same composition or in different compositions. In some embodiments, the MAOI, or a salt thereof, and the 5-$HT_{2A}$ agonist, or a salt thereof, are administered in the same composition. MAOI, or a salt thereof, and the 5-$HT_{2A}$ agonist, or a salt thereof, are administered in different compositions.

In some embodiments, the MAOI, or a salt thereof, and the 5-$HT_{2A}$ agonist, or a salt thereof, are administered with a delaying buffer or delaying layer. In some embodiments, the MAOI, or a salt thereof, and the 5-$HT_{2A}$ agonist, or a salt thereof, are administered as an extended-release product, a delayed-release product, or a targeted-release product. In another embodiment, the administered modified release product may additionally comprise a combination of copovidone, microcrystalline cellulose, hypromellose, colloidal silicon dioxide, and magnesium stearate. Exemplary such formulations include those described elsewhere herein and in WO2010/080977, WO2010/080970, and U.S. Pat. No. 8,313,766.

In a preferred embodiment, the MAOI is CX157, or a salt thereof; and the 5-$HT_{2A}$ agonist is DMT, or a salt thereof, and the administered modified release product comprises a combination of copovidone, microcrystalline cellulose, hypromellose, colloidal silicon dioxide, and magnesium stearate. In some embodiments, the MAOI is CX157, or a salt thereof; and the 5-$HT_{2A}$ agonist is DMT, or a salt thereof, and the administered modified release product comprises a combination of copovidone, microcrystalline cellulose, hypromellose, colloidal silicon dioxide, and magnesium stearate.

In embodiments, administering to the subject a therapeutically effective amount of a MAOI, such as CX157, or a salt thereof, comprises administering the MAOI in a dose of between about 0.8 mg/kg and 5.0 mg/kg, 1.0 mg/kg and 3.5 mg/kg, 1.3 mg/kg and 3.3 mg/kg, 1.4 mg/kg and 3.5 mg/kg, or 1.7 mg/kg and 2.5 mg/kg. In embodiments, the dose of the MAOI is between about 0.8 mg/kg and 5.0 mg/kg. In embodiments, the dose of the MAOI is between about 1.0 mg/kg and 3.5 mg/kg. In embodiments, the dose of the MAOI is between about 1.3 mg/kg and 3.3 mg/kg. In embodiments, the dose of the MAOI is between about 1.4 mg/kg and 3.5 mg/kg. In embodiments, the dose of the MAOI is between about 1.7 mg/kg and 2.5 mg/kg. In embodiments, the dose of the MAOI is about 2.1 mg/kg. In embodiments, the dose of the MAOI is about 1.4 mg/kg. In embodiments, the dose of the MAOI is about 3.5 mg/kg.

In embodiments, administering to the subject a therapeutically effective amount of a MAOI, such as CX157, or a salt thereof, comprises administering the MAOI in a dose of between about 50 mg and 300 mg, 75 mg and 200 mg, or 100 and 150 mg. In embodiments, the dose of the MAOI is between about 50 mg and 300 mg. In embodiments, the dose of the MAOI is between about 75 mg and 200 mg. In embodiments, the dose of the MAOI is between about 100 mg and 150 mg. In embodiments, the dose of the MAOI is about 125 mg. In embodiments, the dose of MAOI is about 175 mg.

FIGS. 1-4 show exemplary embodiments which demonstrate potential dosing regimens for administration to a subject of a 5-$HT_{2A}$ agonist, or a salt thereof, and a MAOI, or a salt thereof, wherein the 5-$HT_{2A}$ agonist is DMT, and the MAOI is CX157.

As shown in FIGS. 1-4, in some embodiments, administration to a subject of about 0.1 mg/kg of DMT may induce pre-hallucinogenic effects. "Pre-hallucinogenic effects" refer to somaesthetic and emotional responses a subject may experience after administration of a dose of DMT that provides certain threshold psychedelic effects, and which can be described as a feeling as if one is on the verge of a psychedelic experience, but without the aggregate subjective effects described as "hallucinogenic" or as a "full" psychedelic experience; as discussed, e.g., in Strassman, R. J., Archives Gen'l Psychiatry, 1994; 51(2):98.

Examples of pre-hallucinogenic effects include feelings of stress, dysphoria, tensity, and uncomfortability, and may be distinguished from subjective effects at doses below "pre-hallucinogenic" that are phenomenologically distinct, and generally positive (e.g., calming, mood uplifting). A subject may have pre-hallucinogenic effects leading up to a psychedelic experience, or may have pre-hallucinogenic effects and not achieve a full psychedelic experience. In some embodiments, and for some subjects, administration of about 0.2 mg/kg of DMT and greater may induce hallucinogenic effects. Pre-hallucinogenic effects may be experienced by certain such subjects at a range of, for example, between 0.1 mg/kg and 0.2 mg/kg of DMT.

In some embodiments, the 5-$HT_{2A}$ agonist, or a salt thereof, is administered to a subject in the amount of a microdose. Herein, a "microdose" refers to the use of a low dose of a psychedelic compound or composition, which causes no to negligible psychedelic effects in a subject. (See, e.g., id. and Barker, 2022).

In embodiments, administering to a subject a therapeutically effective amount of a 5-$HT_{2A}$ agonist, such as DMT, or a salt thereof, comprises administering the 5-$HT_{2A}$ agonist in a dose of between about 0.02 mg/kg and 0.20 mg/kg, 0.03 mg/kg and 0.13 mg/kg, 0.03 mg/kg and 0.07 mg/kg, 0.05 mg/kg and 0.10 mg/kg, or about 0.08 mg/kg. In embodiments, the dose of the 5-$HT_{2A}$ agonist is between about 0.02 mg/kg and 0.20 mg/kg. In embodiments, the dose of the 5-$HT_{2A}$ agonist is between about 0.03 mg/kg and 0.13 mg/kg. In embodiments, the dose of the 5-$HT_{2A}$ agonist is between about 0.03 mg/kg and 0.07 mg/kg. In embodiments, the dose of the 5-$HT_{2A}$ agonist is between about 0.05 mg/kg and 0.10 mg/kg.

In embodiments, the dose of the 5-$HT_{2A}$ agonist is about 0.08 mg/kg. In embodiments, the dose of the 5-$HT_{2A}$ agonist is about 0.05 mg/kg. In some embodiments, a "microdose" of the 5-$HT_{2A}$ agonist is between about 0.05 rg/kg and 0.10 mg/kg.

Figure 2:
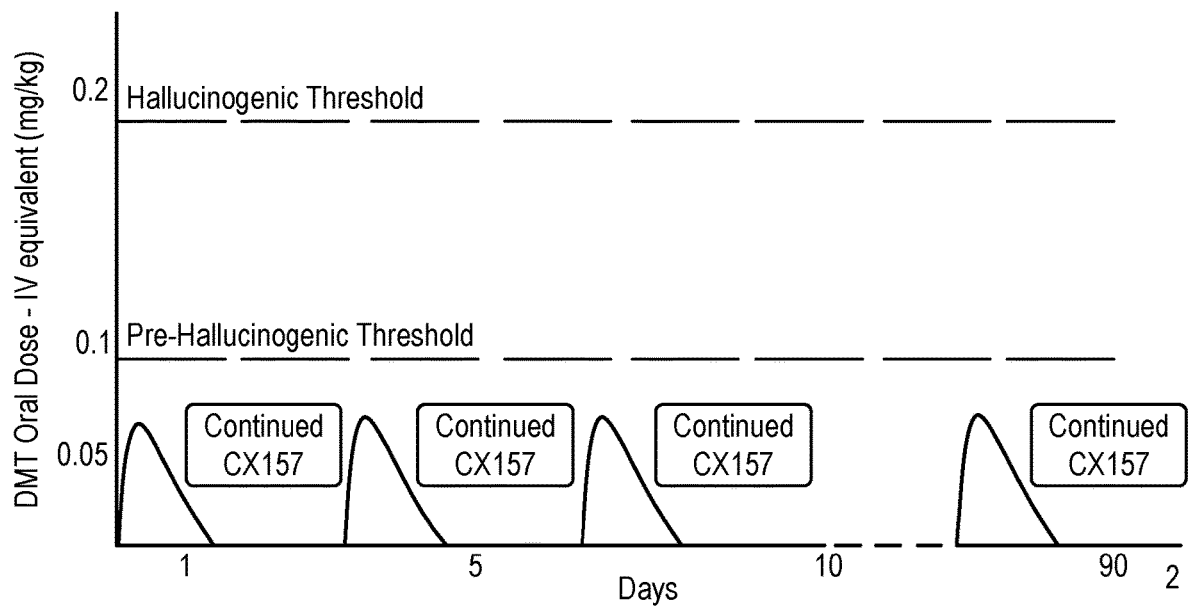
FIG. 2 illustrates an exemplary dosing regimen, wherein a subject takes a given microdose of DMT intermittently and an effective amount of CX157 daily.

FIG. 1 and FIG. 2 illustrate exemplary dosing regimens wherein a subject takes a single microdose of DMT in an amount between about 0.05 mg/kg and 0.10 mg/kg, and an effective amount of CX157, which in exemplary embodiments is 175 mg.

In some embodiments, administering to the subject a therapeutically effective amount of a 5-$HT_{2A}$ agonist, such as DMT, or a salt thereof, comprises administering the 5-$HT_{2A}$ agonist in a dose of between about 0.20 mg/kg and 1.0 mg/kg, 0.20 mg/kg and 0.80 mg/kg, 0.20 mg/kg and 0.60 mg/kg, 0.30 mg/kg and 0.80 mg/kg, or 0.30 mg/kg and 0.60 mg/kg. In embodiments, the dose of the 5-$HT_{2A}$ agonist is between about 0.20 mg/kg and 1.0 mg/kg. In embodiments, the dose of the 5-$HT_{2A}$ agonist is between about 0.20 mg/kg and 0.80 mg/kg. In embodiments, the dose of the 5-$HT_{2A}$ agonist is between about 0.20 mg/kg and 0.60 mg/kg. In embodiments, the dose of the 5-HT$_{2A}$ agonist is between about 0.30 mg/kg and 0.80 mg/kg. In embodiments, the dose of the 5-HT$_{2A}$ agonist is between about 0.30 mg/kg and 0.60 mg/kg.

In some embodiments, administering to the subject a therapeutically effective amount of a 5-HT$_{2A}$ agonist, such as DMT, or a salt thereof, comprises administering the 5-HT$_{2A}$ agonist in a dose of between about 1 mg and 10 mg, 2 mg and 8 mg, 3 mg and 6 mg, or about 5 mg. In embodiments, the dose of the 5-HT$_{2A}$ agonist is between about 1 mg and 10 mg. In embodiments, the dose of the 5-HT$_{2A}$ agonist is between about 2 mg and 8 mg. In embodiments, the dose of the 5-HT$_{2A}$ agonist is between about 3 mg and 6 mg. In embodiments, the dose of the 5-HT$_{2A}$ agonist is about 3 mg. In embodiments, the dose of the 5-HT$_{2A}$ agonist is about 5 mg. In embodiments, the dose of the 5-HT$_{2A}$ agonist is about 10 mg.

In some embodiments, administering to the subject a therapeutically effective amount of a 5-HT$_{2A}$ agonist, such as DMT, or a salt thereof, comprises administering the 5-HT$_{2A}$ agonist in a dose of between about 15 mg and 300 mg, 25 mg and 200 mg, 20 mg and 50 mg, or 50 mg and 100 mg. In embodiments, the dose of the 5-HT$_{2A}$ agonist is between about 15 mg and 300 mg. In embodiments, the dose of the 5-HT$_{2A}$ agonist is between about 25 mg and 200 mg. In embodiments, the dose of the 5-HT$_{2A}$ agonist is between about 20 mg and 50 mg. In embodiments, the dose of the 5-HT$_{2A}$ agonist is between about 50 mg and 100 mg. In embodiments, the dose of the 5-HT$_{2A}$ agonist is about 50 mg. In embodiments, the dose of the 5-HT$_{2A}$ agonist is about 75 mg. In embodiments, the dose of the 5-HT$_{2A}$ agonist is about 100 mg.

In some embodiments, the 5-HT$_{2A}$ agonist, or a salt thereof, is administered to a subject in the amount of a psychedelic dose. Herein, a "psychedelic dose" refers to a dose of a psychedelic compound or composition which is capable of inducing a full psychedelic experience or "trip" in a subject. In embodiments, such as exemplary embodiments of DMT administered with an MAOI, such as CX157, a "psychedelic" dose is between about 0.6 mg/kg and 3 mg/kg, such as between about 60 mg and about 250 mg.

In embodiments, the 5-HT$_{2A}$ agonist, or a salt thereof, is administered to a subject in the amount of a psycholytic dose. Herein, a "psycholytic dose" refers to a dose of a psychedelic compound or composition, which is sufficiently lower than that of a psychedelic dose such that it does not induce a full psychedelic experience or "trip" in a subject, although it may still cause some psychedelic effects. In embodiments, such as exemplary embodiments of DMT administered with an MAOI, such as CX157, a "psycholytic" dose is between about 0.10 mg/kg and 0.6 mg/kg, such as between about 10 mg and about 60 mg.

Figure 3:
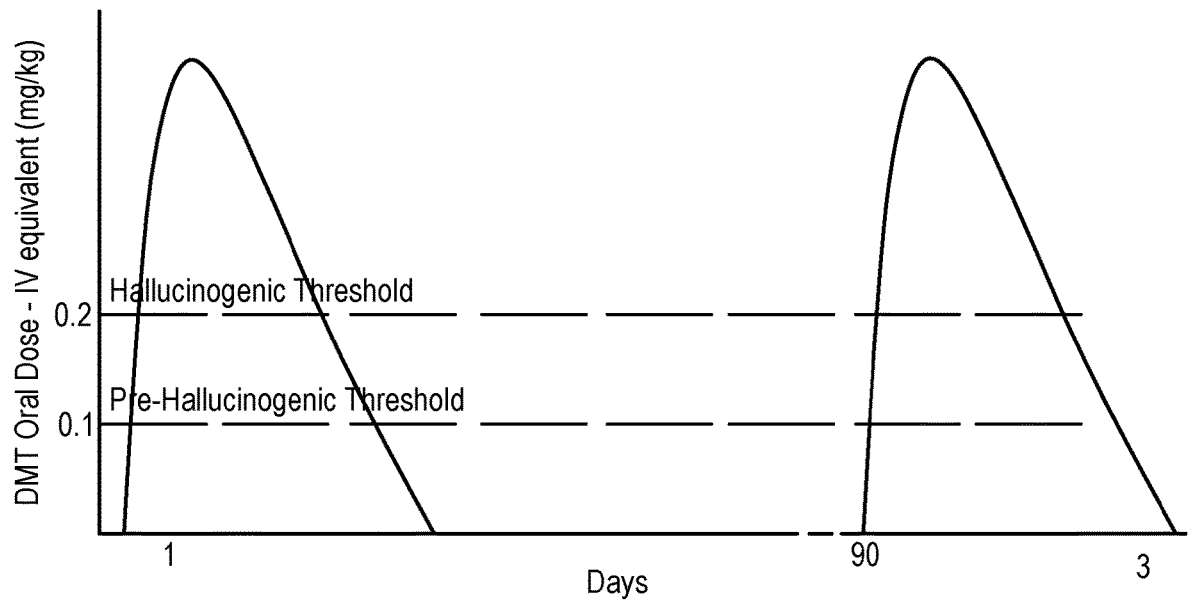
FIG. 3 illustrates an exemplary dosing regimen, wherein a subject takes a given psychedelic dose of DMT intermittently according to need, and an effective amount of CX157.
Figure 4:
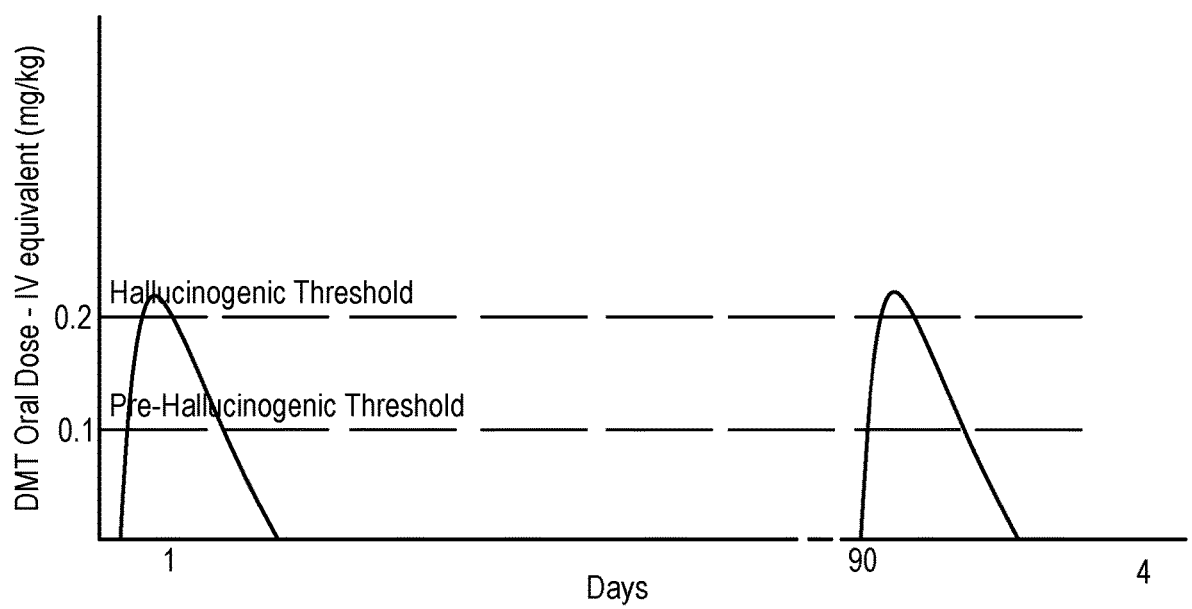
FIG. 4 illustrates an exemplary dosing regimen, wherein a subject takes a given psycholytic dose of DMT intermittently according to need, and an effective amount of CX157.

FIG. 3 illustrates an exemplary dosing regimen wherein a subject takes a single psychedelic dose of DMT in an amount greater than about 60 mg and up to about 250 mg and an effective amount of CX157. FIG. 4 illustrates an exemplary dosing regimen wherein a subject takes a single psycholytic dose of DMT in an amount greater than about 10 mg and up to about 60 mg and an effective amount of CX157.

It will be readily appreciated that specific dose amounts, as well as dose ranges, for "microdoses," "psycholytic doses," and "psychedelic doses" will vary for different 5-HT$_{2A}$ agonists, and will vary for the same 5-HT$_{2A}$ agonist for different people and for different dosing methods; however, the determination of such dose ranges and specific dose amounts, including to provide a "microdose," "psycholytic dose," and "psychedelic dose," will be understood for different compounds and for different people and different dosing methods, according to the teachings herein and the general knowledge in the art.

It will be further appreciated that dosing ranges may overlap, including for the same drug compound.

In some embodiments, the MAOI, or a salt thereof, is administered by a variety of routes including oral, mucosal (e.g., buccal, sublingual), rectal, vaginal, transdermal, subcutaneous, intravenous, intramuscular, inhaled, intraocular, topical, and intranasal. In some preferred embodiments, the MAOI, or a salt thereof, is administered orally. In further particularly preferred embodiments, wherein the MAOI is CX157, or a salt thereof, the MAOI is administered orally.

In some embodiments, the 5-HT$_{2A}$ agonist, or a salt thereof, is administered by a variety of routes including oral, mucosal (e.g., buccal, sublingual), rectal, vaginal, transdermal, subcutaneous, intravenous, intramuscular, inhaled, intraocular, topical, and intranasal. In preferred embodiments, the 5-HT$_{2A}$ agonist, or a salt thereof, is administered orally. In other embodiments, the 5-HT$_{2A}$ agonist, or a salt thereof, is administered parenterally. In other preferred embodiments, the 5-HT$_{2A}$ agonist, or a salt thereof, is administered intravenously or intramuscularly. Further formulations and routes of administration for disclosed MAO inhibitors and 5-HT$_{2A}$ agonists are described in various embodiments herein.

In some embodiments, wherein the 5-HT$_{2A}$ agonist is DMT, or a salt thereof, and the MAOI is CX157, or a salt thereof, the MAOI is administered to a subject orally. In some embodiments, wherein the 5-HT$_{2A}$ agonist is DMT, or a salt thereof, and the MAOI is CX157, or a salt thereof, the 5-HT$_{2A}$ agonist is administered to a subject orally.

It will be appreciated that the frequency or duration of a disclosed method may be increased or reduced, as indicated by the clinical outcome desired, status of the pathology or symptom, any adverse side effects of the treatment or therapy, or concomitant medications. In embodiments, the subject is subjected to a disclosed method daily, every second day, every third day, every fourth day, every fifth day, every sixth day, every seventh day, every eighth day, every ninth day, every tenth day, every eleventh day, every twelfth day, every thirteenth day, or every fourteenth day, for the duration of a treatment cycle. In embodiments, a treatment cycle is repeated every week, every two weeks, every three weeks, monthly, every two months, every three months, every six months, every year, every two years, every five years, or every ten years. For example, in some embodiments, the subject is subjected to a disclosed method daily. In embodiments, the subject is subjected to a disclosed method every other day. In other embodiments, the subject is subjected to a disclosed method every third day for one month. In embodiments, the treatment cycle is a weekly cycle that consists of subjecting the subject to a disclosed method for five consecutive days, followed by two "off" days during which the subject is not subjected to a disclosed method. In other embodiments, the treatment cycle is a three-week cycle that consists of subjecting the subject to a disclosed method for fourteen consecutive days, followed by seven "off" days during which the subject is not subjected to a disclosed method. In embodiments, the treatment cycle is a four-week cycle that consists of subjecting the subject to a disclosed method for seven consecutive days, followed by twenty-one "off" days during which the subject is not subjected to a disclosed method. In embodiments, the treatment cycle is a four-week cycle that consists of subjecting the subject to a disclosed method for fourteen consecutive days, followed by fourteen "off" days during which the subject is not subjected to a disclosed method. In embodiments, the treatment cycle is a four-week cycle that consists of subjecting the subject to a disclosed method for twenty-one consecutive days, followed by seven "off" days during which the subject is not subjected to a disclosed method.

In embodiments, the 5-HT$_{2A}$ agonist is administered daily for a period of at least 90 days; and the MAOI is administered daily for a period of at least 90 days. For example, FIG. 1 illustrates an exemplary dosing regimen for administration to a subject of a single dose of DMT daily and an effective amount of CX157 daily for a period of 90 days.

In embodiments, the 5-HT$_{2A}$ agonist is administered intermittently, such as by taking a single dose every third day, for a period of at least 90 days; and the MAOI is administered daily for a period of at least 90 days. In embodiments, the 5-HT$_{2A}$ agonist is administered intermittently, such as by taking a single dose weekly, for a period of at least 90 days; and the MAOI is administered daily for a period of at least 90 days. For example, FIG. 2 illustrates an exemplary dosing regimen for administration to a subject of a dose of DMT intermittently and an effective amount of CX157 daily for a period of 90 days. FIGS. 3 and 4 illustrate exemplary dosing regimens for administration to a subject of a single dose of DMT and an effective amount of CX157 every 90 days.

The individual disclosed compounds (e.g., the MAOI, the 5-HT$_{2A}$ agonist) will be understood to also encompass pharmaceutically acceptable salts of such compounds. The term "pharmaceutically acceptable salt" (or equivalently herein as shorthand, "salt," as "pharmaceutically acceptable" will be implied), refers to salts prepared from pharmaceutically acceptable non-toxic acids or bases, and which may be synthesized by conventional chemical methods. Generally, such salts are prepared by reacting the free acid or base forms of these agents with a stoichiometric amount of the appropriate base or acid in water or in an organic solvent, or in a mixture of the two; generally, nonaqueous media (e.g., ether, ethyl acetate, ethanol, isopropanol, or acetonitrile) are preferred. For therapeutic use, and as the word is used in this disclosure, "salts" of the compounds are those wherein the counter-ion is pharmaceutically acceptable.

Exemplary salts include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d-lactate, decanoate, dichloroacetate, digluconate, dodecylsulfate, edentate, edetate, edisylate, estolate, esylate, ethanesulfonate, ethyl sulfate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, hippurate, hybenzate, hydrabamine, hydrobromide, hydrobromide/bromide, hydrochloride, hydroiodide, hydroxide, hydroxybenzoate, hydroxynaphthoate, iodide, isethionate, isothionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like (see Berge et al., *J Pharm Sci.*, 1977; 66:1-19).

Certain disclosed compounds may contain one or more ionizable groups (groups from which a proton can be removed (e.g., —COOH) or added (e.g., amines) or which can be quaternized (e.g., amines)). All possible ionic forms of such molecules and salts thereof are included in the present disclosure.

A compound used in a disclosed method or composition can exist in solid or liquid form. In the solid state, a compound may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The subject matter described herein includes such solvates.

The skilled artisan will further appreciate that certain compounds that exist in crystalline form, including the various solvates thereof, may exhibit polymorphism (i.e. the capacity to occur in different crystalline structures). These different crystalline forms are typically known as "polymorphs." The subject matter disclosed herein includes such polymorphs. Polymorphs include the different crystal packing arrangements of the same elemental composition of a compound. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. All polymorphic forms of compounds used in disclosed methods or compositions are included in the present disclosure.

Compounds used in disclosed methods or compositions may contain one or more asymmetric centers and give rise to enantiomers, diastereomers, and other stereoisomeric forms. Each chiral center may be defined, in terms of absolute stereochemistry, as (R)- or (S)-. The invention includes all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. Various methods are known in the art for preparing optically active forms and determining activity. Such methods include standard tests described herein and other similar tests which are well known in the art. All stereochemical forms of compounds used in disclosed methods or compositions are included in the present disclosure.

V. PHARMACEUTICAL COMPOSITIONS

In some aspects, provided herein is a pharmaceutical composition comprising: a MAOI, or a salt thereof; and a 5-HT$_{2A}$ agonist, or a salt thereof; wherein the MAOI is a MAO-A-selective inhibitor; and wherein the 5-HT$_{2A}$ agonist is susceptible to degradation by MAO-A. Herein, the terms "disclosed compound," "active compound," "active ingredient," and "active agent" are used interchangeably to refer to a disclosed MAOI or 5-HT$_{2A}$ agonist of the disclosed methods or compositions.

"Pharmaceutical compositions" are compositions that include the disclosed compound(s) together in an amount (for example, in a unit dosage form) with a pharmaceutically acceptable carrier, diluent, or excipient. Some embodiments will not have a single carrier, diluent, or excipient alone, but will include multiple carriers, diluents, and/or excipients. Compositions can be prepared by standard pharmaceutical formulation techniques such as disclosed in, e.g., Remington: The Science & Practice of Pharmacy (2020) 23th ed., Academic Press., Cambridge, Mass.; The Merck Index (1996) 12th ed., Merck Pub. Group, Whitehouse, N.J.; Pharm. Principles of Solid Dosage Forms (1993), Technomic Pub. Co., Inc., Lancaster, Pa.; and Ansel & Stoklosa, Pharm. Calculations (2001) 11th ed., Lippincott Williams & Wilkins, Baltimore, Md.; & Poznansky et al. Drug Delivery Systems (1980), R. L. Juliano, ed., Oxford, N.Y., pp. 253-315).

"Pharmaceutically acceptable" used in connection with an excipient, carrier, diluent, or other ingredient means the ingredient is generally safe and, within the scope of sound medical judgment, suitable for use in contact with cells of humans and animals without undue toxicity, irritation, allergic response, or complication, commensurate with a reasonable risk/benefit ratio.

In embodiments, pharmaceutical compositions comprising a disclosed compound can be administered by a variety of routes including oral, mucosal (e.g., buccal, sublingual), rectal, transdermal, subcutaneous, intravenous, intramuscular, inhaled, and intranasal. In embodiments, the compounds employed in the methods of this invention are effective as oral, mucosal (e.g., buccal, sublingual), rectal, transdermal, subcutaneous, intravenous, intramuscular, inhaled, and intranasal compositions. Such compositions are prepared in a manner well known in the pharmaceutical art and comprise at least one active compound. (See, e.g., Remington, 2020).

The disclosed compositions are preferably formulated in a unit dosage form, each dosage containing a therapeutically effective amount of the active ingredients, for example in the dosage amounts disclosed below. The term "unit dosage form" refers to a physically discrete unit suited as unitary dosages for the subject to be treated, each unit containing a predetermined quantity of active material calculated to produce the desired therapeutic effect(s), in association with a suitable pharmaceutical carrier, diluent, or excipient. Unit dosage forms are often used for ease of administration and uniformity of dosage. Unit dosage forms can contain a single or individual dose or unit, a sub-dose, or an appropriate fraction thereof (e.g., one half a "full" dose for a "booster" dose as described below), of the pharmaceutical composition administered.

Unit dosage forms include capsules, troches, cachets, lozenges, tablets, ampules and vials, which may include a composition in a freeze-dried or lyophilized state; a sterile liquid carrier may be added prior to administration or delivery in vivo. Unit dosage forms include ampules and vials with liquid compositions disposed therein. Unit dosage forms include compounds for transdermal administration, like "patches" that contact the epidermis (including the mucosa) of a subject for an extended or brief period of time.

In embodiments, a disclosed composition is formulated in a pharmaceutically acceptable oral dosage form. Oral dosage forms include oral liquid dosage forms (such as tinctures, drops, emulsions, syrups, elixirs, suspensions, and solutions, and the like) and oral solid dosage forms. A disclosed pharmaceutical composition may be prepared as a formulation suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

In embodiments, a disclosed composition is formulated as an oral solid dosage form. Oral solid dosage forms may include but are not limited to, lozenges, troches, tablets, capsules, caplets, powders, pellets, multiparticulates, beads, spheres, and/or any combinations thereof. Oral solid dosage forms may be formulated as immediate release, controlled release, sustained release, extended release, or modified release formulations. Accordingly, in some embodiments, the disclosed oral solid dosage forms may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including a fast-melt tablet. Additionally, pharmaceutical formulations may be administered as a single capsule or in multiple capsule dosage form. In embodiments, the pharmaceutical formulation is administered in two, three, four, or more capsules or tablets.

Oral solid dosage forms may contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof. Oral solid dosage forms also can comprise one or more pharmaceutically acceptable additives such as a compatible carrier, complexing agent, ionic dispersion modulator, disintegrating agent, surfactant, lubricant, colorant, moistening agent, plasticizer, stabilizer, penetration enhancer, wetting agent, anti-foaming agent, alone or in combination, as well as supplementary active compound(s).

Supplementary active compounds include preservatives, antioxidants, antimicrobial agents including biocides and biostats such as antibacterial, antiviral and antifungal agents. Preservatives can be used to inhibit microbial growth or increase stability of the active ingredient thereby prolonging the shelf life of the formulation. Suitable preservatives are known in the art and include EDTA, EGTA, benzalkonium chloride or benzoic acid or benzoates, such as sodium benzoate. Antioxidants include vitamin A, vitamin C (ascorbic acid), vitamin E, tocopherols, other vitamins or provitamins, and compounds such as alpha lipoic acid.

In embodiments, a disclosed composition is formulated as an oral liquid dosage form. Oral liquid dosage forms include tinctures, drops, emulsions, syrups, elixirs, suspensions, and solutions, and the like. These oral liquid dosage forms may be formulated with any pharmaceutically acceptable excipient known to those of skill in the art for the preparation of liquid dosage forms, and with solvents, diluents, carriers, excipients, and the like chosen as appropriate to the solubility and other properties of the active agents and other ingredients. Solvents may be, for example, water, glycerin, simple syrup, alcohol, medium chain triglycerides (MCT), and combinations thereof.

Liquid dosage forms for oral administration may be in the form of pharmaceutically acceptable emulsions, syrups, elixirs, suspensions, and solutions, which may contain an inactive diluent, such as water. Pharmaceutical formulations may be prepared as liquid suspensions or solutions using a sterile liquid, such as an oil, water, an alcohol, and combinations of these pharmaceutically suitable surfactants, suspending agents, emulsifying agents, may be added for oral or parenteral administration. Liquid formulations also may be prepared as single dose or multi-dose beverages. Suspensions may include oils. Such oils include peanut oil, sesame oil, cottonseed oil, corn oil, and olive oil. Suitable oils also include carrier oils such as MCT and long chain triglyceride (LCT) oils. Suspension preparation may also contain esters of fatty acids such as ethyl oleate, isopropyl myristate, fatty acid glycerides, and acetylated fatty acid glycerides. Suspension formulations may include alcohols, (such as ethanol, isopropyl alcohol, hexadecyl alcohol), glycerol, and propylene glycol. Ethers, such as poly(ethylene glycol), petroleum hydrocarbons such as mineral oil and petrolatum, and water may also be used in suspension formulations. Suspension can thus include an aqueous liquid or a non-aqueous liquid, an oil-in-water liquid emulsion, or a water-in-oil emulsion.

In embodiments, formulations are provided comprising the disclosed compositions and at least one dispersing agent or suspending agent for oral administration to a subject. The formulation may be a powder and/or granules for suspension, and upon admixture with water, a substantially uniform suspension is obtained. The aqueous dispersion can comprise amorphous and non-amorphous particles consisting of multiple effective particle sizes such that a drug is absorbed in a controlled manner over time.

Dosage forms for oral administration can be aqueous suspensions selected from the group including pharmaceutically acceptable aqueous oral dispersions, emulsions, solutions, and syrups (see, e.g., Singh et al., Encyclopedia of Pharm. Tech., 2nd Ed., 754-757 (2002). In addition to disclosed compounds, the liquid dosage forms may comprise additives, such as one or more disintegrating agents, dispersing agents, wetting agents, preservatives, viscosity enhancing agents, sweetening agents, or flavoring agents.

Disclosed compositions also may be prepared as formulations suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

Examples of suitable aqueous and non-aqueous carriers, diluents, solvents, or vehicles include water, ethanol, polyols, suitable mixtures thereof, vegetable oils, and injectable organic esters such as ethyl oleate. Additionally, the disclosed compositions can be dissolved at concentrations of >1 mg/ml using water-soluble beta cyclodextrins (e.g., beta-sulfobutyl-cyclodextrin and 2-hydroxypropyl-betacyclodextrin. Proper fluidity can be maintained, for example, by the use of a coating such as a lecithin, by the maintenance of the required particle size in the case of dispersions, and by the use of surfactants.

Formulations suitable for subcutaneous injection also may contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, and sorbic acid. Isotonic agents, such as sugars and sodium chloride may be used. Prolonged drug absorption of an injectable form can be brought about by use of agents delaying absorption, e.g., aluminum monostearate or gelatin.

Disclosed compositions also may be prepared as suspension formulations designed for extended-release via subcutaneous or intramuscular injection. Such formulations avoid first-pass metabolism, and lower dosages of the active agents will be necessary to maintain equivalent plasma levels when compared to oral formulations. In such formulations, the mean particle size of the active agents and the range of total particle sizes can be used to control the release of those agents by controlling the rate of dissolution in fat or muscle. The compositions also may be prepared for microinjection or injection cannula.

In embodiments, disclosed pharmaceutical compositions may be formulated into a topical dosage form. Topical dosage forms include transmucosal and transdermal formulations, such as aerosols, emulsions, sprays, ointments, salves, gels, pastes, lotions, liniments, oils, and creams. For such formulations, penetrants and carriers can be included in the pharmaceutical composition. Penetrants are known in the art, and include, for transmucosal administration, detergents, bile salts, and fusidic acid derivatives. For transdermal administration, carriers which may be used include Vaseline®, lanolin, PEG, alcohols, transdermal enhancers, and combinations thereof.

In some aspects are provided various forms of preparations including as a delaying buffer or delaying layer. Another embodiment includes forms of preparations including as an extended-release product, a delayed-release product, or a targeted-release product. For example, the MAOI (e.g., CX157) may be formulated for rapid or extended release (see, e.g., as disclosed in WO2010/080977); with or without stabilizers and/or excipients (see, e.g., U.S. Pat. No. 8,313,766); and in various formulations with or without coatings, such as enteric coatings (see, e.g., WO2010/080970) to further alter the release profile. In some embodiments, a composition comprising a MAOI additionally comprises a combination of copovidone, microcrystalline cellulose, hypromellose, colloidal silicon dioxide, and magnesium stearate.

In embodiments, a pharmaceutical composition comprising a MAOI and a 5-$HT_{2A}$ agonist comprises both the MAOI and the 5-$HT_{2A}$ agonist, together with one or more pharmaceutically acceptable carriers, diluents, or excipients, formulated as a single pharmaceutical combination product, such as a fixed-dose combination (FDC) or single-pill combination (SPC).

In some embodiments, a pharmaceutical composition comprises CX157 and a 5-HT$_{2A}$ agonist. In embodiments, a pharmaceutical composition comprises CX157 and DMT. In embodiments, a pharmaceutical composition comprises CX157 and 5-MeO-DMT. In embodiments, a pharmaceutical composition comprises CX157 and DPT. In embodiments, a pharmaceutical composition comprises CX157 and psilocin. In embodiments, a pharmaceutical composition comprises CX157 and psilocybin.

In some embodiments, a pharmaceutical composition comprises CX157 and a deuterated 5-HT$_{2A}$ agonist. In embodiments, a pharmaceutical composition comprises CX157 and deuterated DMT. In embodiments, a pharmaceutical composition comprises CX157 and deuterated 5-MeO-DMT. In embodiments, a pharmaceutical composition comprises CX157 and deuterated DPT. In embodiments, a pharmaceutical composition comprises CX157 and deuterated psilocin. In embodiments, a pharmaceutical composition comprises CX157 and deuterated psilocybin.

In some embodiments, a pharmaceutical composition comprises CX009 and a 5-HT$_{2A}$ agonist. In embodiments, a pharmaceutical composition comprises CX009 and DMT. In embodiments, a pharmaceutical composition comprises CX009 and 5-MeO-DMT. In embodiments, a pharmaceutical composition comprises CX009 and DPT. In embodiments, a pharmaceutical composition comprises CX009 and psilocin. In embodiments, a pharmaceutical composition comprises CX009 and psilocybin.

In some embodiments, a pharmaceutical composition comprises CX009 and a deuterated 5-HT$_{2A}$ agonist. In embodiments, a pharmaceutical composition comprises CX009 and deuterated DMT. In embodiments, a pharmaceutical composition comprises CX009 and deuterated 5-MeO-DMT. In embodiments, a pharmaceutical composition comprises CX009 and deuterated DPT. In embodiments, a pharmaceutical composition comprises CX009 and deuterated psilocin. In embodiments, a pharmaceutical composition comprises CX009 and deuterated psilocybin.

In some embodiments, a pharmaceutical composition comprises brofaromine and a 5-HT$_{2A}$ agonist. In embodiments, a pharmaceutical composition comprises brofaromine and DMT. In embodiments, a pharmaceutical composition comprises brofaromine and 5-MeO-DMT. In embodiments, a pharmaceutical composition comprises brofaromine and DPT. In embodiments, a pharmaceutical composition comprises brofaromine and psilocin. In embodiments, a pharmaceutical composition comprises brofaromine and psilocybin.

In some embodiments, a pharmaceutical composition comprises brofaromine and a deuterated 5-HT$_{2A}$ agonist. In embodiments, a pharmaceutical composition comprises brofaromine and deuterated DMT. In embodiments, a pharmaceutical composition comprises brofaromine and deuterated 5-MeO-DMT. In embodiments, a pharmaceutical composition comprises brofaromine and deuterated DPT. In embodiments, a pharmaceutical composition comprises brofaromine and deuterated psilocin. In embodiments, a pharmaceutical composition comprises brofaromine and deuterated psilocybin.

In some embodiments, a pharmaceutical composition comprises caroxazone and a 5-HT$_{2A}$ agonist. In embodiments, a pharmaceutical composition comprises caroxazone and DMT. In embodiments, a pharmaceutical composition comprises caroxazone and 5-MeO-DMT. In embodiments, a pharmaceutical composition comprises caroxazone and DPT. In embodiments, a pharmaceutical composition comprises caroxazone and psilocin. In embodiments, a pharmaceutical composition comprises caroxazone and psilocybin.

In some embodiments, a pharmaceutical composition comprises caroxazone and a deuterated 5-HT$_{2A}$ agonist. In embodiments, a pharmaceutical composition comprises caroxazone and deuterated DMT. In embodiments, a pharmaceutical composition comprises caroxazone and deuterated 5-MeO-DMT. In embodiments, a pharmaceutical composition comprises caroxazone and deuterated DPT. In embodiments, a pharmaceutical composition comprises caroxazone and deuterated psilocin. In embodiments, a pharmaceutical composition comprises caroxazone and deuterated psilocybin.

In some embodiments, a pharmaceutical composition comprises eprobemide and a 5-HT$_{2A}$ agonist. In embodiments, a pharmaceutical composition comprises eprobemide and DMT. In embodiments, a pharmaceutical composition comprises eprobemide and 5-MeO-DMT. In embodiments, a pharmaceutical composition comprises eprobemide and DPT. In embodiments, a pharmaceutical composition comprises eprobemide and psilocin. In embodiments, a pharmaceutical composition comprises eprobemide and psilocybin.

In some embodiments, a pharmaceutical composition comprises eprobemide and a deuterated 5-HT$_{2A}$ agonist. In embodiments, a pharmaceutical composition comprises eprobemide and deuterated DMT. In embodiments, a pharmaceutical composition comprises eprobemide and deuterated 5-MeO-DMT. In embodiments, a pharmaceutical composition comprises eprobemide and deuterated DPT. In embodiments, a pharmaceutical composition comprises eprobemide and deuterated psilocin. In embodiments, a pharmaceutical composition comprises eprobemide and deuterated psilocybin.

In some embodiments, a pharmaceutical composition comprises metralindole and a 5-HT$_{2A}$ agonist. In embodiments, a pharmaceutical composition comprises metralindole and DMT. In embodiments, a pharmaceutical composition comprises metralindole and 5-MeO-DMT. In embodiments, a pharmaceutical composition comprises metralindole and DPT. In embodiments, a pharmaceutical composition comprises metralindole and psilocin. In embodiments, a pharmaceutical composition comprises metralindole and psilocybin.

In some embodiments, a pharmaceutical composition comprises metralindole and a deuterated 5-HT$_{2A}$ agonist. In embodiments, a pharmaceutical composition comprises metralindole and deuterated DMT. In embodiments, a pharmaceutical composition comprises metralindole and deuterated 5-MeO-DMT. In embodiments, a pharmaceutical composition comprises metralindole and deuterated DPT. In embodiments, a pharmaceutical composition comprises metralindole and deuterated psilocin. In embodiments, a pharmaceutical composition comprises metralindole and deuterated psilocybin.

In some embodiments, a pharmaceutical composition comprises minaprine and a 5-HT$_{2A}$ agonist. In embodiments, a pharmaceutical composition comprises minaprine and DMT. In embodiments, a pharmaceutical composition comprises minaprine and 5-MeO-DMT. In embodiments, a pharmaceutical composition comprises minaprine and DPT. In embodiments, a pharmaceutical composition comprises minaprine and psilocin. In embodiments, a pharmaceutical composition comprises minaprine and psilocybin.

In some embodiments, a pharmaceutical composition comprises minaprine and a deuterated 5-HT$_{2A}$ agonist. In embodiments, a pharmaceutical composition comprises minaprine and deuterated DMT. In embodiments, a pharmaceutical composition comprises minaprine and deuterated 5-MeO-DMT. In embodiments, a pharmaceutical composition comprises minaprine and deuterated DPT. In embodiments, a pharmaceutical composition comprises minaprine and deuterated psilocin. In embodiments, a pharmaceutical composition comprises minaprine and deuterated psilocybin.

In some embodiments, a pharmaceutical composition comprises pirlindole and a 5-$HT_{2A}$ agonist. In embodiments, a pharmaceutical composition comprises pirlindole and DMT. In embodiments, a pharmaceutical composition comprises pirlindole and 5-MeO-DMT. In embodiments, a pharmaceutical composition comprises pirlindole and DPT. In embodiments, a pharmaceutical composition comprises pirlindole and psilocin. In embodiments, a pharmaceutical composition comprises pirlindole and psilocybin.

In some embodiments, a pharmaceutical composition comprises pirlindole and a deuterated 5-$HT_{2A}$ agonist. In embodiments, a pharmaceutical composition comprises pirlindole and deuterated DMT. In embodiments, a pharmaceutical composition comprises pirlindole and deuterated 5-MeO-DMT. In embodiments, a pharmaceutical composition comprises pirlindole and deuterated DPT. In embodiments, a pharmaceutical composition comprises pirlindole and deuterated psilocin. In embodiments, a pharmaceutical composition comprises pirlindole and deuterated psilocybin.

In some embodiments, a pharmaceutical composition comprises rosiridin and a 5-$HT_{2A}$ agonist. In embodiments, a pharmaceutical composition comprises rosiridin and DMT. In embodiments, a pharmaceutical composition comprises rosiridin and 5-MeO-DMT. In embodiments, a pharmaceutical composition comprises rosiridin and DPT. In embodiments, a pharmaceutical composition comprises rosiridin and psilocin. In embodiments, a pharmaceutical composition comprises rosiridin and psilocybin.

In some embodiments, a pharmaceutical composition comprises rosiridin and a deuterated 5-$HT_{2A}$ agonist. In embodiments, a pharmaceutical composition comprises rosiridin and deuterated DMT. In embodiments, a pharmaceutical composition comprises rosiridin and deuterated 5-MeO-DMT. In embodiments, a pharmaceutical composition comprises rosiridin and deuterated DPT. In embodiments, a pharmaceutical composition comprises rosiridin and deuterated psilocin. In embodiments, a pharmaceutical composition comprises rosiridin and deuterated psilocybin.

In some embodiments, a pharmaceutical composition comprises amiflamine and a 5-$HT_{2A}$ agonist. In embodiments, a pharmaceutical composition comprises amiflamine and DMT. In embodiments, a pharmaceutical composition comprises amiflamine and 5-MeO-DMT. In embodiments, a pharmaceutical composition comprises amiflamine and DPT. In embodiments, a pharmaceutical composition comprises amiflamine and psilocin. In embodiments, a pharmaceutical composition comprises amiflamine and psilocybin.

In some embodiments, a pharmaceutical composition comprises amiflamine and a deuterated 5-$HT_{2A}$ agonist. In embodiments, a pharmaceutical composition comprises amiflamine and deuterated DMT. In embodiments, a pharmaceutical composition comprises amiflamine and deuterated 5-MeO-DMT. In embodiments, a pharmaceutical composition comprises amiflamine and deuterated DPT. In embodiments, a pharmaceutical composition comprises amiflamine and deuterated psilocin. In embodiments, a pharmaceutical composition comprises amiflamine and deuterated psilocybin.

In some embodiments, a pharmaceutical composition comprises befloxatone and a 5-$HT_{2A}$ agonist. In embodiments, a pharmaceutical composition comprises befloxatone and DMT. In embodiments, a pharmaceutical composition comprises befloxatone and 5-MeO-DMT. In embodiments, a pharmaceutical composition comprises befloxatone and DPT. In embodiments, a pharmaceutical composition comprises befloxatone and psilocin. In embodiments, a pharmaceutical composition comprises befloxatone and psilocybin.

In some embodiments, a pharmaceutical composition comprises befloxatone and a deuterated 5-$HT_{2A}$ agonist. In embodiments, a pharmaceutical composition comprises befloxatone and deuterated DMT. In embodiments, a pharmaceutical composition comprises befloxatone and deuterated 5-MeO-DMT. In embodiments, a pharmaceutical composition comprises befloxatone and deuterated DPT. In embodiments, a pharmaceutical composition comprises befloxatone and deuterated psilocin. In embodiments, a pharmaceutical composition comprises befloxatone and deuterated psilocybin.

In some embodiments, a pharmaceutical composition comprises cimoxatone and a 5-$HT_{2A}$ agonist. In embodiments, a pharmaceutical composition comprises cimoxatone and DMT. In embodiments, a pharmaceutical composition comprises cimoxatone and 5-MeO-DMT. In embodiments, a pharmaceutical composition comprises cimoxatone and DPT. In embodiments, a pharmaceutical composition comprises cimoxatone and psilocin. In embodiments, a pharmaceutical composition comprises cimoxatone and psilocybin.

In some embodiments, a pharmaceutical composition comprises cimoxatone and a deuterated 5-$HT_{2A}$ agonist. In embodiments, a pharmaceutical composition comprises cimoxatone and deuterated DMT. In embodiments, a pharmaceutical composition comprises cimoxatone and deuterated 5-MeO-DMT. In embodiments, a pharmaceutical composition comprises cimoxatone and deuterated DPT. In embodiments, a pharmaceutical composition comprises cimoxatone and deuterated psilocin. In embodiments, a pharmaceutical composition comprises cimoxatone and deuterated psilocybin.

In some embodiments, a pharmaceutical composition comprises esuprone and a 5-$HT_{2A}$ agonist. In embodiments, a pharmaceutical composition comprises esuprone and DMT. In embodiments, a pharmaceutical composition comprises esuprone and 5-MeO-DMT. In embodiments, a pharmaceutical composition comprises esuprone and DPT. In embodiments, a pharmaceutical composition comprises esuprone and psilocin. In embodiments, a pharmaceutical composition comprises esuprone and psilocybin.

In some embodiments, a pharmaceutical composition comprises esuprone and a deuterated 5-$HT_{2A}$ agonist. In embodiments, a pharmaceutical composition comprises esuprone and deuterated DMT. In embodiments, a pharmaceutical composition comprises esuprone and deuterated 5-MeO-DMT. In embodiments, a pharmaceutical composition comprises esuprone and deuterated DPT. In embodiments, a pharmaceutical composition comprises esuprone and deuterated psilocin. In embodiments, a pharmaceutical composition comprises esuprone and deuterated psilocybin.

In some embodiments, a pharmaceutical composition comprises sercloremine and a 5-$HT_{2A}$ agonist. In embodiments, a pharmaceutical composition comprises sercloremine and DMT.

In embodiments, a pharmaceutical composition comprises sercloremine and 5-MeO-DMT. In embodiments, a pharmaceutical composition comprises sercloremine and DPT. In embodiments, a pharmaceutical composition comprises sercloremine and psilocin. In embodiments, a pharmaceutical composition comprises sercloremine and psilocybin.

In some embodiments, a pharmaceutical composition comprises sercloremine and a deuterated 5-$HT_{2A}$ agonist. In embodiments, a pharmaceutical composition comprises sercloremine and deuterated DMT. In embodiments, a pharmaceutical composition comprises sercloremine and deuterated 5-MeO-DMT. In embodiments, a pharmaceutical composition comprises sercloremine and deuterated DPT. In embodiments, a pharmaceutical composition comprises sercloremine and deuterated psilocin. In embodiments, a pharmaceutical composition comprises sercloremine and deuterated psilocybin.

In some embodiments, a pharmaceutical composition comprises tetrindole and a 5-$HT_{2A}$ agonist. In embodiments, a pharmaceutical composition comprises tetrindole and DMT. In embodiments, a pharmaceutical composition comprises tetrindole and 5-MeO-DMT. In embodiments, a pharmaceutical composition comprises tetrindole and DPT. In embodiments, a pharmaceutical composition comprises tetrindole and psilocin. In embodiments, a pharmaceutical composition comprises tetrindole and psilocybin.

In some embodiments, a pharmaceutical composition comprises tetrindole and a deuterated 5-$HT_{2A}$ agonist. In embodiments, a pharmaceutical composition comprises tetrindole and deuterated DMT. In embodiments, a pharmaceutical composition comprises tetrindole and deuterated 5-MeO-DMT. In embodiments, a pharmaceutical composition comprises tetrindole and deuterated DPT. In embodiments, a pharmaceutical composition comprises tetrindole and deuterated psilocin. In embodiments, a pharmaceutical composition comprises tetrindole and deuterated psilocybin.

In a preferred embodiment, the composition comprises CX157, or a salt thereof, as the MAO inhibitor; and DMT, or a salt thereof, as the deuterated 5-$HT_{2A}$ agonist; and the modified release product comprises a combination of copovidone, microcrystalline cellulose, hypromellose, colloidal silicon dioxide, and magnesium stearate. In another preferred embodiment, the composition comprises CX157, or a salt thereof, as the MAO inhibitor; and deuterated DMT, or a salt thereof, as the deuterated 5-$HT_{2A}$ agonist; and the modified release product comprises a combination of copovidone, microcrystalline cellulose, hypromellose, colloidal silicon dioxide, and magnesium stearate.

A. Dose and Dosage, Additional Agents, and Kits

In some embodiments, pharmaceutical compositions comprise a therapeutically effective amount or an effective amount of a disclosed compound, such as for administration to a subject. Administration of pharmaceutical compositions in a "therapeutically effective amount," or an "effective amount" to a subject means administration of an amount of composition sufficient to achieve the desired effect. When an "effective amount" means an amount effective in treating the stated disorder or symptoms in a subject, "therapeutic effect" would be understood to mean the responses(s) in a mammal after treatment that are judged to be desirable and beneficial. Hence, depending on the mental health disorder to be treated, or improvement in mental health or functioning sought, and depending on the particular constituent(s) in the disclosed compositions under consideration, those responses shall differ, but would be readily understood by those of ordinary skill, through an understanding of the disclosure herein and the general knowledge of the art (e.g., by reference to the symptoms listed in the Diagnostic and Statistical Manual of Mental Disorders, 5th Edition (DSM-5) for the stated disorder).

In embodiments, the compositions comprise therapeutic amounts of the disclosed compounds and in some embodiments other active or inactive ingredients. Dosage amounts will be understood by reference to all of the teachings herein as well as the general knowledge in the art, but certain exemplary dosage amounts, known to be useful in the practice of the invention, are listed below for ease of reference.

In some embodiments, where a pharmaceutical composition includes a disclosed MAOI, such as CX157, the MAOI may be present in an amount so that a single dose is (in a mg dosage amount calculated based on the kg weight of the patient), e.g., between about 0.8 mg/kg and 5.0 mg/kg, 1.0 mg/kg and 3.5 mg/kg, 1.3 mg/kg and 3.3 mg/kg, 1.4 mg/kg and 3.5 mg/kg, or 1.7 mg/kg and 2.5 mg/kg. In embodiments, the MAOI is present in an amount so that a single dose is between about 0.8 mg/kg and 5.0 mg/kg. In embodiments, the MAOI is present in an amount so that a single dose is between about 1.0 mg/kg and 3.5 mg/kg. In embodiments, the MAOI is present in an amount so that a single dose is between about 1.3 mg/kg and 3.3 mg/kg. In embodiments, the MAOI is present in an amount so that a single dose is between about 1.4 mg/kg and 3.5 mg/kg. In embodiments, the MAOI is present in an amount so that a single dose is between about 1.7 mg/kg and 2.5 mg/kg. In embodiments, the MAOI is present in an amount so that a single dose is about 2.1 mg/kg. In embodiments, the MAOI is present in an amount so that a single dose is about 1.4 mg/kg. In embodiments, the MAOI is present in an amount so that a single dose is about 3.5 mg/kg.

In embodiments, where a pharmaceutical composition includes a disclosed MAOI, such as CX157, the MAOI may be present in an amount so that a single dose is (whether or not such dose is present in a unit dosage form), e.g., between about 50 mg and 300 mg, 75 mg and 200 mg, or 100 and 150 mg. In embodiments, the MAOI is present in an amount so that a single dose is between about 50 mg and 300 mg. In embodiments, the MAOI is present in an amount so that a single dose is between about 75 mg and 200 mg. In embodiments, the MAOI is present in an amount so that a single dose is between about 100 mg and 150 mg. In embodiments, the MAOI is present in an amount so that a single dose is about 125 mg. In embodiments, the MAOI is present in an amount so that a single dose is about 175 mg.

In some embodiments, where a pharmaceutical composition includes a disclosed 5-$HT_{2A}$ agonist, such as DMT, the 5-$HT_{2A}$ agonist may be present in an amount so that a single dose is (in a milligram dosage amount calculated based on the kilogram weight of the patient), e.g., between about 0.02 mg/kg and 0.20 mg/kg, 0.03 mg/kg and 0.13 mg/kg, 0.03 mg/kg and 0.07 mg/kg, 0.05 mg/kg and 0.10 mg/kg, or about 0.08 mg/kg. In embodiments, the 5-$HT_{2A}$ agonist is present in an amount so that a single dose is between about 0.02 mg/kg and 0.20 mg/kg. In embodiments, the 5-$HT_{2A}$ agonist is present in an amount so that a single dose is between about 0.03 mg/kg and 0.13 mg/kg. In embodiments, the 5-$HT_{2A}$ agonist is present in an amount so that a single dose is between about 0.03 mg/kg and 0.07 mg/kg. In embodiments, the 5-$HT_{2A}$ agonist is present in an amount so that a single dose is between about 0.05 mg/kg and 0.10 mg/kg. In embodiments, the 5-$HT_{2A}$ agonist is present in an amount so that a single dose is about 0.08 mg/kg. In embodiments, the 5-$HT_{2A}$ agonist is present in an amount so that a single dose is about 0.05 mg/kg.

In some embodiments, where a pharmaceutical composition includes a disclosed 5-$HT_{2A}$ agonist, such as DMT, the 5-$HT_{2A}$ agonist may be present in an amount so that a single dose is (in a milligram dosage amount calculated based on the kilogram weight of the patient), e.g., between about 0.20 mg/kg and 1.0 mg/kg, 0.20 mg/kg and 0.80 mg/kg, 0.20 mg/kg and 0.60 mg/kg, 0.30 mg/kg and 0.80 mg/kg, or 0.30 mg/kg and 0.60 mg/kg. In embodiments, the dose of the 5-HT$_{2A}$ agonist is between about 0.20 mg/kg and 1.0 mg/kg. In embodiments, the dose of the 5-HT$_{2A}$ agonist is between about 0.20 mg/kg and 0.80 mg/kg. In embodiments, the dose of the 5-HT$_{2A}$ agonist is between about 0.20 mg/kg and 0.60 mg/kg. In embodiments, the dose of the 5-HT$_{2A}$ agonist is between about 0.30 mg/kg and 0.80 mg/kg. In embodiments, the dose of the 5-HT$_{2A}$ agonist is between about 0.30 mg/kg and 0.60 mg/kg.

In some embodiments, where a pharmaceutical composition includes a disclosed 5-HT$_{2A}$ agonist, such as DMT, the 5-HT$_{2A}$ agonist may be present in an amount so that a single dose is (whether or not such dose is present in a unit dosage form), e.g., between about 1 mg and 10 mg, 2 mg and 8 mg, 3 mg and 6 mg, or about 5 mg. In embodiments, the 5-HT$_{2A}$ agonist may be present in an amount so that a single dose is between about 1 mg and 10 mg. In embodiments, the 5-HT$_{2A}$ agonist is present in an amount so that a single dose is between about 2 mg and 8 mg. In embodiments, the 5-HT$_{2A}$ agonist is present in an amount so that a single dose is between about 3 mg and 6 mg. In embodiments, the 5-HT$_{2A}$ agonist is present in an amount so that a single dose is about 3 mg. In embodiments, the 5-HT$_{2A}$ agonist is present in an amount so that a single dose is about 5 mg. In embodiments, the 5-HT$_{2A}$ agonist is present in an amount so that a single dose is about 10 mg.

In some embodiments, where a pharmaceutical composition includes a disclosed 5-HT$_{2A}$ agonist, such as DMT, the 5-HT$_{2A}$ agonist may be present in an amount so that a single dose is (whether or not such dose is present in a unit dosage form), e.g., between about 15 mg and 300 mg, 25 mg and 200 mg, 20 mg and 50 mg, or 50 mg and 100 mg. In embodiments, the 5-HT$_{2A}$ agonist is present in an amount so that a single dose is between about 15 mg and 300 mg. In embodiments, the 5-HT$_{2A}$ agonist is present in an amount so that a single dose is between about 25 mg and 200 mg. In embodiments, the 5-HT$_{2A}$ agonist is present in an amount so that a single dose is between about 20 mg and 50 mg. In embodiments, the 5-HT$_{2A}$ agonist is present in an amount so that a single dose is between about 50 mg and 100 mg. In embodiments, the 5-HT$_{2A}$ agonist is present in an amount so that a single dose is about 50 mg. In embodiments, the 5-HT$_{2A}$ agonist is present in an amount so that a single dose is about 75 mg. In embodiments, the 5-HT$_{2A}$ agonist is present in an amount so that a single dose is about 100 mg.

It will be readily appreciated that dosages may vary depending upon whether the treatment is therapeutic or prophylactic, the onset, progression, severity, frequency, duration, probability of or susceptibility of the symptom to which treatment is directed, clinical endpoint desired, previous, simultaneous or subsequent treatments, general health, age, gender, and race of the subject, bioavailability, potential adverse systemic, regional or local side effects, the presence of other disorders or diseases in the subject, and other factors that will be appreciated by the skilled artisan (e.g., medical or familial history).

Dose amount, frequency or duration may be increased or reduced, as indicated by the clinical outcome desired, status of the pathology or symptom, any adverse side effects of the treatment or therapy, or concomitant medications. The skilled artisan with the teaching of this disclosure in hand will appreciate the factors that may influence the dosage, frequency, and timing required to provide an amount sufficient or effective for providing a therapeutic effect or benefit, and to do so depending on the type of therapeutic effect desired, as well as to avoid or minimize adverse effects.

It will be understood that, in some embodiments, the dose actually administered will be determined by a physician, in light of the relevant circumstances, including the disorder to be treated, the chosen route of administration, the actual composition or formulation administered, the age, weight, and response of the individual patient, and the severity of the patient's symptoms, and therefore any dosage ranges disclosed herein are not intended to limit the scope of the invention. In some instances, dosage levels below the lower limit of a disclosed range may be more than adequate, while in other cases doses above a range may be employed without causing any harmful side effects, provided for instance that such larger doses also may be divided into several smaller doses for administration, either taken together or separately.

In embodiments, disclosed compositions will be administered and dosed in accordance with good medical practice, taking into account the method and scheduling of administration, prior and concomitant medications and medical supplements, the clinical condition of the individual patient and the severity of the underlying disease, the patient's age, sex, body weight, and other such factors relevant to medical practitioners, and knowledge of the particular compound(s) used. Starting and maintenance dosage levels thus may differ from patient to patient, for individual patients across time, and for different pharmaceutical compositions and formulations, but shall be able to be determined with ordinary skill in view of the disclosure.

It should be appreciated that in other embodiments, e.g., when the disclosed compositions are taken without the direct intervention or guidance of a medical professional, appropriate dosages to achieve a therapeutic effect, including the upper and lower bounds of any dose ranges, can be determined by an individual by reference to available public information and knowledge, and reference to subjective considerations regarding desired outcomes and effects.

Determination of appropriate dosing shall include not only the determination of single dosage amounts, but also the determination of the number and timing of doses, e.g., administration of a particular dosage amount once per day, twice per day, or more than twice per day, and the time(s) of day or time(s) during a therapy session preferable for their administration.

In embodiments, especially where a formulation is prepared in single unit dosage form, such as a capsule, tablet, or lozenge, suggested dosage amounts may be known by reference to the format of the preparation itself. In embodiments, where a formulation is prepared in multiple dosage form, for instance liquid suspensions and topical preparations, suggested dosage amounts may be known by reference to the means of administration or by reference to the packaging, labeling, package insert(s), marketing materials, training materials, or other information and knowledge available to those of skill or the public.

In another aspect of this disclosure is provided pharmaceutical kits and kits of parts containing pharmaceutical compositions or formulations of the invention, optionally together with suggested administration guidelines or prescribing information therefor, and optionally in a suitable container. Individual unit dosage forms can be included in multi-dose kits or containers. pharmaceutical formulations also can be packaged in single or multiple unit dosage forms for uniformity of dosage and ease of administration.

In an exemplary pharmaceutical kit, comprising a suitable container, capsules, tablets, caplets, or other unit dosage forms are packaged in blister packs. "Blister pack" refers to any of several types of pre-formed container, especially plastic packaging, containing separate receptacles (e.g., cavities or pockets) for single unit doses, where such separate receptacles are individually sealed and can be opened individually. Blister packs include such pharmaceutical blister packs known to those of ordinary skill, including Aclar® Rx160, Rx20e, SupRx, and UltRx 2000, 3000, 4000, and 6000 (Honeywell). Within the definition of multi-dose containers, and also often referred to as blister packs, are blister trays, blister cards, strip packs, push-through packs, and the like.

Information pertaining to dosing and proper administration (if needed) may be printed onto a multi-dose kit directly (e.g., on a blister pack or other interior packaging holding the compositions or formulations of the invention). In embodiments, disclosed kits also can contain package inserts and other printed instructions (e.g., on exterior packaging) for administering the disclosed compositions and for their appropriate therapeutic use.

In some embodiments, a patient will have the option of using online software such as a website, or downloadable software such as a mobile application, to assist with compliance or to provide data relating to treatment. Such software can be used to, e.g., keep track of last dose taken and total doses taken, provide reminders and alerts for upcoming doses, provide feedback to discourage taking doses outside of set schedules, and allow for recording of specific subjective effects, or provide means for unstructured journaling. Such data collection can assist with individual patient compliance, can be used to improve or tailor individual patient care plans, and can be anonymized, aggregated, and analyzed (including by AI or natural language processing means) to allow research into the effects of various methods of treatment.

It should be readily appreciated that the disclosed compositions are not limited to combinations of a single compound, or (when formulated as a pharmaceutical composition) limited to a single carrier, diluent, and/or excipient alone, but may also include combinations of multiple compounds (including additional active compounds), and/or multiple carriers, diluents, and excipients. Pharmaceutical compositions of this invention thus may comprise a compound of Formula (1) together with one or more other active agents (or their derivatives and analogs) in combination, together with one or more pharmaceutically-acceptable carriers, diluents, and/or excipients, and additionally with one or more other active compounds.

In some embodiments, a formulation of the invention will be prepared so as to increase an existing therapeutic effect, provide an additional therapeutic effect, increase a desired property such as stability or shelf-life, decrease an unwanted effect or property, alter a property in a desirable way (such as pharmacokinetics or pharmacodynamics), modulate a desired system or pathway (e.g., a neurotransmitter system), or provide synergistic effects.

"Therapeutic effects" that may be increased or added in embodiments of the invention include, but are not limited to, antioxidant, anti-inflammatory, analgesic, antineuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, empathogenic, psychedelic, sedative, and stimulant effects.

"Synergistic effects" should be understood to include increases in potency, bioactivity, bioaccessibility, bioavailability, or therapeutic effect, that are greater than the additive contributions of the components acting alone. Numerous methods known to those of skill in the art exist to determine whether there is synergy as to a particular effect, e.g., whether, when two or more components are mixed together, the effect is greater than the sum of the effects of the individual components applied alone, thereby producing "1+1>2." Suitable methods include isobologram (or contour) analysis (Huang, Front *Pharmacol.*, 2019; 10:1222), or the equation of Loewe additivity (Loewe & Muischnek, *Arch. Exp. Pathol Pharmacol.*, 1926, 114:313-326). A synergistic effect also may be calculated using methods such as the Sigmoid-Emax equation (Holford & Scheiner, *Clin. Pharmacokinet.*, 1981; 6:429-453) and the median-effect equation (Chou & Talalay, *Adv. Enzyme Regul.* 1984; 22:27-55). The corresponding graphs associated with the equations referred to above are the concentration-effect curve and combination index curve, respectively. Each equation referred to above may be applied to experimental data to generate a corresponding graph to aid in assessing the effects of the drug combination.

In embodiments, a disclosed pharmaceutical composition comprises an additional active compound. In some embodiments, the additional active compound is selected from the group consisting of: amino acids, antioxidants, anti-inflammatory agents, analgesics, antineuropathic and antinociceptive agents, antimigraine agents, anxiolytics, antidepressants, antipsychotics, anti-PTSD agents, dissociatives, cannabinoids, immunostimulants, anti-cancer agents, antiemetics, orexigenics, antiulcer agents, antihistamines, antihypertensives, anticonvulsants, antiepileptics, bronchodilators, neuroprotectants, nootropics, empathogens, psychedelics, plasticity-inducing agents (e.g., "psychoplastogens" or "neuroplastogens"), additional monoamine oxidase inhibitors, tryptamines, terpenes, phenethylamines, sedatives, stimulants, serotonergic agents, and vitamins. In some embodiments, the additional active compound acts to increase a therapeutic effect, provide an additional therapeutic effect, decrease an unwanted effect, increase stability or shelf-life, improve bioavailability, induce synergy, increase plasticity (e.g., neural plasticity), or alter pharmacokinetics or pharmacodynamics. In some embodiments, the additional therapeutic effect is an antioxidant, anti-inflammatory, analgesic, antineuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, empathogenic, psychedelic, sedative, or stimulant effect.

In some embodiments, disclosed methods and compositions are administered in combination with a serotonergic agent to a subject. In embodiments, disclosed methods and compositions are administered to a subject along with any of a serotonin agonist, e.g., a compound activating a serotonin receptor, a serotonin antagonist, e.g., a compound binding but not activating a serotonin receptor, or a serotonin effector molecule, e.g., a compound binding to an enzyme for allosteric regulation. In embodiments, a serotonergic agent acts (either directly or indirectly) at more than one type of receptor, including receptors other than serotonergic or other monoaminergic receptors. In embodiments, a serotonergic agent blocks the serotonin transporter (SERT) and results in an elevation of the synaptic concentration of serotonin, and an increase of neurotransmission. In embodiments, a serotonergic agent acts as a reuptake modulator and inhibits the plasmalemmal transporter-mediated reuptake of serotonin from the synapse into the presynaptic neuron, leading to an increase in extracellular concentrations of serotonin and an increase in neurotransmission. In embodiments, a serotonergic agent inhibits the activity of one or both monoamine oxidase enzymes, resulting in an increase in concentrations of serotonin and an increase in neurotransmission. In embodiments, a serotonergic agent is an antidepressant or anxiolytic, e.g., an SSRI, serotonin-norepinephrine reuptake inhibitor (SNRI), tricyclic (TCA), MAOI, or atypical antidepressant.

In some embodiments, an additional active compound is mesembrine, or another bioactive alkaloid present in *Sceletium tortuosum* (kanna).

In some embodiments, an additional active compound is a tryptamine. As understood by those in the art, tryptamines are compounds having the general structure below, wherein $R^{N1}$, $R^{N2}$, $R^{\alpha}$, $R^{\beta}$, $R^2$, $R^4$, $R^5$, $R^6$, and $R^7$ are as defined herein and as generally understood in the art:

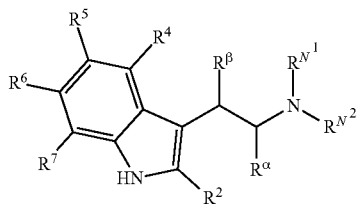

In some embodiments, $R^{N1}$, $R^{N2}$, $R^{\alpha}$, $R^{\beta}$, $R^2$, $R^4$, $R^5$, $R^6$, and $R^7$ are each independently hydrogen, deuterium, halogen (F, Cl, Br, or I), OH, phosphoryloxy, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl. Additionally, any two of $R^{N1}$, $R^{N2}$, $R^{\alpha}$, $R^{\beta}$, $R^2$, $R^4$, $R^5$, $R^6$, and $R^7$ and the intervening atoms can be taken together to form an optionally substituted optionally substituted cycloalkyl, optionally substituted cycloalkenyl, optionally substituted aryl, or optionally substituted heterocyclyl. In embodiments, the tryptamine is a quaternary salt, in which an additional $R^{N3}$ is connected to the nitrogen to which $R^{N1}$ and $R^{N2}$ are bound; wherein $R^{N3}$ is optionally substituted alkyl, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl.

In some embodiments, the additional active compound is a tryptamine selected from the group consisting of psilocybin, psilocin, or one of the TiHKAL tryptamines (see supra), or a pharmaceutically acceptable salt, hydrate, solvate, prodrug, stereoisomer, or tautomer thereof, or a combination thereof.

In embodiments, an additional tryptamine will be a "complex tryptamine" or other indolamine and including iboga alkaloids such as ibogaine, and their analogs, metabolites, and derivatives, and β-carbolines.

In some embodiments, the additional active compound is a phenethylamine. As understood by those in the art, phenethylamines are compounds having the general structure below, wherein $R^{N1}$, $R^{N2}$, $R^{\alpha}$, $R^{\beta}$, and each of $R^2$-$R^6$ are as taught herein and as generally understood in the art:

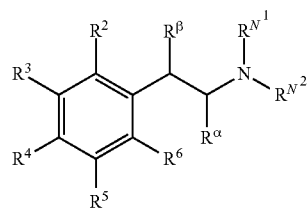

In some embodiments, $R^{N1}$, $R^{N2}$, $R^{\alpha}$, $R^{\beta}$, and each of $R^{2-6}$ are independently hydrogen, deuterium, halogen, optionally substituted alkyl, optionally substituted alkenyl, optionally substituted alkynyl, optionally substituted cycloalkyl, optionally substituted cycloalkenyl, optionally substituted aryl, or optionally substituted heterocyclyl. In embodiments, $R^3$ and $R^4$ are joined together to form an optionally substituted heterocyclyl, such as a dioxole (as with MDMA), a furan, a tetrahydrofuran, a thiophene, a pyrrole, a pyridine, a pyrrolidine, an ethylene oxide, an ethylenimine, a trimethylene oxide, a pyran, a piperidine, an imidazole, a thiazole, a dioxane, a morpholine, or a pyrimidine. In embodiments, $R^3$ and $R^4$ are joined together to form an optionally substituted aryl, such as a phenyl. In embodiments, the phenethylamine comprises a quaternary ammonium cation wherein each of $R^{N1}$, $R^{N2}$, and an additional $R^{N3}$ are independently an alkyl group or an aryl group, and with all other substituents as above. In embodiments, the phenethylamine is a quaternary salt, in which an additional $R^{N3}$ is connected to the nitrogen to which $R^{N1}$ and $R^{N2}$ are bound; wherein $R^{N3}$ is optionally substituted alkyl, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl.

In some embodiments, the additional active compound is a phenethylamine selected from the group consisting of α-ethyl-3,4,5-trimethoxy-phenethylamine (AEM), 4-allyloxy-3,5-dimethoxyphenethylamine (AL), 2,5-dimethoxy-4-methylthioamphetamine (ALEPH), 2,5-dimethoxy-4-ethylthioamphetamine (ALEPH-2), 2,5-dimethoxy-4-isopropylthioamphetamine (ALEPH-4), 2,5-dimethoxy-4-phenylthio-amphetamine (ALEPH-6), 2,5-dimethoxy-4-propylthio-amphetamine (ALEPH-7), 2,5-dimethoxy-α-ethyl-4-methy-lphenethylamine (ARIADNE), 3,4-diethoxy-5-methoxy-phenethylamine (ASB), 4-butoxy-3,5-dimethoxy-phenethylamine (B), 2,5-dimethoxy-4,N-dimethylamphetamine (BEATRICE), 2,5-bismethylthio-4-methyl-amphetamine (BIS-TOM), 4-bromo-2,5,β-trimethoxyphenethylamine (BOB), 2,5,β-trimethoxy-4-methylphenethylamine (BOD), β-methoxy-3,4-methylenedioxyphenethylamine (BOH), 2,5-dimethoxy-β-hydroxy-4-methylphenethylamine (BOHD), 3,4,5,β-tetramethoxy-phenethylamine (BOM), 4-bromo-3,5-dimethoxyamphetamine (4-Br-3,5-DMA), 2-bromo-4,5-methylenedioxyamphetamine (2-Br-4,5-MDA), 3,4-methylenedioxy-N-ethyl-amphetamine (MDEA), 4-bromo-2,5-dimethoxyphenethylamine (2C-B), 4-benzyloxy-3,5-dimethoxyamphetamine (3C-BZ), 4-chloro-2,5-dimethoxyphenethylamine (2C-C), 2,5-dimethoxy-4-methyl-phenethylamine (2C-D), 2,5-dimethoxy-4-ethylphenethylamine (2C-E), 3,5-dimethoxy-4-ethoxyamphetamine (3C-E), 2,5-dimethoxy-4-fluorophenethylamine (2C-F), 2,5-dimethoxy-3,4-dimethylphenethylamine (2C-G), 2,5-dimethoxy-3,4- trimethylene-phenethylamine (2C-G-3), 2,5-dimethoxy-3,4-tetramethylenephenethylamine (2C-G-4), 3,4-norbornyl-2,5-dimethoxy-phenethylamine (2C-G-5), 1,4-dimethoxynaphthyl-2-ethylamine (2C-G-N), 2,5-dimethoxyphenethylamine (2C-H), 4-iodo-2,5-dimethoxyphenethylamine (2C-I), 2,5-dimethoxy-4-nitro-phenethylamine (2C-N), 2,5-dimethoxy-4-isopropoxyphenethylamine (2C-O-4), 2,5-dimethoxy-4-propylphenethylamine (2C-P), 4-cyclopropylmethoxy-3,5-dimethoxyphenethylamine (CPM), 2,5-dimethoxy-4-methylselenophenethylamine (2C-SE), 2,5-dimethoxy-4-methylthiophenethylamine (2C-T), 2,5-dimethoxy-4-ethylthiophenethylamine (2C-T-2), 2,5-dimethoxy-4-isopropylthiophenethylamine (2C-T-4), 2,6-dimethoxy-4-isopropylthio-phenethylamine (psi-2C-T-4), 2,5-dimethoxy-4-propylthiophenethylamine (2C-T-7), 4-cyclopropylmethylthio-2,5-dimethoxyphenethylamine (2C-T-8), 4-(t)-butylthio-2,5-dimethoxy-phenethylamine (2C-T-9), 2,5-dimethoxy-4-(2-methoxyethylthio)phenethyl-amine (2C-T-13), 4-cyclopropylthio-2,5-dimethoxyphen-ethyl-amine (2C-T-15), 4-(s)-butylthio-2,5-dimethoxy-phenethylamine (2C-T-17), 2,5-dimethoxy-4-(2-fluoro-ethylthio)phenethylamine (2C-T-21), 3,5-dimethoxy-4-trideuteromethylphenethylamine (4-D), B,β-dideutero-3,4,5-trimethoxy-phenethylamine (β-D), 3,5-dimethoxy-4-methyl-phenethylamine (DESOXY), 2,4-dimethoxy-amphetamine (2,4-DMA), 2,5-dimethoxyamphetamine (2,5-DMA), 3,4-dimethoxyamphetamine (3,4-DMA), 2-(2,5-dimethoxy-4-methylphenyl)cyclopropylamine (DMCPA), 3,4-dimethoxy-β-hydroxyphenethylamine (DME), 2,5-dimethoxy-3,4-methylenedioxyamphetamine (DMMDA), 2,3-dimethoxy-4,5-methylenedioxy-amphetamine (DMMDA-2), 3,4-dimethoxyphenethylamine (DMPEA), 4-amyl-2,5-dimethoxyamphetamine (DOAM), 4-bromo-2,5-dimethoxyamphetamine (DOB), 4-butyl-2,5-dimethoxyamphetamine (DOBU), 4-chloro-2,5-dimethoxyamphetamine (DOC), 2,5-dimethoxy-4-(2-fluoroethyl)amphetamine (DOEF), 2,5-dimethoxy-4-ethyl-amphetamine (DOET), 4-iodo-2,5-dimethoxyamphetamine (DOI), 2,5-dimethoxy-4-methylamphetamine (DOM (STP)), 2,6-dimethoxy-4-methylamphetamine (psi-DOM), 2,5-dimethoxy-4-nitro-amphetamine (DON), 2,5-dimethoxy-4-propylamphetamine (DOPR), 3,5-dimethoxy-4-ethoxyphenethylamine (E), 2,4,5-triethoxyamphetamine (EEE), 2,4-diethoxy-5-methoxyamphetamine (EEM), 2,5-diethoxy-4-methoxyamphetamine (EME), 4,5-dimethoxy-2-ethoxyamphetamine (EMM), 2-ethylamino-1-(3,4-methylenedioxyphenyl)butane (ETHYL-J), 2-ethylamino-1-(3,4-methylenedioxyphenyl)pentane (ETHYL-K), 6-(2-aminopropyl)-5-methoxy-2-methyl-2,3-dihydrobenzofuran (F-2), 6-(2-aminopropyl)-2,2-dimethyl-5-methoxy-2,3-dihydrobenzofuran (F-22), N-hydroxy-N-methyl-3,4-methylenedioxyamphetamine (FLEA), 2,5-dimethoxy-3,4-(trimethylene)amphetamine (G-3), 2,5-dimethoxy-3,4-(tetramethylene)amphetamine (G-4), 3,6-dimethoxy-4-(2-aminopropyl)benzonorbornane (G-5), 2,5-dimethoxy-3,4-dimethyl-amphetamine (GANESHA), 1,4-dimethoxynaphthyl-2-isopropyl-amine (G-N), 2,5-dimethoxy-4-ethylthio-N-hydroxy-phenethylamine (HOT-2), 2,5-dimethoxy-N-hydroxy-4-(n)-propylthiophenethylamine (HOT-7), 4-(s)-butylthio-2,5-dimethoxy-N-hydroxy-phenethylamine (HOT-17), 2,5-dimethoxy-N,N-dimethyl-4-iodo-amphetamine (IDNNA), 2,3,4-trimethoxy-phenethylamine (IM), 3,5-dimethoxy-4-isopropoxyphenethylamine (IP), 5-ethoxy-2-methoxy-4-methylamphetamine (IRIS), 2-amino-1-(3,4-methylenedioxyphenyl)butane (J, BDB), 3-methoxy-4,5-methylenedioxyphenethylamine (LOPHOPHINE), 3,4,5-trimethoxy-phenethylamine (M), 4-methoxyamphetamine (4-MA, PMA), 2,N-dimethyl-4,5-methylenedioxyamphetamine (MADAM-6), 3,5-dimethoxy-4-methallyloxyphenethylamine (MAL), 3,4-methylenedioxyamphetamine (MDA), N-allyl-3,4-methylenedioxyamphetamine (MDAL), N-butyl-3,4-methylenedioxyamphetamine (MDBU), N-benzyl-3,4-methylenedioxy-amphetamine (MDBZ), N-cyclopropylmethyl-3,4-methylenedioxyamphetamine (MDCPM), N,N-dimethyl-3,4-methylenedioxyamphetamine (MDDM), N-ethyl-3,4-methylenedioxyamphetamine (MDE), N-(2-hydroxyethyl)-3,4-methylenedioxyamphetamine (MDHOET), N-isopropyl-3,4-methylenedioxyamphetamine (MDIP), N-methyl-3,4-methylenedioxy-amphetamine (MDMA), 3,4-ethylenedioxy-N-methylamphetamine (MDMC), N-methoxy-3,4-methylenedioxyamphetamine (MDMEO), N-(2-methoxyethyl)-3,4-methylenedioxyamphetamine (MDMEOET), 3,4-methylenedioxy-α,α,N-trimethyl-phenethylamine (MDMP), N-hydroxy-3,4-methylenedioxyamphetamine (MDOH), 3,4-methylenedioxy-phenethylamine (MDPEA), α,α-dimethyl-3,4-methylenedioxyphenethylamine (MDPH), 3,4-methylenedioxy-N-propargyl-amphetamine (MDPL), 3,4-methylenedioxy-N-propyl-amphetamine (MDPR), 3,4-dimethoxy-5-ethoxyphenethylamine (ME), 4,5-ethylenedioxy-3-methoxyamphetamine (MEDA), 4,5-diethoxy-2-methoxyamphetamine (MEE), 2,5-dimethoxy-4-ethoxyamphetamine (MEM), 4-ethoxy-3-methoxyphenethylamine (MEPEA), 5-bromo-2,4-dimethoxyamphetamine (META-DOB), 2,4-dimethoxy-5-methylthioamphetamine (META-DOT), 2,5-dimethoxy-N-methylamphetamine (METHYL-DMA), 4-bromo-2,5-dimethoxy-N-methylamphetamine (METHYL-DOB), 2-methylamino-1-(3,4-methylenedioxyphenyl)butane (METHYL-J, MBDB), 2-methylamino-1-(3,4-methylenedioxyphenyl)pentane (METHYL-K), 4-methoxy-N-methyl-amphetamine (METHYL-MA, PMMA), 2-methoxy-N-methyl-4,5-methylenedioxyamphetamine (METHYL-MMDA-2), 3-methoxy-4,5-methylenedioxyamphetamine (MMDA), 2-methoxy-4,5-methylenedioxy-amphetamine (MMDA-2), 2-methoxy-3,4-methylenedioxyamphetamine (MMDA-3a), 4-methoxy-2,3-methylenedioxyamphetamine (MMDA-3b), 2,4-dimethoxy-5-ethoxyamphetamine (MME), 3,4-dimethoxy-5-(n)-propoxyphenethylamine (MP), 2,5-dimethoxy-4-(n)-propoxyamphetamine (MPM), 4,5-dimethoxy-2-methylthioamphetamine (ORTHO-DOT), 3,5-dimethoxy-4-propoxyphenethylamine (P), 3,5-dimethoxy-4-phenethyloxyphenethylamine (PE), phenethylamine (PEA), 3,5-dimethoxy-4-(2-propynyloxy) phenethylamine (PROPYNYL), 3,5-diethoxy-4-methoxyphenethylamine (SB), 2,3,4,5-tetra-methoxyamphetamine (TA), 4-ethoxy-3-ethylthio-5-methoxyphenethylamine (3-TASB), 3-ethoxy-4-ethylthio-5-methoxyphenethylamine (4-TASB), 3,4-diethoxy-5-methylthio-phenethylamine (5-TASB), 4-(n)-butylthio-3,5-dimethoxy-phenethylamine (TB), 4-ethoxy-5-methoxy-3-methylthiophenethylamine (3-TE), 3,5-dimethoxy-4-ethylthio-phenethylamine (TE, 4-TE), 3,4-dimethoxy-2-methylthiophenethylamine (2-TIM), 2,4-dimethoxy-3-methylthio-phenethylamine (3-TIM), 2,3-dimethoxy-4-methylthiophenethylamine (4-TIM), 3,4-dimethoxy-5-methylthiophenethylamine (3-TM), 3,5-dimethoxy-4-methylthiophenethylamine (4-TM), 3,4,5-trimethoxy-amphetamine (TMA), 2,4,5-trimethoxyamphetamine (TMA-2), 2,3,4-trimethoxyamphetamine (TMA-3), 2,3,5-trimethoxyamphetamine (TMA-4), 2,3,6-trimethoxyamphetamine (TMA-5), 2,4,6-trimethoxyamphetamine (TMA-6), 4,5-dimethoxy-3-ethylthiophenethylamine (3-TME), 3-ethoxy-5-methoxy-4-methylthiophenethylamine (4-TME), 3-ethoxy-4-methoxy-5-methylthiophenethylamine (5-TME), 3,4-methylenedioxy-2-methylthioamphetamine (2T-MMDA-3a), 2-methoxy-4,5-methylenethiooxy-amphetamine (4T-MMDA-2), 2,4,5-trimethoxyphenethylamine (TMPEA), 4-ethyl-5-methoxy-2-methylthioamphetamine (2-TOET), 4-ethyl-2-methoxy-5-methylthio-amphetamine (5-TOET), 5-methoxy-4-methyl-2-methylthioamphetamine (2-TOM), 2-methoxy-4-methyl-5-methylthioamphetamine (5-TOM), 2-methoxy-4-methyl-5-methyl-sulfinylamphetamine (TOMSO), 3,5-dimethoxy-4-propylthio-phenethylamine (TP), 3,4,5-triethoxyphenethylamine (TRIS), 3-ethoxy-5-ethylthio-4-methoxyphenethylamine (3-TSB), 3,5-diethoxy-4-methylthiophenethylamine (4-TSB), 3,4-diethoxy-5-ethylthio-phenethylamine (3-T-TRIS), 3,5-diethoxy-4-ethylthiophenethylamine (4-T-TRIS), (R)-2,5-dimethoxy-4-iodoamphetamine (R-DOI), or a salt, hydrate, solvate, prodrug, stereoisomer, or tautomer thereof, or a combination thereof.

In embodiments, the additional active compound is an ergoline. In embodiments, the additional active compound is an ergot alkaloid. In embodiments, the additional active compound is a lysergamide. As understood in the art, lysergamides are compounds with the general structure below, wherein $R^{N1}$, $R^{N2}$, $R^1$, $R^2$, $R^4$, $R^6$, $R^7$, $R^8$, $R^9$, $R^{12}$, $R^{13}$, and $R^{14}$ are as taught herein and as generally understood in the art:

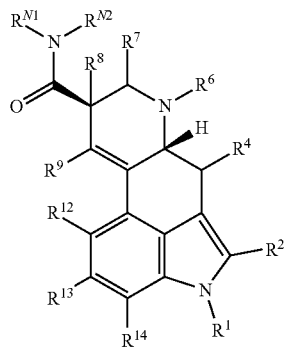

In some embodiments, $R^{N1}$, $R^{N2}$, $R^1$, $R^2$, $R^4$, $R^6$, $R^7$, $R^8$, $R^9$, $R^{12}$, $R^{13}$, and $R^{14}$ are each independently H, deuterium, halogen, optionally substituted alkyl, optionally substituted alkenyl, optionally substituted alkynyl, optionally substituted cycloalkyl, optionally substituted cycloalkenyl, optionally substituted aryl, or optionally substituted heterocyclyl. Additionally, any two of $R^{N1}$, $R^{N2}$, $R^1$, $R^2$, $R^4$, $R^6$, $R^7$, $R^1$, $R^9$, $R^{12}$, $R^{13}$, and $R^{14}$ and the intervening atoms can be taken together to form an optionally substituted cycloalkyl, optionally substituted cycloalkenyl, optionally substituted aryl, or optionally substituted heterocyclyl. In embodiments, the lysergamide is a quaternary salt, in which an additional $R^{6A}$ is connected to the nitrogen to which $R^6$ is bound; wherein $R^{6A}$ is optionally substituted alkyl, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl.

In some embodiments, the additional active compound is a lysergamide selected from the group consisting of lysergic acid diethylamide (i.e., LSD, LSD-25, LAD, Delysid), 6-ethyl-6-nor-lysergic acid diethylamide (ETH-LAD), 6-propynyl-6-nor-lysergic acid diethylamide (PARGY-LAD), 6-allyl-6-nor-lysergic acid diethylamide (AL-LAD), 6-propyl-6-nor-lysergic acid diethylamide (PRO-LAD), 6-isopropyl-6-nor-lysergic acid diethylamide (IP-LAD), 6-cylopropyl-6-nor-lysergic acid diethylamide (CIP-LAD), 6-butyl-6-nor-lysergic acid diethylamide (BU-LAD), 6-(2-fluoroethyl)-6-nor-lysergic acid diethylamide (FLUORO-ETH-LAD), 1-acetyl-lysergic acid diethylamide (i.e., ALD, ALD-52, N-acetyl-LSD), 1-propionyl-lysergic acid diethylamide (1P-LSD), 1-butyryl-lysergic acid diethylamide (1P-LSD), 1-valeryl-lysergic acid diethylamide (1V-LSD), 1-(cyclopropylmethanoyl)-lysergic acid diethylamide (1 cP-LSD), 1-(1,2-dimethylcyclobutane-1-carbonyl)-lysergic acid diethylamide (1D-LSD), 1-propionyl-6-allyl-6-nor-lysergic acid diethylamide (1P-AL-LAD), 1-(cyclopropyl-methanoyl)-6-allyl-6-nor-lysergic acid diethylamide (lcP-AL-LAD), 1-propionyl-6-ethyl-6-nor-lysergic acid diethylamide (1P-ETH-LAD), lysergic acid 2,4-dimethyl-azetidide (i.e., LA-SS-Az, LSZ), lysergic acid piperidide (LSD-Pip), and lysergic acid methylisopropyl amide (MIPLA).

Other tryptamines, phenethylamines, and lysergamides useful as additional active compounds for purposes of the invention and thus contemplated for inclusion therein will be as generally known in the art (see, e.g., Shulgin and Shulgin, PiHKAL: A Chemical Love Story, Transform Press (1991); TiHKAL, op cit.; Grob & Grigsby, Handbook of Medical Hallucinogens, 2021; Luethi & Liechti, Arch. Toxicol., 2020; 94: 1085-1133; Nichols, Pharmacol Reviews, 2016; 68(2):264-355; Glennon, Pharmacol Biochem Behavior, 1999; 64:251-256; each of which is incorporated by reference as if fully set forth herein).

VI. METHODS OF USE

In embodiments, disclosed methods and compositions are used to modulate neurotransmission. In embodiments, disclosed methods and compositions are used to treat a condition, such as a disease or a disorder. In embodiments, disclosed methods and compositions are used in the manufacture of a medicament for the therapeutic and/or the prophylactic treatment of a condition, such as a disease or a disorder. In embodiments, disclosed methods and compositions are administered as part of therapy. In embodiments, disclosed methods and compositions are administered along with psychotherapy, psychological support, or patient monitoring. In embodiments, disclosed methods and compositions are administered in a therapeutically effective amount to a subject having a condition, such as a disease or a disorder. In embodiments, the condition is a mental health disorder. In embodiments, the condition is a neurodegenerative disorder. In embodiments, the condition is a pain disorder. In embodiments, disclosed methods and compositions are administered to a subject that is healthy.

Herein, the terms "subject," "user," "patient," and "individual" are used interchangeably, and refer to any mammal, including murines, simians, mammalian farm animals, mammalian sport animals, and mammalian pets, such as canines and felines, although preferably humans. Such terms will be understood to include one who has an indication for which a compound, composition, or method described herein may be efficacious, or who otherwise may benefit by the disclosed invention. In general, all of the disclosed compounds, compositions, and methods will be appreciated to work for all individuals, although individual variation is to be expected, and will be understood. The disclosed methods of treatment also can be modified to treat multiple patients at once, including couples (e.g., as part of couples therapy), families, and groups (e.g., as part of group therapy). Hence, these terms will be understood to also mean two or more individuals.

In preferred embodiments, disclosed compositions are administered to a subject orally. In other embodiments, disclosed compositions may be mucosally (e.g., buccally, sublingually), rectally, subcutaneously, intravenously, intramuscularly, intranasally, by inhalation, or transdermally administered to a subject, as well as administered by a combination of any two or more such routes. In embodiments, when administered through one or more such routes, disclosed methods and compositions are useful in methods for treating a patient in need of such treatment.

A. Modulating Neurotransmission

In embodiments, disclosed compositions modulate neurotransmission in a subject, such as following administration of a therapeutically effective amount thereof to said subject. In embodiments, modulating neurotransmission by administering a disclosed compound to a subject treats a disease or disorder in the subject. In embodiments, modulating neurotransmission comprises regulating levels of monoamines in, for example, the CNS and peripheral tissues. In embodiments, modulating neurotransmission by administering a disclosed compound to a subject treats a disease or disorder in the subject.

In embodiments, disclosed compositions, when administered in a pharmacologically effective amount, inhibit the reuptake of one or more neurotransmitters. In embodiments, disclosed compositions, when administered in a pharmacologically effective amount, increase the extracellular concentration of one or more neurotransmitters, including the amount of extracellular serotonin, dopamine, or norepinephrine.

In some embodiments, disclosed methods and compositions are used to modulate neurotransmission, such as neurotransmission in a subject. In some methods herein, the disclosed compositions, when administered in a pharmacologically effective amount, thus affect monoaminergic neurotransmission, including serotonergic, dopaminergic, and noradrenergic neurotransmission. Accordingly, in some embodiments, the disclosed compositions, when administered in a pharmacologically effective amount, are used to treat a medical condition linked to dysregulation or inadequate functioning of neurotransmission, and in specific embodiments, are used to treat a medical condition linked to monoaminergic neurotransmission.

In embodiments, disclosed compositions, when administered in a pharmacologically effective amount (e.g., according to a disclosed method), act on or modulate one or more monoamine receptors, such as a serotonin receptor, a dopamine receptor, and a norepinephrine receptor. In embodiments, the compositions are agonists or partial agonists of a monoamine receptor, including any one or more of a serotonin receptor, a dopamine receptor, and a norepinephrine receptor.

B. Modulating Neuroplasticity

In some embodiments, disclosed methods and compositions are used to increase neural plasticity. Neural plasticity, also known as neuroplasticity or brain plasticity, refers to the brain's ability to change and adapt in response to experiences, learning, and environmental factors. Neural plasticity occurs through several mechanisms, including synaptic plasticity, which involves the strengthening or weakening of connections (synapses) between neurons. Synaptic plasticity is often associated with learning and memory processes. Another form of plasticity is called structural plasticity, which involves changes in the physical structure of neurons, such as the growth of new dendritic branches or the formation of new synapses.

Neural plasticity can be defined in terms of neuritogenesis, spinogenesis, and synaptogenesis in neurons. Neuritogenesis refers to the process by which neurons generate and extend their neurites (i.e., to form axons and dendrites). Neuritogenesis is a critical step in neural development and the formation of neuronal circuits. Spinogenesis refers to the formation of dendritic spines, which are small protrusions on the dendrites of neurons. Dendritic spines are crucial for synaptic connections and play a vital role in synaptic transmission and plasticity. Synaptogenesis refers to the formation of synapses, which is crucial for the establishment and refinement of neural circuits, and is a fundamental process underlying learning, memory, and information processing in the brain.

In some embodiments, administration of a disclosed composition to a subject (e.g., according to a disclosed method) results in an increase in the number of dendritic branches, the number of dendritic crossings, the density of dendritic spines, the density of synapses (i.e., number of synapses per neuron), or total dendritic length. These factors can be measured using a Sholl analysis and other techniques known to those of skill in the art (Ly C et al., *ACS Pharmacology & Translational Science*. 2020:4(2); 452-460).

C. Treatment

In some embodiments, disclosed methods and compositions are used to treat a medical condition, such as a disease or disorder. In some embodiments, disclosed compositions are used in the manufacture of a medicament to treat a condition, such as a disease or disorder. Also provided are methods of administering disclosed compounds and compositions to a subject having a condition, such as a disease or disorder, thereby treating said condition.

In some embodiments, disclosed methods and compositions are administered to a subject by one or more routes of administration, including, e.g., oral, mucosal, rectal, subcutaneous, intravenous, intramuscular, intranasal, inhaled, ocular, intraocular, topical, and transdermal routes. When administered through one or more of such routes, the compound(s) and composition(s) are useful in methods for treating a patient in need of such treatment.

In some embodiments are provided methods of treating and/or preventing a condition in a mammal, the method comprising administering to the mammal a therapeutically effective amount of a disclosed compound or pharmaceutical composition. In some embodiments, "treating" or "treatment" refers to treating a disease or disorder in a mammal, and preferably in a human, and includes causing a desired biological or pharmacological effect, such as: (a) preventing a disorder from occurring in a subject who may be predisposed to the disorder but has not yet been diagnosed with it; (b) inhibiting a disorder, i.e. arresting its development; (c) relieving a disorder, e.g., causing regression thereof; (d) protecting from or relieving a symptom or pathology caused by or related to a disorder; (e) reducing, decreasing, inhibiting, ameliorating, or preventing the onset, severity, duration, progression, frequency or probability of one or more symptoms or pathologies associated with a disorder; and (f) preventing or inhibiting of a worsening or progression of symptoms or pathologies associated with a disorder or comorbid with a disorder. In embodiments, treatment includes prevention. In other embodiments, treatment does not include prevention. Other such measurements, benefits, and surrogate or clinical endpoints, alone or in combination, will be understood to one of skill in view of the teachings herein and the knowledge in the art.

In some embodiments, disclosed methods and compositions are used to treat a central nervous system (CNS) disorder. Broadly, CNS disorders include diseases of the nervous system (e.g., movement disorders, neurodegenerative disorders) as well as mental, behavioral, and neurodevelopmental disorders, such as those characterized by the DSM-5, Merck Manual, ICD-11, or other such diagnostic resources known to those of skill.

1. Mental, Behavioral, or Neurodevelopmental Disorders

In some embodiments, disclosed methods and compositions are used to treat a mental, behavioral, or neurodevelopmental disorder. In some embodiments, disclosed methods and compositions are administered to a subject having a mental, behavioral, or neurodevelopmental disorder, thereby treating said mental, behavioral, or neurodevelopmental disorder. In some methods herein, disclosed compositions, when administered in a therapeutically effective amount, provide beneficial therapeutic effects for the treatment of a mental, behavioral, or neurodevelopmental disorder.

The ICD-11, which is incorporated by reference herein in its entirety, defines "mental, behavioral, or neurodevelopmental disorders" as syndromes characterized by clinically significant disturbance in an individual's cognition, emotional regulation, or behavior that reflects a dysfunction in the psychological, biological, or developmental processes that underlie mental and behavioral functioning. Such disorders include, but are not limited to, neurodevelopmental disorders, schizophrenia or other primary psychotic disorders, catatonia, mood disorders, anxiety or fear-related disorders, obsessive-compulsive or related disorders, disorders specifically associated with stress, dissociative disorders, feeding (or eating) disorders, elimination disorders, disorders of bodily distress or bodily experience, disorders due to substance use or addictive behaviors, impulse control disorders, disruptive behavior or dissocial disorders, personality disorders (and related traits), paraphilic disorders, factitious disorders, neurocognitive disorders, mental or behavioral disorders associated with pregnancy, childbirth or the puerperium, sleep-wake disorders, sexual dysfunctions, and gender incongruence.

A mental, behavioral, or neurodevelopmental disorder where otherwise undefined, will be understood to refer to the disorder as defined in the ICD-11. Within the category of mental, behavioral, or neurodevelopmental disorders, the term mental disorder (or "mental health disorder") generally refers to a disease condition that involves negative changes in emotion, mood, thinking, and/or behavior. In general, mental health disorders are characterized by clinically significant disturbances in cognition, emotion, behavior, or a combination thereof, resulting in impaired functioning, distress, or increased risk of suffering. Although the terms "mental disorder" and "mental health disorder," as well as terms that define specific diseases and disorders, generally shall refer to the criteria in the ICD-11, or a patient with a diagnosis based thereon, it will be appreciated that disclosed methods are equally applicable to patients having an equivalent underlying disorder, whether that disorder is diagnosed based on the criteria in ICD-11, ICD-10, DSM-5, or DSM-IV (each of which is incorporated by reference herein in its entirety) whether the diagnosis is based on other clinically acceptable criteria, or whether the patient has not yet had a formal clinical diagnosis.

In some embodiments, a microdose of a disclosed 5-HT$_{2A}$ agonist, or a salt thereof, and an effective amount of a MAOI, or a salt thereof, are used to treat a mental, behavioral, or neurodevelopmental disorder. In some embodiments, a psycholytic dose of a disclosed 5-HT$_{2A}$ agonist, or a salt thereof, and an effective amount of a MAOI, or a salt thereof, are used to treat a mental, behavioral, or neurodevelopmental disorder. In some embodiments, a psychedelic dose of a disclosed 5-HT$_{2A}$ agonist, or a salt thereof, and an effective amount of a MAOI, or a salt thereof, are used to treat a mental, behavioral, or neurodevelopmental disorder.

In some embodiments, disclosed methods and compositions are used to treat a mental health disorder. In some methods herein, disclosed compositions, when administered in a therapeutically effective amount, provide beneficial therapeutic effects for the treatment of a mental health disorder. In some embodiments, disclosed methods and compositions are used to reduce the symptoms of a mental health disorder. The symptoms of the mental health disorder to be treated shall be able to be determined by one of skill in the art, by reference to the general understanding of the art regarding that disorder.

In some embodiments, measures of therapeutic efficacy include reports by a subject or an observer. In some embodiments, measures of therapeutic efficacy include responses to a questionnaire. Non-limiting representative examples of applicable measures of symptom improvement include the Generalized Anxiety Disorder Scale-7 (GAD-7), Montgomery-Asberg Depression Rating Scale (MADRS), Global Assessment of Functioning (GAF) Scale, Clinical Global Impression (CGI), Substance Abuse Questionnaire (SAQ), Mini International Neuropsychiatric Interview 5 (MINI 5), Columbia Suicide Severity Rating Scale (C-SSRS), Patient Health Questionnaire (PHQ-9), Pittsburgh Sleep Quality Index (PSQI), Interpersonal Reactivity Index (IRI), Short Form (36) Health Survey (SF-36), Self-Compassion Scale (SCS), Trauma History Questionnaire (THQ), Beck Depression Index (BDI), and related subject- or observer-reported measures.

In some embodiments, disclosed methods and compositions are used to treat a neurodevelopmental disorder. In some embodiments, a "neurodevelopmental disorder" is a neurological and/or cognitive disorder that arises during the developmental period that involves significant difficulties in the acquisition and execution of specific neurological functions (e.g., intellectual, motor, language, or social functions). In some embodiments, the neurodevelopmental disorder is a disorder of intellectual development, a developmental speech or language disorder, autism spectrum disorder, a developmental learning disorder, a developmental motor coordination disorder, attention deficit hyperactivity disorder, or stereotypic movement disorder.

In some embodiments, disclosed methods and compositions are used to treat schizophrenia or another primary psychotic disorder. In general, these disorders are characterized by significant impairments in reality and alterations in behavior manifest in positive symptoms like persistent delusions, persistent hallucinations, disorganized thinking and speech, grossly disorganized behavior, as well as experience of negative symptoms such as blunted or flat affect and avolition and psychomotor disturbances. In embodiments, disclosed methods and compositions are used to treat schizophrenia, schizoaffective disorder, schizotypal disorder, acute and transient psychotic disorder, delusional disorder, or a substance-induced psychotic disorder.

In embodiments, disclosed methods and compositions are used to treat catatonia. In embodiments, "catatonia" refers to a category of syndromes characterized by the co-occurrence of several symptoms of decreased, increased, or abnormal psychomotor activity. In embodiments, the catatonia is associated with another mental disorder. In embodiments, the catatonia is induced by substances or medications.

In embodiments, disclosed methods and compositions are used to treat a mood disorder. As defined in the ICD-11, mood disorders are categorized according to the specific type(s) of mood episodes, and their pattern over time. The primary types of mood episodes are depressive episodes, manic episodes, mixed episodes, and hypomanic episodes. In embodiments, the mood disorder is a bipolar or related disorder (e.g., bipolar type I disorder, bipolar type II disorder, cyclothymic disorder), a depressive disorder, or a substance-induced mood disorder. In embodiments, the mood disorder is a depressive disorder. In embodiments, the depressive disorder is single-episode depressive disorder, major depressive episode disorder, persistent depressive disorder (formally known as dysthymia), disruptive mood dysregulation disorder, premenstrual dysphoric disorder, postpartum depression, substance/medication-induced depressive disorder, depressive disorder due to another medical condition, seasonal affective disorder, mixed depressive and anxiety disorder, or an unspecified depressive disorder. In embodiments, depression is assessed through the Patient Health Questionnaire-9 (PHQ-9) screening tool, Montgomery-Asberg Depression Rating Scale (MADRS), Hamilton Depression Rating Scale, Beck Depression Inventory (BDI-II), Zung Self-Rating Depression Scales (SDS), Major Depression Inventory (MDI), Center for Epidemiologic Studies Depression Scale (CED-D), Rome Depression Inventory (RDI), Hamilton Rating Scale for Depression (HRSD), and Carroll Rating Scale (CRS).

In embodiments, a microdose of a disclosed 5-HT$_{2A}$ agonist, or a salt thereof, and an effective amount of a MAOI, or a salt thereof, are used to treat major depressive disorder (MDD). In embodiments, a psychedelic dose of a disclosed 5-HT$_{2A}$ agonist, or a salt thereof, and an effective amount of a MAOI, or a salt thereof, are used to treat MDD. In embodiments, a psycholytic dose of a disclosed 5-HT$_{2A}$ agonist, or a salt thereof, and an effective amount of a MAOI, or a salt thereof, are used to treat MDD.

In embodiments, a microdose of a disclosed 5-HT$_{2A}$ agonist, or a salt thereof, and an effective amount of a MAOI, or a salt thereof, are used to treat treatment-resistant depression (TRD). In embodiments, a psychedelic dose of a disclosed 5-HT$_{2A}$ agonist, or a salt thereof, and an effective amount of a MAOI, or a salt thereof, are used to treat TRD. In embodiments, a psycholytic dose of a disclosed 5-HT$_{2A}$ agonist, or a salt thereof, and an effective amount of a MAOI, or a salt thereof, are used to treat TRD.

In embodiments, a microdose of a disclosed 5-HT$_{2A}$ agonist, or a salt thereof, and an effective amount of a MAOI, or a salt thereof, are used to treat PTSD. In embodiments, a psychedelic dose of a disclosed 5-HT$_{2A}$ agonist, or a salt thereof, and an effective amount of a MAOI, or a salt thereof, are used to treat PTSD. In embodiments, a psycholytic dose of a disclosed 5-HT$_{2A}$ agonist, or a salt thereof, and an effective amount of a MAOI, or a salt thereof, are used to treat PTSD.

In embodiments, a microdose of a disclosed 5-HT$_{2A}$ agonist, or a salt thereof, and an effective amount of a MAOI, or a salt thereof, are used to treat prolonged grief disorder. In embodiments, a psychedelic dose of a disclosed 5-HT$_{2A}$ agonist, or a salt thereof, and an effective amount of a MAOI, or a salt thereof, are used to treat prolonged grief disorder. In embodiments, a psycholytic dose of a disclosed 5-HT$_{2A}$ agonist, or a salt thereof, and an effective amount of a MAOI, or a salt thereof, are used to treat prolonged grief disorder.

In embodiments, a microdose of a disclosed 5-HT$_{2A}$ agonist, or a salt thereof, and an effective amount of a MAOI, or a salt thereof, are used to treat ADHD. In embodiments, a psychedelic dose of a disclosed 5-HT$_{2A}$ agonist, or a salt thereof, and an effective amount of a MAOI, or a salt thereof, are used to treat ADHD. In embodiments, a psycholytic dose of a disclosed 5-HT$_{2A}$ agonist, or a salt thereof, and an effective amount of a MAOI, or a salt thereof, are used to treat ADHD.

In embodiments, disclosed methods and compositions are used to treat an anxiety or fear-related disorder. An "anxiety disorder" refers to a class of mental disorders that induce excessive or abnormal fear, dread, or worry. In embodiments, the anxiety disorder is selected from the group consisting of generalized anxiety disorder, panic disorder, agoraphobia, specific phobia, social anxiety disorder, separation anxiety disorder, selective mutism, or a substance-induced anxiety disorder.

In embodiments, disclosed methods and compositions are used to treat an obsessive-compulsive or related disorder. In general, these disorders are characterized by repetitive thoughts and behaviors, such as cognitive phenomena (obsessions, intrusive thoughts and preoccupations). In embodiments, the disorder is characterized by a compulsive need to accumulate possessions and distress related to discarding them (i.e., hoarding disorder). In embodiments, the disorder is body-focused and can be characterized by recurrent and habitual actions (hair-pulling, skin-picking). In embodiments, the disorder is obsessive-compulsive disorder, body dysmorphic disorder, olfactory reference disorder, hypochondriasis, hoarding disorder, a body-focused repetitive behavior disorder, or a substance-induced obsessive-compulsive disorder.

In embodiments, disclosed methods and compositions are used to treat a disorder associated with stress. In embodiments, the disorder associated with stress has an identifiable stressor that is a causal factor, like exposure to a stressful or traumatic event, or a series of such events or adverse experiences. Stressors may be within the normal range of life experiences (e.g., divorce, socioeconomic problems), or from a threatening or traumatizing experience. In general, the nature and duration of the symptoms that arise in response to the stressor can distinguish the disorder from everyday stress. In embodiments, disclosed methods and compositions are used to treat post-traumatic stress disorder, complex post-traumatic stress disorder, prolonged grief disorder, adjustment disorder, reactive attachment disorder, or disinhibited social engagement disorder.

In embodiments, disclosed methods and compositions are used to treat a dissociative disorder. Dissociative disorders can be characterized by involuntary disruption or discontinuity in the normal integration of one or more of the following: identity, sensations, perceptions, affects, thoughts, memories, control over body movements, or behavior. In some subjects, dissociative disorder symptoms can be severe, and may result in impairment in personal, social, educational, occupational or other areas of functioning. In embodiments, disclosed methods and compositions are used to treat dissociative neurological symptom disorder, dissociative amnesia (including amnesia with dissociative fugue and without dissociative fugue), trance disorder, possession trance disorder, dissociative identity disorder, partial dissociative identity disorder, or depersonalization-derealization disorder.

In embodiments, disclosed methods and compositions are used to treat a feeding or eating disorder. Feeding or eating disorders generally involve abnormal eating or feeding behaviors that are not explained by another health condition, and are not developmentally appropriate or culturally sanctioned. These disorders can involve preoccupation with food as well as body weight and shape concerns. In embodiments, disclosed methods and compositions are used to treat anorexia nervosa (including anorexia with significantly low body weight, anorexia with dangerously low body weight, or anorexia in recovery with normal body weight), bulimia nervosa, binge eating disorder, avoidant-restrictive food intake disorder, pica, or rumination-regurgitation disorder.

In embodiments, disclosed methods and compositions are used to treat an elimination disorder. Elimination disorders include, for example, the repeated voiding of urine into clothes or bed, and the repeated passage of feces in inappropriate places once the individual has reached a developmental age when continence is ordinarily expected. In embodiments, disclosed methods and compositions are used to treat enuresis (including nocturnal enuresis, diurnal enuresis, and nocturnal and diurnal enuresis) or encopresis (including both with encopresis constipation or overflow incontinence, and encopresis without constipation or overflow incontinence).

In embodiments, disclosed methods and compositions are used to treat a disorder of bodily distress or bodily experience. Disorders of bodily stress typically involve bodily symptoms that the subject finds distressing and to which the subject devotes excessive attention. Bodily integrity dysphoria typically involves a disturbance in the person's experience of the body manifested by persistent discomfort or intense feelings of body configuration. In embodiments, disclosed methods and compositions are used to treat a bodily distress disorder (including mild, moderate, and severe bodily distress disorder) or body integrity dysphoria.

In embodiments, disclosed methods and compositions are used to treat a disorder due to substance use or addictive behaviors. Disorders due to substance use or addictive behaviors are mental and/or behavioral disorders that develop predominantly as a result of the use of psychoactive substances (including medications and illegal or illicit substances), or specific repetitive rewarding and reinforcing behaviors. In embodiments, disclosed methods and compositions are used to treat disorders due to substance use (i.e., a substance use disorder, or SUD). In embodiments, the substance use disorder (SUD) is associated with alcohol, cannabis, synthetic cannabinoids, opioids, sedatives, hypnotics or anxiolytics, cocaine, stimulants (e.g., amphetamines, methamphetamines, methcathinone, synthetic cathinones, caffeine), hallucinogens, nicotine, volatile inhalants, MDMA or MDA, dissociative drugs like ketamine and phencyclidine, or another substance (including medications and non-psychoactive substances). In embodiments, the SUD is selected from alcohol use disorder, cannabis use disorder, caffeine use disorder, phencyclidine use disorder, inhalants use disorder, opioids use disorder, sedatives use disorder, hypnotics use disorder, anxiolytics use disorder, stimulants use disorder, and tobacco use disorder. In embodiments, the SUD is alcohol use disorder. In embodiments, the SUD is cannabis use disorder. In embodiments, the SUD is caffeine use disorder. In embodiments, the SUD is phencyclidine use disorder. In embodiments, the SUD is inhalant use disorder. In embodiments, the SUD is opioids use disorder. In embodiments, the SUD is sedatives use disorder. In embodiments, the SUD is hypnotics use disorder. In embodiments, the SUD is anxiolytics use disorder. In embodiments, the SUD is stimulants use disorder. In embodiments, the SUD is tobacco use disorder. In embodiments, the SUD is alcohol use disorder, wherein said alcohol use disorder is selected from alcohol abuse, alcohol dependence, and alcoholism. In embodiments, the disorder is associated with another addictive behavior (e.g., gambling disorders, gaming disorder). In embodiments, a SUD can be screened using a Screening to Brief Intervention (S2BI), Alcohol, Smoking, and Substance Involvement Screening Test (ASSIST), Brief Screener for Alcohol, Tobacco, and other Drugs (BSTAD), Tobacco, Alcohol, Prescription medication, and other Substance use (TAPS), the Opioid Risk Tool-OUD (ORT-OUD) Chart, Drug Abuse Screen Test (DAST-10), and Tobacco, Alcohol, Prescription medication, and other Substance use (TAPS).

In embodiments, disclosed methods and compositions are used to treat an impulse control disorder. In general, impulse control disorders are characterized by the repeated failure to resist an impulse, drive, or urge to perform an act that is rewarding to the subject despite negative long-term consequences, such as harm to the subject or a significant impairment in important areas of the subject's functioning. In embodiments, impulse control behaviors include fire-setting, stealing, inappropriate sexual behavior, and explosive outbursts. In some embodiments, disclosed methods and compositions are used to treat pyromania, kleptomania, compulsive sexual behavior disorder, or intermittent explosive disorder.

In some embodiments, disclosed methods and compositions are used to treat a disruptive behavior disorder or a dissocial disorder. Such disorders may be broadly characterized by persistent behavior problems that range from persistently defiant, disobedient, provocative or spiteful behaviors to behaviors that violate the rights of others or norms, rules, or laws. In some embodiments, disclosed methods and compositions are used to treat oppositional defiant disorder (including oppositional defiant disorder with chronic irritability-anger and oppositional defiant disorder without chronic irritability-anger) or conduct-dissocial disorder (including childhood-onset conduct-dissocial disorder and adolescent-onset conduct-dissocial disorder).

In some embodiments, disclosed methods and compositions are used to treat a personality disorder. Personality disorders may be generally characterized by problems in perceiving one's identity, self-worth, accuracy of self-view, and self-discretion that is manifest in patterns of cognition, emotional experience, emotional expression, and maladaptive behavior. In embodiments, disclosed methods and compositions are used to treat a mild, moderate, or severe personality disorders. In embodiments, disclosed methods and compositions are used to treat a prominent personality trait or patterns (e.g., negative affectivity, detachment, dissociality, disinhibition, anankastia, borderline pattern). In embodiments, the personality disorder is antisocial personality disorder, avoidant personality disorder, borderline personality disorder, dependent personality disorder, histrionic personality disorder, masochistic or sadistic behavior, narcissistic personality disorder, obsessive-compulsive personality disorder, paranoid personality disorder, psychopathy, sociopathy, schizoid personality disorder, or schizotypal personality disorder.

In embodiments, disclosed methods and compositions are used to treat a paraphilic disorder. Paraphilic disorders can be characterized by persistent and intense patterns of atypical sexual arousal, the focus of which involves others whose age or status renders them unwilling or unable to consent. In embodiments, disclosed methods and compositions are used to treat exhibitionistic disorder, voyeuristic disorder, pedophilic disorder, coercive sexual sadism disorder, frotteuristic disorder, other paraphilic disorders involving non-consenting individuals, or paraphilic disorders involving solitary behavior or consenting individuals.

In embodiments, disclosed methods and compositions are used to treat a factitious disorder. In general, factitious disorders may be characterized by intentionally feigning, falsifying, inducing or aggravating medical, psychological, or behavior signs and symptoms or injury to oneself or another person. Subjects with factitious disorders may seek treatment or otherwise present themselves or another person as ill, injured, or impaired. In embodiments, disclosed methods and compositions are used to treat factitious disorder imposed on self or a factitious disorder imposed on another.

In embodiments, disclosed methods and compositions are used to treat a neurocognitive disorder. Neurocognitive disorders may be characterized by primary clinical defects in cognitive functioning that are acquired (rather than developmental), and therefore the subject experiences a decline from a previously attained level of functioning. In embodiments, disclosed methods and compositions are used to treat delirium. In embodiments, the delirium is associated with another disease or disorder. In embodiments, the delirium is associated with a psychoactive substance (including medications and illicit or illegal substances). In embodiments, disclosed methods and compositions are used to treat mild neurocognitive disorder. In embodiments, disclosed methods and compositions are used to treat an amnestic disorder. In embodiments, the amnestic disorder is associated with another disease or disorder. In embodiments, the delirium is associated with a psychoactive substance (including medications and illicit or illegal substances). In embodiments, disclosed methods and compositions are used to treat dementia. In embodiments, the dementia is associated with Alzheimer's disease, Parkinson's disease, cerebrovascular disease, Lewy body disease, a psychoactive substance (including medications and illicit or illegal substances). In embodiments, disclosed methods and compositions are used to treat a behavioral or psychological disturbance associated with dementia. In embodiments, dementia is assessed using a Functional Activities Questionnaire (FAQ), Ascertain Dementia 8 (AD8), Mini-Cog, Mini-Mental State Exam (MMSE), the Montreal Cognitive Assessment (MoCA), and the Neuropsychiatric Inventory Questionnaire (NPI-Q).

In embodiments, disclosed methods and compositions are used to treat a mental or behavioral disorder associated with pregnancy, childbirth, or the puerperium. In embodiments, the syndrome associated with pregnancy or the puerperium involves significant mental and behavioral features, including a depressive symptom. In embodiments, the disorder includes psychotic symptoms. In embodiments, disclosed methods and compositions are used to treat mental or behavioral disorders associated with pregnancy, childbirth or the puerperium, with psychotic symptoms. In embodiments, disclosed methods and compositions are used to treat mental or behavioral disorders associated with pregnancy, childbirth or the puerperium, without psychotic symptoms.

In embodiments, disclosed methods and compositions are used to treat a sleep-wake disorder. In general, sleep-wake disorders are associated with difficulty initiating or maintaining sleep (e.g., insomnia), excessive sleepiness (e.g., hypersomnolence disorders), respiratory disturbance during sleep (e.g., sleep-related breathing disorders (SRBDs), such as obstructive sleep apnea (OSA), central sleep apnea (CSA), sleep-related hypoventilation disorders, sleep-related hypoxemia disorder, snoring, catathrenia, Cheyne-Stokes breathing, and sleep-disordered breathing), disorders of the sleep-wake schedule (e.g., circadian rhythm sleep-wake disorders), abnormal movements during sleep, or problematic behavioral or psychological events that occur while falling asleep, during sleep, or upon arousal from sleep (e.g., parasomnia disorders). In embodiments, disclosed methods and compositions are used to treat an insomnia disorder, a hypersomnolence disorder, a sleep-related breathing disorder, a circadian rhythm sleep-wake disorder, or a parasomnia disorder.

In embodiments, disclosed methods and compositions are used to treat sexual dysfunction. Sexual dysfunctions can be defined as syndromes wherein a subject may have difficulty experiencing personally satisfying, non-coercive sexual activities. In embodiments, disclosed methods and compositions are used to treat hypoactive sexual desire dysfunction, sexual arousal dysfunction, orgasmic dysfunction, ejaculatory dysfunction, or sexual dysfunction associated with pelvic organ prolapse.

In embodiments, a disclosed compound or composition is administered together with psychotherapy, such as psychosocial or behavioral therapy, including any of (or adapted from any of) cognitive behavioral therapy (e.g., as described in Arch Gen Psychiatry 1999; 56:493-502), interpersonal therapy (e.g., as described in Psychol Addict Behav 2009; 23(1):168-174), contingency management based therapy (e.g., as described in Psychol Addict Behav 2009; 23(1): 168-174; in J Consul Clin Psychol 2005; 73(2):354-59; or in Case Reports in Psychiatry, Vol. 2012, Article ID 731638), motivational interviewing based therapy (e.g., as described in J Consul Clin Psychol 2001; 69(5):858-62), meditation based therapy, such as transcendental meditation based therapy (e.g., as described in J Consul Clin Psychol 2000; 68(3): 515-52), or the therapeutic approach used by MAPS to treat patients with PTSD (e.g., as in Mithoefer, M (2017). Manual for MDMA-Assisted Psychotherapy in the Treatment of Post-traumatic Stress Disorder).

In embodiments, disclosed methods and compositions may be administered in conjunction with or as an adjunct to psychotherapy. In other embodiments, psychotherapy is neither necessitated nor desired, or no specific type of psychotherapy is necessitated or desired, however any of the disclosed methods can be used in combination with one or more psychotherapy sessions. In embodiments, a subject may take a microdose of a disclosed psychedelic compound or composition without the participation or guidance of a therapist. In embodiments, a subject may take a psychedelic dose of a disclosed psychedelic compound or composition with the participation or guidance of a therapist. In embodiments, a subject may take a psycholytic dose of a disclosed psychedelic compound or composition with the participation or guidance of a therapist, including one or more preparation and integration sessions, in addition to the drug administration session(s). The flexibility to participate in specific therapies, as well as to choose between any such therapies (or to decide to forgo any specific therapy), while still receiving clinically significant therapeutic effects, is among the advantages of some embodiments of the disclosure. Furthermore, a patient can participate in numerous other therapeutically beneficial activities, where such participation follows or is in conjunction with the administration of the composition, including breathing exercises, meditation and concentration practices, focusing on an object or mantra, listening to music, physical exercise, stretching or bodywork, journaling, grounding techniques, positive self-talk, or engaging with a pet or animal, and it should be understood that such participation can occur with or without the participation or guidance of a therapist.

In embodiments, "psychotherapy" is specifically "psychedelic-assisted psychotherapy." Psychedelic-assisted psychotherapy, broadly, includes a range of related approaches that involve at least one session where the patient ingests a psychedelic and is monitored, supported, or otherwise engaged by one or more trained mental health professionals while under the effects of the psychedelic (see, e.g., Schenberg, 2018). In embodiments, psychedelic-assisted psychotherapy includes psychedelic therapy and psycholytic therapy. "Psychedelic therapy" refers to a form of psychotherapeutic treatment wherein a subject attends psychotherapy sessions which involve taking high dosage amounts of a psychedelic compound, such as a disclosed $5\text{-}HT_{2A}$ agonist, or composition thereof to induce a significantly altered state of consciousness. In embodiments, a subject may be administered a psychedelic dose of a disclosed $5\text{-}HT_{2A}$ agonist or composition thereof during a psychedelic therapy session. In embodiments, a subject during a drug administration session as part of psychedelic therapy may experience hallucinogenic or psychedelic effects. In embodiments, a subject may attend three single-dose psychotherapy sessions in a hospital setting over the course of 12 weeks. "Psycholytic therapy" may in some embodiments refer to a form of psychotherapeutic treatment wherein a subject attends psychotherapy sessions which involve administration of relatively medium or low dosage amounts of a disclosed $5\text{-}HT_{2A}$ agonist or composition thereof to induce a mildly altered state of consciousness. In embodiments, a subject may be administered a psycholytic dose of a disclosed $5\text{-}HT_{2A}$ agonist or composition during a psycholytic therapy session. In embodiments, a subject attending psycholytic therapy may experience feelings of relaxation, comfort, warmth, an elevation in mood, and reduced anxiety. In embodiments, a subject attending psycholytic therapy does not experience pre-hallucinogenic effects. Protocols have been developed for the standardization of procedures which emphasize a high degree of care (see, e.g., Johnson, 2008), such as the therapeutic approach used by MAPS to treat patients with PTSD using MDMA (e.g., as described in Mithoefer, 2017).

In embodiments, the psychotherapy conducted with disclosed methods and compositions are conducted in widely spaced sessions. These sessions can be as frequently as weekly but are more often approximately monthly or less frequently. In most cases, a small number of sessions, on the order of one to three, is needed for a patient to experience significant clinical progress, as indicated, e.g., by a reduction in symptoms of the mental health disorder being treated. In embodiments, psychotherapy comprises multiple sessions, during some of which disclosed methods and compositions are administered ("drug-assisted psychotherapy"); in others, the patient participates in psychosocial or behavioral therapy without concomitant administration of a drug, or without administration of a disclosed compound or composition.

In embodiments, a disclosed compound or composition is administered together with standardized psychological treatment or support, which refers to any accepted modality of standard psychotherapy or counseling sessions, whether once a week, twice a week, or as needed; whether in person or virtual (e.g., over telemedicine or by means of a web program or mobile app); and whether with a human therapist or a virtual or AI "therapist." Herein, "therapist" refers to a person who treats a patient using the disclosed compositions and methods, whether that person is a psychiatrist, clinical psychologist, clinical therapist, registered therapist, psychotherapist, or other trained clinician, counselor, facilitator, or guide, although it will be understood that certain requirements will be appropriate to certain aspects of the drug-assisted therapy (e.g., prescribing, dispensing, or administering a drug, offering psychotherapeutic support). In embodiments, a "person" may also include an AI.

In embodiments, a patient is administered a psychedelic dose of a disclosed $5\text{-}HT_{2A}$ agonist during psychedelic therapy. In embodiments, a patient is administered a psycholytic dose of a disclosed $5\text{-}HT_{2A}$ agonist during psycholytic therapy. In embodiments, a patient is administered a psychedelic dose of a disclosed $5\text{-}HT_{2A}$ agonist during psychedelic therapy, wherein said $5\text{-}HT_{2A}$ agonist is DMT. In embodiments, a patient is administered a psycholytic dose of a disclosed $5\text{-}HT_{2A}$ agonist during psycholytic therapy, wherein said $5\text{-}HT_{2A}$ agonist is DMT.

In embodiments, a patient will participate in a treatment protocol or a disclosed method, or be administered a disclosed composition as part of such a method, if the patient meets certain specified inclusion criteria, does not meet certain specified exclusion criteria, does not meet any specified withdrawal criteria during the course of treatment, and otherwise satisfies the requirements of the embodiment of the invention as claimed.

Preferably, where the disclosed pharmaceutical compositions are administered, such administration occurs without or with reduced risk of side effects that would require physician supervision, and therefore allow for treatment at home or otherwise outside of a clinic and without the need for such supervision, and/or additionally without the requirement of adjunctive psychotherapy (although it also may be provided in certain embodiments herein).

In embodiments, personalized approaches (i.e., "personalized" or "precision" medicine) may be used, based on individual characteristics, including drug metabolism (e.g., CYP2D6 or CYP3A4) or individual genetic variation. The term "genetic variation" refers to a change in a gene sequence relative to a reference sequence (e.g., a commonly-found and/or wild-type sequence). Genetic variation may be recombination events or mutations such as substitution/deletion/insertion events like point and splice site mutations.

In one embodiment, the genetic variation is a genetic variation in one or more cytochrome P450 (CYP or CYP450) enzymes that affects drug metabolism, including metabolism of a disclosed composition, and including CYP1A2, CYP2C$_9$, CYP2D6, CYP2C$_{19}$, CYP3A4 and CYP3A5. Other examples of CYP enzymes include CYP1A1, CYP1B1, CYP2A6, CYP2A13, CYP2B6, CYP2C$_8$, CYP2C$_9$, CYP2C$_{18}$, CYP2E1, CYP2G1, CYP2J2, CYP2R1, CYP2S1, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

In embodiments, a disclosed composition is taken together with a compound that is metabolized by the same CYP enzyme(s) as the disclosed composition, so as to permit a lower dose to be taken, increase the effective bioavailability of one or both, or otherwise affect drug metabolism or pharmacokinetics. In embodiments, the dose of a disclosed composition is adjusted, such as reduced, when administered to a subject known to be a poor metabolizer of an active compound in the composition (e.g., having a genetic variation in CYP2D6 and/or CYP3A4), or increased when administered to a subject known to be a rapid metabolizer. In embodiments, a patient is tested using ordinary means known to those of skill to determine if the patient is a poor or rapid metabolizer for one or more such CYP enzymes.

In one embodiment, the genetic variation is a genetic variation in metabotropic glutamate receptor type 5 (mGluR5), which has been implicated in mood and anxiety symptoms in humans. In another embodiment, the genetic variation is one or more single nucleotide polymorphisms (SNPs) in the FKBP5 gene that are associated with elevated levels of FKBP51 protein relative to persons lacking such SNPs. The FKBP5 gene has been implicated in responses to stress and trauma, and such SNPs are correlated with susceptibility to certain depression, PTSD, and anxiety disorders. In embodiments, a genetic variation is an inclusion criteria for the administration of a disclosed compound. In embodiments, a genetic variation is an exclusion criteria for the administration of a disclosed compound.

In one embodiment, the mammal being treated has altered epigenetic regulation of a gene, the expression of which is associated with a mental health condition or susceptibility to a mental health treatment, such as the SIGMAR1 gene for the non-opioid sigma-1 receptor.

2. Neurodegenerative Disorders

In some embodiments, disclosed methods and compositions are used to treat a neurodegenerative disorder. In some methods herein, the disclosed compositions, when administered in a therapeutically effective amount, provide beneficial therapeutic effects for the treatment of a neurodegenerative disorder.

The term "neurodegenerative disorder" refers to a class of progressive, chronic, and debilitating conditions characterized by the gradual loss of structure and function of neurons within the central nervous system (CNS) or peripheral nervous system (PNS). These disorders involve the degeneration, impairment, or death of neuronal cells, leading to a decline in cognitive, motor, and/or sensory abilities.

Neurodegenerative disorders can be classified according to primary clinical features, e.g., dementia, parkinsonism, or motor neuron disease, anatomic distribution of neurodegeneration, e.g., frontotemporal degenerations, extrapyramidal disorders, or spinocerebellar degenerations, or principal molecular abnormality (Dugger B, Dickson D W. Pathology of Neurodegenerative Diseases. Cold Spring Harbor Perspectives in Biology. 2017:9(7); a028035). These disorders may involve various etiologies, including presence of pathogenic proteins, age, environmental stressors, and genetic predisposition (Armstrong R. Folia Neuropathologica. 2020: 58(2); 93-112).

Without being bound by theory, a feature of neurodegenerative conditions is neuronal cell death, which, among other aspects, is implicated in the promotion of inflammation. (See, e.g., Chan et al., Annu Rev Immunol. 2015; 33:79-106; Chi et al., Int J Mol Sci. 2018; 19(10):3082. Neurodegeneration may be assessed, e.g., by measuring markers of neuronal loss, such as cerebrospinal fluid markers, e.g., visinin-like protein 1 (VILIP-1), tau, and p-tau181 (Tarawneh et al., Neurol. 2015; 72(6):656-665). Anti-inflammatory pathways could involve activation of 5-HT$_{2A}$ receptors. (See, e.g., Figiel et al., Psychedelics & Neurochemistry. Journal of Neurochemistry. 2021; 162(1):89-108; Calleja-Conde et al., Transl. Psychiatry 2020; 10:331; and Olson et al., Psychedelics & Neurochemistry. Journal of Neurochemistry. 2021; 162(1): 109-27). Recent evidence suggests a role of 5-HT$_{2A}$ receptors, which are found throughout the body, including in both the central nervous system and peripheral tissues, in mediating the termination of the inflammatory response (Flanagan & Nichols. Int Rev Psychiatry. 2018 August; 30(4):363-375). In the periphery, 5-HT$_{2A}$ receptors are found in multiple immune related tissues such as the spleen, thymus, and circulating lymphocytes, as well as in components of both the innate and adaptive immune systems (Stefulj et al., Brain Behav Immun. 2000 September; 14(3):219-24; Cloëz-Tayarani et al., Int Immunol. 2003 February; 15(2):233-40).

Some 5-HT$_{2A}$ agonists, such as DMT, also target the Sigma-1 receptor, which is reported to protect cells from various insults. For example, endoplasmic reticulum stress (ERS) induces up-regulation of Sigma-1 expression. (Figiel et al., 2021). ERS damage is reported in several neurodegenerative disorders. Id. In addition, inflammation-based blood-brain barrier leakage could be prevented to some degree by the presence of 5-HT$_{2A}$ agonists, such as DMT and 5-MeO-DMT. Id. In another example, Alzheimer's disease may be assessed using any of biomarket PET scans, blood tests, CSF tests, and neuropsychological assessments, e.g., to assess the presence of amyloid plaque and aggregated tau. Cognitive decline may also be used as a measure of neurodegeneration. Methods for assessing cognitive decline, e.g., comprehensive neuropsychological testing, are known. Exemplary cognitive evaluations include Mini-Mental State Examination (MMSE) and Montreal Cognitive Assessment (MoCA). See Toh et al., Transl Neurodegener. 2014; 3:15. Cognitive decline and the progression of disease state also may be assessed using a condition-specific measure, e.g., the Unified Huntington's Disease Rating Scale (UHDRS).

In embodiments, a microdose of a disclosed 5-HT$_{2A}$ agonist, or a salt thereof, and an effective amount of a MAOI, or a salt thereof, are used to treat a neurodegenerative disorder. In embodiments, a psycholytic dose of a disclosed 5-HT$_{2A}$ agonist, or a salt thereof, and an effective amount of a MAOI, or a salt thereof, are used to treat a neurodegenerative disorder. In embodiments, a psychedelic dose of a disclosed 5-HT$_{2A}$ agonist, or a salt thereof, and an effective amount of a MAOI, or a salt thereof, are used to treat a neurodegenerative disorder.

In some embodiments, the neurodegenerative disorder is any of Alzheimer's disease (AD); corticobasal degeneration (CBD); amyotrophic lateral sclerosis or Charcot's disease; chronic traumatic encephalopathy; corticobasal degeneration; a form of dementia, such as frontotemporal dementia (FTD), Lewy body dementia, tangle-predominant senile dementia, Pick's disease (PiD), argyrophilic grain disease, Guam parkinsonism-dementia complex, frontotemporal dementia with parkinsonism-17 (FTDP-17) and vascular dementia; Huntington's disease; Lytico-Bodig disease; mild cognitive impairment (MCI); multiple sclerosis; ischemic cerebral infarction; hemorrhagic cerebral infarction; frontotemporal lobar degeneration; primary progressive aphasia; multiple systems atrophy; Creutzfeld-Jakob disease; a motor neuron disease, such as amyotrophic lateral sclerosis (ALS), progressive bulbar palsy (PBP), pseudobulbar palsy, progressive muscular atrophy (PMA), primary lateral sclerosis (PLS), spinal muscular atrophy (SMA) and monomelic amyotrophy (MMA); neuromyelitis optica spectrum disorder; Parkinson's disease or Parkinsonisms; prion diseases; progressive supranuclear palsy (PSP); and traumatic brain injury (TBI).

In embodiments, a microdose of a disclosed 5-HT$_{2A}$ agonist, or a salt thereof, and an effective amount of a MAOI, or a salt thereof, are used to treat traumatic brain injury. In embodiments, a psychedelic dose of a disclosed 5-HT$_{2A}$ agonist, or a salt thereof, and an effective amount of a monoamine MAOI, or a salt thereof, are used to treat traumatic brain injury. In embodiments, a psycholytic dose of a disclosed 5-$HT_{2A}$ agonist, or a salt thereof, and an effective amount of a MAOI, or a salt thereof, are used to treat traumatic brain injury.

3. Pain Disorders

In some embodiments, disclosed methods and compositions are used to treat a pain disorder. In some methods herein, the disclosed compositions, when administered in a therapeutically effective amount, provide beneficial therapeutic effects for the treatment of a pain disorder.

A "pain disorder" refers to a class of medical conditions characterized by the experience of persistent or recurrent physical or psychological pain, either localized or widespread, that significantly impairs an individual's daily functioning and quality of life. These disorders may involve various etiologies, including nociceptive, neuropathic, psychogenic, idiopathic or radicular origins. In embodiments, disclosed methods and compositions are used to treat neuropathic pain. In embodiments, disclosed methods and compositions are used to treat psychogenic pain. In embodiments, disclosed methods and compositions are used to treat idiopathic pain. In embodiments, disclosed methods and compositions are used to treat radicular pain.

Pain disorders may manifest as acute or chronic pain, and they can affect different parts of the body, such as musculoskeletal, neurological, gastrointestinal, or visceral systems. Pain can be expressed as, but is not limited to, post-herpetic pain, trigeminal pain, occipital pain, or pudendal pain. In embodiments, disclosed methods and compositions are used to treat pain associated with chemotherapy (e.g., chemotherapy associated neuropathy). In embodiments, disclosed methods and compositions are used to treat arthritis, back pain, central pain, chronic fatigue syndrome, cluster headaches, migraine headaches, phantom limb pain, complex regional pain syndrome, compression mononeuropathy, diabetic neuropathy, fibromyalgia, focal neuropathy, herniated disc pain, or sciatica.

In some embodiments, a microdose of a disclosed 5-$HT_{2A}$ agonist, or a salt thereof, and an effective amount of a MAOI, or a salt thereof, are used to treat a pain disorder. In some embodiments, a psycholytic dose of a disclosed 5-$HT_{2A}$ agonist, or a salt thereof, and an effective amount of a MAOI, or a salt thereof, are used to treat a pain disorder. In some embodiments, a psychedelic dose of a disclosed 5-$HT_{2A}$ agonist, or a salt thereof, and an effective amount of a MAOI, or a salt thereof, are used to treat a pain disorder.

In some embodiments, pain is assessed using the Pain, Enjoyment, and General Activity Scale (PEG), the Numeric Rating Scale (NRS), the Visual Analog Scale (VAS), Behavioral Pain Scale (BPS), and the Faces Pain Scale-Revised (FPS-R).

4. Inflammatory Disorders

In some embodiments, disclosed methods and compositions are used to treat an inflammatory disorder. In some embodiments, disclosed methods and compositions are useful for reducing inflammation. In some embodiments, disclosed methods and compositions are used in the manufacture of a medicament to treat an inflammatory disorder or reduce inflammation.

Evidence suggesting a role of 5-$HT_{2A}$ receptors and thus of 5-$HT_{2A}$ receptor agonists in treating inflammation is discussed above and elsewhere herein.

In some embodiments, a microdose of a disclosed 5-$HT_{2A}$ agonist, or a salt thereof, and an effective amount of a MAOI, or a salt thereof, are used to treat an inflammatory disorder. In some embodiments, a psycholytic dose of a disclosed 5-$HT_{2A}$ agonist, or a salt thereof, and an effective amount of a MAOI, or a salt thereof, are used to treat an inflammatory disorder. In some embodiments, a psychedelic dose of a disclosed 5-$HT_{2A}$ agonist, or a salt thereof, and an effective amount of a MAOI, or a salt thereof, are used to treat an inflammatory disorder.

In some embodiments, disclosed methods and compositions are useful for treating skin inflammation, muscle inflammation, tendon inflammation, ligament inflammation, bone inflammation, cartilage inflammation, lung inflammation, heart inflammation, liver inflammation, pancreatic inflammation, kidney inflammation, bladder inflammation, gastric inflammation, intestinal inflammation, neuroinflammation, ocular inflammation, or brain inflammation.

In some embodiments, the inflammatory disorder is any of acne vulgaris, oxalic acid/heartburn, age-related macular degeneration (AMD), allergies, allergic rhinitis, Alzheimer's disease, amyotrophic lateral sclerosis, Anemia, appendicitis, arteritis, arthritis, including osteoarthritis, rheumatoid arthritis, juvenile idiopathic arthritis, spondyloarthropathy such as ankylosing spondylitis, reactive arthritis (Reiter syndrome), psoriatic arthritis, enteroarthritis associated with inflammatory bowel disease, Whipple and Behcet's disease, septic arthritis, gout (also known as gouty arthritis, crystalline synovitis, metabolic arthritis), pseudogout (calcium pyrophosphate deposition disease), and Still's disease. Arthritis can affect a single joint (monoarthritis), two to four joints (oligoarthritis), or five or more joints (polyarthritis).

In some embodiments, the inflammatory disorder is any of long COVID, a food allergy, post-treatment lyme disease syndrome, and an ulcer. In some embodiments, an inflammatory disorder is any of asthma, atherosclerosis, autoimmune disorder, balanitis, blepharitis, bronchiolitis, bronchitis, bullous pemphigoid, burns, bursitis, cancer, including NF-κB-induced inflammatory cancer; cardiovascular disease, including hypertension, endocarditis, myocarditis, heart valve dysfunction, congestive heart failure, myocardial infarction, diabetic heart abnormalities, vascular inflammation, including arteritis, phlebitis, and vasculitis; arterial occlusive disease, including arteriosclerosis and stenosis; inflammatory cardiac hypertrophy, peripheral arterial disease, aneurysm, embolism, incision, pseudoaneurysm, vascular malformation, vascular nevus, thrombosis, thrombophlebitis, varicose veins, stroke, cardiac arrest, and carditis; celiac disease, cellulitis, cervicitis, cholangitis, cholecystitis, chorioamnionitis, chronic obstructive pulmonary disease (COPD), cirrhosis, congestive heart failure, conjunctivitis, colitis, cyclophosphamide-induced cystitis, cystic fibrosis, cystitis, lacrimal inflammation, and dementia.

A reduction in inflammation, such as chronic systemic inflammation, may be measured according to various methods available to one of skill. Inflammatory biomarkers may be detected from biological specimens, for example, a subject's blood, such as plasma or serum, or saliva. In one example, inflammation may be detected by measuring high-sensitivity C-reactive protein (CRP) and white blood cell count from a blood test. CRP may also be detected in a saliva sample. Salivary CRP is not synthesized locally in the mouth and may reflect more systemic levels of inflammation compared to other inflammatory biomarkers, such as cytokines (Szabo & Slavish, Psychoneuroendocrin. 2021; 124: 105069). Additionally clinical pathology data, e.g., hematology data on erythrocyte parameters, platelet count, total number of leukocytes, and leukocyte differentials and morphology, coagulation data on clotting times and fibrinogen, and clinical chemistry data on total protein, albumin and globulin, liver enzymes, renal parameters, electrolytes, and bilirubin can provide an initial indication of the presence and potentially the location of inflammation, in the absence of specific data on immune tissues. See e.g., Germolec et al. *Methods Mol Biol.* 2018; 1803:57-79 and Luo et al. *Clin Lab.* 2019; 65(3).

VII. ADDITIONAL EXAMPLES

The following examples are included for illustrative purposes only and are not intended to limit the scope of the invention.

Example 12: In Vitro Inhibition of MAO-A and MAO-B by CX157

Objective: The purpose of this in vitro study was to determine the ability of CX157 to inhibit MAO-A and MAO-B in rat brain and rat liver.

Methods: The soluble extract of the mitochondrial enriched fraction (P2 pellet), which was prepared from brain homogenates of male Sprague-Dawley rats, served as the source of MAO-A enzymatic activity. The P2 fraction was prepared and was stored frozen until being thawed for use on the day of assay. Final concentrations of 50 µM [$^{14}$C]-serotonin (5-HT) and 10 µM [$^{14}$C]-phenylethylamine (PEA) were employed as specific substrates for MAO-A and MAO-B, respectively. Test compound inhibition was based on competition for oxidation of these radio-labeled substrates. MAO-A assay specificity was enhanced by inclusion of 0.1 µM deprenyl to prevent substrate oxidation by MAO-B. Likewise, MAO-B assays included 0.1 µM clorgyline to block MAO-A activity. The investigational drug candidate CX157, as well as RO-41-1049 and RO-16-6491, exemplary MAO inhibitors used as positive controls for inhibition of MAO-A and MAO-B, respectively, were analyzed over a concentration range of 7 log units. Inhibition of enzymatic activities was expressed as $IC_{50}$ and as the $K_i$, which was calculated using the Cheng-Prusoff equation.

Results: The inhibitory properties of CX157 are described below.

Figure 5:
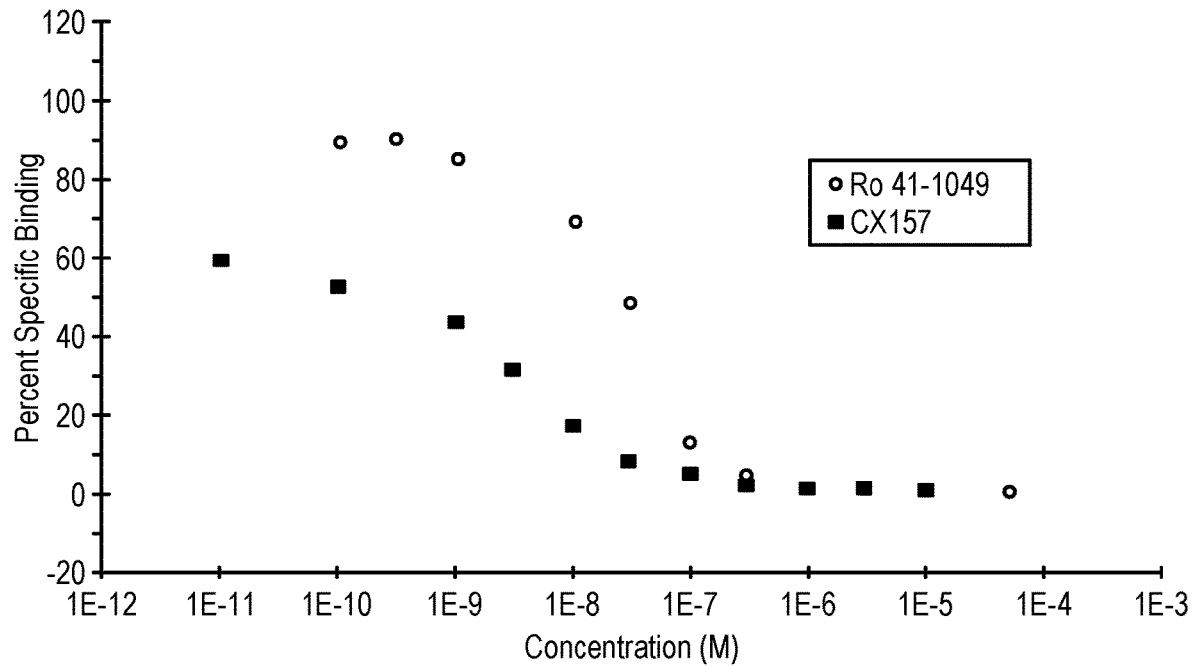
FIG. 5 illustrates exemplary binding profiles of CX157 and a reference compound in rat brain monoamine oxidase-A (MAO-A) assay to measure inhibition of MAO-A by CX157 in rat brain tissue.
Figure 6:
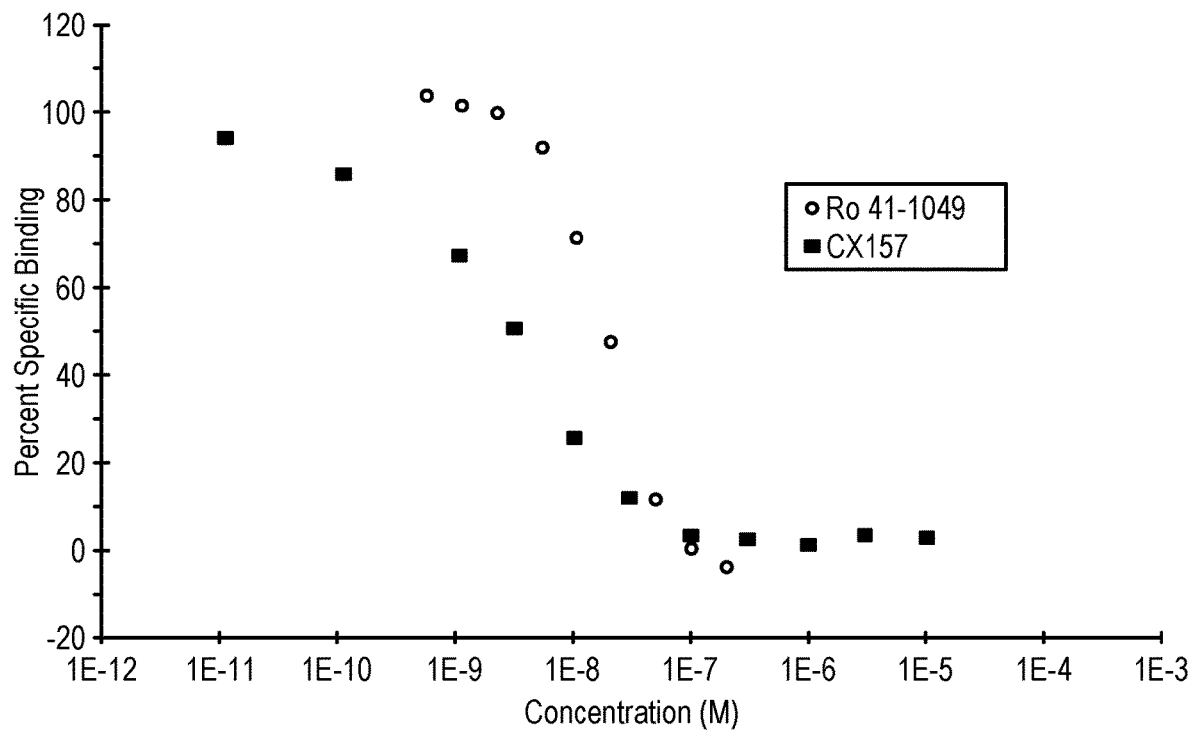
FIG. 6 illustrates exemplary binding profiles of CX157 and a reference compound in rat liver MAO-A assay to measure inhibition of MAO-A by CX157 in rat liver tissue.

MAO-A: FIG. 5 details exemplary binding profiles of CX157 and RO-41-1049 (as a positive control) in rat brain MAO-A assays. FIG. 6 details exemplary binding profiles of CX157 and RO-41-1049 (as a positive control) in rat liver MAO-A assays. The substrate concentrations (M) used in both the rat brain MAO-A assays and the rat liver MAO-A assays were varied. The specific binding percentages of CX157 at MAO-A in both types of assays were measured and plotted based on the varying substrate concentrations used. In rat brain MAO-A, the $IC_{50}$ and $K_i$ values for CX157 were both 0.09 nM. In rat liver MAO-A, the $IC_{50}$ and $K_i$ values for CX157 were 2.22 nM and 0.91 nM, respectively. The $K_i$ ratios (CX157/RO-41-1049) were:

|  | $K_i$ for CX157/$K_i$ for RO-41-1049 |
| --- | --- |
| Brain MAO-A | 0.006 |
| Liver MAO-A | 0.126 |

Figure 7:
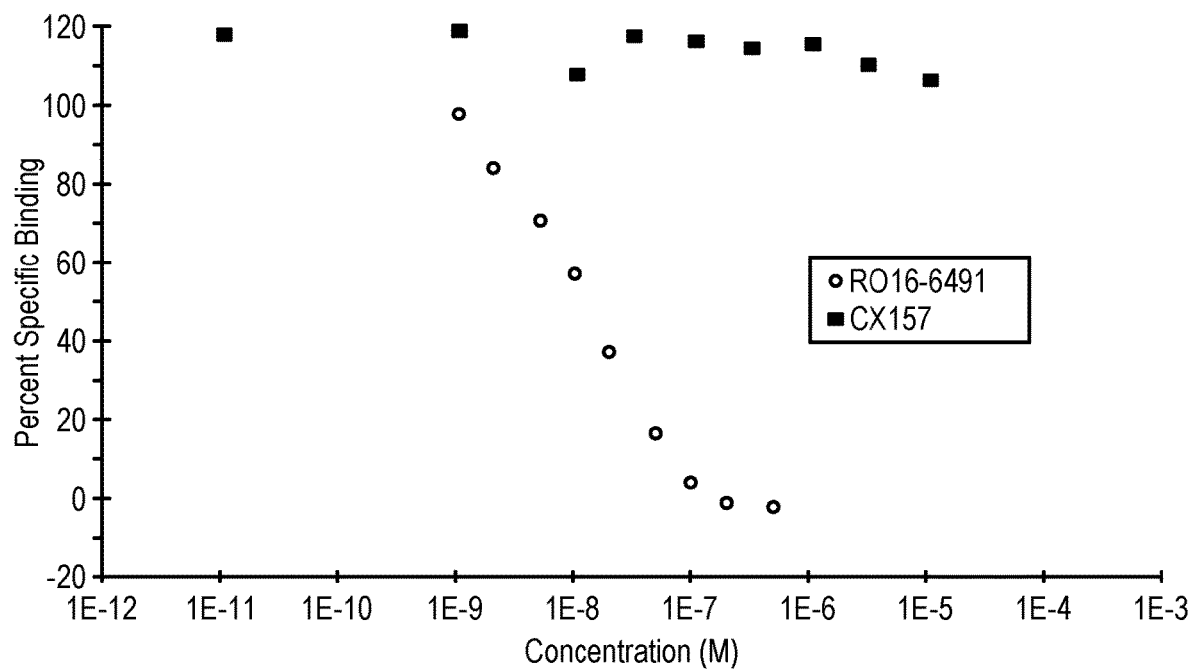
FIG. 7 illustrates exemplary binding profiles of CX157 and a reference compound in rat brain MAO-B assay to measure inhibition of MAO-B by CX157 in rat brain tissue.
Figure 8:
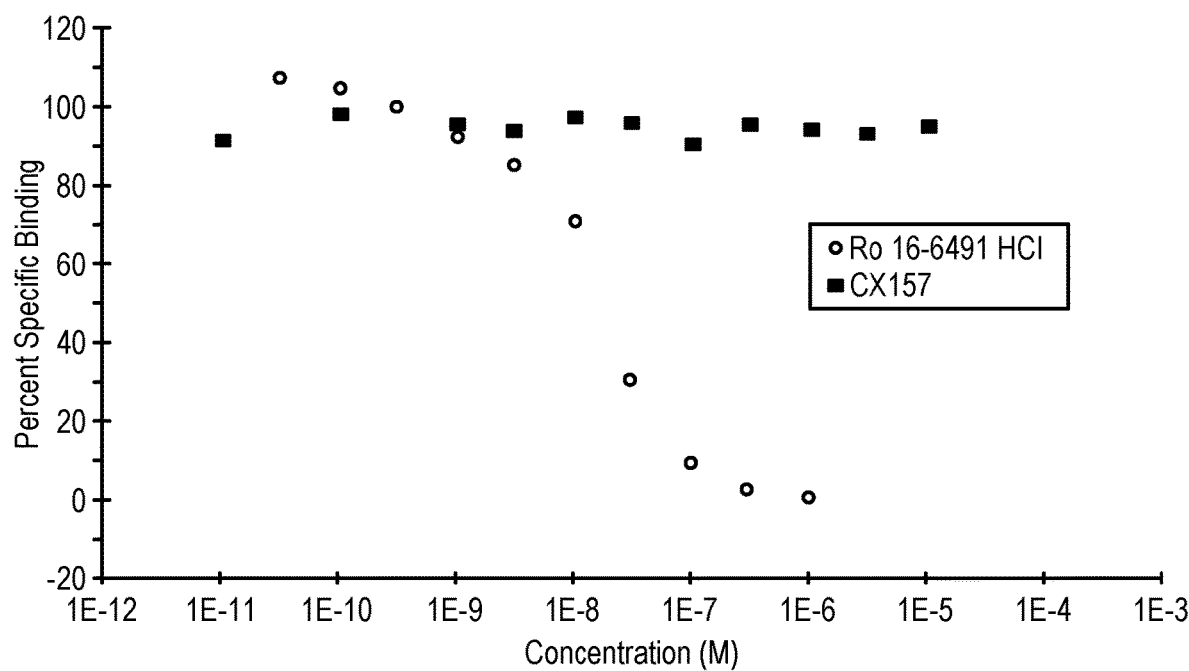
FIG. 8 illustrates exemplary binding profiles of CX157 and a reference compound in rat liver MAO-B assay to measure inhibition of MAO-B by CX157 in rat liver tissue.

MAO-B: FIG. 7 details exemplary binding profiles of CX157 and RO-16-6491 (as a positive control) in rat brain MAO-B assays. FIG. 8 details exemplary binding profiles of CX157 and RO-16-6491 (as a positive control) in rat liver MAO-B assays. The substrate concentrations (M) used in both the rat brain MAO-B assays and the rat liver MAO-B assays were varied. The specific binding percentages of CX157 at MAO-B in both types of assays were measured and plotted based on the varying substrate concentrations used. CX157 did not inhibit rat brain or liver MAO-B under the conditions of this study. In these same assays, the reference compound for MAO-B inhibition, RO 16-6491, generated graded concentration-inhibition relationships, with $K_i$ values in the 12 nM range.

Conclusions: Under the conditions of this study, CX157 inhibited rat brain MAO-A with $K_i$ values generally >10 fold lower than the reference compound RO 41-1049, and did not inhibit rat brain MAO-B at any of the concentrations tested.

Example 13: Ex Vivo Inhibition of MAO-A Activity by CX157 in Rat Brain

Objective: The purpose of this ex vivo study was to examine the dose-response relationship and time-course of action of CX157 as an inhibitor of brain MAO-A activity in rats when administered orally. This ex vivo study also measures brain penetration of CX157 in rats, which can be assessed by determining the concentration of MAO-A inhibitor in the brain compared to the plasma concentration.

Methods: Sprague-Dawley male rats (average weight of 190 g) were segregated into three groups for testing of the effects of CX157 on brain MAO-A enzyme activity. The three groups consisted of animals who received either 1, 5, and 10 mg/kg of CX157. Each group consisted of twenty-four subjects. Test animals were administered the doses of CX157 orally, by the gavage method in accordance with White & Scates, Drug Dev Res. 1992; 25:191-199.

In each drug group, four animals were sacrificed at each time period (0, 2, 4, 8, 18 and 24 hours) on four different days following drug administration. Brains were removed from the animal, bisected, frozen immediately on dry ice and placed in a −80° C. freezer. Trunk blood was collected in tubes containing sodium heparin and centrifuged at 5000 rpm for 10 minutes at 4° C. to extract the plasma. The frozen brain samples were thawed, weighed, and homogenized (3:1 tissue weight/buffer volume) in 0.25 M sucrose, containing 50 mM $KHPO_4$(pH 7.4), with a Teflon glass homogenizer. Deprenyl HCl (at a final concentration of 100 nM) was added to each sample of homogenate to block MAO-B enzyme activity. A volume of 400 µl of homogenate was pipetted into each assay tube. A 50 µl volume of 500 µM [$^{14}$C]-5HT (specific activity of 1.6 Curies/mmol) was added to each assay tube to give a final concentration of 50 m. Blank assay tubes (included to correct for nonspecific deamination of [$^{14}$C]-5HT) also contained 50 µl of RO-41-1049, while total activity assay tubes (specific and nonspecific deaminating activity) contained 50 µl of buffer. The final concentration of RO-41-1049 in the blank activity tubes was 100 µM. This yielded a total assay volume of 500 µl. All assays were incubated for 7.5 minutes at 37° C. The reaction was terminated by the addition of 500 µl of 2 M citric acid. The deaminated [$^{14}$C]-5HT metabolite was extracted into a liquid scintillation fluor mixture of xylene/ethyl acetate and 0.4% PPO and quantified using a liquid scintillation spectrometer.

The specific activity of MAO-A in each of the samples was determined by subtraction of the values obtained in the nonspecific tubes from those in the total activity tubes. Methylcellulose was prepared by weighing 17.5 grams in a weigh boat on a Mettler balance and poured into a 4 liter flask. Two liters of distilled water was added to the 4 liter flask. The mixture was placed on a stir plate/hot plate and stirred overnight (for 24 hours) until completely dissolved. After the methylcellulose dissolved, distilled water was added until the volume in the flask reached 3.5 liters. The CX157 was prepared in a 0.5% methylcellulose/Tween 80 mixture to obtain the following dosages 1, 5, and 10 mg/kg. Initially, 52 mg of CX157 was placed in a 7 ml amber vial. A volume of 52 µl of Tween 80 was added to the amber vial containing CX157. A volume of 5.2 ml of methylcellulose was added to this vial to yield a solution of 10 mg/ml; this solution was used to deliver the 10 mg/kg dose. For the 5 mg/kg dose, a 5 mg/ml solution was prepared as follows; a volume of 1 ml of 10 mg/ml stock was mixed with 1 ml of methylcellulose and sonicated until mixed thoroughly. For the 1 mg/kg dose, a 1:10 dilution of the stock dose of 10 mg/ml was performed by pipetting 0.5 ml of 10 mg/ml stock into an amber vial with an addition of 4.5 ml of methylcellulose followed by sonication to disperse the drug into solution. All drugs were then administered on a 1 ml/kg basis with an average volume of 200 µl.

Figure 18:
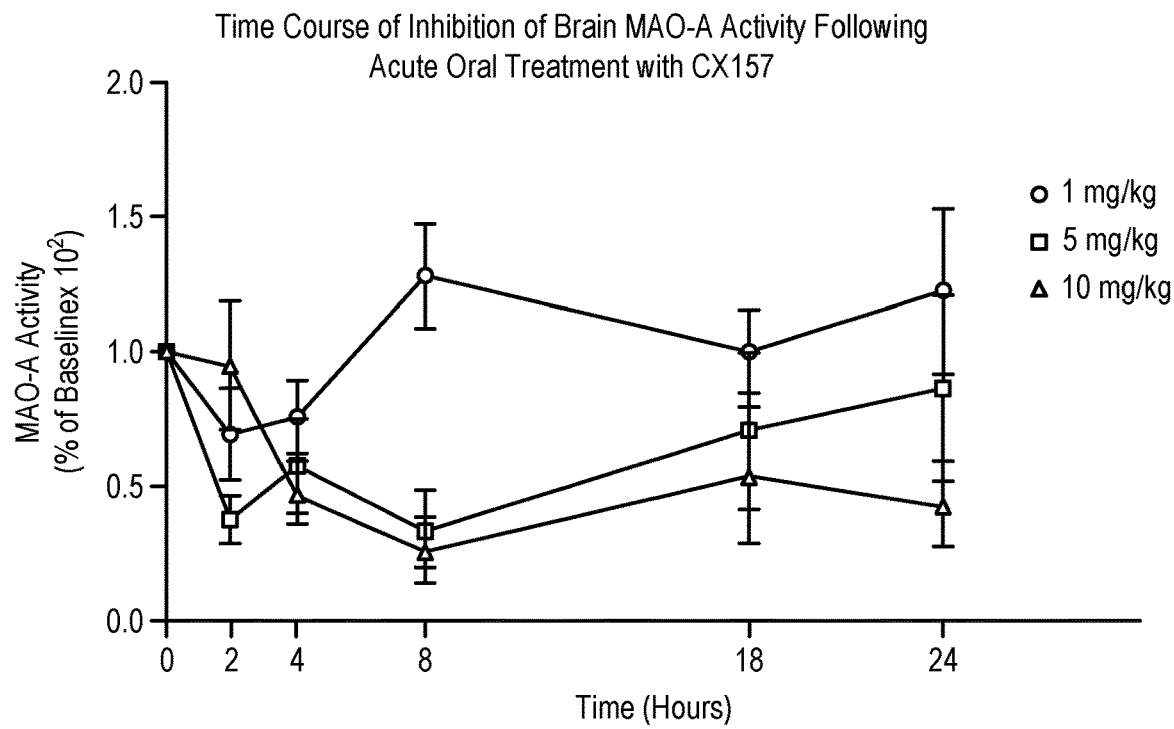
FIG. 18 illustrates exemplary mean percentages of baseline brain MAO-A activity in rats over a 24-hour time period following oral administration of CX157 at three different dosage amounts.
Figure 19:
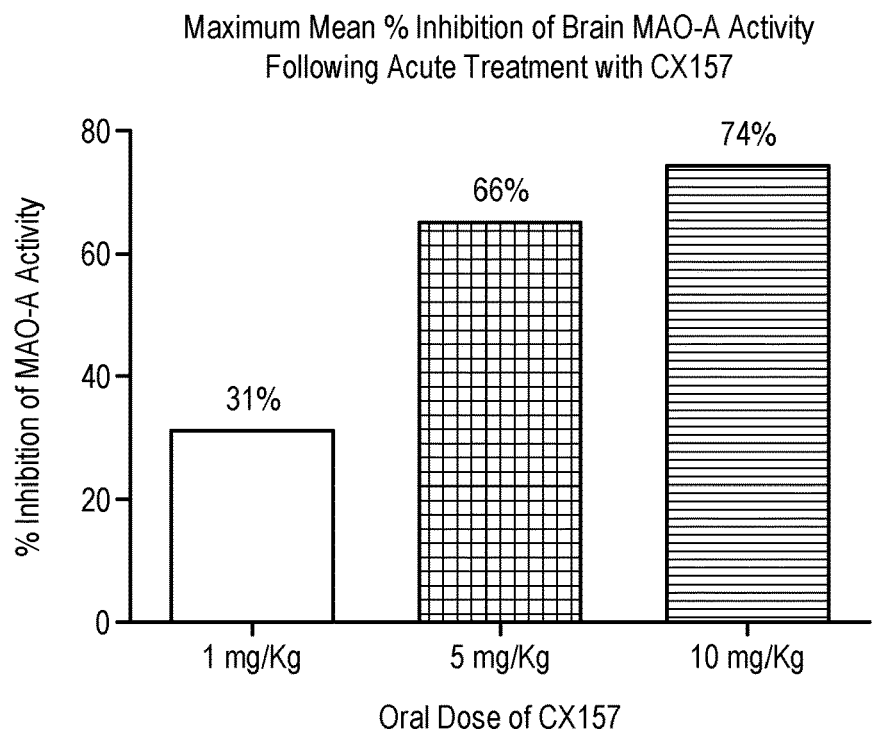
FIG. 19 illustrates exemplary mean percentages of inhibition of brain MAO-A activity following acute treatment of rats with CX157 at three different dosage amounts.

Results: The mean brain MAO-A activity values at 0, 2, 4, 8, 18, and 24 hours following the administration of 1, 5, and 10 mg/kg of CX157 (gavage method) on four different experimental days is shown in the table below. FIG. 18 illustrates the mean (±SEM) percentages of baseline brain MAO-A activity in groups of rats sacrificed at 0, 2, 4, 8, 18 and 24 hours following the administration of 1, 5, and 10 mg/kg of CX157. FIG. 19 illustrates the maximum mean percentage of inhibition of rat brain MAO-A activity following administration of 1, 5, and 10 mg/kg of CX157, irrespective of the time following drug administration.

| Group # | Dose | Time (h) | Day #1 | Day #2 | Day #3 | Day #4 | Avg. | St. Dev. |
|---|---|---|---|---|---|---|---|---|
| 1 | 1 mg/kg | 0 | 5051 | 3995 | 3520 | 1980 | 3636 | 1276 |
| 1 | 1 mg/kg | 2 | 4637 | 2548 | 1338 | 2587 | 2778 | 1369 |
| 1 | 1 mg/kg | 4 | 2921 | 3478 | 1577 | 4117 | 3023 | 1081 |
| 1 | 1 mg/kg | 8 | 7232 | 4979 | 3565 | 4707 | 5121 | 1535 |
| 1 | 1 mg/kg | 18 | 5071 | 5019 | 3071 | 2811 | 3993 | 1220 |
| 1 | 1 mg/kg | 24 | 6414 | 6981 | 4646 | 1491 | 4883 | 2470 |
| 2 | 5 mg/kg | 0 | 5661 | 5499 | 3070 | 3687 | 4479 | 1298 |
| 2 | 5 mg/kg | 2 | 1596 | 1578 | 537 | 2271 | 1496 | 716 |
| 2 | 5 mg/kg | 4 | 3817 | 958 | 1263 | 3154 | 2298 | 1403 |
| 2 | 5 mg/kg | 8 | 2957 | 1014 | 1266 | 225 | 1366 | 1150 |
| 2 | 5 mg/kg | 18 | 5925 | 3160 | 1717 | 472 | 2818 | 2344 |
| 2 | 5 mg/kg | 24 | 6207 | 1250 | 5433 | 880 | 3443 | 2767 |
| 3 | 10 mg/kg | 0 | 6953 | 4824 | 2623 | 1158 | 3889 | 2538 |
| 3 | 10 mg/kg | 2 | 4330 | 1001 | 5292 | 4600 | 3806 | 1914 |
| 3 | 10 mg/kg | 4 | 1207 | 946 | 2637 | 2784 | 1894 | 951 |
| 3 | 10 mg/kg | 8 | 601 | 295 | 2476 | 766 | 1035 | 980 |
| 3 | 10 mg/kg | 18 | 3244 | 4482 | 391 | 482 | 2150 | 2042 |
| 3 | 10 mg/kg | 24 | 2419 | 3047 | 219 | 1162 | 1712 | 1267 |

The table below provides the mean brain MAO-A activity and SEM in groups sacrificed at various times following oral administration of 1 mg/kg of CX157.

| Time (h) | Mean (DPM) | SEM (DPM) | % Baseline | N |
|---|---|---|---|---|
| 0 | 4002.0 | 482.7 | 100% | 12 |
| 2 | 2777.5 | 684.3 | 69% | 4 |
| 4 | 3023.3 | 540.5 | 76% | 4 |
| 8 | 5120.8 | 767.5 | 128% | 4 |
| 18 | 3993.0 | 609.8 | 100% | 4 |
| 24 | 4883.0 | 1235.2 | 122% | 4 |

Figure 16:
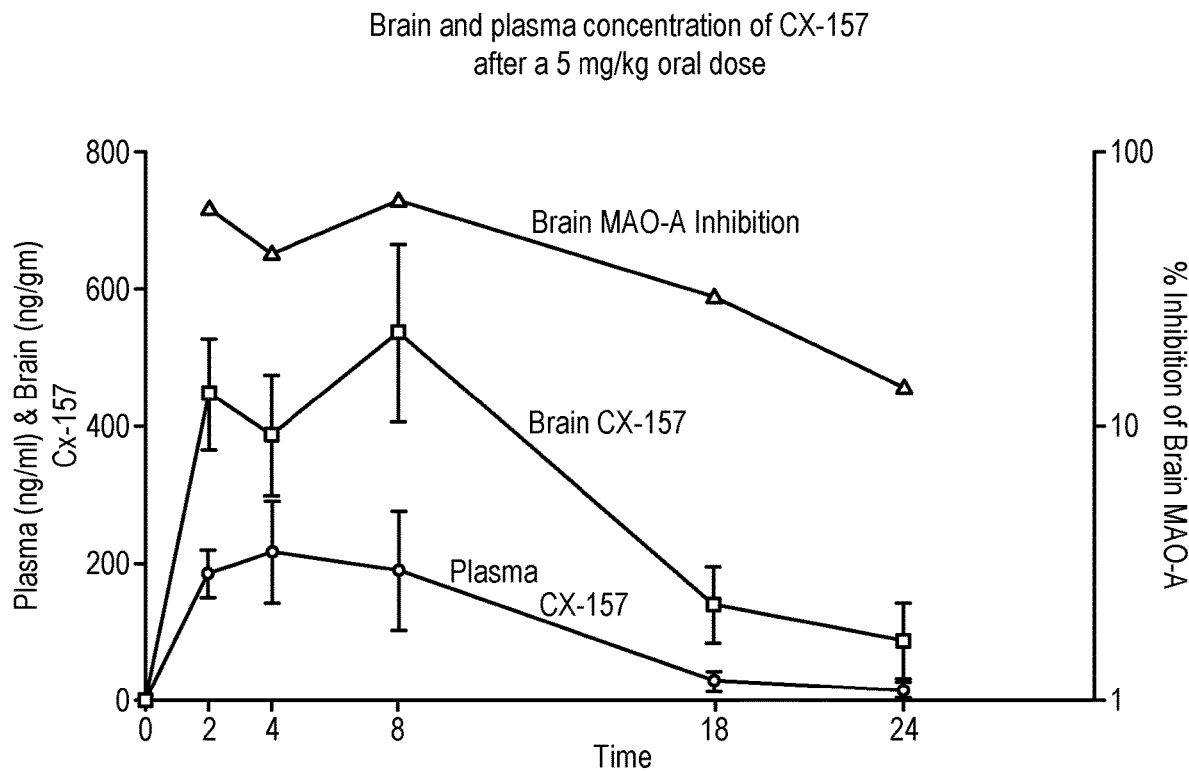
FIG. 16 illustrates exemplary concentrations of CX157 in rat brain and plasma and the percentage of inhibition of rat brain MAO-A over a 24-hour period after administering 5 mg/kg of CX157 by oral gavage.

The table below provides the mean brain MAO-A activity and SEM in groups sacrificed at various times following oral administration of 5 mg/kg of CX157. FIG. 16 illustrates mean percentages of inhibition on brain MAO-A following a single oral dose of CX157 at 5 mg/kg.

| Time (h) | Mean (DPM) | SEM (DPM) | % Baseline | N |
|---|---|---|---|---|
| 0 | 4002.0 | 482.7 | 100% | 12 |
| 2 | 1495.5 | 357.9 | 37% | 4 |
| 4 | 2298.0 | 701.6 | 57% | 4 |
| 8 | 1365.5 | 575.0 | 34% | 4 |
| 18 | 2818.5 | 1172.1 | 70% | 4 |
| 24 | 3442.5 | 1383.8 | 86% | 4 |

The table below provides the mean brain MAO-A activity and SEM in groups sacrificed at various times following oral administration of 10 mg/kg of CX157.

| Time (h) | Mean (DPM) | SEM (DPM) | % Baseline | N |
|---|---|---|---|---|
| 0 | 4002.0 | 482.7 | 100% | 12 |
| 2 | 3805.8 | 956.6 | 95% | 4 |
| 4 | 1893.5 | 475.6 | 47% | 4 |
| 8 | 1034.5 | 490.3 | 26% | 4 |
| 18 | 2149.8 | 1021.1 | 54% | 4 |
| 24 | 1711.8 | 633.4 | 43% | 4 |

The table below provides the mean and SEM plasma CX157 concentrations in groups sacrificed at various times following oral administration of 1 mg/kg of CX157.

| Time (h) | Mean CX157 Concentration (ng/ml) | SEM (ng/ml) | N |
|---|---|---|---|
| 0 | 0 | 0 | 4 |
| 2 | 20.0 | 11.6 | 4 |
| 4 | 9.9 | 4.8 | 4 |
| 8 | 13.4 | 4.2 | 4 |
| 18 | 4.5 | 2.3 | 4 |
| 24 | 3.2 | 0.5 | 3 |

The table below provides the mean and SEM brain CX157 concentrations in groups sacrificed at various times following oral administration of 1 mg/kg of CX157.

| Time (h) | Mean CX157 Concentration (ng/ml) | SEM (ng/ml) | N |
|---|---|---|---|
| 0 | 0 | 0 | 4 |
| 2 | 102.7 | 33.1 | 4 |
| 4 | 71.7 | 15.5 | 4 |
| 8 | 76.5 | 18.5 | 4 |
| 18 | 17.3 | 4.5 | 4 |
| 24 | 13.2 | 2.6 | 4 |

The table below provides the mean brain/plasma ratios of CX157 concentrations in groups sacrificed at various times following oral administration of 1 mg/kg of CX157.

| Time (h) | Mean CX157 Concentration (ng/ml) | SEM (ng/ml) | N |
|---|---|---|---|
| 0 | N/A | N/A | 4 |
| 2 | 7.4 | 1.5 | 4 |
| 4 | 10.3 | 3.2 | 4 |
| 8 | 6.5 | 0.9 | 4 |
| 18 | 5.7 | 2.0 | 4 |
| 24 | 4.8 | 1.5 | 3 |

The table below provides the mean and SEM plasma CX157 concentrations in groups sacrificed at various times following oral administration of 5 mg/kg of CX157.

| Time (h) | Mean CX157 Concentration (ng/ml) | SEM (ng/ml) | N |
|---|---|---|---|
| 0 | 0 | 0 | 4 |
| 2 | 183.8 | 35.5 | 4 |
| 4 | 214.1 | 74.2 | 4 |
| 8 | 188.8 | 87.2 | 4 |
| 18 | 26.8 | 14.6 | 4 |
| 24 | 14.3 | 10.2 | 4 |

The table below provides the mean and SEM brain CX157 concentrations in groups sacrificed at various times following oral administration of 5 mg/kg of CX157.

| Time (h) | Mean CX157 Concentration (ng/ml) | SEM (ng/ml) | N |
|---|---|---|---|
| 0 | 0 | 0 | 4 |
| 2 | 446.8 | 81.4 | 4 |
| 4 | 386.0 | 89.1 | 4 |
| 8 | 535.0 | 129.2 | 4 |
| 18 | 140.0 | 71.6 | 4 |
| 24 | 85.8 | 54.9 | 4 |

The table below provides the mean brain/plasma ratios of CX157 concentrations in groups sacrificed at various times following oral administration of 5 mg/kg of CX157.

| Time (h) | Mean CX157 Concentration (ng/ml) | SEM (ng/ml) | N |
|---|---|---|---|
| 0 | N/A | N/A | 4 |
| 2 | 2.5 | 0.2 | 4 |
| 4 | 2.2 | 0.4 | 4 |
| 8 | 5.0 | 2.7 | 4 |
| 18 | 3.7 | 1.2 | 4 |
| 24 | 7.4 | 0.9 | 4 |

The table below provides the mean and SEM plasma CX157 concentrations in groups sacrificed at various times following oral administration of 10 mg/kg of CX157.

| Time (h) | Mean CX157 Concentration (ng/ml) | SEM (ng/ml) | N |
|---|---|---|---|
| 0 | 0 | 0 | 4 |
| 2 | 158.2 | 51.5 | 4 |
| 4 | 412.3 | 95.2 | 4 |
| 8 | 257.3 | 54.1 | 4 |
| 18 | 8.5 | 3.0 | 4 |
| 24 | 5.4 | 1.8 | 4 |

The table below provides the mean and SEM brain CX157 concentrations in groups sacrificed at various times following oral administration of 10 mg/kg of CX157.

| Time (h) | Mean CX157 Concentration (ng/ml) | SEM (ng/ml) | N |
|---|---|---|---|
| 0 | 0 | 0 | 4 |
| 2 | 386.8 | 82.6 | 4 |
| 4 | 513.3 | 141.0 | 4 |
| 8 | 539.8 | 89.7 | 4 |
| 18 | 56.6 | 15.5 | 4 |
| 24 | 86.6 | 34.7 | 4 |

The table below provides the mean brain/plasma ratios of CX157 concentrations in groups sacrificed at various times following oral administration of 10 mg/kg of CX157.

| Time (h) | Mean CX157 Concentration (ng/ml) | SEM (ng/ml) | N |
|---|---|---|---|
| 0 | N/A | N/A | 4 |
| 2 | 3.1 | 0.8 | 4 |
| 4 | 1.9 | 0.0 | 4 |
| 8 | 2.2 | 0.3 | 4 |
| 18 | 7.2 | 0.7 | 4 |
| 24 | 8.5 | 0.7 | 4 |

Figure 14:
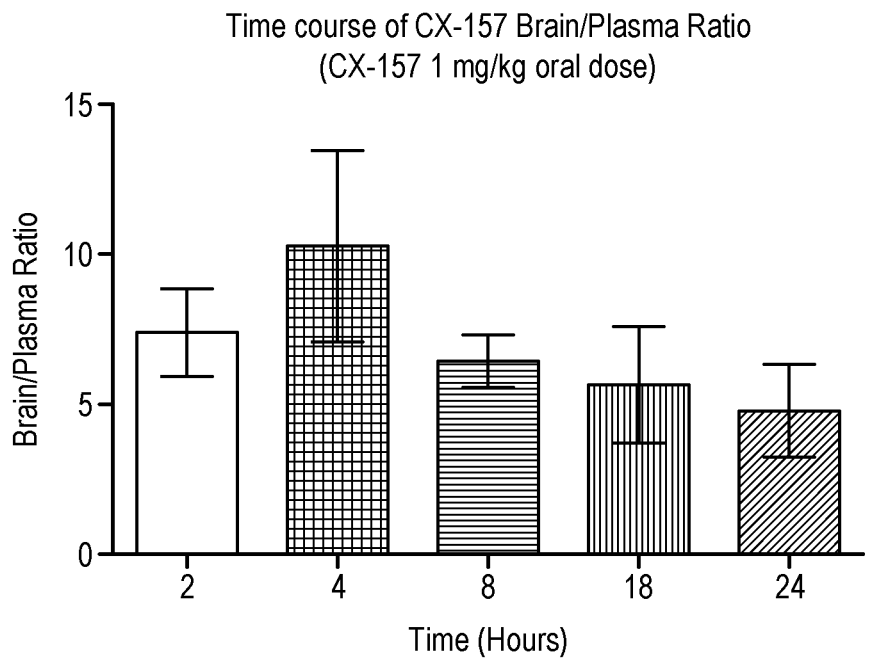
FIG. 14 illustrates exemplary concentrations of CX157 in rat brain and plasma over a 24-hour time period after administering 1 mg/kg of CX157 by oral gavage.
Figure 15:
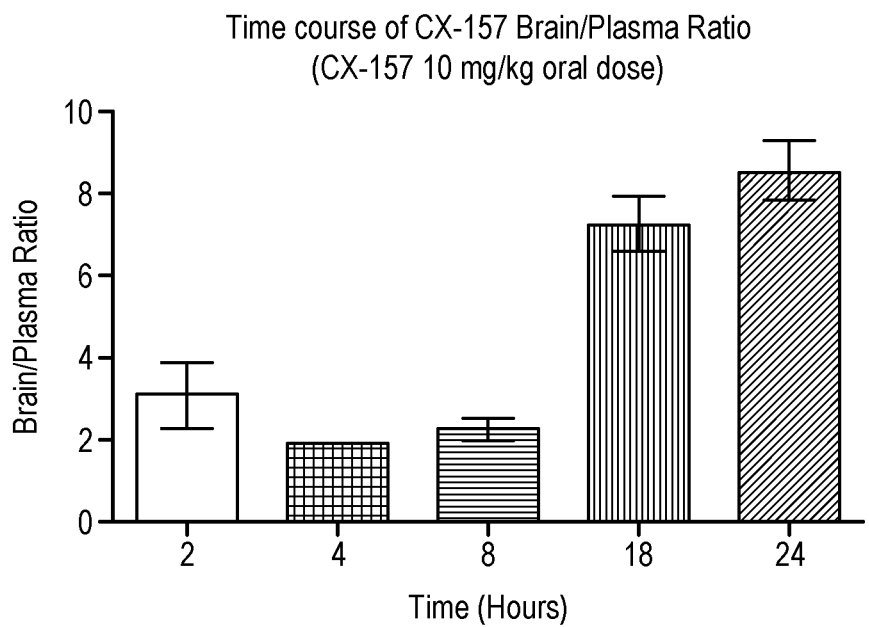
FIG. 15 illustrates exemplary concentrations of CX157 in rat brain and plasma over a 24-hour time period after administering 10 mg/kg of CX157 by oral gavage.
Figure 17:
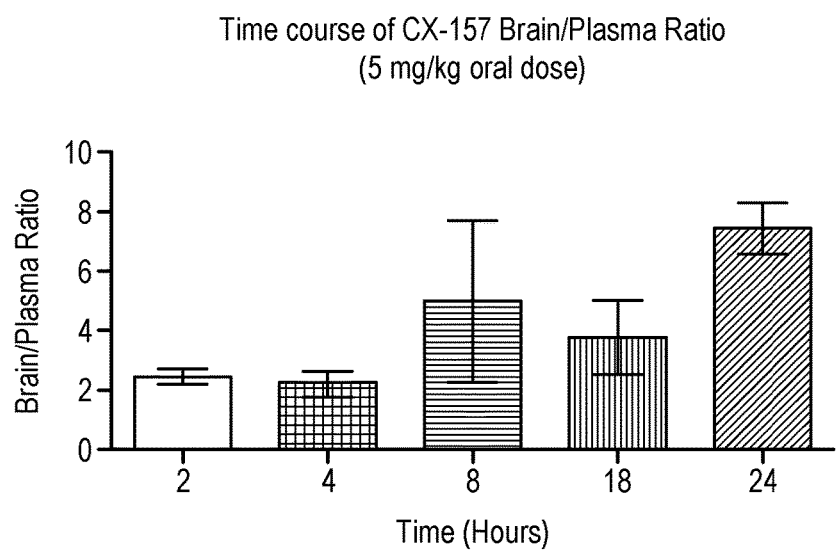
FIG. 17 illustrates exemplary concentrations of CX157 in rat brain and plasma over a 24-hour time period after administering 5 mg/kg of CX157 by oral gavage.
Figure 20:
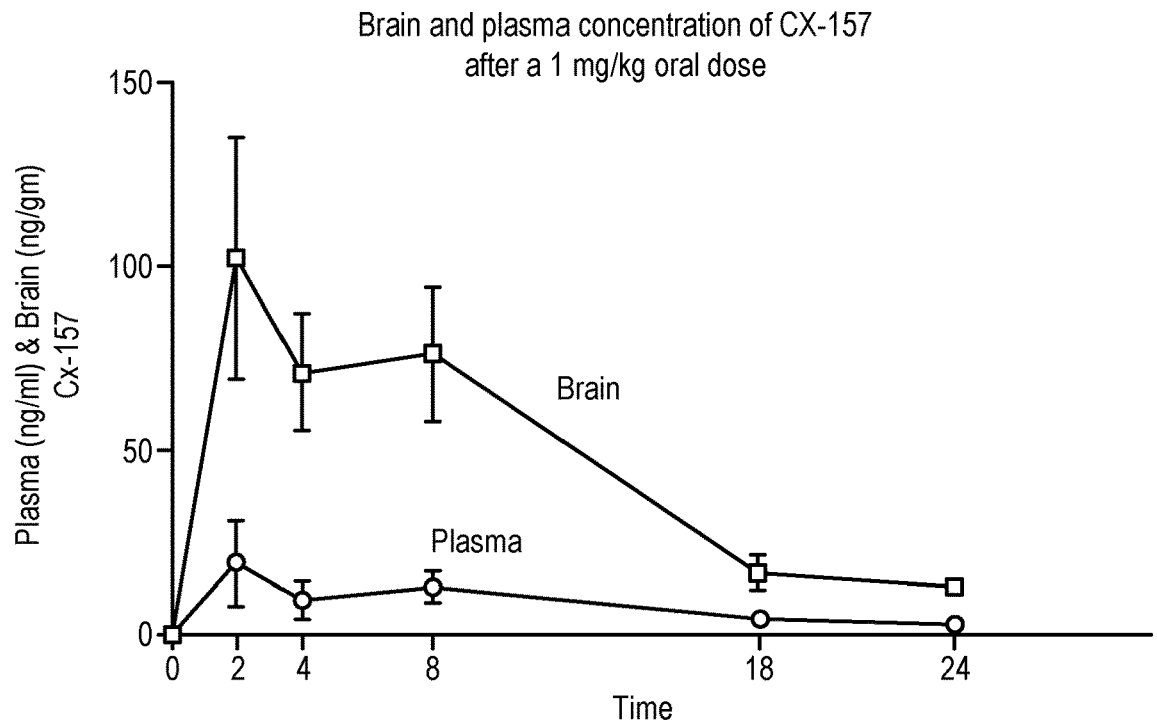
FIG. 20 illustrates exemplary concentrations of CX157 in rat brain and plasma over a 24-hour time period after orally administering 1 mg/kg of CX157 to rats by gavage method.
Figure 21:
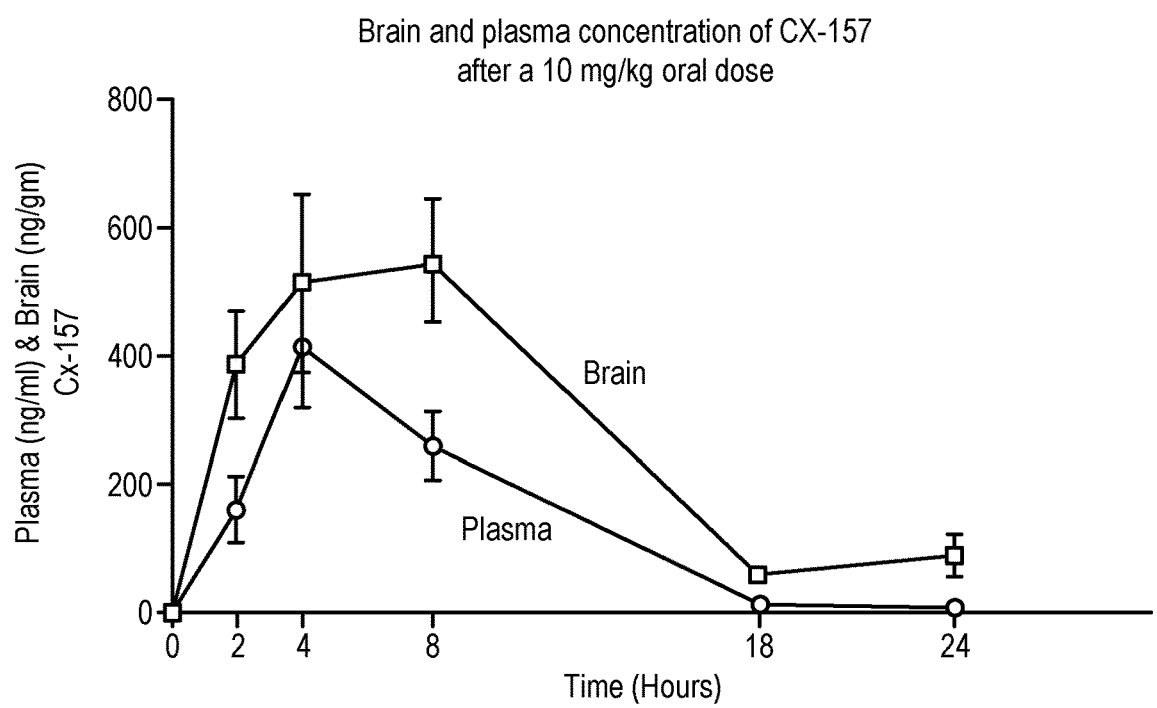
FIG. 21 illustrates exemplary concentrations of CX157 in rat brain and plasma over a 24-hour time period after orally administering 10 mg/kg of CX157 to rats by gavage method.

FIGS. 14, 17 and 15 illustrate mean (±SEM) brain to plasma concentration ratios following single oral CX157 doses of 1, 5, and 10 mg/kg, respectively. FIGS. 20, 16, and 21 illustrate mean (±SEM) plasma and brain concentrations of CX157 following single oral doses of CX157 at 1, 5, and 10 mg/kg, respectively.

The experimental results from this study indicated that orally administered CX157 inhibited MAO-A enzymatic activity in the brains of rats in a dose and time dependent manner. The data shows that CX157 is effective orally at inhibiting MAO-A enzyme activity in the brain, even at the lowest dose of 1 mg/kg. After oral administration, plasma levels rose initially during drug absorption, reaching maximum levels at two to four hours, and then fell over the rest of the twenty-four hour study period. Plasma exposures increased in proportion to the dose over the range of doses studied. These data indicate that CX157 brain/plasma ratios are high, with brain concentrations of up to 10-fold higher than plasma concentrations (e.g., 4 hours after a 1 mg/kg oral dose). In addition, FIGS. 14-18 show that at each dose tested (i.e., 1, 5, and 10 mg/kg), CX157 concentrations in the brain are maintained over the 24-hour time course of the experiments, and that CX157 appeared to demonstrate a longer pharmacokinetic half-life in the brain than in plasma, particularly at a dose of 10 mg/kg, where an increase in brain/plasma ratio was observed at the later post-treatment time points.

Conclusions: CX157 was rapidly absorbed, penetrated the blood-brain-barrier, achieved brain concentrations that were higher than observed in the plasma, and inhibited brain MAO-A enzyme activity in a dose-dependent and reversible fashion following oral administration. The MAO-A inhibition time-course closely paralleled the CX157 concentration in plasma and brain, with a rapid onset and similar duration of action. These observations demonstrate that CX157 is a potent, dose-dependent, and reversible inhibitor of brain MAO-A enzyme activity with good permeability and rapid distribution into the brain tissue following a single, oral administration to rats.

Example 14: Inhibitory Kinetics of Brain MAO-A Activity by CX157

Objective: The objective of this study was to determine the in vitro kinetics ($K_m$ and $V_{max}$ values) of human brain MAO-A inhibition by CX157.

Figure 9:
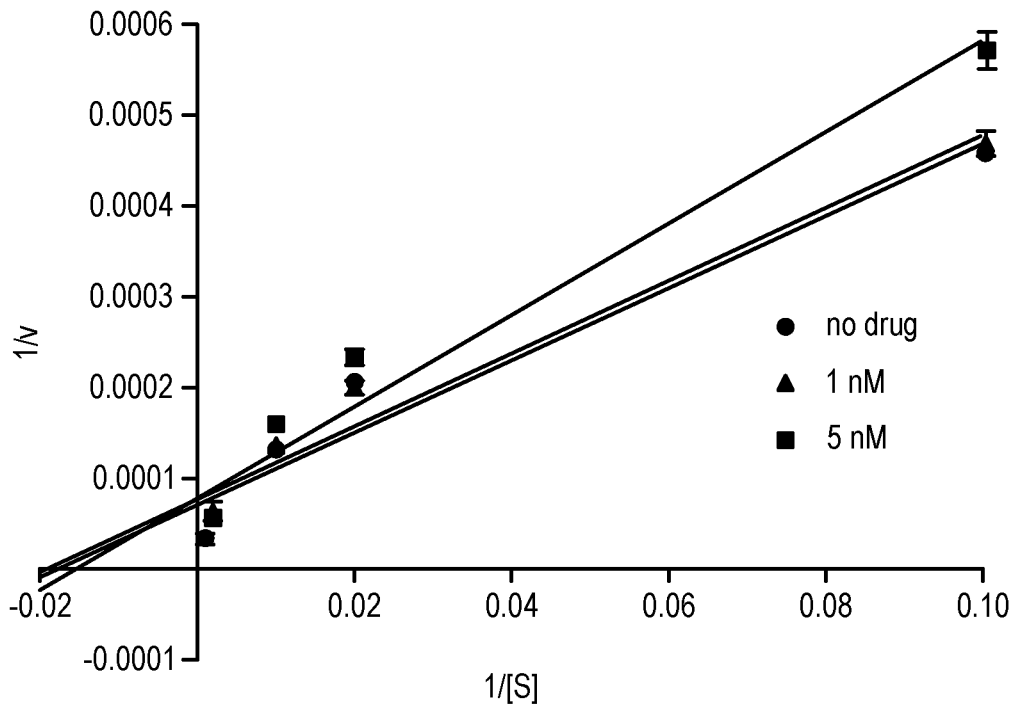
FIG. 9 illustrates an exemplary Lineweaver-Burke plot of CX157 for purposes of calculating terms relating to enzyme kinetics, such as $K_m$ and $V_{max}$.

Methods: The soluble extract of the mitochondrial enriched fraction (P2 pellet), which was prepared from homogenates of a post-mortem sample of the human brain striatum, served as the source of MAO-A enzymatic activity for this assay. After preparation, the P2 fraction was stored frozen until it was thawed for use on the day of assay. The MAO-A activity was assayed using [$^{14}$C]-serotonin (5-HT) as the substrate over a 2 log unit concentration range (10, 50, 100, 500 & 1000 µM) to both span the 5-HT $K_m$ (170 µM) and saturate the enzyme. The MAO-A assay specificity was enhanced by inclusion of 0.1 µM deprenyl to prevent substrate oxidation by MAO-B. The CX157 competition for MAO-A activity was measured using either 1.0 nM or 5.0 nM CX157 against the 2 log unit concentration range of [$^{14}$C]-5-HT. The reference standard, RO 41-1049, was tested at 10 µM. Deprenyl (0.1 µM) was included in all MAO-A assays to prevent any potential for MAO-B mediated oxidation of the [$^{14}$C]-5-HT substrate. FIG. 9 details an exemplary form of a Lineweaver-Burke plot for CX157. On the horizontal axis of the Lineweaver-Burke plot, FIG. 9 describes values for the reciprocals of the substrate concentrations used for the MAO-A assays. On the vertical axis of the plot, FIG. 9 details values representing the reciprocals of the reaction rates induced by CX157 based on the varying substrate concentrations used for the MAO-A assays. The MAO-A assays were performed using CX157 at concentrations of 0 nM (as a positive control), 1 nM and 5 nM. The $K_m$ and $V_{max}$ values were calculated from Lineweaver-Burke plots.

Results: The inhibitory kinetics in human brain striatum are described below:

MAO-A: In the present study with MAO-A derived from human brain striatum, the 5.0 nM concentration of CX157 also increased the $K_m$ (34.6%) of the enzyme for [$^{14}$C]-5-HT, with no meaningful change in the $V_{max}$, confirming that CX157 functioned as a competitive inhibitor of MAO-A. $V_{max}$ and $K_m$ values of 1 nM and 5 nM of compound CX157 are as noted below. CX157 was found to exhibit a $K_i$ of 10 nM for MAO-A from a plot of said values.

|  | No Drug | 1 nM CX157 | 5 nM CX157 |
|---|---|---|---|
| $V_{max}$ | 51906 | 50777 | 59161 |
| $K_m$ | 794 | 836 | 1069 |

Statistical analysis of interactions between CX157 and MAO-A indicate inhibition of MAO-A by CX157 at low concentrations. CX157 was found to exhibit a K, of 10 nM for MAO-A.

Summary Output of Collected Data:

| Regression Statistics | |
|---|---|
| Multiple R | 0.99885342 |
| R Square | 0.99770815 |
| Adjusted R Square | 0.99541631 |
| Standard Error | 10.0297177 |
| Observations | 3 |

| ANOVA | | | | | |
|---|---|---|---|---|---|
|  | df | SS | MS | F | Significance F |
| Regression | 1 | 43792.0714 | 43792.0714 | 435.329467 | 0.0304887 |
| Residual | 1 | 100.595238 | 100.595238 | | |
| Total | 2 | 43892.6667 | | | |

|  | Coefficient | Standard Error | t Stat | P-value |
|---|---|---|---|---|
| Intercept | 787.809524 | 7.89133972 | 99.8321643 | 0.00637669 |
| X Variable 1 | 55.9285714 | 2.68055482 | 20.8645505 | 0.0304887 |

|  | Lower 95% | Upper 95% | Lower 95.0% | Upper 95.0% |
|---|---|---|---|---|
| Intercept | 687.540546 | 888.078502 | 687.540546 | 888.078502 |
| X Variable 1 | 21.8688931 | 89.9882498 | 21.8688931 | 89.9882498 |

Figure 10:
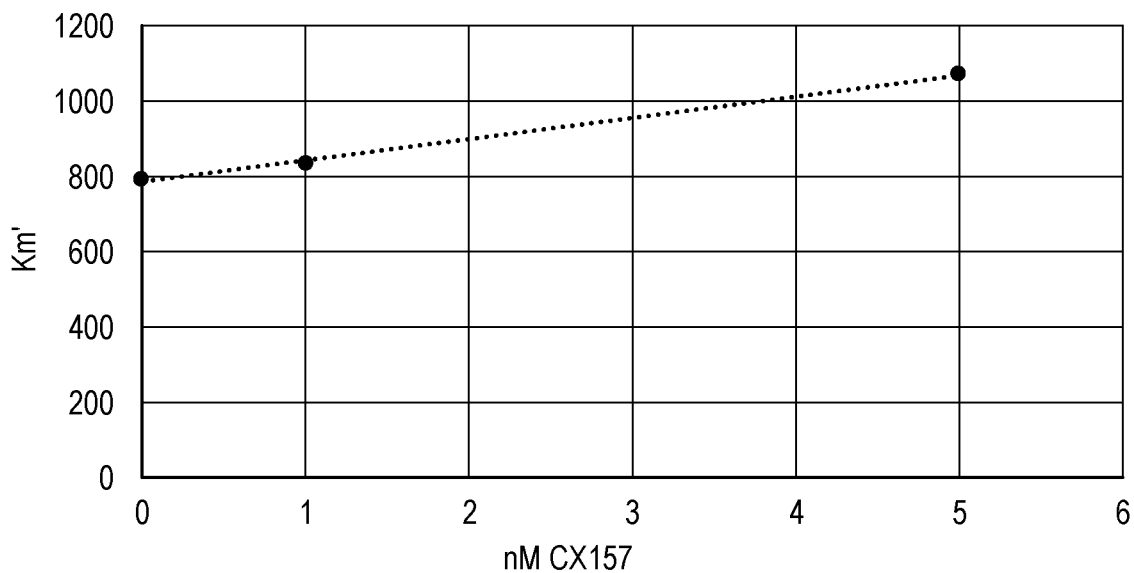
FIG. 10 illustrates exemplary kinetic data, including $K_m$ values, for CX157 at various substrate concentrations demonstrating its effects on MAO-A inhibition in human brain striatum.

Conclusions: FIG. 10 illustrates an increase in the $K_m$ values for CX157 as its concentration was increased from 0 nM to 6 nM in exemplary MAO-A assays. CX157 is a competitive inhibitor of MAO-A from human brain striatum based on the kinetic data. Increases in $K_m$ with added amounts of CX157 were not accompanied by appreciable changes in the $V_{max}$ of the enzyme reaction and thus appeared to follow kinetics of previous experiments.

Example 15: Binding Selectivity of CX157 In Vitro

Objective: The purpose of this in vitro screening study was to assess the selectivity of CX157 using ligand-receptor interactions that were representative of a broad spectrum of physiological systems. The identification of receptor affinity was based on the in vitro competition between CX157 and a specific radioactive ligand-receptor interaction.

Methods: Investigational drug candidates CX157 were analyzed in NovaScreen's bank of ligand-binding reactions to test for specificity. CX157 was screened at concentrations of both 10.0 nM and 100 nM as potential competitors in binding reactions involving nine classes containing 69 binding sites. The following binding reactions are tested: Adenosine Non-selective, Adrenergic Alpha 1 Non-selective, Adrenergic Alpha 2 Non-selective, Adrenergic Beta Non-selective, Dopamine Transporter, Dopamine Non-selective, GABA A Agonist Site, GABA A BDZ alpha 1 site, GABA B, Glutamate AMPA Site (Ionotropic), Glutamate Kainate Site (Ionotropic), Glutamate NMDA Agonist Site (Ionotropic), Glutamate NMDA Glycine (Stry-insens Site) (Ionotrophic), Glycine Strychnine-sensitive, Histamine $H_1$, Histamine $H_2$, Histamine $H_3$, Melatonin Non-selective, Muscarinic M1 (hr), Muscarinic M2 (hr), Muscarinic Non-selective Central, Muscarinic Non-selective Peripheral, Nicotinic (α-BnTx insensitive) Neuronal, Norepinephrine Transporter, Opioid Non-selective, Orphanin (hr), Serotonin Transporter, Serotonin Non-selective, Sigma Non-selective, Estrogen, Testosterone (cytosolic), Calcium Channel Type L (Dihydropyridine Site), Calcium Channel Type N, Potassium Channel ATP-Sensitive, Potassium Channel Ca2+ Act. VI, Potassium Channel I[Kr] (hERG) (hr), Sodium Site 2, Nitric Oxide NOS (Neuronal-Binding), Leukotriene LTB4 (BLT), Leukotriene LTD4 (CysLT1), Thromboxane A2 (h), Corticotropin Releasing Factor Non-selective, Oxytocin, Platelet Activating Factor PAF, Thyrotropin Releasing Hormone TRH, Angiotensin II AT1 (h), Angiotensin II AT2, Bradykinin BK2, Cholecystokinin CCK1 (CCKA), Cholecystokinin CCK2 (CCKB), Endothelin ET-A (h), Endothelin ET-B (h), Galanin Non-Selective, Neurokinin NK1, Neurokinin NK2 (NKA) (hr), Neurokinin NK3 (NKB), Vasoactive Intestinal Peptide Non-selective, Vasopressin 1, Choline Acetyltransferase, Esterase Acetylcholine, Glutamic Acid Decarboxylase, Oxidase MAO-A Peripheral, Oxidase MAO-B Peripheral, CYP3A4 (h), CYP1A2 (h), CYP2A6 (h), CYP2C$_{19}$ (h), CYP2C$_{9*1}$ (h), and CYP2D6 (h).

Results: CX157 only exhibited an affinity for MAO-A, when measured by competition for [$^{14}$C]-serotonin (5-HT) binding (Kd=8.7 nM). At 10.0 nM and 100 nM, CX157 reduced [$^{14}$C]-5-HT binding by 63.4% and 100.6%, respectively. There were no interactions with any of the other binding sites in this screen.

Conclusions: In a screening study with 9 classes of ligand-receptor interactions representing a broad spectrum of physiological systems, containing 69 different specific binding sites, CX157 had a high affinity for MAO-A and did not bind to MAO-B. There were no interactions with any of the other sites in this screen.

Example 16: Safety, Tolerance, and Pharmacokinetics (PK) of CX157

Objective: The primary objective of this study was to examine the safety, tolerability, and PK properties of up to seven (7) dose levels of CX157 compared to placebo in healthy male volunteers.

Methods: The trial was a Phase 1, single center, double-blind, placebo-controlled, sequential group, acute dose escalation study of the safety and pharmacokinetics of seven (7) CX157 dose levels in healthy male volunteers. Each of the seven (7) dose groups consisted of six (6) subjects, with the exception of cohort 2 (CX157 10 mg or placebo) which enrolled only five (5) subjects. Within each dose group, four (4) subjects were randomized to CX157 and two (2) subjects to placebo. Subjects were normal healthy volunteers confined to the study center for approximately 4 days, beginning approximately 16 hours before exposure to study drug and ending approximately 48 hours after exposure to study drug. Safety and tolerability was assessed for each dose group by the Principal Investigator before advancing to the next scheduled dose group. CX157 was administered as a fully solubilized microemulsion in Labrasol™

Figure 11:
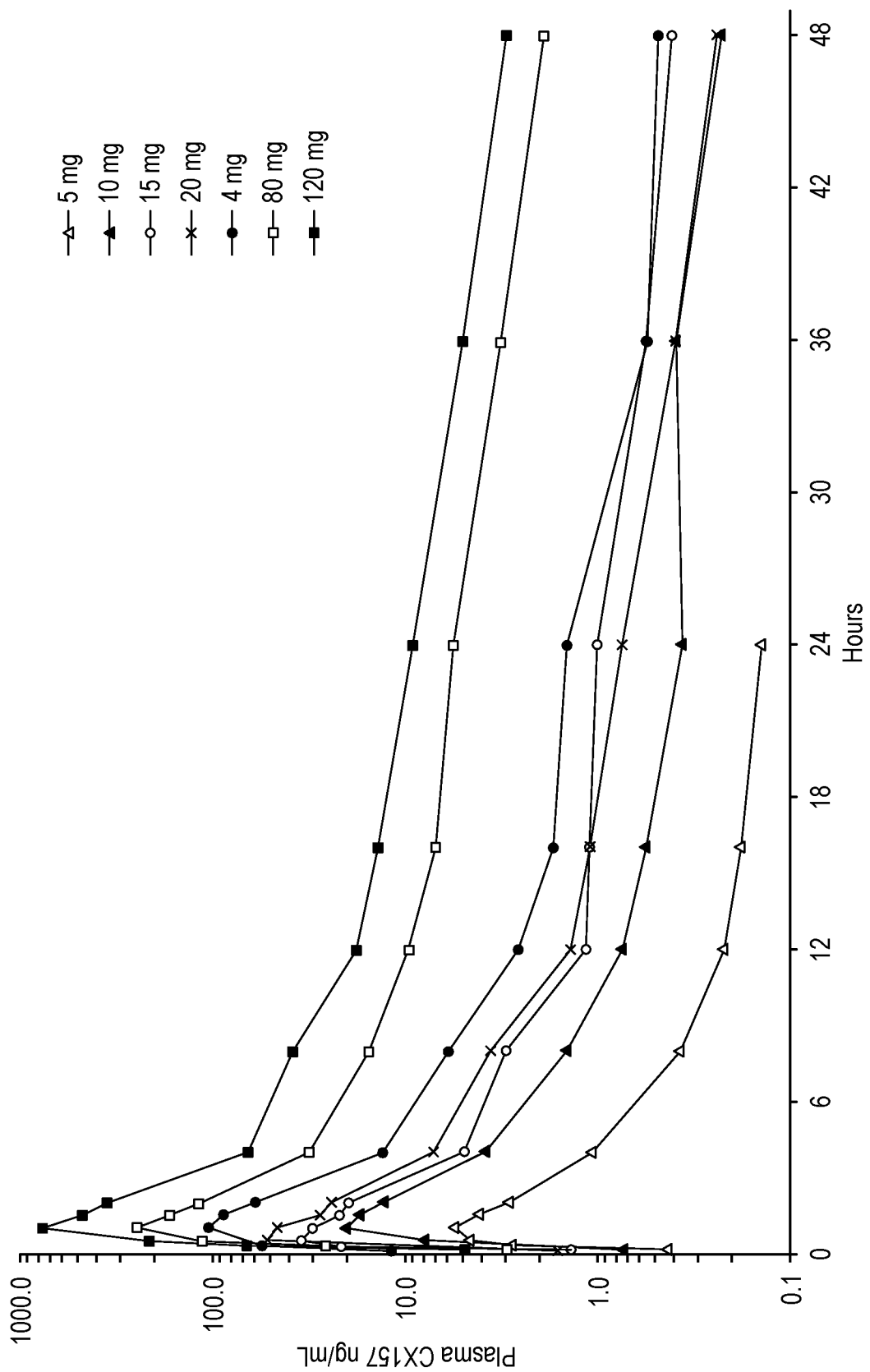
FIG. 11 illustrates exemplary plasma concentrations of subjects after administration of CX157 at seven different dosage amounts.

Plasma samples for the pharmacokinetic analysis of CX157 were obtained at predose (30 minutes prior to dosing), 10, 20, 30, 60 and 90 minutes, 2, 4, 8, 12, 16, 24, 36 and 48 hours after dosing. Plasma concentrations of CX157 were used to estimate the following PK parameters: $C_{max}$, $T_{max}$, $C_{last}$, $T_{last}$, $AUC_{0-24h}$, $AUC_{0-48h}$, $AUC_{last}$, $AUC_{inf}$, $k_{el}$, % $AUC_{extrap}$, $t_{1/2}$, CL/F, and Vd/F. FIG. 11 details exemplary concentrations of CX157 (in ng/mL) in the plasma of subjects, measured from predose until 48 hours following administration of CX157. FIG. 11 details the plasma concentrations of CX157 (in ng/mL) of subjects for each of the seven dose groups, wherein the dosage amounts of CX157 administered to the subjects were 5 mg, 10 mg, 15 mg, 20 mg, 40 mg, 80 mg, and 120 mg.

Formulation: Each natural/transparent Licaps® size 0 hard gelatin capsule contains 5 mg or 10 mg CX157 in Labrasol™; each capsule is banded with a green gelatin band that is comprised of gelatin NF and polysorbate-80 NF. CX157 Liquid Filled Capsules are packaged in white, opaque, high density polyethylene (HDPE) bottles with screw-top polypropylene child resistant caps. Each bottle contains 30 capsules per bottle. CX157 Liquid Filled Capsules, 5 mg and 10 mg are stored long-term at controlled room temperature conditions [i15° C. to 30° C. (59° F. to 86° F.)].

Results: Safety, tolerance, and pharmacokinetics are described below:

Summary of CX157 Pharmacokinetic Parameters by Treatment Group:

|  |  | Group | | | | | |
| --- | --- | --- | --- | --- | --- | --- | --- |
|  |  | 1 | | 2 | | 3 | |
|  |  | Dose (mg) | | | | | |
|  |  | 5 | | 10 | | 15 | |
| Parameter | Units | Mean | SD | Mean | SD | Mean | SD |
| Dose | mg/kg | 0.066 | 0.005 | 0.12 | 0.018 | 0.198 | 0.022 |
| Cmax | ng/ml | 5.8 | 2 | 20.8 | 14.7 | 42.2 | 18.1 |
| Tmax | h | 0.75 | 0.29 | 1.17 | 0.29 | 0.88 | 0.48 |
| Clast | ng/ml | 0.15 | 0.04 | 0.2 | 0.07 | 0.38 | 0.37 |
| Tlast | h | 17 | 8.25 | 40 | 13.86 | 45 | 6 |
| C24h | ng/ml | 0.14 | 0.05 | 0.37 | 0.21 | 1 | 1.2 |
| AUC0-24 | ng h/mL | 21.6 | 1.7 | 63 | 46 | 107 | 40 |
| AUC0-48 | ng h/mL | ND | ND | 96 | 33 | 129 | 67 |
| AUClast | ng h/mL | 16.5 | 6.5 | 69 | 51 | 122 | 57 |

-continued

| | | Group | | | | | |
|---|---|---|---|---|---|---|---|
| | | 1 | | 2 | | 3 | |
| | | Dose (mg) | | | | | |
| | | 5 | | 10 | | 15 | |
| Parameter | Units | Mean | SD | Mean | SD | Mean | SD |
| AUCinf | ng h/mL | ND | ND | 102 | 34 | 129 | 64.9 |
| % AUCextrap | % | ND | ND | 6.2 | 1.1 | 5 | 3 |
| kel | 1/h | ND | ND | 0.0371 | 0.006 | 0.0529 | 0.008 |
| t1/2 | h | ND | ND | 18.9 | 3.12 | 13.3 | 1.81 |
| CL/F | mL/min kg | ND | ND | 19.7 | 7.3 | 30.2 | 13.5 |
| Vd/F | L/kg | ND | ND | 33.3 | 17.2 | 33.7 | 13.1 |
| Cmax/Dose | ratio | 87 | 26 | 182 | 137 | 212 | 79.5 |
| AUCinf/Dose | ratio | ND | ND | 906 | 334 | 673 | 382 |

| | | Group | | | | | |
|---|---|---|---|---|---|---|---|
| | | 4 | | 5 | | 6 | |
| | | Dose (mg) | | | | | |
| | | 20 | | 40 | | 80 | |
| Parameter | Units | Mean | SD | Mean | SD | Mean | SD |
| Dose | mg/kg | 0.23 | 0.038 | 0.53 | 0.06 | 1.1 | 0.18 |
| Cmax | ng/mL | 56.1 | 14.9 | 123 | 61.4 | 244.8 | 18.2 |
| Tmax | h | 0.75 | 0.29 | 0.83 | 0.33 | 1 | 0 |
| Clast | ng/ml | 0.24 | 0.16 | 0.48 | 0.29 | 1.9 | 1 |
| Tlast | h | 48 | 0 | 48 | 0 | 48 | 0 |
| C24h | ng/ml | 0.74 | 0.3 | 1.4 | 0.4 | 5.5 | 2.8 |
| AUC0-24 | ng h/mL | 139 | 45 | 291 | 95 | 647 | 222 |
| AUC0-48 | ng h/mL | 149 | 50 | 309 | 100 | 730 | 261 |
| AUClast | ng h/mL | 149 | 50 | 309 | 100 | 730 | 261 |
| AUCinf | ng h/mL | 154 | 53 | 321 | 107.9 | 772 | 281 |
| % AUCextrap | % | 3.1 | 1.3 | 3.3 | 2 | 5.2 | 1.3 |
| kel | 1/h | 0.0488 | 0.006 | 0.0459 | 0.009 | 0.0456 | 0.005 |
| t1/2 | h | 14.4 | 1.78 | 15.6 | 3.52 | 15.3 | 1.59 |
| CL/F | mL/min kg | 26.5 | 9.8 | 29.9 | 10.7 | 25.3 | 9.1 |
| Vd/F | L/kg | 32.9 | 11.9 | 38.1 | 7.2 | 33.5 | 13.1 |
| Cmax/Dose | ratio | 251 | 73.5 | 234 | 112 | 232 | 42.2 |
| AUCinf/Dose | ratio | 701 | 272 | 619 | 230 | 720 | 230 |

Safety: Overall the percent of subjects experiencing adverse events was higher in the placebo group (93%) than in the CX157 groups (89%, range 67%-100%) and the most frequently reported adverse events (by MedDRA® term) were pharyngolaryngeal pain (n=18), tachycardia (n=14), throat irritation (n=7), and nausea (n=7).

There was one report of Blood Creatine Phosphokinase Increased (857.2 U/L; reference range 38.0-174.0 U/L) which, in the opinion of the Investigator, was secondary to vigorous exercise prior to confinement to the clinic and subsequent CX157 dosing. Review of the subject's electrocardiograms during the study (predose, 1, 2, 4, 6, 8, 24, and 48 hours after dosing) were normal with regards to rate, rhythm, and morphology further supporting this conclusion.

Adverse events were relatively evenly distributed across the CX157 dose levels and no dose response was identified. The most commonly reported findings in both the CX157 and placebo treatment groups were respiratory, thoracic, mediastinal, or gastrointestinal disorders and this was most likely due to the vehicle, Labrasol™, used in compounding CX157 as a fully solubilized microemulsion for oral delivery. Labrasol is known to be poorly palatable when administered as a liquid taken by mouth.

Conclusions: The safety analysis of this single dose, dose escalation study of CX157 in normal healthy volunteers indicated that CX157 was safe and well tolerated, as demonstrated by no subject premature discontinuations, the lack of serious adverse experiences, and the lack of clinically significant findings on vital signs, ECGs, and laboratory tests. In addition, there were no significant differences between the cumulative active and placebo treatment groups in terms of the incidence of AEs.

Example 17: Safety, Tolerance, and Pharmacokinetics of CX157 at Three Doses

Objectives: The primary objectives of this study were to examine the safety and the pharmacodynamic and pharmacokinetic properties of three doses of CX157 administered for 14 days compared to placebo in healthy male and female volunteers.

Methods: The study was a Phase I, single-center, randomized, parallel-group, multiple-dose, placebo-controlled, pharmacodynamic, pharmacokinetic and safety study in healthy volunteers. To obtain 24 enrolled subjects, screening procedures and inclusion/exclusion criteria were evaluated for 54 subjects during a variable screening period of up to 28 days. Once enrolled, subjects were randomized to either CX157 10 mg, 20 mg or 40 mg or matching placebo administered twice daily for 14 consecutive days.

Formulations: Each natural/transparent Licaps® size 0 hard gelatin capsule contains 10 mg CX157 in Labrasol™; each capsule is banded with a green gelatin band comprised of gelatin NF and polysorbate-80 NF. CX157 Liquid Filled Capsules are packaged in white, opaque, high density polyethylene (HDPE) bottles with screw-top polypropylene child resistant caps. Each bottle contains 30 capsules. CX157 Liquid Filled Capsules, 5 and 10 mg are stored long-term at controlled room temperature conditions [15-30° C. (59-86° F.)].

Results: CX157 was rapidly absorbed after oral administration of 10 mg liquid-filled capsules, resulting in generally proportional exposures after doses of 10, 20 and 40 mg. Plasma concentrations rose during twice-daily dosing, and reached steady-state levels during the 14-day study.

Although the mean terminal half-life was 33.3 to 35.3 hours, a dose interval of 12-h appears to be pharmacokinetically appropriate for oral CX157 Liquid Filled Capsules. At the highest (40 mg) dose, the Day 14 $C_{max}$ was 166±179 ng/mL, the mean $AUC_{0-12h}$ was 355±235 ng/h-mL, and the $C_{SS}$ was 29.6±19.6 ng/mL. The degree of pharmacokinetic variability observed may be a result of factors other than differences in body weight, race and gender.

Overall, 15 (62.5%) study subjects reported mild adverse events, and 3 (12.5%) reported moderate events. All 3 of the subjects who reported having moderate events were in the placebo group. The most frequently reported AEs by primary system organ class were characterized as occurring within the cardiac, nervous system and vascular disorder system organ class. The most frequently reported AEs (by MedDRA® term) were tachycardia (n=10), headache (n=7), diastolic hypertension (n=4) and systolic hypertension (n=4).

Summary of PK Parameters:

| | | Group | | | | | |
|---|---|---|---|---|---|---|---|
| | | 1 | | 1 | | 2 | |
| | | Dose (mg) | | | | | |
| | | 10 | | 10 | | 20 | |
| | | Day | | | | | |
| | | 1 | | 14 | | 1 | |
| Parameter | Units | Mean | SD | Mean | SD | Mean | SD |
| Dose | mg/kg | 0.13 | 0.01 | 0.13 | 0.01 | 0.27 | 0.05 |
| Cmax | ng/ml | 18.1 | 16.2 | 24.2 | 21.5 | 32.3 | 43.9 |
| Tmax | h | 1 | b | 1 | b | 1.25 | b |
| Cmin | ng/ml | 0.6 | 0.6 | 3 | 3.9 | 1.13 | 1.32 |
| Tmin | h | 10.7 | 2.07 | 12 | 0 | 12 | 0 |
| C12h | ng/ml | 0.63 | 0.56 | 3 | 3.9 | 1.13 | 1.3 |
| AUC0-12h | ng h/mL | 50 | 35 | 97 | 99 | 83.5 | 55.2 |
| AUClast | ng h/mL | NA | | 180 | 209 | NA | |
| AUCinf | ng h/mL | NA | | NA | | NA | |
| % AUCextrap | % | NA | | NA | | NA | |
| t1/2 | h | NA | | NA | | NA | |
| CSS | ng/mL | NA | | 8.1 | 8.3 | NA | |
| Cmax/Cmin | ratio | 31.4 | 29 | 6.64 | 1 | 36.7 | 39 |
| Cmax/Dose | ratio | 137 | 121 | 185 | 169 | 128 | 186 |
| AUC0-12h/Dose | ratio | 380 | 249 | 753 | 783 | 312 | 220 |

NA = Could not be determined from the data. Values shown are means (n = 6) unless noted.
a N = 4 for all Group 3 day 14 values;
b Median values shown for Tmax;
c N = 2

| | | Group | | | | | |
|---|---|---|---|---|---|---|---|
| | | 2 | | 3 | | 3 | |
| | | Dose (mg) | | | | | |
| | | 20 | | 40 | | 40 | |
| | | Day | | | | | |
| | | 14 | | 1 | | 14 | |
| Parameter | Units | Mean | SD | Mean | SD | Meana | SD |
| Dose | mg/kg | 0.27 | 0.05 | 0.52 | 0.04 | 0.52 | 0.04 |
| Cmax | ng/ml | 30.1 | 27.1 | 69.5 | 52 | 166 | 179 |
| Tmax | h | 1.5 | b | 1.08 | b | 0.5 | b |
| Cmin | ng/ml | 3.05 | 2.2 | 2.52 | 1.23 | 8.8 | 5.7 |
| Tmin | h | 12 | 0 | 12 | 0 | 12 | 0 |
| C12h | ng/ml | 3.05 | 2.2 | 2.52 | 1.24 | 8.8 | 5.7 |
| AUC0-12h | ng h/mL | 115 | 96 | 186 | 113 | 355 | 235 |

-continued

| | | Group | | | | | |
|---|---|---|---|---|---|---|---|
| | | 2 | | 3 | | 3 | |
| | | Dose (mg) | | | | | |
| | | 20 | | 40 | | 40 | |
| | | Day | | | | | |
| | | 14 | | 1 | | 14 | |
| Parameter | Units | Mean | SD | Mean | SD | Mean a | SD |
| AUClast | ng h/mL | 191 | 173 | NA | | 602 | 330 |
| AUCinf | ng h/mL | 433c | 310 | NA | | 712 | 340 |
| % AUCextrap | % | 19.0c | 1.3 | NA | | 16.5 | 13 |
| t1/2 | h | 33.3c | 4.3 | NA | | 35.3 | 16.8 |
| CSS | ng/ml | 9.6 | 8 | NA | | 29.6 | 19.6 |
| Cmax/Cmin | ratio | 10.8 | 9.3 | 28.2 | 19 | 15.6 | 6.9 |
| Cmax/Dose | ratio | 104 | 75 | 136 | 105 | 320 | 340 |
| AUC0-12h/Dose | ratio | 400 | 250 | 363 | 224 | 687 | 455 |

NA = Could not be determined from the data. Values shown are means (n = 6) unless noted.
a N = 4 for all Group 3 day 14 values;
b Median values shown for Tmax;
cN = 2

Conclusions: The safety analysis of CX157 10 mg, 20 mg and 40 mg administered twice daily for 14 days in normal healthy volunteers indicated that CX157 was generally safe and well tolerated, based upon the lack of clinically significant safety findings.

Pharmacokinetically, CX157 was rapidly absorbed resulting in generally proportional exposures after doses of 10, 20 and 40 mg. Plasma concentrations rose during twice-daily dosing, and reached steady-state levels during the 14-day study. Although the mean terminal half-life was 33.3 to 35.3 hours, a dose interval of 12-h appears to be pharmacokinetically appropriate for oral CX157 Liquid Filled Capsules. Variability identified in pharmacokinetic parameters may be a result of factors other than differences in body weight, race and gender.

With regards to pharmacodynamic activity, the data suggest that CX157 inhibits MAO-A activity when administered repeatedly at the doses tested in this study, and the extent of the inhibition of MAO-A activity was variable and did not appear to be dose-related.

Example 18: Safety, Tolerance, and PK of CX157 Administered Via Modified Release Tablets Objectives: This was a Phase I, single-center, randomized, double-blind, placebo-controlled, two-period, sequential dose comparison study in healthy male and female subjects. Safety, tolerance, and PK of CX157 administered via a modified release tablet were monitored.

Methods: A total of 20 Subjects (16 on CX157 and 4 on placebo) were dosed with CX157 Modified Release Tablets, 125 mg BID (total daily dose of 250 mg) or placebo in Period 1 for 7 days. Of the 20 subjects, 19 continued in Period 2 of the study where they received CX157 Modified Release Tablets, 175 mg BID (total daily dose of 350 mg) or placebo in the fed state for 7 days. Subjects who were randomized to CX157 125 mg BID in Period 1 received CX157 175 mg BID in Period 2, after a washout of 7 days. Subjects randomized to placebo in Period 1 received placebo in Period 2, after a washout of 7 days. Blood samples for PK analysis were collected during both periods of the study.

Formulations: Each CX157 Film Coated Tablet, 125 mg contains 125 mg CX157 and the following inactive ingredients: copovidone (Plasdone S630) NF; microcrystalline cellulose (Avicel PH 102) NF; hypromellose (Metalose 90SH-100SR) USP; colloidal silicon dioxide (Cabosil M-5P) NF; and magnesium stearate (Hyqual 5712) NF. Each oval, biconvex CX157 Film Coated Tablet, 125 mg has a white opaque film coating (Advantia™ Prime) and is stored long-term at controlled room temperature conditions [25° C. (77° F.); excursions 15-30° C. (59-86° F.)].

CX157 Modified Release Tablets contains 175 mg CX157 and the following inactive ingredients: copovidone (Plasdone S630) NF; microcrystalline cellulose (Avicel PH 102) NF; hypromellose (Metalose 90SH-4000SR) USP; colloidal silicon dioxide (Cabosil M-5P) NF; and magnesium stearate (Hyqual 5712) NF. Each CX157 Modified Release Tablet, 175 mg is stored long-term at controlled room temperature conditions [25° C. (77° F.), excursions 15-30° C. (59-86° F.)]; the tablets are a modified caplet shape, pale pink in color, and plain on both sides.

Figure 12:
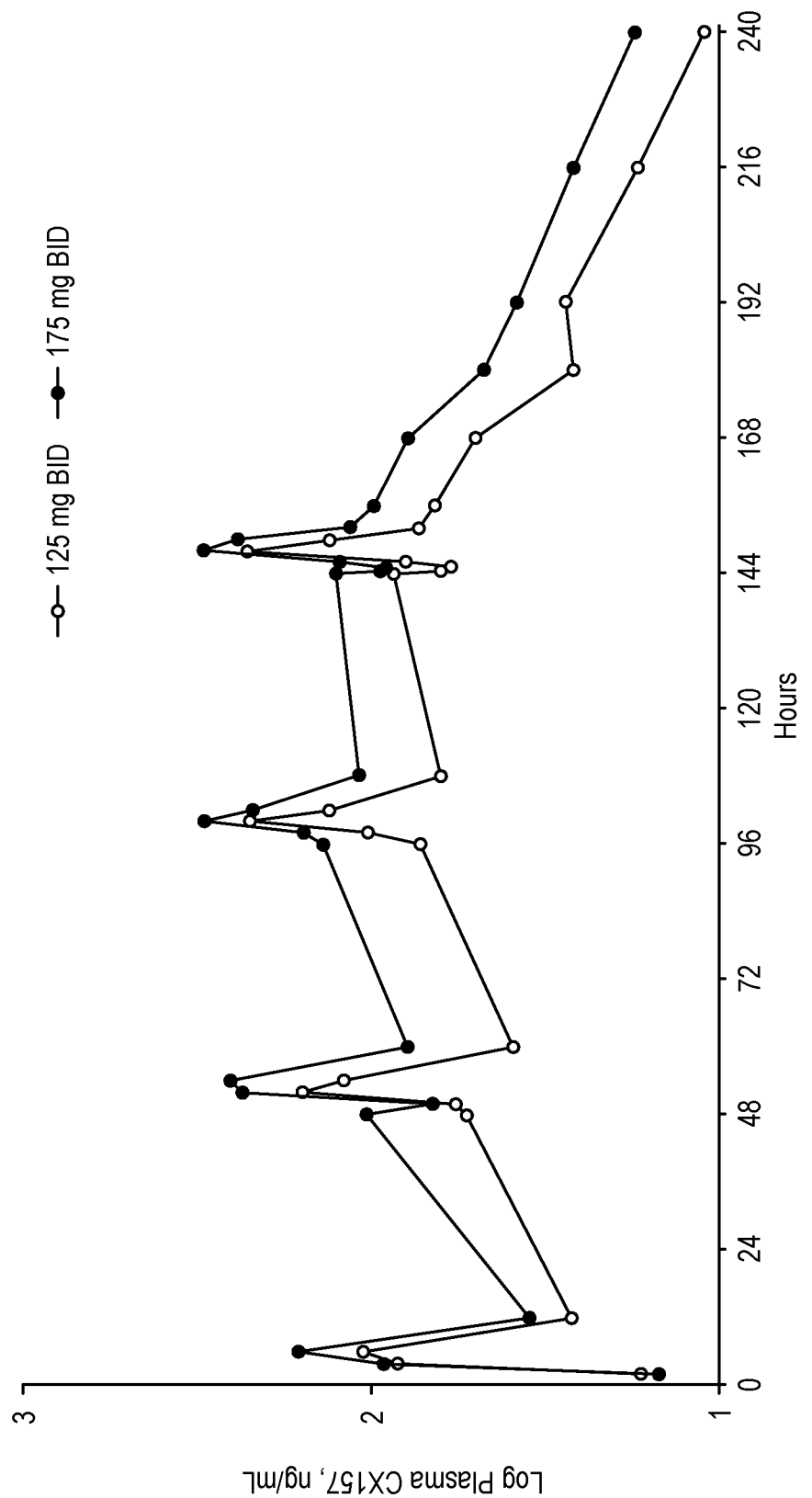
FIG. 12 illustrates exemplary mean plasma profiles of subjects after administration of CX157 twice a day, at two different dosage amounts, in the form of modified release tablets.

Results: FIG. 12 details exemplary logarithmic mean concentrations of CX157 (in ng/ml) in the plasma of subjects, measured from the time of administration of CX157 to 48 hours following administration. FIG. 12 details the logarithmic mean plasma concentrations of CX157 (in ng/ml) of subjects after administration of CX157 twice a day, at dosage amounts of 125 mg and 175 mg, in the form of modified release tablets. Overall, both doses of CX157 were well tolerated. All of the adverse events reported were mild to moderate in severity and resolved. After the last dose of CX157 125 mg on Day 7, the mean Cmax was 231.3±114 ng/mL and the Cmin was 54.9±32 ng/mL, representing a fluctuation in CX157 concentrations of 4.6-fold during each 12-h dosing interval at steady state. The AUCss was 1283±651 ng h/mL, resulting in an average plasma concentration (Css) at steady state of 106.9±54 ng/mL. The mean Cmax increased from 134±103 ng/mL on Day 1 to 231.3±114 ng/mL on Day 7, and the 12-hour AUC increased from 702±500 ng h/mL on Day 1 to 1283±651 ng h/mL on Day 7. Accumulation of CX157 during BID dosing with 125 mg MR tablets was 2.6-fold based on the Day 7 versus Day 1 exposures. After absorption of the last dose on Day 7, plasma concentrations fell in a log-linear manner over the rest of the study period. The terminal half-life observed for CX157 MR tablets, 125 mg was 39.4±14 h, a value similar to those observed in other repeated-dose studies of CX157 in humans.

Summary of Pharmacokinetic Parameters for CX157 MR Tablets at 125 mg:

| Parameter | Unit | Mean | SD | Median | Geometric mean | Min | Max | CV | n |
|---|---|---|---|---|---|---|---|---|---|
| $C_{max}$ | ng/ml | 231.3 | 114.0 | 202.5 | 200.1 | 36.4 | 435.0 | 49 | 16 |
| $T_{max}$ | h | 4.1 | 0.9 | 4.0 | 4.0 | 2.0 | 6.0 | 21 | 16 |
| $C_{min}$ | ng/ml | 54.9 | 32.1 | 48.9 | 45.3 | 7.8 | 136.0 | 59 | 16 |
| $T_{min}$ | h | 3.9 | 4.8 | 1.5 | 2.0 | 0.5 | 12.0 | 123 | 16 |
| $C_{12h}$ | ng/mL | 65.5 | 36.4 | 62.2 | 54.6 | 11.1 | 136.0 | 56 | 16 |
| $C_{last}$ | ng/ml | 11.1 | 8.3 | 11.2 | 8.2 | 0.58 | 35.9 | 75 | 16 |
| $T_{last}$ | h | 94.5 | 6.0 | 96.0 | 94.3 | 72.0 | 96.0 | 6 | 16 |
| $AUC_{SS}$ | ng h/mL | 1283 | 651.2 | 1169 | 1102 | 214 | 2496 | 51 | 16 |
| $C_{SS}$ | ng/ml | 106.9 | 54.3 | 97.4 | 91.8 | 17.8 | 208.0 | 51 | 16 |
| kel | h-1 | 0.0 | 0.01 | 0.0 | 0.0 | 0.0 | 0.1 | 64 | 16 |
| $t_{1/2}$ | h | 39.4 | 14.3 | 40.5 | 36.1 | 11.6 | 62.8 | 36 | 16 |
| $C_{max}$/dose | ratio | 134.1 | 62.44 | 117.0 | 117.3 | 22.9 | 229.7 | 47 | 16 |
| $AUC_{SS}$/dose | ratio | 748 | 378 | 692 | 646 | 134 | 1458 | 51 | 16 |
| $C_{max}/C_{min}$ | ratio | 4.6 | 1.3 | 4.7 | 4.4 | 2.5 | 7.4 | 28 | 16 |
| R (AUC) | ratio | 2.6 | 2.3 | 1.8 | 2.1 | 1.1 | 10.7 | 89 | 16 |
| CL/F | mL/min kg | 31.8 | 27.2 | 24.1 | 25.8 | 11.4 | 124.0 | 86 | 16 |

Summary of Pharmacokinetic Parameters for CX157 MR Tablets at 175 mg:

| Parameter | Unit | Mean | SD | Median | Geometric mean | Min | Max | CV | n |
|---|---|---|---|---|---|---|---|---|---|
| $C_{max}$ | ng/ml | 339 | 153 | 344 | 302 | 85.4 | 692 | 45 | 15 |
| $T_{max}$ | h | 4.4 | 1.1 | 4.0 | 4.3 | 2.0 | 6.0 | 25 | 15 |
| $C_{min}$ | ng/ml | 83.2 | 45.8 | 87.1 | 69.2 | 10.0 | 188.0 | 55 | 15 |
| $T_{min}$ | h | 4.7 | 5.4 | 1.0 | 2.2 | 0.5 | 12.0 | 114 | 15 |
| $C_{12h}$ | ng/ml | 98.2 | 55.0 | 87.1 | 80.9 | 11.0 | 215 | 56 | 15 |
| $C_{last}$ | ng/ml | 17.5 | 16.7 | 9.8 | 11.6 | 1.7 | 65.8 | 95 | 15 |
| $T_{last}$ | h | 92.8 | 12.4 | 96.0 | 91.7 | 48.0 | 96.0 | 13 | 15 |
| $AUC_{SS}$ | ng h/mL | 1955 | 992 | 1973 | 1697 | 352 | 4119 | 51 | 15 |
| $C_{SS}$ | ng/ml | 163 | 82.7 | 164 | 141 | 29.3 | 343 | 51 | 15 |
| kel | h-1 | 0.0 | 0.01 | 0.0 | 0.0 | 0.0 | 0.1 | 49 | 15 |
| $t_{1/2}$ | h | 32.4 | 12.0 | 30.4 | 30.1 | 11.0 | 54.4 | 37 | 15 |
| $C_{max}$/dose | ratio | 141 | 63.93 | 140 | 126 | 38.4 | 269.7 | 45 | 15 |
| $AUC_{SS}$/dose | ratio | 816 | 417 | 702 | 709 | 158 | 1638 | 51 | 15 |
| $C_{max}/C_{min}$ | ratio | 4.9 | 2.6 | 3.9 | 4.4 | 2.3 | 11.4 | 54 | 15 |
| R (AUC) | ratio | 2.5 | 1.5 | 2.0 | 2.2 | 1.1 | 7.4 | 62 | 15 |
| CL/F | mL/min kg | 28.5 | 23.3 | 23.7 | 23.5 | 10.2 | 105 | 82 | 15 |

Conclusions: Analysis of the data for CX157 Modified Release Tablets, 125 mg and 175 mg, showed that plasma concentrations reached or approached steady-state levels after 6 days of repeated BID dosing, and that significant plasma levels of CX157 were maintained over the 12-hour dose interval in most subjects on these regimens. The 125 mg and 175 mg formulations produced similar plasma profiles that were dose proportional, with approximately 50% higher exposures for the 175 mg formulation.

Example 19: Fed and Fasted Pharmacokinetics of CX157 Modified Release Tablet

Objectives: This was a Phase I, single-center, open-label, randomized, two-period, cross-over study in healthy male and female subjects. Comparison of CX157 with fed versus fasted subjects was observed.

Methods: A total of 18 subjects were to participate and receive a single dose of CX157 Modified Release Tablet, 175 mg in fed or fasted states according to a randomization schedule. There was a six to seven-day washout period between the two study drug administrations.

Formulations: CX157 Modified Release Tablets contains 175 mg CX157 and the following inactive ingredients: copovidone (Plasdone S630) NF; microcrystalline cellulose (Avicel PH 102) NF; hypromellose (Metalose 90SH-4000SR) USP; colloidal silicon dioxide (Cabosil M-5P) NF; and magnesium stearate (Hyqual 5712) NF. Each CX157 Modified Release Tablet, 175 mg is stored long-term at controlled room temperature conditions [25° C. (77° F.), excursions 15-30° C. (59-86° F.)]; the tablets are a modified caplet shape, pale pink in color, and plain on both sides.

Results: CX157 Modified Release Tablet, 175 mg was well tolerated in both fed and fasted states. There were no deaths or SAEs reported during the study. The two-period crossover food-effect study of CX157 Modified Release Tablets, 175 mg, in which 18 healthy subjects, who were randomly assigned to receive the drug orally after an overnight fast or after a high-fat breakfast, completed the study. Analysis of data from this study demonstrated the presence of a food effect for this formulation, which altered both the rate and extent of CX157 absorption.

The mean AUCinf was increased approximately 3-fold, from 554±468 ng h/mL in fasted subjects to 1782±2271 ng h/mL in fed subjects. The mean Cmax rose by approximately 5-fold, from 45±38 ng/mL in fasted subjects to 234±269 ng/mL in fed subjects. In addition to being more complete, absorption took place over a longer period of time in fed subjects compared to fasted subjects. The median Tmax was increased from 3 h in fasted subjects to 5 h in fed subjects, and plasma levels were 3 to 9-fold higher in fed subjects during the period between 4 and 12 h after dosing. Mean plasma concentrations for the two treatments fell in parallel during the elimination phase (from 24 to 72 h) with similar half-lives for fed (23.5±9.7 h) and fasted (20.6±8.5 h) treatments, suggesting there was no food effect on the halflife of the drug. Summary of PK Parameters by Treatment:

| Parameter | Unit | Fed | | Fasted | | Fed/Fasted Ratio | P* |
|---|---|---|---|---|---|---|---|
| | | Mean | SD | Mean | SD | | |
| Dose | mg/kg | 2.3 | 0.39 | 2.3 | 0.39 | ND | ND |
| $C_{max}$ | ng/ml | 234 | 269 | 45.3 | 38.0 | 5.2 | <0.0001 |
| $T_{max}$ | h | 5.22 | 1.1 | 3.31 | 1.6 | 1.6 | 0.0007 |
| $C_{last}$ | ng/mL | 4.69 | 7.1 | 2.48 | 3.2 | 1.9 | ND |
| $T_{last}$ | h | 66.7 | 13.2 | 60.0 | 16.5 | 1.1 | ND |
| $C_{12h}$ | ng/ml | 26.5 | 28.6 | 8.97 | 6.5 | 3.0 | <0.0001 |
| $AUC_{0-12h}$ | ng h/mL | 893 | 1045 | 207 | 151 | 4.3 | ND |
| $AUC_{last}$ | ng h/mL | 1480 | 1807 | 476 | 398 | 3.1 | <0.0001 |
| $AUC_{inf}$ | ng h/mL | 1782 | 2271 | 554 | 468 | 3.2 | ND |
| half-life | h | 23.5 | 9.7 | 20.6 | 8.5 | 1.1 | 0.1353 |
| $C_{max}$/dose | ratio | 92.1 | 87.9 | 18.3 | 14.0 | 5.0 | <0.0001 |
| $AUC_{inf}$/dose | ratio | 698 | 737 | 229 | 172 | 3.1 | 0.0002 |
| CL/F | mL/min kg | 44.2 | 29.3 | 122 | 91.4 | 0.4 | ND |
| Vd/F | L/kg | 76.3 | 43.5 | 184 | 122.9 | 0.4 | ND |
| $T_{lag}$ | h | 1.36 | 0.45 | 1.03 | 0.40 | 1.3 | 0.0161 |

Figure 13:
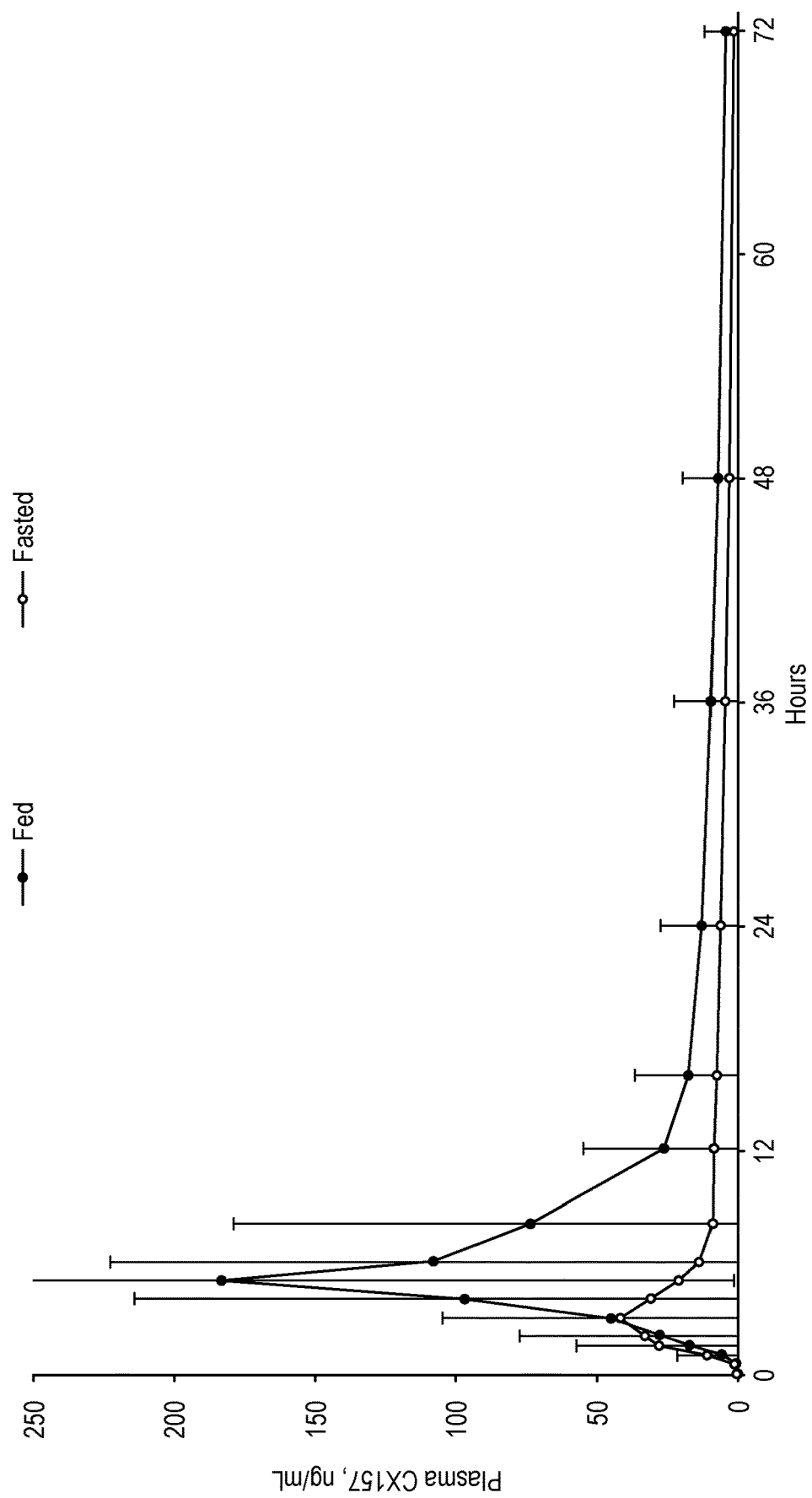
FIG. 13 illustrates exemplary mean plasma concentrations of subjects after taking a single dose of CX157 in the form of a modified release tablet, in fed or fasted states according to a randomization schedule.

Conclusions: FIG. 13 details exemplary mean plasma concentrations of CX157 (in ng/ml) in the plasma of subjects in fed and fasted subjects, measured from predose until 72 hours following administration of CX157. A significant pharmnacokinetic food effect was observed for CX157 Modified Release Tablets, 175 mg after oral administration to healthy male and female subjects in a crossover study comparing administration after an overnight fast and after a high-fat, high-calorie meal. In nearly all subjects, feeding resulted in substantial (approximately 3 to 5-fold) increases in Cmax and AUC, with plasma levels in fed subjects remaining at least 2-fold higher than those in fasted subjects from 3 h to at least 72 h after dosing. Food also prolonged absorption, with increases in $T_{max}$ and lag time observed after feeding. The half-life of CX157 (mean, 20.6 to 23.5 h) was not significantly different between treatments.

Example 20: In Vivo Assessment of Efficacy of Chronic CX157 and Low-Dose DMT in Mouse Model Objectives: The primary objective of this study is to examine the efficacy of disclosed methods for treating depression in a rodent in vivo experimental model. Specifically, a mouse model is used to determine the efficacy of CX157 in combination with DMT for treating depression.

Methods: Mice are given a first dose and a second dose by oral gavage, with the doses given consecutively 30 minutes apart. The substances administered of dose one and two are outlined below in groups 1 to 5. This two-dose regimen is repeated daily for 5 weeks. CX157 can be dosed approximately at 31 mg/kg. DMT can be dosed approximately at 1.2 mg/kg.

| Dose Article | Dose Amount |
|---|---|
| CX157 | 31 mg/kg |
| DMT | 1.2 mg/kg |

Mice are divided into 5 groups with 10 mice in each group. Each group receives a test article according to the grouping below.

| Group | First Dose | Second Dose (30 min. After first dose) |
|---|---|---|
| 1 | Vehicle | Vehicle |
| 2 | CX157 | Vehicle |
| 3 | Vehicle | DMT |
| 4 | CX157 | DMT |
| 5 | Phenelzine | DMT |

Head-twitch response (HTR) assessment is a well-known assay for evaluating the hallucinogenic activity of a compound in mice. HTR assessment is conducted in 2 minute periods, every 10 minutes, for 60 minutes post-administration of test articles. HTR assessment is initiated immediately following administration of test articles. Two additional sub-groups with 5 mice from group 4 and 5 mice from group 5 are implicated in a tyramine challenge experiment via blood pressure analysis.

After the conclusion of two full weeks of the dosing regimen described above, depression is evaluated by performing a forced swim test 1 hour after the second dose. The forced swim test assay is repeated after the conclusion of the fourth full week of the dosing regimen. After the conclusion of three full weeks of the dosing regimen described above, depression is evaluated by performing a fear conditioning and extinction assay 1 hour after the second dose. The fear conditioning and extinction assay is repeated after the conclusion of the fourth full week of the dosing regimen. These assays are described in, e.g., Cameron et al., ACS Chem Neurosci. 2019; 10(7):3261-3270 and other general references known in the art.

Five mice from each of Groups 4 (CX157/DMT) and 5 (phenelzine/DMT) will be further subjected to a tyramine challenge. In this experiment, mice are administered tyramine by oral gavage. Blood pressure is assessed 1 hour following tyramine administration by the tail-cuff technique, as described in Bunag RD, J Applied Physiology. 1973 February; 34(2):279-82. After termination of the mice in Groups 1-5, blood samples are analyzed to determine levels of test article in the blood and brain tissue.

Results: This experiment provides preclinical insight into the efficacy of treating depression according to disclosed methods. Results further provide insight into the safety of subjecting a subject to a disclosed method without modification of diet with respect to tyramine-containing foods.

Example 21: Human Clinical Study of Combined Therapy with CX157 and DMT

Objectives: The objective of this study is to determine the appropriate dose for low-dose treatment of human subjects with DMT following administration of CX157.

Study Design: This open label, single-dose study will treat three groups (n=10/group) of healthy volunteers with "micro" (low) doses of orally administered DMT 2 hours after receiving 175 mg of oral CX157.

| Group | CX157 Dose | DMT Dose |
| --- | --- | --- |
| 1 | 0 (not administered) | 0.5 mg/kg |
| 2 | 175 mg | 0.03 mg/kg |
| 3 | 175 mg | 0.05 mg/kg |
| 4 | 175 mg | 0.07 mg/kg |

Additional groups may be added, in which subjects are treated with higher or lower doses of CX157 or DMT, depending on preliminary or interim results from the study. Groups can be dosed sequentially; specifically, Group 3 and Group 4 can follow depending on the results from the previous (lower dose) group. For Example, if the outcome from Group 2 is appropriate, Group 3 will be dosed according to the dosing schedule above. However, if the dose of Group 2 is too high (as determined by the occurrence of unpleasant side effects), the doses for Groups 3 and 4 can be adjusted down; or another Group (i.e., Group 5) can be added with an additional dose (such as 0.04 mg/kg).

Formulation: The formulation of CX157 can be a modified release tablet containing 175 mg CX157 and can include the following inactive ingredients: copovidone (Plasdone S630) NF; microcrystalline cellulose (Avicel PH 102) NF; hypromellose (Metalose 90SH-4000SR) USP; colloidal silicon dioxide (Cabosil M-5P) NF; and magnesium stearate (Hyqual 5712) NF. Each CX157 Modified Release Tablet, 175 mg is stored long-term at controlled room temperature conditions [25° C. (77° F.), excursions 15-30° C. (59-86° F.)]; the tablets can be a modified caplet shape, pale pink in color, and plain on both sides.

Inclusion Criteria: Healthy adult volunteers aged 18-65 years old will be eligible for this study.

Exclusion Criteria: Subjects with acute or chronic heart failure, liver failure, kidney failure, resistant hypertension, arrhythmia, valvular heart disease, chronic obstructive pulmonary disease, asthma, severe obesity, epilepsy, pregnancy, thyroid disorders; and those with a family diagnosis or suspicion of genetic monoamine oxidase deficiency, previous adverse response to psychedelic substances, present or past symptoms or family members with a psychotic disorder, dissociative identity disorder, bipolar disorder, prodromal symptoms of schizophrenia, abuse of alcohol or other substances, except tobacco, acute or sub-acute risk of suicide, flu-like symptoms; and those for whom CX157 or DMT is otherwise contraindicated.

Dosing Regimen:

| Hour | Group 1 | Group 2 | Group 3 | Group 4 |
| --- | --- | --- | --- | --- |
| 0 | Free breakfast: encourage all to eat well | | | |
| 1 (oral CX157) | X (no CX157) | 175 mg CX157 modified release tablet | | |
| | Subject Assessment: e.g., Hallucinogen Rating Scale (HRS) | | | |
| 3 DMT dose (mg/kg) | 0.5 | 0.03 | 0.05 | 0.07 |
| PK determinations (Minutes) | 15, 30, 45, 60 | 30, 60, 90, 120, 180 | | |
| 5 | Provide lunch | | | |
| 6 | Subject Assessment: e.g., Hallucinogen Rating Scale (HRS) | | | |

Primary Outcome Measures: Safety and pharmacokinetics (PK) will be assessed as described in Table 1. Blood pressure, heart rate, respiratory rate, and oxygen saturation will be measured at 1, 2, and 3 hours after the oral DMT dose. Plasma levels of glucose, urea, creatinine, AST, and ALT will be measured at 2 and 4 hours after the oral DMT dose. Serotonin Syndrome Scale will be administered at 2 hours and 4 hours after the oral DMT dose.

Secondary Outcome Measures: Subjects will be administered the Hallucinogen Rating Scale (HRS) 3 hours after receiving the oral DMT dose. Higher scores will indicate a more intense psychedelic experience. Preferably, subjects will indicate low HRS scores, indicating a sub-hallucinogenic dose. Subjects will further evaluate the impact of DMT on the Satisfaction with Life Scale (SWL), State-Trait Anxiety Inventory, WHO Quality of Life Assessment Instrument, and Positive and Negative Affect Schedule (PANAS) both prior to study participation and 1 month after study participation.

Example 22: In Vivo Treatment Efficacy of Chronic CX157 and Deuterated 5-$HT_{2A}$ Receptor Agonist Objectives: The primary objective of this study is to examine the efficacy of disclosed methods for treating depression in a rodent in vivo experimental model. Specifically, a mouse model is used to determine the efficacy of CX157 in combination with a deuterated or non-deuterated 5-$HT_{2A}$ agonist for treating depression. In this example, the deuterated 5-$HT_{2A}$ agonist is deuterated DMT, and the non-deuterated 5-$HT_{2A}$ agonist is DMT.

Methods: Mice are given a first dose and a second dose by oral gavage, with the doses given consecutively 30 minutes apart. The substances administered of dose one and two are outlined below in groups 1 to 6. This two-dose regimen is repeated daily for 5 weeks. CX157 can be dosed approximately at 31 mg/kg. DMT and deuterated DMT can be dosed approximately at 1.2 mg/kg.

| Dose Article | Dose Amount |
| --- | --- |
| CX157 | 31 mg/kg |
| Deuterated DMT | 1.2 mg/kg |

Mice are divided into 6 groups with 10 mice in each group. Each group receives a test article according to the grouping below.

| Group | First Dose | Second Dose (30 min. After first dose) |
|---|---|---|
| 1 | Vehicle | Vehicle |
| 2 | CX157 | Vehicle |
| 3 | Vehicle | Deuterated DMT |
| 4 | CX157 | Deuterated DMT |
| 5 | Phenelzine | Deuterated DMT |
| 6 | CX157 | DMT |

Head-twitch response (HTR) assessment is a well-known assay for evaluating the hallucinogenic activity of a compound in mice. HTR assessment is conducted in 2 minute periods, every 10 minutes, for 60 minutes post-administration of test articles. HTR assessment is initiated immediately following administration of test articles. Two additional sub-groups with 5 mice from group 4 and 5 mice from group 5 are implicated in a tyramine challenge experiment via blood pressure analysis. After the conclusion of two full weeks of the dosing regimen described above, depression is evaluated by performing a forced swim test 1 hour after the second dose. The forced swim test assay is repeated after the conclusion of the fourth full week of the dosing regimen. After the conclusion of three full weeks of the dosing regimen described above, depression is evaluated by performing a fear conditioning and extinction assay 1 hour after the second dose. The fear conditioning and extinction assay is repeated after the conclusion of the fourth full week of the dosing regimen. These assays are described in, e.g., Cameron et al., ACS Chem Neurosci. 2019; 10(7):3261-3270 and other references known in the art. Five mice from each of Groups 4 (CX157/deuterated DMT), 5 (phenelzine/deuterated DMT), and 6 (CX157/DMT) will be further subjected to a tyramine challenge. In this experiment, mice are administered tyramine by oral gavage. Blood pressure is assessed 1 hour following tyramine administration by the tail-cuff technique, as described in Bunag RD. Validation in awake rats of a tail-cuff method for measuring systolic pressure. See, e.g., J Applied Physiology. 1973; 34(2):279-82.

After termination of the mice in Groups 1-6, blood samples are analyzed to determine levels of test article in the blood and brain tissue.

Results: This experiment provides preclinical insight into the efficacy of treating depression according to disclosed methods. Results also provide insight into the safety of subjecting a subject to a disclosed method without modification of diet with respect to tyramine-containing foods.

Example 23: Human Clinical Study of Combined Therapy with CX157 and Deuterated 5-HT$_{2A}$ Agonist Objectives: The objective of this study is to determine the appropriate dose for low-dose treatment of human subjects with a deuterated 5-HT$_{2A}$ agonist following administration of CX157. In this example, the deuterated 5-HT$_{2A}$ agonist is deuterated DMT.

Study Design: This open label, single-dose study will treat three groups (n=10/group) of healthy volunteers with "micro" (low) doses of orally administered DMT 2 hours after receiving 175 mg of oral CX157.

| Group | CX157 Dose | Deuterated DMT Dose |
|---|---|---|
| 1 | 0 (not administered) | 0.5 mg/kg |
| 2 | 175 mg | 0.03 mg/kg |
| 3 | 175 mg | 0.05 mg/kg |
| 4 | 175 mg | 0.07 mg/kg |

Additional groups may be added, in which subjects are treated with higher or lower doses of CX157 or deuterated DMT, depending on preliminary or interim study results. Groups can be dosed sequentially; specifically, Groups 3 and 4 can follow depending on results from the previous (lower dose) group. For Example, if the outcome from Group 2 is appropriate, Group 3 will be dosed according to the dosing schedule above. However, if the dose of Group 2 is too high (as determined by the occurrence of unpleasant side effects), the doses for Groups 3 and 4 can be adjusted down; or another Group (i.e., Group 5) can be added with an additional dose (e.g., 0.04 mg/kg).

Formulation: The formulation of CX157 can be a modified release tablet containing 175 mg CX157 and can include the following inactive ingredients: copovidone (Plasdone S630) NF; microcrystalline cellulose (Avicel PH 102) NF; hypromellose (Metalose 90SH-4000SR) USP; colloidal silicon dioxide (Cabosil M-5P) NF; and magnesium stearate (Hyqual 5712) NF. Each CX157 Modified Release Tablet, 175 mg is stored long-term at controlled room temperature conditions [25° C. (77° F.), excursions 15-30° C. (59-86° F.)]; the tablets can be a modified caplet shape, pale pink in color, and plain on both sides.

Inclusion Criteria: Healthy adult volunteers aged 18-65 years will be eligible for this study.

Exclusion Criteria: Subjects with acute or chronic heart failure, liver failure, kidney failure, resistant hypertension, arrhythmia, valvular heart disease, chronic obstructive pulmonary disease, asthma, severe obesity, epilepsy, pregnancy, thyroid disorders; and those with a family diagnosis or suspicion of genetic monoamine oxidase deficiency, previous adverse response to psychedelic substances, present or past symptoms or family members with a psychotic disorder, dissociative identity disorder, bipolar disorder, prodromal symptoms of schizophrenia, abuse of alcohol or other psychoactive substances, except tobacco, acute or sub-acute risk of suicide, flu-like symptoms; and those for whom CX157 or deuterated DMT is otherwise contraindicated.

Dosing Regimen:

| Hour | Group 1 | Group 2 | Group 3 | Group 4 |
|---|---|---|---|---|
| 0 | Free breakfast: encourage all to eat well | | | |
| 1 (oral CX157) | X (no CX157) | 175 mg CX157 modified release tablet | | |
| | Subject Assessment: e.g., Hallucinogen Rating Scale (HRS) | | | |
| 3 Deuterated DMT dose (mg/kg) | 0.5 | 0.03 | 0.05 | 0.07 |
| PK determinations (Minutes) | 15, 30, 45, 60 | 30, 60, 90, 120, 180 | | |
| 5 | Provide lunch | | | |
| 6 | Subject Assessment: e.g., Hallucinogen Rating Scale (HRS) | | | |

Primary Outcome Measures: Safety and pharmacokinetics (PK) will be assessed as described in Table 1. Blood pressure, heart rate, respiratory rate, and oxygen saturation will be measured at 1, 2, and 3 hours after the oral DMT dose. Plasma levels of glucose, urea, creatinine, AST, and ALT will be measured at 2 and 4 hours after the oral deuterated DMT dose. Serotonin Syndrome Scale will be administered at 2 hours and 4 hours after the oral deuterated DMT dose.

Secondary Outcome Measures: Subjects will be administered the Hallucinogen Rating Scale (HRS) 3 hours after receiving the oral deuterated DMT dose. Higher scores will indicate a more intense psychedelic experience. Preferably, subjects will indicate low HRS scores, indicating a sub-hallucinogenic dose. Subjects will further evaluate the impact of DMT on the Satisfaction with Life Scale (SWL), State-Trait Anxiety Inventory, WHO Quality of Life Assessment Instrument, and Positive and Negative Affect Schedule (PANAS) both prior to study participation and 1 month after study participation.

Example 24: Exemplary Administration of CX157, DMT, and Combinations Thereof

Administration Example 1: Subjects are administered 175 mg CX157 alone. No subjective effects are noticeable during a period of 2.5 hours after administration, and no significant antidepressant activity was detected in the trial subjects, in accordance with similar findings, e.g., Clinical Trial No. NCT01633437.

Administration Example 2: Subjects are administered 25 mg, 37.5 mg, 50 mg, 75 mg, or 100 mg DMT freebase in a capsule. No subjective effects are noticeable at any dose during a period for over 1 hour after administration, in accordance with similar findings published in the literature, e.g., Barker, S. A., 2022.

Administration Example 3: Subjects are administered 175 mg CX157, and then from between 2-3 hours later, such as at 2 hours 40 minutes later, a dose of 0.03 mg/kg, 0.05 mg/kg, or 0.07 mg/kg DMT freebase in capsule. Alternatively, subjects are administered a capsule containing 2.5 mg, 3.75 mg, 5 mg, 7.5 mg, 10 mg, 12.5 mg, 15 mg, 17.5 mg, or 20 mg DMT freebase. Subjective effects are noticeable from around one hour, such as a feeling of focus, followed by a smooth, steady, calm energy, lasting around 6 hours, such as 5 hours 40 minutes, with a feeling of tranquility about 1 hour later, and a total duration of around 8 hours, such as 8 hours 15 minutes.

Administration Example 4: Subjects are administered 175 mg CX157, and then from between 2-3 hours later, such as at 2 hours 15 minutes later, a dose of 0.2 mg/kg, 0.4 mg/kg, or 0.6 mg/kg DMT freebase in capsule. Alternatively, subjects are administered a capsule containing 25 mg, 37.5 mg, 50 mg, 75 mg, 100 mg, 125 mg, 150 mg, 175 mg, or 200 mg DMT freebase. At lower doses of DMT, subjects report effects that are relaxing, comforting, and "warm," and describe mildly mood-elevating and anxiolytic properties. At higher doses of DMT, subjects report psychedelic effects that are noticeable from around 40 minutes, with heightening of effects at one hour, a peak of about 30 minutes, a diminishing of effects returning to baseline of about 30 minutes, and a total duration of around 2 hours, during which subjects note changes in auditory and visual perception, such as closed- and open-eye visuals, and including at sufficient doses, a 'breakthrough' into perceptual and hallucinogenic effects typical of DMT.

In any of the above Administration Examples, the CX157 may be prepared as a 175 mg modified release tablet, such as described in U.S. Pat. No. 8,313,766.

The foregoing description, for purposes of explanation, uses specific nomenclature to provide a thorough understanding of the invention. However, it will be apparent that specific details are not required in order to practice the invention. Thus, the description of specific embodiments is presented for purposes of illustration and description, but is not intended to be exhaustive or to limit the invention to the precise compositions, formulations, methods, or the like disclosed; many modifications and variations are possible in view of the above teachings. Embodiments were chosen and described in order to best explain the principles of the invention and its practical applications, through the elucidation of specific examples, and to thereby enable others in the art to best utilize the invention and various embodiments with various modifications as are suited to the particular use contemplated, when such uses are beyond the specific examples disclosed. Accordingly, the scope of the invention shall be defined solely by the following claims and their equivalents.

The invention claimed is:

1. A pharmaceutical composition or kit of parts, useful to treat a mental health disorder in a human, comprising therapeutically effective amounts of:
   a) a compound having the formula:

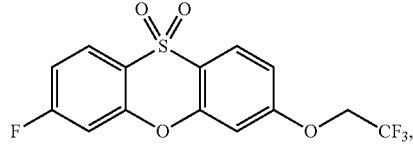

(CX157), or a pharmaceutically acceptable salt thereof; and
   b) N,N-dimethyltryptamine (DMT), or a pharmaceutically acceptable salt thereof;
wherein the DMT is formulated for oral administration.

2. A method of treating a mental health in a subject, comprising administering to the subject the composition or kit of parts of claim 1.

3. The method of claim 2, wherein the CX157 is administered prior to administration of the DMT.

4. The method of claim 2, wherein the mental health disorder is any of post-traumatic stress disorder (PTSD), an adjustment disorder, an affective disorder, a depressive disorder, major depressive disorder (MDD), treatment-resistant depression (TRD), atypical depression, postpartum depression, catatonic depression, a depressive disorder due to a medical condition, premenstrual dysphoric disorder, seasonal affective disorder, dysthymia, an anxiety disorder, an anxiety related disorder, generalized anxiety disorder (GAD), a phobia disorder, binge eating disorder, body dysmorphic disorder, an alcohol or drug abuse or dependence disorder, a substance use disorder, substance-induced mood disorder, a mood disorder related to another health condition, a disruptive behavior disorder, an eating disorder, an impulse control disorder, obsessive compulsive disorder (OCD), attention deficit hyperactivity disorder (ADHD), prolonged grief disorder, a personality disorder, autism, autism spectrum disorder, social anxiety in autism, an attachment disorder, and a dissociative disorder.

5. The composition or kit of parts of claim 1, comprising between about 50 mg and about 300 mg, between about 75 mg and about 200 mg, between about 100 mg and about 150 mg, about 125 mg, or about 175 mg of CX157, or a pharmaceutically acceptable salt thereof.

6. The composition or kit of parts of claim 5, comprising about 175 mg of CX157, or a pharmaceutically acceptable salt thereof.

7. The composition or kit of parts of claim 1, comprising between about 1 mg and about 300 mg of DMT, or a pharmaceutically acceptable salt thereof.

8. The composition or kit of parts of claim 7, comprising between about 1 mg and about 10 mg of DMT, or a pharmaceutically acceptable salt thereof.

9. The composition or kit of parts of claim 7, comprising between about 10 mg and about 60 mg of DMT, or a pharmaceutically acceptable salt thereof.

10. The composition or kit of parts of claim 7, comprising between about 60 mg and about 250 mg of DMT, or a pharmaceutically acceptable salt thereof.

11. The composition or kit of parts of claim 1, wherein the CX157 or the DMT is formulated for modified release.

12. The composition or kit of parts of claim 1, further comprising a pharmaceutically acceptable carrier, diluent, or excipient.

13. The composition of claim 12, wherein the pharmaceutically acceptable carrier, diluent, or excipient comprises copovidone, microcrystalline cellulose, hypromellose, colloidal silicon dioxide, or magnesium stearate.

14. The method of claim 2, wherein the amount administered to the subject of CX157, or a pharmaceutically acceptable salt thereof, is between about 50 mg and about 300 mg, between about 75 mg and about 200 mg, between about 100 mg and about 150 mg, about 125 mg, or about 175 mg.

15. The method of claim 14, wherein the amount administered to the subject of CX157, or a pharmaceutically acceptable salt thereof, is about 175 mg.

16. The method of claim 2, wherein the amount administered to the subject of DMT, or a pharmaceutically acceptable salt thereof, is between about 0.05 mg/kg and about 3 mg/kg.

17. The method of claim 16, wherein the amount administered to the subject of DMT, or a pharmaceutically acceptable salt thereof, is between about 0.05 mg/kg and about 0.10 mg/kg.

18. The method of claim 16, wherein the amount administered to the subject of DMT, or a pharmaceutically acceptable salt thereof, is between about 0.30 mg/kg and about 0.60 mg/kg.

19. The method of claim 16, wherein the amount administered to the subject of DMT, or a pharmaceutically acceptable salt thereof, is between about 0.60 mg/kg and about 3 mg/kg.

* * * * *